United States Patent
Henry et al.

(10) Patent No.: US 10,870,837 B2
(45) Date of Patent: *Dec. 22, 2020

(54) FUSION PROTEINS COMPRISING ENZYME REPLACEMENT THERAPY ENZYMES

(71) Applicant: Denali Therapeutics Inc., South San Francisco, CA (US)

(72) Inventors: Anastasia Henry, South San Francisco, CA (US); Mihalis Kariolis, South San Francisco, CA (US); Cathal Mahon, South San Francisco, CA (US); Adam P. Silverman, South San Francisco, CA (US); Ankita Srivastava, South San Francisco, CA (US)

(73) Assignee: Denali Therapeutics Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/355,339

(22) Filed: Mar. 15, 2019

(65) Prior Publication Data

US 2019/0249155 A1 Aug. 15, 2019

Related U.S. Application Data

(63) Continuation of application No. PCT/US2018/053747, filed on Oct. 1, 2018.

(60) Provisional application No. 62/721,396, filed on Aug. 22, 2018, provisional application No. 62/678,183, filed on May 30, 2018, provisional application No. 62/626,365, filed on Feb. 5, 2018, provisional application No. 62/583,276, filed on Nov. 8, 2017, provisional application No. 62/566,898, filed on Oct. 2, 2017.

(51) Int. Cl.
| | | |
|---|---|---|
| *A61K 39/395* | (2006.01) | |
| *C12N 9/16* | (2006.01) | |
| *C07K 14/00* | (2006.01) | |
| *A61K 47/68* | (2017.01) | |
| *C07K 19/00* | (2006.01) | |
| *C12N 15/62* | (2006.01) | |
| *C07K 16/28* | (2006.01) | |
| *C12N 9/18* | (2006.01) | |
| *C12N 9/24* | (2006.01) | |
| *A61K 38/00* | (2006.01) | |

(52) U.S. Cl.
CPC .......... *C12N 9/16* (2013.01); *A61K 47/68* (2017.08); *C07K 14/00* (2013.01); *C07K 16/28* (2013.01); *C07K 16/2881* (2013.01); *C07K 19/00* (2013.01); *C12N 9/18* (2013.01); *C12N 9/2402* (2013.01); *C12N 15/62* (2013.01); *C12Y 301/06013* (2013.01); *A61K 38/00* (2013.01); *C07K 2317/55* (2013.01); *C07K 2317/622* (2013.01); *C07K 2317/92* (2013.01); *C07K 2319/30* (2013.01); *C12Y 301/04012* (2013.01); *C12Y 302/01045* (2013.01); *C12Y 310/01001* (2013.01)

(58) Field of Classification Search
None
See application file for complete search history.

(56) References Cited

U.S. PATENT DOCUMENTS

| | | | |
|---|---|---|---|
| 7,396,811 B2 | 7/2008 | Lebowitz et al. | |
| 7,442,372 B2 | 10/2008 | Kakkis | |
| 7,560,424 B2 | 7/2009 | Lebowitz et al. | |
| 7,569,544 B2 | 8/2009 | Zankel et al. | |
| 7,829,537 B2 | 11/2010 | Zankel et al. | |
| 7,871,624 B2 | 1/2011 | Grubb et al. | |
| 7,981,864 B2 | 7/2011 | Lebowitz | |
| 8,124,073 B2 | 2/2012 | Stefano | |
| 8,128,925 B2 | 3/2012 | Vellard et al. | |
| 8,207,114 B2 | 6/2012 | Lebowitz et al. | |
| 8,227,212 B2 | 7/2012 | Von et al. | |
| 8,486,399 B2 | 7/2013 | Pardridge et al. | |
| 8,536,315 B2 | 9/2013 | Hyden et al. | |
| 8,545,837 B2 | 10/2013 | Zhu et al. | |
| 8,546,319 B2 | 10/2013 | Starr et al. | |
| 8,658,162 B2 | 2/2014 | Schuchman et al. | |
| 8,715,661 B2 | 5/2014 | Pardridge et al. | |
| 8,722,019 B2 | 5/2014 | Jefferies et al. | |
| 8,748,567 B2 | 6/2014 | Narasimhaswamy et al. | |
| 8,834,874 B2 | 9/2014 | Pardridge et al. | |
| 8,858,950 B2 | 10/2014 | Pardridge et al. | |
| 8,889,127 B2 | 11/2014 | Muro Galindo et al. | |
| 8,906,379 B2 | 12/2014 | Stefano | |
| 8,920,801 B2 | 12/2014 | Pardridge et al. | |
| 8,926,967 B2 | 1/2015 | Dodge et al. | |

(Continued)

FOREIGN PATENT DOCUMENTS

| | | |
|---|---|---|
| EP | 2842969 A1 | 3/2015 |
| EP | 3409771 A1 | 12/2018 |

(Continued)

OTHER PUBLICATIONS

Chung, et al., "A biochemical and physicochemical comparison of two recombinant enzymes used for enzyme replacement therapies of hunter syndrome", Glycoconj J 31, 309-315 (2014).

Karpova, et al., "A fluorimetric enzyme assay for the diagnosis of Sanfilippo disease type A (MPS IIIA)", J Inher Metab Dis 19, 278-285 (1996).

Muenzer, et al., "A phase II/III clinical study of enzyme replacement therapy with idursulfase in mucopolysaccharidosis II (Hunter syndrome)", Genetics in Medicine 8(8), 465-473 (2006).

(Continued)

*Primary Examiner* — Michael D Pak
(74) *Attorney, Agent, or Firm* — Viksnins Harris Padys Malen LLP

(57) ABSTRACT

Provided herein are fusion proteins that comprise an enzyme replacement therapy enzyme and an Fc region, as well as methods of using such proteins to treat a lysosomal storage disorder. Methods for transporting agents across the blood-brain barrier are also provided herein.

47 Claims, 26 Drawing Sheets

Specification includes a Sequence Listing.

(56) References Cited

U.S. PATENT DOCUMENTS

| | | |
|---|---|---|
| 9,044,473 B2 | 6/2015 | Kakkis |
| 9,051,556 B2 | 6/2015 | Nichols |
| 9,089,566 B2 | 7/2015 | Kakkis |
| 9,150,841 B2 | 10/2015 | Boldog et al. |
| 9,206,402 B2 | 12/2015 | Jin et al. |
| 9,279,109 B2 | 3/2016 | Mihara et al. |
| 9,283,181 B2 | 3/2016 | Calias et al. |
| 9,364,567 B2 | 6/2016 | Vitalis et al. |
| 9,487,766 B2 | 11/2016 | Ballabio et al. |
| 9,492,511 B2 | 11/2016 | Nichols |
| 9,545,450 B2 | 1/2017 | Do |
| 9,579,366 B2 | 2/2017 | Quinn et al. |
| 9,603,908 B2 | 3/2017 | Xie et al. |
| 9,611,323 B2 | 4/2017 | Dennis et al. |
| 9,657,310 B2 | 5/2017 | Takahashi et al. |
| 9,682,129 B2 | 6/2017 | Barbier et al. |
| 9,689,015 B2 | 6/2017 | Piens et al. |
| 9,708,406 B2 | 7/2017 | Zhang et al. |
| 9,757,470 B2 | 9/2017 | Narasimhaswamy et al. |
| 9,814,762 B2 | 11/2017 | Lebowitz et al. |
| 9,834,587 B2 | 12/2017 | Aoyagi-Scharber et al. |
| 9,834,588 B2 | 12/2017 | Aoyagi-Scharber et al. |
| 9,845,327 B2 | 12/2017 | Krainc et al. |
| 9,862,939 B2 | 1/2018 | Radin et al. |
| 9,880,151 B2 | 1/2018 | Watt et al. |
| 9,896,672 B2 | 2/2018 | Jin et al. |
| 9,957,489 B2 | 5/2018 | Fogh et al. |
| 9,975,955 B2 | 5/2018 | Pardridge et al. |
| 9,982,243 B2 | 5/2018 | Berghard et al. |
| 9,994,641 B2 | 6/2018 | Sonoda et al. |
| 10,058,619 B2 | 8/2018 | Jefferies et al. |
| 10,080,783 B2 | 9/2018 | Dodge et al. |
| 10,174,299 B2 | 1/2019 | Jin et al. |
| 10,457,717 B2 | 10/2019 | Chen et al. |
| 2004/0229250 A1 | 11/2004 | Figura et al. |
| 2005/0100986 A1 | 5/2005 | Verma et al. |
| 2005/0142141 A1 | 6/2005 | Pardridge |
| 2008/0025995 A1 | 1/2008 | Grubb et al. |
| 2010/0183577 A1 | 7/2010 | Stern et al. |
| 2010/0303797 A1 | 12/2010 | Starr et al. |
| 2012/0171120 A1 | 7/2012 | Dennis et al. |
| 2012/0276125 A1 | 11/2012 | Ast et al. |
| 2013/0224797 A1 | 8/2013 | Takahashi |
| 2013/0244231 A1 | 9/2013 | Takahashi |
| 2014/0004097 A1 | 1/2014 | Zhang et al. |
| 2014/0050666 A1 | 2/2014 | Calhoun et al. |
| 2014/0242059 A1 | 8/2014 | Jin et al. |
| 2014/0335163 A1 | 11/2014 | Boivin et al. |
| 2015/0023956 A1 | 1/2015 | Pardridge et al. |
| 2015/0037311 A1 | 2/2015 | Boivin et al. |
| 2015/0093399 A1 | 4/2015 | Jefferies |
| 2015/0094451 A1 | 4/2015 | Fischer et al. |
| 2015/0147310 A1 | 5/2015 | Boivin et al. |
| 2015/0290341 A1 | 10/2015 | Boivin et al. |
| 2015/0322149 A1 | 11/2015 | Bohrmann et al. |
| 2015/0353639 A1 | 12/2015 | Watts et al. |
| 2016/0083707 A1 | 3/2016 | Radin |
| 2016/0120958 A1 | 5/2016 | Chuang et al. |
| 2016/0145589 A1 | 5/2016 | Jin et al. |
| 2016/0152719 A1 | 6/2016 | Pardridge et al. |
| 2016/0208006 A1 | 7/2016 | Pardridge et al. |
| 2016/0324984 A1 | 11/2016 | Brinkmann et al. |
| 2017/0042979 A1 | 2/2017 | Stefano |
| 2017/0051071 A1 | 2/2017 | Rueger et al. |
| 2017/0073652 A1 | 3/2017 | Nichols |
| 2017/0152524 A1 | 6/2017 | Passini et al. |
| 2017/0191041 A1 | 7/2017 | Radin |
| 2017/0204386 A1 | 7/2017 | Vitalis et al. |
| 2017/0218085 A1 | 8/2017 | Geierstanger et al. |
| 2017/0226493 A1 | 8/2017 | Callewaert et al. |
| 2017/0232076 A1 | 8/2017 | Concino et al. |
| 2017/0355744 A1 | 12/2017 | Aoyagi-Scharber et al. |
| 2017/0362632 A1 | 12/2017 | Bernhardt et al. |
| 2018/0015180 A1 | 1/2018 | Castaigne et al. |
| 2018/0021445 A1 | 1/2018 | Starr et al. |
| 2018/0028677 A1 | 2/2018 | Narasimhaswamy et al. |
| 2018/0055911 A1 | 3/2018 | Lebowitz et al. |
| 2018/0080033 A1 | 3/2018 | Melnyk et al. |
| 2018/0125949 A1 | 5/2018 | Lebowitz et al. |
| 2018/0171012 A1 | 6/2018 | Sonoda et al. |
| 2018/0209960 A1 | 7/2018 | Watt et al. |
| 2018/0221459 A1 | 8/2018 | Dickson et al. |
| 2018/0251535 A1 | 9/2018 | Pardridge et al. |
| 2018/0303914 A1 | 10/2018 | Lee et al. |
| 2019/0002852 A1 | 1/2019 | Vitalis et al. |
| 2020/0223935 A1 | 7/2020 | Chen et al. |

FOREIGN PATENT DOCUMENTS

| | | |
|---|---|---|
| EP | 3556399 A1 | 10/2019 |
| JP | 2015096063 A | 5/2015 |
| WO | 2003057179 A2 | 7/2003 |
| WO | 2005021064 A2 | 3/2005 |
| WO | 2005047337 A1 | 5/2005 |
| WO | 2006007560 A2 | 1/2006 |
| WO | 2006072620 A1 | 7/2006 |
| WO | 2008003103 A2 | 1/2008 |
| WO | 2008089339 A2 | 7/2008 |
| WO | 2009091994 A9 | 12/2009 |
| WO | 2011044542 A1 | 4/2011 |
| WO | 2012063799 A1 | 5/2012 |
| WO | 2012075037 A1 | 6/2012 |
| WO | 2012101671 A1 | 8/2012 |
| WO | 2012101998 A1 | 8/2012 |
| WO | 2012177020 A9 | 2/2013 |
| WO | 2013078562 A2 | 6/2013 |
| WO | 20140105014 A2 | 1/2014 |
| WO | 2014022515 A1 | 2/2014 |
| WO | 2014033074 A1 | 3/2014 |
| WO | 2014082080 A2 | 5/2014 |
| WO | 2014152940 A1 | 9/2014 |
| WO | 2014194427 A1 | 12/2014 |
| WO | 2015009052 A1 | 1/2015 |
| WO | 2015012944 A1 | 1/2015 |
| WO | 2015098989 A1 | 7/2015 |
| WO | 2016025519 A1 | 2/2016 |
| WO | 2016077775 A1 | 5/2016 |
| WO | 2016081643 A1 | 5/2016 |
| WO | 20160881640 A1 | 5/2016 |
| WO | 2016126339 A1 | 8/2016 |
| WO | 2016207240 A1 | 12/2016 |
| WO | 2016208695 A1 | 12/2016 |
| WO | 2016077356 A9 | 1/2017 |
| WO | 2017003270 A1 | 1/2017 |
| WO | 2017055570 A1 | 4/2017 |
| WO | 2017055586 A1 | 4/2017 |
| WO | 2017062666 A2 | 4/2017 |
| WO | 2017100467 A2 | 6/2017 |
| WO | 2017103612 A1 | 6/2017 |
| WO | 2017116066 A1 | 7/2017 |
| WO | 2017131496 A1 | 8/2017 |
| WO | 2017147414 A1 | 8/2017 |
| WO | 2017151791 A1 | 9/2017 |
| WO | 2017181113 A1 | 10/2017 |
| WO | 2018031424 A1 | 2/2018 |
| WO | 2018038243 A1 | 3/2018 |
| WO | 2018117613 A1 | 6/2018 |
| WO | 2018124121 A1 | 7/2018 |
| WO | 2018124277 A1 | 7/2018 |
| WO | 2018146473 A1 | 8/2018 |
| WO | 2018152326 A1 | 8/2018 |
| WO | 2018152359 A1 | 8/2018 |
| WO | 2018152375 A2 | 8/2018 |
| WO | 2018153581 A1 | 8/2018 |
| WO | 2018155443 A1 | 8/2018 |
| WO | 2019009684 A2 | 1/2019 |
| WO | 2019022563 A2 | 1/2019 |
| WO | 2019032955 A1 | 2/2019 |
| WO | 2019033046 A1 | 2/2019 |

(56) References Cited

FOREIGN PATENT DOCUMENTS

| | | |
|---|---|---|
| WO | 2019049967 A1 | 3/2019 |
| WO | 2019246071 A1 | 12/2019 |

OTHER PUBLICATIONS

Patent Cooperation Treaty, International Searching Authority, Search Report and Written Opinion for PCT/U82018/053747, 18 pages, dated Jan. 14, 2019.

Roeser, et al., "A general binding mechanism for all human sulfatases by the formylglycine-generating enzyme", PNAS 103(1), 81-86 (2006).

Scarpa, et al., "Treatment of brain disease in the mucopolysaccharidoses", Molecular Genetics and Metabolism 122S, 25-34 (2017).

Sonoda, et al., "A blood-brain barrier-penetrating anti-human transferrin receptor antibody fusion protein for neuronopathic mucopolysaccharidosis II", Molecular Therapy 26(5), 1366-1374 (2018).

Sonoda, et al., "Abstract 319: Correction of central nervous system deficits in the mouse model of Hunter syndrome by recombinant iduronate 2-sulfatase crossing the blood-brain barrier", Molecular Genetics and Metabolism (Abstracts) 120, S125-S126 (2016).

Zareba, et al., "Idursulfase in Hunter Syndrome Treatment", Drugs of Today 43(11), 759-767 (2007).

Zhou. et al., "Brain-Penetrating igG-Iduronate 2-Sulfatase Fusion Protein for the Mouse", Drug Metabolism and Dispostion 40(2), 329-335 (2012).

Database Geneseq [Online], "Immunostimulatory fusion protein production related protein, SEQ ID 6", Accession No. GSP:AYM2804, 2 pages (Feb. 3, 2011).

Liu, H, et al., "Fc Engineering for Developing Therapeutic Bispecific Antibodies and Novel Scaffolds", Frontiers in Immunology 8, 1-15 (2017).

Lobner, E, et al., "Engineered IgG1-Fc—one fragment to bind them all", Immunological Reviews 270(1), 113-131 (2016).

Pardridge, W, "Blood-brain barrier drug delivery of IgG fusion proteins with a transferrin receptor monoclonal antibody", Expert Opinion on Drug Deli, Informa Healthcare 12(2), 207-222 (2015).

Park, Hye In, et al., "The Highly Evolvable Antibody Fc Domain", Trends in Biotechnology 34(11), 895-908 (2016).

Wozniak-Knopp, G, et al., "Introducing antigen-binding sites in structural loops of immunoglobulin constant domains: Fc fragments with engineered HER2/neu-binding sites and antibody properties", Protein Engineering, Design and Selection, Oxford Journal, 23(4), 289-297 (2010).

Yu, Y, et al., "Therapeutic bispecific antibodies cross the blood-brain barrier in nonhuman primates", Science Translational Medicine 6(261), 261ra154, 10 pages (2014).

U.S. Appl. No. 16/782,984.
U.S. Appl. No. 16/782,669.
U.S. Appl. No. 16/649,943.

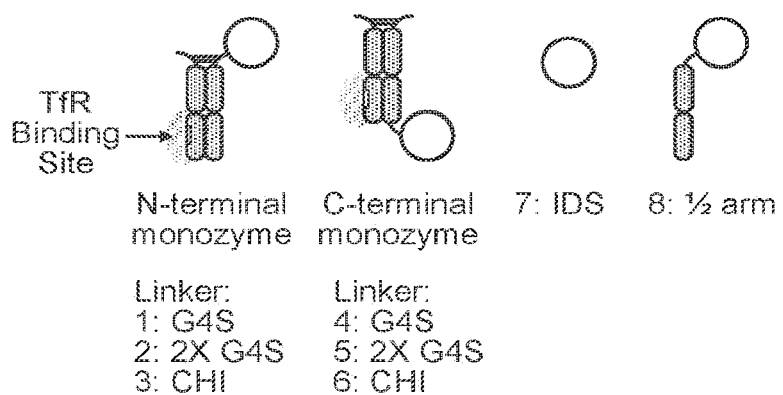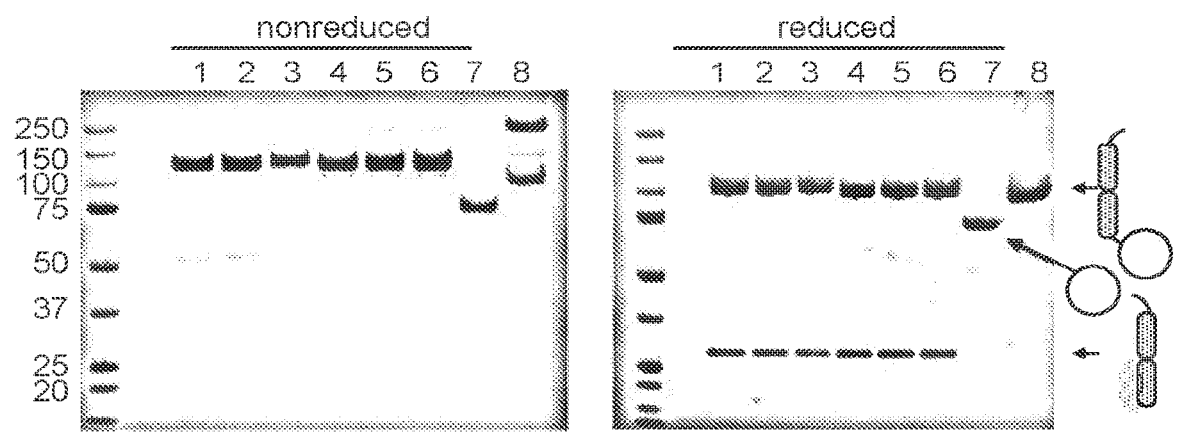
FIG. 1

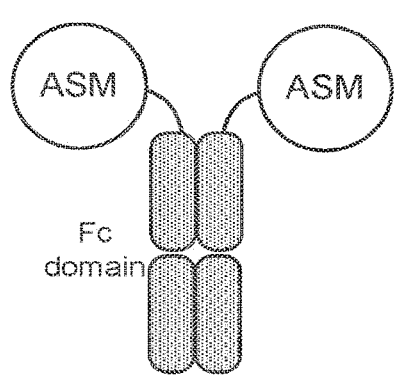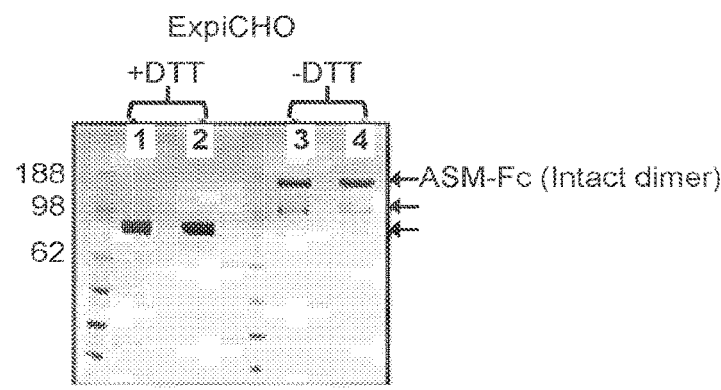
FIG. 11

SEQUENCE LISTING

<160> NUMBER OF SEQ ID NOS: 242

<210> SEQ ID NO 1
<211> LENGTH: 217
<212> TYPE: PRT
<213> ORGANISM: Homo sapiens

<400> SEQUENCE: 1

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110
```

```
Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 2
<211> LENGTH: 110
<212> TYPE: PRT
<213> ORGANISM: Homo sapiens

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 3
<211> LENGTH: 107
<212> TYPE: PRT
<213> ORGANISM: Homo sapiens

<400> SEQUENCE: 3

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 4
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Leu Gly Leu Val Trp Val Gly
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ala Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 5
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Val Trp Ser His
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Ser Glu Trp Gln Gln Gly Tyr Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 6
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Ser Gln
145                 150                 155                 160

Tyr Lys Thr Thr Pro Pro Val Leu Asp Ser Asp Gly Ser Phe Phe Leu
                165                 170                 175

Tyr Ser Lys Leu Thr Val Glu Lys Ser Asp Trp Gln Gln Gly His Val
            180                 185                 190

Phe Ser Cys Ser Val Met His Glu Ala Leu His Asn His Tyr Thr Gln
```

```
                195                 200                 205

Lys Ser Leu Ser Leu Ser Pro Gly Lys
    210                 215

<210> SEQ ID NO 7
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Val Gly Thr Pro Trp Ala Leu
145                 150                 155                 160

Tyr Lys Thr Thr Pro Pro Val Leu Asp Ser Asp Gly Ser Phe Phe Leu
                165                 170                 175

Tyr Ser Lys Leu Thr Val Leu Lys Ser Glu Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 8
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

```
Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Tyr Gly Thr Val Trp Ser Lys
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Ser Glu Trp Gln Gln Gly Phe Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 9
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Leu Gly His Val Trp Ala Val
145                 150                 155                 160

Tyr Lys Thr Thr Pro Pro Val Leu Asp Ser Asp Gly Ser Phe Phe Leu
                165                 170                 175
```

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 10
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Leu Gly Leu Val Trp Val Gly
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 11
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val

```
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Asp Glu Leu
        115                 120                 125
Thr Lys Asn Gln Val Ser Leu Thr Cys Leu Val Lys Gly Phe Tyr Pro
    130                 135                 140
Ser Asp Ile Ala Val Glu Trp Glu Ser Met Gly His Val Trp Val Gly
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Thr Trp Gln Gln Gly Trp Val
            180                 185                 190
Phe Ser Cys Ser Val Met His Glu Ala Leu His Asn His Tyr Thr Gln
        195                 200                 205
Lys Ser Leu Ser Leu Ser Pro Gly Lys
    210                 215

<210> SEQ ID NO 12
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Asp Glu Leu
        115                 120                 125
Thr Lys Asn Gln Val Ser Leu Thr Cys Leu Val Lys Gly Phe Tyr Pro
    130                 135                 140
Ser Asp Ile Ala Val Glu Trp Glu Ser Leu Gly Leu Val Trp Val Phe
145                 150                 155                 160
```

```
Ser Lys Thr Thr Pro Pro Val Leu Asp Ser Asp Gly Ser Phe Phe Leu
            165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215

<210> SEQ ID NO 13
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
            165                 170                 175

Tyr Ser Lys Leu Thr Val Thr Lys Ser Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215

<210> SEQ ID NO 14
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14
```

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Ser Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 15
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
```

```
                130                 135                 140
Ser Asp Ile Ala Val Glu Trp Glu Ser Leu Gly His Val Trp Val Gly
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Ser Glu Trp Gln Gln Gly Trp Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
                210                 215

<210> SEQ ID NO 16
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Leu Gly His Val Trp Val Ala
145                 150                 155                 160

Thr Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
                210                 215

<210> SEQ ID NO 17
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 17

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Leu Gly Pro Val Trp Val His
145                 150                 155                 160

Thr Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 18
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Leu Gly His Val Trp Val Asp
145                 150                 155                 160

Gln Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 19
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Leu Gly His Val Trp Val Asn
145                 150                 155                 160

Gln Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 20
<211> LENGTH: 217
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Leu Gly His Val Trp Val Asn
145                 150                 155                 160

Phe Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 21
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Trp Trp Glu Ser Leu Gly His Val Trp Ala Val
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 22
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 22

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Leu Trp Glu Ser Leu Gly His Val Trp Ala Val
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

```
<210> SEQ ID NO 23
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Tyr Trp Glu Ser Leu Gly His Val Trp Ala Val
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 24
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
```

```
                    65                  70                  75                  80
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
                115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Leu Gly His Val Trp Ala Val
145                 150                 155                 160

Tyr Gln Thr Thr Pro Pro Val Leu Asp Ser Asp Gly Ser Phe Phe Leu
                    165                 170                 175

Tyr Ser Lys Leu Thr Val Pro Lys Ser Thr Trp Gln Gln Gly Trp Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
        210                 215

<210> SEQ ID NO 25
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
                115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Leu Gly His Val Trp Ala Val
145                 150                 155                 160

Tyr Phe Thr Thr Pro Pro Val Leu Asp Ser Asp Gly Ser Phe Phe Leu
                    165                 170                 175

Tyr Ser Lys Leu Thr Val Pro Lys Ser Thr Trp Gln Gln Gly Trp Val
                180                 185                 190

Phe Ser Cys Ser Val Met His Glu Ala Leu His Asn His Tyr Thr Gln
                195                 200                 205
```

Lys Ser Leu Ser Leu Ser Pro Gly Lys
    210             215

<210> SEQ ID NO 26
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Leu Gly His Val Trp Ala Val
145                 150                 155                 160

Tyr His Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210             215

<210> SEQ ID NO 27
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
            50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
130                 135                 140

Ser Asp Ile Ala Val Trp Trp Glu Ser Leu Gly His Val Trp Ala Val
145                 150                 155                 160

Tyr Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
210                 215

<210> SEQ ID NO 28
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
            50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Leu Gly His Val Trp Ala Val
145                 150                 155                 160

Tyr Gln Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val

```
                    180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 29
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Leu Gly His Val Trp Ala Val
145                 150                 155                 160

Tyr Gln Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 30
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Trp Trp Glu Ser Leu Gly His Val Trp Val Asn
145                 150                 155                 160

Gln Lys Thr Thr Pro Pro Val Leu Asp Ser Asp Gly Ser Phe Phe Leu
                165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 31
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

Ala Pro Glu Leu Leu Gly Gly Pro Ser Val Phe Leu Phe Pro Pro Lys
1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Leu Gly His Val Trp Val Asn
145                 150                 155                 160

Gln Gln Thr Thr Pro Pro Val Leu Asp Ser Asp Gly Ser Phe Phe Leu
                    165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 32
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Leu Gly His Val Trp Val Asn
145                 150                 155                 160

Gln Gln Thr Thr Pro Pro Val Leu Asp Ser Asp Gly Ser Phe Phe Leu
                    165                 170                 175

Tyr Ser Lys Leu Thr Val Pro Lys Ser Thr Trp Gln Gln Gly Trp Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 33
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Ala Pro Glu Leu Leu Gly Gly Pro Ser Val Phe Leu Phe Pro Pro Lys

```
  1               5                  10                 15
Pro Lys Asp Thr Leu Met Ile Ser Arg Thr Pro Glu Val Thr Cys Val
            20                  25                 30

Val Val Asp Val Ser His Glu Asp Pro Glu Val Lys Phe Asn Trp Tyr
            35                  40                 45

Val Asp Gly Val Glu Val His Asn Ala Lys Thr Lys Pro Arg Glu Glu
         50                  55                 60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
             100                 105                110

Pro Arg Glu Pro Gln Val Tyr Thr Leu Pro Pro Ser Arg Asp Glu Leu
             115                 120                 125

Thr Lys Asn Gln Val Ser Leu Thr Cys Leu Val Lys Gly Phe Tyr Pro
         130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Ser Glu Trp Gln Gln Gly Phe Val
             180                 185                 190

Phe Ser Cys Ser Val Met His Glu Ala Leu His Asn His Tyr Thr Gln
             195                 200                 205

Lys Ser Leu Ser Leu Ser Pro Gly Lys
         210                 215

<210> SEQ ID NO 34
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Ala Pro Glu Leu Leu Gly Gly Pro Ser Val Phe Leu Phe Pro Pro Lys
1               5                  10                 15

Pro Lys Asp Thr Leu Met Ile Ser Arg Thr Pro Glu Val Thr Cys Val
            20                  25                 30

Val Val Asp Val Ser His Glu Asp Pro Glu Val Lys Phe Asn Trp Tyr
            35                  40                 45

Val Asp Gly Val Glu Val His Asn Ala Lys Thr Lys Pro Arg Glu Glu
         50                  55                 60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
             100                 105                110

Pro Arg Glu Pro Gln Val Tyr Thr Leu Pro Pro Ser Arg Asp Glu Leu
             115                 120                 125

Thr Lys Asn Gln Val Ser Leu Thr Cys Leu Val Lys Gly Phe Tyr Pro
         130                 135                 140
```

Ser Asp Ile Ala Val Glu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
            165                 170                 175

Tyr Ser Lys Leu Thr Val Thr Lys Glu Glu Trp Gln Gln Gly Phe Val
        180                 185                 190

Phe Ser Cys Ser Val Met His Glu Ala Leu His Asn His Tyr Thr Gln
    195                 200                 205

Lys Ser Leu Ser Leu Ser Pro Gly Lys
    210                 215

<210> SEQ ID NO 35
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
            165                 170                 175

Tyr Ser Lys Leu Thr Val Thr Lys Glu Glu Trp Gln Gln Gly Phe Val
        180                 185                 190

Phe Ser Cys Ser Val Met His Glu Ala Leu His Asn His Tyr Thr Gln
    195                 200                 205

Lys Ser Leu Ser Leu Ser Pro Gly Lys
    210                 215

<210> SEQ ID NO 36
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Ser Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 37
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
```

```
                115                 120                 125
Thr Lys Asn Gln Val Ser Leu Thr Cys Leu Val Lys Gly Phe Tyr Pro
        130                 135                 140
Ser Asp Ile Ala Val Glu Trp Glu Ser Tyr Gly Thr Glu Trp Ser Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Thr Lys Glu Glu Trp Gln Gln Gly Phe Val
        180                 185                 190
Phe Ser Cys Ser Val Met His Glu Ala Leu His Asn His Tyr Thr Gln
                195                 200                 205
Lys Ser Leu Ser Leu Ser Pro Gly Lys
        210                 215

<210> SEQ ID NO 38
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Asp Glu Leu
        115                 120                 125
Thr Lys Asn Gln Val Ser Leu Thr Cys Leu Val Lys Gly Phe Tyr Pro
    130                 135                 140
Ser Asp Ile Ala Val Trp Trp Glu Ser Tyr Gly Thr Glu Trp Ser Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Thr Lys Glu Glu Trp Gln Gln Gly Phe Val
            180                 185                 190
Phe Ser Cys Ser Val Met His Glu Ala Leu His Asn His Tyr Thr Gln
        195                 200                 205
Lys Ser Leu Ser Leu Ser Pro Gly Lys
    210                 215

<210> SEQ ID NO 39
<211> LENGTH: 217
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 39
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Ser Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

```
<210> SEQ ID NO 40
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Tyr Gly Thr Glu Trp Ser Ser
145                 150                 155                 160

Tyr Gln Thr Thr Pro Pro Val Leu Asp Ser Asp Gly Ser Phe Phe Leu
                165                 170                 175

Tyr Ser Lys Leu Thr Val Thr Lys Ser Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 41
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Tyr Gly Thr Glu Trp Ser Asn
145                 150                 155                 160

Tyr Gln Thr Thr Pro Pro Val Leu Asp Ser Asp Gly Ser Phe Phe Leu
                165                 170                 175

Tyr Ser Lys Leu Thr Val Thr Lys Ser Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215
```

```
<210> SEQ ID NO 42
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Ser Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 43
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Lys Ser Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 44
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Arg Glu Glu Trp Gln Gln Gly Phe Val
            180                 185                 190

Phe Ser Cys Ser Val Met His Glu Ala Leu His Asn His Tyr Thr Gln
        195                 200                 205
```

```
Lys Ser Leu Ser Leu Ser Pro Gly Lys
    210                 215
```

<210> SEQ ID NO 45
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Gly Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 46
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
```

```
            50                  55                  60
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Leu Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Arg Glu Glu Trp Gln Gln Gly Phe Val
            180                 185                 190

Phe Ser Cys Trp Val Met His Glu Ala Leu His Asn His Tyr Thr Gln
        195                 200                 205

Lys Ser Leu Ser Leu Ser Pro Gly Lys
    210                 215

<210> SEQ ID NO 47
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Leu Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190
```

```
Phe Ser Cys Trp Val Met His Glu Ala Leu His Asn His Tyr Thr Gln
        195                 200                 205

Lys Ser Leu Ser Leu Ser Pro Gly Lys
    210                 215

<210> SEQ ID NO 48
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Arg Glu Glu Trp Gln Gln Gly Phe Val
            180                 185                 190

Phe Thr Cys Trp Val Met His Glu Ala Leu His Asn His Tyr Thr Gln
        195                 200                 205

Lys Ser Leu Ser Leu Ser Pro Gly Lys
    210                 215

<210> SEQ ID NO 49
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

Val Val Asp Val Ser His Glu Asp Pro Glu Val Lys Phe Asn Trp Tyr
          35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
              85                  90                  95

Ala Leu Pro Ala Pro Ile Glu Lys Thr Ile Ser Lys Ala Lys Gly Gln
             100                 105                 110

Pro Arg Glu Pro Gln Val Tyr Thr Leu Pro Pro Ser Arg Asp Glu Leu
             115                 120                 125

Thr Lys Asn Gln Val Ser Leu Thr Cys Leu Val Lys Gly Phe Tyr Pro
 130                 135                 140

Ser Asp Ile Ala Val Leu Trp Glu Ser Tyr Gly Thr Glu Trp Ser Ser
 145                 150                 155                 160

Tyr Arg Thr Thr Pro Pro Val Leu Asp Ser Asp Gly Ser Phe Phe Leu
             165                 170                 175

Tyr Ser Lys Leu Thr Val Thr Arg Glu Glu Trp Gln Gln Gly Phe Val
             180                 185                 190

Phe Thr Cys Gly Val Met His Glu Ala Leu His Asn His Tyr Thr Gln
             195                 200                 205

Lys Ser Leu Ser Leu Ser Pro Gly Lys
             210                 215

<210> SEQ ID NO 50
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
              20                  25                  30

Val Val Asp Val Ser His Glu Asp Pro Glu Val Lys Phe Asn Trp Tyr
          35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
              85                  90                  95

Ala Leu Pro Ala Pro Ile Glu Lys Thr Ile Ser Lys Ala Lys Gly Gln
             100                 105                 110

Pro Arg Glu Pro Gln Val Tyr Thr Leu Pro Pro Ser Arg Asp Glu Leu
             115                 120                 125

Thr Lys Asn Gln Val Ser Leu Thr Cys Leu Val Lys Gly Phe Tyr Pro
 130                 135                 140

Ser Asp Ile Ala Val Leu Trp Glu Ser Tyr Gly Thr Glu Trp Ser Ser
 145                 150                 155                 160

Tyr Arg Thr Thr Pro Pro Val Leu Asp Ser Asp Gly Ser Phe Phe Leu 165                 170                 175

Tyr Ser Lys Leu Thr Val Thr Arg Glu Glu Trp Gln Gln Gly Phe Val
            180                 185                 190

Phe Glu Cys Trp Val Met His Glu Ala Leu His Asn His Tyr Thr Gln
        195                 200                 205

Lys Ser Leu Ser Leu Ser Pro Gly Lys
        210                 215

<210> SEQ ID NO 51
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Arg Glu Glu Trp Gln Gln Gly Phe Val
            180                 185                 190

Phe Lys Cys Trp Val Met His Glu Ala Leu His Asn His Tyr Thr Gln
        195                 200                 205

Lys Ser Leu Ser Leu Ser Pro Gly Lys
        210                 215

<210> SEQ ID NO 52
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Ala Pro Glu Leu Leu Gly Gly Pro Ser Val Phe Leu Phe Pro Pro Lys
1               5                   10                  15

```
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Pro Glu Glu Trp Gln Gln Gly Phe Val
            180                 185                 190

Phe Lys Cys Trp Val Met His Glu Ala Leu His Asn His Tyr Thr Gln
            195                 200                 205

Lys Ser Leu Ser Leu Ser Pro Gly Lys
    210                 215

<210> SEQ ID NO 53
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
    130                 135                 140
```

```
Ser Asp Ile Ala Val Trp Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Arg Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 54
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 54

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
        100                 105                 110

Pro Arg Glu Pro Gln Val Tyr Thr Leu Pro Pro Ser Arg Asp Glu Leu
    115                 120                 125

Thr Lys Asn Gln Val Ser Leu Thr Cys Leu Val Lys Gly Phe Tyr Pro
130                 135                 140

Ser Asp Ile Ala Val Trp Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Gly Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 55
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

-continued

<400> SEQUENCE: 55

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Arg Glu Glu Trp Gln Gln Gly Phe Val
            180                 185                 190

Phe Thr Cys Trp Val Met His Glu Ala Leu His Asn His Tyr Thr Gln
        195                 200                 205

Lys Ser Leu Ser Leu Ser Pro Gly Lys
    210                 215
```

<210> SEQ ID NO 56
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125
```

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Gly Glu Glu Trp Gln Gln Gly Phe Val
            180                 185                 190

Phe Thr Cys Trp Val Met His Glu Ala Leu His Asn His Tyr Thr Gln
            195                 200                 205

Lys Ser Leu Ser Leu Ser Pro Gly Lys
    210                 215

<210> SEQ ID NO 57
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
    115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Arg Glu Glu Trp Gln Gln Gly Phe Val
            180                 185                 190

Phe Thr Cys Gly Val Met His Glu Ala Leu His Asn His Tyr Thr Gln
            195                 200                 205

Lys Ser Leu Ser Leu Ser Pro Gly Lys
    210                 215

<210> SEQ ID NO 58
<211> LENGTH: 217
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 58

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 59
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
```

```
              100                 105                 110
Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Leu Trp Glu Ser Tyr Gly Thr Glu Trp Ser Ser
145                 150                 155                 160

Tyr Arg Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215
```

<210> SEQ ID NO 60
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215
```

<210> SEQ ID NO 61

```
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 62
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Val Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 63
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
```

<210> SEQ ID NO 64
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Phe Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 65
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Phe Gly Thr Glu Trp Val Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 66
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 67
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 68
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
```

```
        35                  40                  45
Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
65                   70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Val Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 69
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
65                   70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175
```

```
Tyr Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 70
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Phe Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 71
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Ala Pro Glu Leu Leu Gly Gly Pro Ser Val Phe Leu Phe Pro Pro Lys
1               5                   10                  15
```

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Phe Gly Thr Glu Trp Val Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 72
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Phe Gly Thr Glu Trp Ser Asn

```
145                 150                 155                 160
Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
    210                 215

<210> SEQ ID NO 73
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
    210                 215

<210> SEQ ID NO 74
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 75
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

```
Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 76
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65              70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Phe Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 77
<211> LENGTH: 217
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic polypeptide"

<400> SEQUENCE: 77

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Phe Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 78
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 78

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
        130                 135                 140

Ser Asp Ile Ala Val Trp Trp Glu Ser Phe Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
        210                 215

<210> SEQ ID NO 79
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
        130                 135                 140

Ser Asp Ile Ala Val Trp Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
        210                 215

<210> SEQ ID NO 80
<211> LENGTH: 217
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 81
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
```

```
            85                  90                  95
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Trp Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 82
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
            50                  55                  60

Gln Tyr Asn Ser Thr Tyr Arg Val Val Ser Val Leu Thr Val Leu His
65              70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
            130                 135                 140

Ser Asp Ile Ala Val Trp Trp Glu Ser Phe Gly Thr Glu Trp Ala Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215
```

<210> SEQ ID NO 83
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Phe Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 84
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 84

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 85
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
```

```
                195                 200                 205

Lys Ser Leu Ser Leu Ser Pro Gly Lys
    210                 215

<210> SEQ ID NO 86
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Val Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 87
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

```
Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 88
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Phe Gly Thr Glu Trp Ala Ser
145                 150                 155                 160

Tyr Lys Thr Thr Pro Pro Val Leu Asp Ser Asp Gly Ser Phe Phe Leu
                165                 170                 175
```

```
Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 89
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Leu Trp Glu Ser Phe Gly Thr Glu Trp Val Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 90
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
```

```
            20                  25                  30
Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Ser Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 91
<211> LENGTH: 550
<212> TYPE: PRT
<213> ORGANISM: Homo sapiens

<400> SEQUENCE: 91

Met Pro Pro Pro Arg Thr Gly Arg Gly Leu Leu Trp Leu Gly Leu Val
 1               5                  10                  15

Leu Ser Ser Val Cys Val Ala Leu Gly Ser Glu Thr Gln Ala Asn Ser
             20                  25                  30

Thr Thr Asp Ala Leu Asn Val Leu Leu Ile Ile Val Asp Asp Leu Arg
         35                  40                  45

Pro Ser Leu Gly Cys Tyr Gly Asp Lys Leu Val Arg Ser Pro Asn Ile
 50                  55                  60

Asp Gln Leu Ala Ser His Ser Leu Leu Phe Gln Asn Ala Phe Ala Gln
 65                  70                  75                  80

Gln Ala Val Cys Ala Pro Ser Arg Val Ser Phe Leu Thr Gly Arg Arg
                 85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
        130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175
```

```
Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 92
<211> LENGTH: 517
<212> TYPE: PRT
<213> ORGANISM: Homo sapiens

<400> SEQUENCE: 92
```

```
Thr Asp Ala Leu Asn Val Leu Ile Ile Val Asp Leu Arg Pro
1               5                   10                  15

Ser Leu Gly Cys Tyr Gly Asp Lys Leu Val Arg Ser Pro Asn Ile Asp
            20                  25                  30

Gln Leu Ala Ser His Ser Leu Leu Phe Gln Asn Ala Phe Ala Gln Gln
        35                  40                  45

Ala Val Cys Ala Pro Ser Arg Val Ser Phe Leu Thr Gly Arg Arg Pro
    50                  55                  60

Asp Thr Thr Arg Leu Tyr Asp Phe Asn Ser Tyr Trp Arg Val His Ala
65                  70                  75                  80

Gly Asn Phe Ser Thr Ile Pro Gln Tyr Phe Lys Glu Asn Gly Tyr Val
                85                  90                  95

Thr Met Ser Val Gly Lys Val Phe His Pro Gly Ile Ser Ser Asn His
            100                 105                 110

Thr Asp Asp Ser Pro Tyr Ser Trp Ser Phe Pro Pro Tyr His Pro Ser
        115                 120                 125

Ser Glu Lys Tyr Glu Asn Thr Lys Thr Cys Arg Gly Pro Asp Gly Glu
    130                 135                 140

Leu His Ala Asn Leu Leu Cys Pro Val Asp Val Leu Asp Val Pro Glu
145                 150                 155                 160

Gly Thr Leu Pro Asp Lys Gln Ser Thr Glu Gln Ala Ile Gln Leu Leu
                165                 170                 175

Glu Lys Met Lys Thr Ser Ala Ser Pro Phe Phe Leu Ala Val Gly Tyr
            180                 185                 190

His Lys Pro His Ile Pro Phe Arg Tyr Pro Lys Glu Phe Gln Lys Leu
        195                 200                 205

Tyr Pro Leu Glu Asn Ile Thr Leu Ala Pro Asp Pro Glu Val Pro Asp
    210                 215                 220

Gly Leu Pro Pro Val Ala Tyr Asn Pro Trp Met Asp Ile Arg Gln Arg
225                 230                 235                 240

Glu Asp Val Gln Ala Leu Asn Ile Ser Val Pro Tyr Gly Pro Ile Pro
                245                 250                 255

Val Asp Phe Gln Arg Lys Ile Arg Gln Ser Tyr Phe Ala Ser Val Ser
            260                 265                 270

Tyr Leu Asp Thr Gln Val Gly Arg Leu Leu Ser Ala Leu Asp Asp Leu
    275                 280                 285

Gln Leu Ala Asn Ser Thr Ile Ile Ala Phe Thr Ser Asp His Gly Trp
290                 295                 300

Ala Leu Gly Glu His Gly Glu Trp Ala Lys Tyr Ser Asn Phe Asp Val
305                 310                 315                 320

Ala Thr His Val Pro Leu Ile Phe Tyr Val Pro Gly Arg Thr Ala Ser
                325                 330                 335

Leu Pro Glu Ala Gly Glu Lys Leu Phe Pro Tyr Leu Asp Pro Phe Asp
            340                 345                 350

Ser Ala Ser Gln Leu Met Glu Pro Gly Arg Gln Ser Met Asp Leu Val
        355                 360                 365

Glu Leu Val Ser Leu Phe Pro Thr Leu Ala Gly Leu Ala Gly Leu Gln
    370                 375                 380

Val Pro Pro Arg Cys Pro Val Pro Ser Phe His Val Glu Leu Cys Arg
385                 390                 395                 400

Glu Gly Lys Asn Leu Leu Lys His Phe Arg Phe Arg Asp Leu Glu Glu
                405                 410                 415
```

```
Asp Pro Tyr Leu Pro Gly Asn Pro Arg Glu Leu Ile Ala Tyr Ser Gln
            420                 425                 430

Tyr Pro Arg Pro Ser Asp Ile Pro Gln Trp Asn Ser Asp Lys Pro Ser
            435                 440                 445

Leu Lys Asp Ile Lys Ile Met Gly Tyr Ser Ile Arg Thr Ile Asp Tyr
        450                 455                 460

Arg Tyr Thr Val Trp Val Gly Phe Asn Pro Asp Glu Phe Leu Ala Asn
465                 470                 475                 480

Phe Ser Asp Ile His Ala Gly Glu Leu Tyr Phe Val Asp Ser Asp Pro
                485                 490                 495

Leu Gln Asp His Asn Met Tyr Asn Asp Ser Gln Gly Gly Asp Leu Phe
            500                 505                 510

Gln Leu Leu Met Pro
            515

<210> SEQ ID NO 93
<211> LENGTH: 536
<212> TYPE: PRT
<213> ORGANISM: Homo sapiens

<400> SEQUENCE: 93

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
            85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
            165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
            245                 250                 255

Asp Ala Tyr Ala Glu His Lys Leu Gln Phe Trp Ala Val Thr Ala Glu
            260                 265                 270
```

```
Asn Glu Pro Ser Ala Gly Leu Leu Ser Gly Tyr Pro Phe Gln Cys Leu
            275                 280                 285

Gly Phe Thr Pro Glu His Gln Arg Asp Phe Ile Ala Arg Asp Leu Gly
        290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
                340                 345                 350

Leu Asp Phe Leu Ala Pro Ala Lys Ala Thr Leu Gly Glu Thr His Arg
                355                 360                 365

Leu Phe Pro Asn Thr Met Leu Phe Ala Ser Glu Ala Cys Val Gly Ser
370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                    405                 410                 415

Trp Thr Asp Trp Asn Leu Ala Leu Asn Pro Glu Gly Gly Pro Asn Trp
                420                 425                 430

Val Arg Asn Phe Val Asp Ser Pro Ile Ile Val Asp Ile Thr Lys Asp
                435                 440                 445

Thr Phe Tyr Lys Gln Pro Met Phe Tyr His Leu Gly His Phe Ser Lys
            450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
        530                 535

<210> SEQ ID NO 94
<211> LENGTH: 497
<212> TYPE: PRT
<213> ORGANISM: Homo sapiens

<400> SEQUENCE: 94

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
                20                  25                  30

Ala Leu Gly Thr Phe Ser Arg Tyr Glu Ser Thr Arg Ser Gly Arg Arg
            35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
```

```
                100                 105                 110
Gly Ile Gly Tyr Asn Ile Ile Arg Val Pro Met Ala Ser Cys Asp Phe
            115                 120                 125

Ser Ile Arg Thr Tyr Thr Tyr Ala Asp Thr Pro Asp Asp Phe Gln Leu
            130                 135             140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
            195                 200                 205

Trp Ala Arg Tyr Phe Val Lys Phe Leu Asp Ala Tyr Ala Glu His Lys
            210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
            275                 280                 285

Pro His Trp Ala Lys Val Val Leu Thr Asp Pro Glu Ala Ala Lys Tyr
            290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
            355                 360                 365

Thr Asn Leu Leu Tyr His Val Val Gly Trp Thr Asp Trp Asn Leu Ala
            370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
            435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 95
<211> LENGTH: 15
```

<212> TYPE: PRT
<213> ORGANISM: Homo sapiens

<400> SEQUENCE: 95

Glu Pro Lys Ser Cys Asp Lys Thr His Thr Cys Pro Pro Cys Pro
1               5                   10                  15

<210> SEQ ID NO 96
<211> LENGTH: 760
<212> TYPE: PRT
<213> ORGANISM: Homo sapiens

<400> SEQUENCE: 96

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Asn Ala
            35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

```
Ile Ser Arg Ala Ala Glu Lys Leu Phe Gly Asn Met Glu Gly Asp
                340             345                 350
Cys Pro Ser Asp Trp Lys Thr Asp Ser Thr Cys Arg Met Val Thr Ser
        355                 360                 365
Glu Ser Lys Asn Val Lys Leu Thr Val Ser Asn Val Leu Lys Glu Ile
    370                 375                 380
Lys Ile Leu Asn Ile Phe Gly Val Ile Lys Gly Phe Val Glu Pro Asp
385                 390                 395                 400
His Tyr Val Val Gly Ala Gln Arg Asp Ala Trp Gly Pro Gly Ala
                405                 410                 415
Ala Lys Ser Gly Val Gly Thr Ala Leu Leu Lys Leu Ala Gln Met
                420                 425                 430
Phe Ser Asp Met Val Leu Lys Asp Gly Phe Gln Pro Ser Arg Ser Ile
                435                 440                 445
Ile Phe Ala Ser Trp Ser Ala Gly Asp Phe Gly Ser Val Gly Ala Thr
            450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
                485                 490                 495
Ser Ala Ser Pro Leu Leu Tyr Thr Leu Ile Glu Lys Thr Met Gln Asn
            500                 505                 510
Val Lys His Pro Val Thr Gly Gln Phe Leu Tyr Gln Asp Ser Asn Trp
            515                 520                 525
Ala Ser Lys Val Glu Lys Leu Thr Leu Asp Asn Ala Ala Phe Pro Phe
            530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Ile Glu Arg Ile Pro Glu Leu Asn Lys Val Ala Arg Ala Ala Ala Glu
                580                 585                 590
Val Ala Gly Gln Phe Val Ile Lys Leu Thr His Asp Val Glu Leu Asn
            595                 600                 605
Leu Asp Tyr Glu Arg Tyr Asn Ser Gln Leu Leu Ser Phe Val Arg Asp
            610                 615                 620
Leu Asn Gln Tyr Arg Ala Asp Ile Lys Glu Met Gly Leu Ser Leu Gln
625                 630                 635                 640
Trp Leu Tyr Ser Ala Arg Gly Asp Phe Phe Arg Ala Thr Ser Arg Leu
                645                 650                 655
Thr Thr Asp Phe Gly Asn Ala Glu Lys Thr Asp Arg Phe Val Met Lys
                660                 665                 670
Lys Leu Asn Asp Arg Val Met Arg Val Glu Tyr His Phe Leu Ser Pro
            675                 680                 685
Tyr Val Ser Pro Lys Glu Ser Pro Phe Arg His Val Phe Trp Gly Ser
            690                 695                 700
Gly Ser His Thr Leu Pro Ala Leu Leu Glu Asn Leu Lys Leu Arg Lys
705                 710                 715                 720
Gln Asn Asn Gly Ala Phe Asn Glu Thr Leu Phe Arg Asn Gln Leu Ala
                725                 730                 735
Leu Ala Thr Trp Thr Ile Gln Gly Ala Ala Asn Ala Leu Ser Gly Asp
                740                 745                 750
Val Trp Asp Ile Asp Asn Glu Phe
```

<210> SEQ ID NO 97
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 97

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 98
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 98

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 99
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 99

```
Ala Pro Glu Leu Leu Gly Gly Pro Ser Val Phe Leu Phe Pro Pro Lys
 1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190
```

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 100
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 101
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr

-continued

```
                35                  40                  45
Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 102
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 102

```
Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175
```

```
Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215
```

<210> SEQ ID NO 103
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 103

```
Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215
```

<210> SEQ ID NO 104
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 104

```
Ala Pro Glu Ala Ala Gly Gly Pro Ser Val Phe Leu Phe Pro Pro Lys
1               5                   10                  15
```

```
Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 105
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Trp Trp Glu Ser Tyr Gly Thr Glu Trp Ser Ser
```

```
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
                210                 215

<210> SEQ ID NO 106
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
                210                 215

<210> SEQ ID NO 107
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107
```

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 108
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

```
Thr Lys Asn Gln Val Ser Leu Ser Cys Ala Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 109
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 110
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 110

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 111
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 111

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 112
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 112

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 113
<211> LENGTH: 10

```
<212> TYPE: PRT
<213> ORGANISM: Homo sapiens

<400> SEQUENCE: 113

Asp Lys Thr His Thr Cys Pro Pro Cys Pro
1               5                   10

<210> SEQ ID NO 114
<211> LENGTH: 525
<212> TYPE: PRT
<213> ORGANISM: Homo sapiens
<220> FEATURE:
<221> NAME/KEY: VARIANT
<222> LOCATION: (59)..(59)
<223> OTHER INFORMATION: /replace="Formylglycine"
<220> FEATURE:
<221> NAME/KEY: SITE
<222> LOCATION: (1)..(525)
<223> OTHER INFORMATION: /note="Variant residues given in the sequence
      have no preference with respect to those in the annotations
      for variant positions"

<400> SEQUENCE: 114

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Ala Val Cys Ala Pro Ser Arg Val
    50                  55                  60

Ser Phe Leu Thr Gly Arg Arg Pro Asp Thr Thr Arg Leu Tyr Asp Phe
65              70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285
```

```
Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525

<210> SEQ ID NO 115
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (59)..(59)
<223> OTHER INFORMATION: /replace="Formylglycine"
<220> FEATURE:
<221> NAME/KEY: SITE
<222> LOCATION: (1)..(757)
<223> OTHER INFORMATION: /note="Variant residues given in the sequence
      have no preference with respect to those in the annotations
      for variant positions"

<400> SEQUENCE: 115

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60
```

```
Ser Phe Leu Thr Gly Arg Arg Pro Asp Thr Thr Arg Leu Tyr Asp Phe
 65                  70                  75                  80

Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
            290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
            370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
            450                 455                 460

Tyr Ser Ile Arg Thr Ile Asp Tyr Arg Tyr Thr Val Trp Val Gly Phe
465                 470                 475                 480
```

```
Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
        500                 505                 510

Asp Ser Gln Gly Gly Asp Leu Phe Gln Leu Leu Met Pro Gly Gly Gly
        515                 520                 525

Gly Ser Asp Lys Thr His Thr Cys Pro Pro Cys Pro Ala Pro Glu Ala
        530                 535                 540

Ala Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
            580                 585                 590

Glu Val His Asn Ala Lys Thr Lys Pro Arg Glu Glu Gln Tyr Asn Ser
        595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
            660                 665                 670

Val Ser Leu Ser Cys Ala Val Lys Gly Phe Tyr Pro Ser Asp Ile Ala
        675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
            740                 745                 750

Leu Ser Pro Gly Lys
        755

<210> SEQ ID NO 116
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
```

```
                65                  70                  75                  80
Arg Val Val Ser Val Leu Thr Val Leu His Gln Asp Trp Leu Asn Gly
                    85                  90                  95

Lys Glu Tyr Lys Cys Lys Val Ser Asn Lys Ala Leu Pro Ala Pro Ile
                    100                 105                 110

Glu Lys Thr Ile Ser Lys Ala Lys Gly Gln Pro Arg Glu Pro Gln Val
                    115                 120                 125

Tyr Thr Leu Pro Pro Ser Arg Asp Glu Leu Thr Lys Asn Gln Val Ser
                    130                 135                 140

Leu Trp Cys Leu Val Lys Gly Phe Tyr Pro Ser Asp Ile Ala Val Trp
145                 150                 155                 160

Trp Glu Ser Tyr Gly Thr Glu Trp Ser Ser Tyr Lys Thr Thr Pro Pro
                    165                 170                 175

Val Leu Asp Ser Asp Gly Ser Phe Phe Leu Tyr Ser Lys Leu Thr Val
                    180                 185                 190

Thr Lys Glu Glu Trp Gln Gln Gly Phe Val Phe Ser Cys Ser Val Met
                    195                 200                 205

His Glu Ala Leu His Asn His Tyr Thr Gln Lys Ser Leu Ser Leu Ser
        210                 215                 220

Pro Gly Lys
225

<210> SEQ ID NO 117
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (59)..(59)
<223> OTHER INFORMATION: /replace="Formylglycine"
<220> FEATURE:
<221> NAME/KEY: SITE
<222> LOCATION: (1)..(757)
<223> OTHER INFORMATION: /note="Variant residues given in the sequence
      have no preference with respect to those in the annotations
      for variant positions"

<400> SEQUENCE: 117

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                    20                  25                  30

Leu Val Arg Ser Pro Asn Ile Asp Gln Leu Ala Ser His Ser Leu Leu
                    35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                    85                  90                  95

Tyr Phe Lys Glu Asn Gly Tyr Val Thr Met Ser Val Gly Lys Val Phe
                    100                 105                 110

His Pro Gly Ile Ser Ser Asn His Thr Asp Asp Ser Pro Tyr Ser Trp
                    115                 120                 125

Ser Phe Pro Pro Tyr His Pro Ser Ser Glu Lys Tyr Glu Asn Thr Lys
```

```
             130                 135                 140
Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
        515                 520                 525

Gly Ser Asp Lys Thr His Thr Cys Pro Pro Cys Pro Ala Pro Glu Leu
    530                 535                 540

Leu Gly Gly Pro Ser Val Phe Leu Phe Pro Pro Lys Pro Lys Asp Thr
545                 550                 555                 560
```

```
Leu Met Ile Ser Arg Thr Pro Glu Val Thr Cys Val Val Asp Val
                565                 570                 575

Ser His Glu Asp Pro Glu Val Lys Phe Asn Trp Tyr Val Asp Gly Val
            580                 585                 590

Glu Val His Asn Ala Lys Thr Lys Pro Arg Glu Glu Gln Tyr Asn Ser
        595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
            660                 665                 670

Val Ser Leu Ser Cys Ala Val Lys Gly Phe Tyr Pro Ser Asp Ile Ala
        675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
            740                 745                 750

Leu Ser Pro Gly Lys
        755

<210> SEQ ID NO 118
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (59)..(59)
<223> OTHER INFORMATION: /replace="Formylglycine"
<220> FEATURE:
<221> NAME/KEY: SITE
<222> LOCATION: (1)..(757)
<223> OTHER INFORMATION: /note="Variant residues given in the sequence
      have no preference with respect to those in the annotations
      for variant positions"

<400> SEQUENCE: 118

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95
```

```
Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
130             135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
        210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510
```

Asp Ser Gln Gly Gly Asp Leu Phe Gln Leu Leu Met Pro Gly Gly
            515                 520                 525

Gly Ser Asp Lys Thr His Thr Cys Pro Pro Cys Pro Ala Pro Glu Leu
530                 535                 540

Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
            580                 585                 590

Glu Val His Asn Ala Lys Thr Lys Pro Arg Glu Glu Gln Tyr Asn Ser
        595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
            660                 665                 670

Val Ser Leu Trp Cys Leu Val Lys Gly Phe Tyr Pro Ser Asp Ile Ala
        675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Tyr Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
            740                 745                 750

Leu Ser Pro Gly Lys
            755

<210> SEQ ID NO 119
<211> LENGTH: 502
<212> TYPE: PRT
<213> ORGANISM: Homo sapiens

<400> SEQUENCE: 119

Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
        50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

```
Glu Thr Val Tyr Pro Phe Asp Phe Ala Tyr Thr Glu Glu Asn Gly Ser
        130                 135                 140

Val Leu Gln Val Gly Arg Asn Ile Thr Arg Ile Lys Leu Leu Val Arg
145                 150                 155                 160

Lys Phe Leu Gln Thr Gln Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 120
<211> LENGTH: 482
<212> TYPE: PRT
<213> ORGANISM: Homo sapiens
```

```
<400> SEQUENCE: 120

Arg Pro Arg Asn Ala Leu Leu Leu Ala Asp Asp Gly Gly Phe Glu
1               5                   10                  15

Ser Gly Ala Tyr Asn Asn Ser Ala Ile Ala Thr Pro His Leu Asp Ala
            20                  25                  30

Leu Ala Arg Arg Ser Leu Leu Phe Arg Asn Ala Phe Thr Ser Val Ser
            35                  40                  45

Ser Cys Ser Pro Ser Arg Ala Ser Leu Leu Thr Gly Leu Pro Gln His
50                  55                  60

Gln Asn Gly Met Tyr Gly Leu His Gln Asp Val His His Phe Asn Ser
65                  70                  75                  80

Phe Asp Lys Val Arg Ser Leu Pro Leu Leu Ser Gln Ala Gly Val
                85                  90                  95

Arg Thr Gly Ile Ile Gly Lys Lys His Val Gly Pro Glu Thr Val Tyr
                100                 105                 110

Pro Phe Asp Phe Ala Tyr Thr Glu Glu Asn Gly Ser Val Leu Gln Val
            115                 120                 125

Gly Arg Asn Ile Thr Arg Ile Lys Leu Leu Val Arg Lys Phe Leu Gln
130                 135                 140

Thr Gln Asp Asp Arg Pro Phe Leu Tyr Val Ala Phe His Asp Pro
145                 150                 155                 160

His Arg Cys Gly His Ser Gln Pro Gln Tyr Gly Thr Phe Cys Glu Lys
                165                 170                 175

Phe Gly Asn Gly Glu Ser Gly Met Gly Arg Ile Pro Asp Trp Thr Pro
            180                 185                 190

Gln Ala Tyr Asp Pro Leu Asp Val Leu Val Pro Tyr Phe Val Pro Asn
            195                 200                 205

Thr Pro Ala Ala Arg Ala Asp Leu Ala Ala Gln Tyr Thr Thr Val Gly
210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
                245                 250                 255

Pro Phe Pro Ser Gly Arg Thr Asn Leu Tyr Trp Pro Gly Thr Ala Glu
                260                 265                 270

Pro Leu Leu Val Ser Ser Pro Glu His Pro Lys Arg Trp Gly Gln Val
            275                 280                 285

Ser Glu Ala Tyr Val Ser Leu Leu Asp Leu Thr Pro Thr Ile Leu Asp
290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
                325                 330                 335

Leu Trp Ala Thr Val Phe Gly Ser Gln Ser His His Glu Val Thr Met
            340                 345                 350

Ser Tyr Pro Met Arg Ser Val Gln His Arg His Phe Arg Leu Val His
            355                 360                 365

Asn Leu Asn Phe Lys Met Pro Phe Pro Ile Asp Gln Asp Phe Tyr Val
370                 375                 380

Ser Pro Thr Phe Gln Asp Leu Leu Asn Arg Thr Thr Ala Gly Gln Pro
385                 390                 395                 400

Thr Gly Trp Tyr Lys Asp Leu Arg His Tyr Tyr Arg Ala Arg Trp
                405                 410                 415
```

```
Glu Leu Tyr Asp Arg Ser Arg Asp Pro His Glu Thr Gln Asn Leu Ala
            420                 425                 430

Thr Asp Pro Arg Phe Ala Gln Leu Leu Glu Met Leu Arg Asp Gln Leu
            435                 440                 445

Ala Lys Trp Gln Trp Glu Thr His Asp Pro Trp Val Cys Ala Pro Asp
450                 455                 460

Gly Val Leu Glu Glu Lys Leu Ser Pro Gln Cys Gln Pro Leu His Asn
465                 470                 475                 480

Glu Leu

<210> SEQ ID NO 121
<211> LENGTH: 629
<212> TYPE: PRT
<213> ORGANISM: Homo sapiens

<400> SEQUENCE: 121

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ser
        35                  40                  45

Asp Ser Arg Val Leu Trp Ala Pro Ala Glu Ala His Pro Leu Ser Pro
50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Asp Met Val Glu
130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
            180                 185                 190

Ala Pro Gly Ala Pro Val Ser Arg Ile Leu Phe Leu Thr Asp Leu His
        195                 200                 205

Trp Asp His Asp Tyr Leu Glu Gly Thr Asp Pro Asp Cys Ala Asp Pro
210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
290                 295                 300
```

Lys Phe Leu Gly Pro Val Pro Val Tyr Pro Ala Val Gly Asn His Glu
305                 310                 315                 320

Ser Thr Pro Val Asn Ser Phe Pro Pro Phe Ile Glu Gly Asn His
            325                 330                 335

Ser Ser Arg Trp Leu Tyr Glu Ala Met Ala Lys Ala Trp Glu Pro Trp
            340                 345                 350

Leu Pro Ala Glu Ala Leu Arg Thr Leu Arg Ile Gly Gly Phe Tyr Ala
            355                 360                 365

Leu Ser Pro Tyr Pro Gly Leu Arg Leu Ile Ser Leu Asn Met Asn Phe
            370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
            405                 410                 415

Gly Asp Lys Val His Ile Ile Gly His Ile Pro Pro Gly His Cys Leu
            420                 425                 430

Lys Ser Trp Ser Trp Asn Tyr Tyr Arg Ile Val Ala Arg Tyr Glu Asn
            435                 440                 445

Thr Leu Ala Ala Gln Phe Phe Gly His Thr His Val Asp Glu Phe Glu
            450                 455                 460

Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
            485                 490                 495

Val Tyr Gln Ile Asp Gly Asn Tyr Ser Gly Ser Ser His Val Val Leu
            500                 505                 510

Asp His Glu Thr Tyr Ile Leu Asn Leu Thr Gln Ala Asn Ile Pro Gly
            515                 520                 525

Ala Ile Pro His Trp Gln Leu Leu Tyr Arg Ala Arg Glu Thr Tyr Gly
            530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
            565                 570                 575

Gly His Pro Pro Ser Glu Pro Cys Gly Thr Pro Cys Arg Leu Ala Thr
            580                 585                 590

Leu Cys Ala Gln Leu Ser Ala Arg Ala Asp Ser Pro Ala Leu Cys Arg
            595                 600                 605

His Leu Met Pro Asp Gly Ser Leu Pro Glu Ala Gln Ser Leu Trp Pro
            610                 615                 620

Arg Pro Leu Phe Cys
625

<210> SEQ ID NO 122
<211> LENGTH: 583
<212> TYPE: PRT
<213> ORGANISM: Homo sapiens

<400> SEQUENCE: 122

Leu Ser Asp Ser Arg Val Leu Trp Ala Pro Ala Glu Ala His Pro Leu
1               5                   10                  15

Ser Pro Gln Gly His Pro Ala Arg Leu His Arg Ile Val Pro Arg Leu
            20                  25                  30

Arg Asp Val Phe Gly Trp Gly Asn Leu Thr Cys Pro Ile Cys Lys Gly

```
                35                  40                  45
Leu Phe Thr Ala Ile Asn Leu Gly Leu Lys Lys Glu Pro Asn Val Ala
 50                  55                  60

Arg Val Gly Ser Val Ala Ile Lys Leu Cys Asn Leu Leu Lys Ile Ala
 65                  70                  75                  80

Pro Pro Ala Val Cys Gln Ser Ile Val His Leu Phe Glu Asp Asp Met
                 85                  90                  95

Val Glu Val Trp Arg Arg Ser Val Leu Ser Pro Ser Glu Ala Cys Gly
                100                 105                 110

Leu Leu Leu Gly Ser Thr Cys Gly His Trp Asp Ile Phe Ser Ser Trp
            115                 120                 125

Asn Ile Ser Leu Pro Thr Val Pro Lys Pro Pro Lys Pro Pro Ser
130                 135                 140

Pro Pro Ala Pro Gly Ala Pro Val Ser Arg Ile Leu Phe Leu Thr Asp
145                 150                 155                 160

Leu His Trp Asp His Asp Tyr Leu Glu Gly Thr Asp Pro Asp Cys Ala
                165                 170                 175

Asp Pro Leu Cys Cys Arg Arg Gly Ser Gly Leu Pro Pro Ala Ser Arg
                180                 185                 190

Pro Gly Ala Gly Tyr Trp Gly Glu Tyr Ser Lys Cys Asp Leu Pro Leu
            195                 200                 205

Arg Thr Leu Glu Ser Leu Leu Ser Gly Leu Gly Pro Ala Gly Pro Phe
210                 215                 220

Asp Met Val Tyr Trp Thr Gly Asp Ile Pro Ala His Asp Val Trp His
225                 230                 235                 240

Gln Thr Arg Gln Asp Gln Leu Arg Ala Leu Thr Thr Val Thr Ala Leu
                245                 250                 255

Val Arg Lys Phe Leu Gly Pro Val Pro Val Tyr Pro Ala Val Gly Asn
                260                 265                 270

His Glu Ser Thr Pro Val Asn Ser Phe Pro Pro Pro Phe Ile Glu Gly
            275                 280                 285

Asn His Ser Ser Arg Trp Leu Tyr Glu Ala Met Ala Lys Ala Trp Glu
290                 295                 300

Pro Trp Leu Pro Ala Glu Ala Leu Arg Thr Leu Arg Ile Gly Gly Phe
305                 310                 315                 320

Tyr Ala Leu Ser Pro Tyr Pro Gly Leu Arg Leu Ile Ser Leu Asn Met
                325                 330                 335

Asn Phe Cys Ser Arg Glu Asn Phe Trp Leu Leu Ile Asn Ser Thr Asp
                340                 345                 350

Pro Ala Gly Gln Leu Gln Trp Leu Val Gly Glu Leu Gln Ala Ala Glu
            355                 360                 365

Asp Arg Gly Asp Lys Val His Ile Ile Gly His Ile Pro Pro Gly His
370                 375                 380

Cys Leu Lys Ser Trp Ser Trp Asn Tyr Tyr Arg Ile Val Ala Arg Tyr
385                 390                 395                 400

Glu Asn Thr Leu Ala Ala Gln Phe Phe Gly His Thr His Val Asp Glu
                405                 410                 415

Phe Glu Val Phe Tyr Asp Glu Glu Thr Leu Ser Arg Pro Leu Ala Val
                420                 425                 430

Ala Phe Leu Ala Pro Ser Ala Thr Thr Tyr Ile Gly Leu Asn Pro Gly
            435                 440                 445

Tyr Arg Val Tyr Gln Ile Asp Gly Asn Tyr Ser Gly Ser Ser His Val
450                 455                 460
```

```
Val Leu Asp His Glu Thr Tyr Ile Leu Asn Leu Thr Gln Ala Asn Ile
465                 470                 475                 480

Pro Gly Ala Ile Pro His Trp Gln Leu Leu Tyr Arg Ala Arg Glu Thr
                485                 490                 495

Tyr Gly Leu Pro Asn Thr Leu Pro Thr Ala Trp His Asn Leu Val Tyr
                500                 505                 510

Arg Met Arg Gly Asp Met Gln Leu Phe Gln Thr Phe Trp Phe Leu Tyr
            515                 520                 525

His Lys Gly His Pro Pro Ser Glu Pro Cys Gly Thr Pro Cys Arg Leu
            530                 535                 540

Ala Thr Leu Cys Ala Gln Leu Ser Ala Arg Ala Asp Ser Pro Ala Leu
545                 550                 555                 560

Cys Arg His Leu Met Pro Asp Gly Ser Leu Pro Glu Ala Gln Ser Leu
                565                 570                 575

Trp Pro Arg Pro Leu Phe Cys
                580

<210> SEQ ID NO 123
<211> LENGTH: 574
<212> TYPE: PRT
<213> ORGANISM: Homo sapiens

<400> SEQUENCE: 123

Leu Ser Asp Ser Arg Val Leu Trp Ala Pro Ala Glu Ala His Pro Leu
1               5                   10                  15

Ser Pro Gln Gly His Pro Ala Arg Leu His Arg Ile Val Pro Arg Leu
                20                  25                  30

Arg Asp Val Phe Gly Trp Gly Asn Leu Thr Cys Pro Ile Cys Lys Gly
            35                  40                  45

Leu Phe Thr Ala Ile Asn Leu Gly Leu Lys Lys Glu Pro Asn Val Ala
        50                  55                  60

Arg Val Gly Ser Val Ala Ile Lys Leu Cys Asn Leu Leu Lys Ile Ala
65                  70                  75                  80

Pro Pro Ala Val Cys Gln Ser Ile Val His Leu Phe Glu Asp Asp Met
                85                  90                  95

Val Glu Val Trp Arg Arg Ser Val Leu Ser Pro Ser Glu Ala Cys Gly
                100                 105                 110

Leu Leu Leu Gly Ser Thr Cys Gly His Trp Asp Ile Phe Ser Ser Trp
            115                 120                 125

Asn Ile Ser Leu Pro Thr Val Pro Lys Pro Pro Lys Pro Pro Ser
        130                 135                 140

Pro Pro Ala Pro Gly Ala Pro Val Ser Arg Ile Leu Phe Leu Thr Asp
145                 150                 155                 160

Leu His Trp Asp His Asp Tyr Leu Glu Gly Thr Asp Pro Asp Cys Ala
                165                 170                 175

Asp Pro Leu Cys Cys Arg Arg Gly Ser Gly Leu Pro Ala Ser Arg
            180                 185                 190

Pro Gly Ala Gly Tyr Trp Gly Glu Tyr Ser Lys Cys Asp Leu Pro Leu
            195                 200                 205

Arg Thr Leu Glu Ser Leu Leu Ser Gly Leu Gly Pro Ala Gly Pro Phe
            210                 215                 220

Asp Met Val Tyr Trp Thr Gly Asp Ile Pro Ala His Asp Val Trp His
225                 230                 235                 240

Gln Thr Arg Gln Asp Gln Leu Arg Ala Leu Thr Thr Val Thr Ala Leu
```

```
                    245                 250                 255
Val Arg Lys Phe Leu Gly Pro Val Pro Val Tyr Pro Ala Val Gly Asn
                260                 265                 270

His Glu Ser Thr Pro Val Asn Ser Phe Pro Pro Phe Ile Glu Gly
            275                 280                 285

Asn His Ser Ser Arg Trp Leu Tyr Glu Ala Met Ala Lys Ala Trp Glu
        290                 295                 300

Pro Trp Leu Pro Ala Glu Ala Leu Arg Thr Leu Arg Ile Gly Gly Phe
305                 310                 315                 320

Tyr Ala Leu Ser Pro Tyr Pro Gly Leu Arg Leu Ile Ser Leu Asn Met
                325                 330                 335

Asn Phe Cys Ser Arg Glu Asn Phe Trp Leu Leu Ile Asn Ser Thr Asp
            340                 345                 350

Pro Ala Gly Gln Leu Gln Trp Leu Val Gly Glu Leu Gln Ala Ala Glu
        355                 360                 365

Asp Arg Gly Asp Lys Val His Ile Ile Gly His Ile Pro Pro Gly His
370                 375                 380

Cys Leu Lys Ser Trp Ser Trp Asn Tyr Tyr Arg Ile Val Ala Arg Tyr
385                 390                 395                 400

Glu Asn Thr Leu Ala Ala Gln Phe Phe Gly His Thr His Val Asp Glu
                405                 410                 415

Phe Glu Val Phe Tyr Asp Glu Glu Thr Leu Ser Arg Pro Leu Ala Val
            420                 425                 430

Ala Phe Leu Ala Pro Ser Ala Thr Thr Tyr Ile Gly Leu Asn Pro Gly
        435                 440                 445

Tyr Arg Val Tyr Gln Ile Asp Gly Asn Tyr Ser Gly Ser Ser His Val
450                 455                 460

Val Leu Asp His Glu Thr Tyr Ile Leu Asn Leu Thr Gln Ala Asn Ile
465                 470                 475                 480

Pro Gly Ala Ile Pro His Trp Gln Leu Leu Tyr Arg Ala Arg Glu Thr
                485                 490                 495

Tyr Gly Leu Pro Asn Thr Leu Pro Thr Ala Trp His Asn Leu Val Tyr
            500                 505                 510

Arg Met Arg Gly Asp Met Gln Leu Phe Gln Thr Phe Trp Phe Leu Tyr
        515                 520                 525

His Lys Gly His Pro Pro Ser Glu Pro Cys Gly Thr Pro Cys Arg Leu
530                 535                 540

Ala Thr Leu Cys Ala Gln Leu Ser Ala Arg Ala Asp Ser Pro Ala Leu
545                 550                 555                 560

Cys Arg His Leu Met Pro Asp Gly Ser Leu Pro Glu Ala Gln
                565                 570

<210> SEQ ID NO 124
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                    100                 105                 110

Pro Arg Phe Asp Tyr Val Thr Thr Leu Pro Pro Ser Arg Asp Glu Leu
                115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Gly Phe
            195                 200                 205

His Asp Leu Ser Leu Ser Pro Gly Lys
            210                 215

<210> SEQ ID NO 125
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                    100                 105                 110

Pro Arg Phe Asp Met Val Thr Thr Leu Pro Pro Ser Arg Asp Glu Leu
                115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

```
Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Gly Phe
        195                 200                 205

His Asp Leu Ser Leu Ser Pro Gly Lys
    210                 215

<210> SEQ ID NO 126
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Phe Glu Tyr Val Thr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Gly Phe
        195                 200                 205

His Asp Leu Ser Leu Ser Pro Gly Lys
    210                 215

<210> SEQ ID NO 127
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Ala Pro Glu Leu Leu Gly Gly Pro Ser Val Phe Leu Phe Pro Pro Lys
```

-continued

```
 1               5                  10                 15
Pro Lys Asp Thr Leu Met Ile Ser Arg Thr Pro Glu Val Thr Cys Val
                20                 25                 30

Val Val Asp Val Ser His Glu Asp Pro Glu Val Lys Phe Asn Trp Tyr
                35                 40                 45

Val Asp Gly Val Glu Val His Asn Ala Lys Thr Lys Pro Arg Glu Glu
 50                 55                 60

Gln Tyr Asn Ser Thr Tyr Arg Val Val Ser Val Leu Thr Val Leu His
 65                 70                 75                 80

Gln Asp Trp Leu Asn Gly Lys Glu Tyr Lys Cys Lys Val Ser Asn Lys
                85                 90                 95

Ala Leu Pro Ala Pro Ile Glu Lys Thr Ile Ser Lys Ala Lys Gly Gln
                100                105                110

Pro Arg Phe Glu Met Val Thr Thr Leu Pro Pro Ser Arg Asp Glu Leu
                115                120                125

Thr Lys Asn Gln Val Ser Leu Thr Cys Leu Val Lys Gly Phe Tyr Pro
                130                135                140

Ser Asp Ile Ala Val Glu Trp Glu Ser Asn Gly Gln Pro Glu Asn Asn
145                150                155                160

Tyr Lys Thr Thr Pro Pro Val Leu Asp Ser Asp Gly Ser Phe Phe Leu
                165                170                175

Tyr Ser Lys Leu Thr Val Asp Lys Ser Arg Trp Gln Gln Gly Asn Val
                180                185                190

Phe Ser Cys Ser Val Met His Glu Ala Leu His Asn His Tyr Gly Phe
                195                200                205

His Asp Leu Ser Leu Ser Pro Gly Lys
                210                215
```

<210> SEQ ID NO 128
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 128

```
Ala Pro Glu Leu Leu Gly Gly Pro Ser Val Phe Leu Phe Pro Pro Lys
 1               5                  10                 15

Pro Lys Asp Thr Leu Met Ile Ser Arg Thr Pro Glu Val Thr Cys Val
                20                 25                 30

Val Val Asp Val Ser His Glu Asp Pro Glu Val Lys Phe Asn Trp Tyr
                35                 40                 45

Val Asp Gly Val Glu Val His Asn Ala Lys Thr Lys Pro Arg Glu Glu
 50                 55                 60

Gln Tyr Asn Ser Thr Tyr Arg Val Val Ser Val Leu Thr Val Leu His
 65                 70                 75                 80

Gln Asp Trp Leu Asn Gly Lys Glu Tyr Lys Cys Lys Val Ser Asn Lys
                85                 90                 95

Ala Leu Pro Ala Pro Ile Glu Lys Thr Ile Ser Lys Ala Lys Gly Gln
                100                105                110

Pro Arg Phe Glu Leu Val Thr Thr Leu Pro Pro Ser Arg Asp Glu Leu
                115                120                125

Thr Lys Asn Gln Val Ser Leu Thr Cys Leu Val Lys Gly Phe Tyr Pro
                130                135                140
```

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Gly Phe
        195                 200                 205

His Asp Leu Ser Leu Ser Pro Gly Lys
    210                 215

<210> SEQ ID NO 129
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Glu Phe Ile Trp Tyr
        35                  40                  45

Val Asp Gly Val Asp Val Arg Tyr Glu Trp Gln Leu Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 130
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gly Phe Val Trp Tyr
        35                  40                  45

Val Asp Gly Val Pro Val Ser Trp Glu Trp Tyr Trp Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
    195                 200                 205

Lys Ser Leu Ser Leu Ser Pro Gly Lys
        210                 215

<210> SEQ ID NO 131
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asp Trp Tyr
        35                  40                  45

Val Asp Gly Val Met Val Arg Arg Glu Trp His Arg Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu

```
                115                 120                 125
Thr Lys Asn Gln Val Ser Leu Thr Cys Leu Val Lys Gly Phe Tyr Pro
            130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
                195                 200                 205
Lys Ser Leu Ser Leu Ser Pro Gly Lys
            210                 215

<210> SEQ ID NO 132
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Ser Phe Glu Trp Tyr
        35                  40                  45
Val Asp Gly Val Pro Val Arg Trp Glu Trp Gln Trp Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Asp Glu Leu
        115                 120                 125
Thr Lys Asn Gln Val Ser Leu Thr Cys Leu Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Lys
    210                 215

<210> SEQ ID NO 133
<211> LENGTH: 217
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 133

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Ala Phe Thr Trp Tyr
        35                  40                  45

Val Asp Gly Val Pro Val Arg Trp Glu Trp Gln Asn Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 134
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Pro Gln Thr Pro Pro Trp Glu Val Lys Phe Asn Trp Tyr
        35                  40                  45

Val Asp Gly Val Glu Val His Asn Ala Lys Thr Lys Pro Arg Glu Glu
    50                  55                  60

Glu Tyr Tyr Thr Tyr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 135
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Pro Pro Ser Pro Pro Trp Glu Val Lys Phe Asn Trp Tyr
        35                  40                  45

Val Asp Gly Val Glu Val His Asn Ala Lys Thr Lys Pro Arg Glu Glu
    50                  55                  60

Glu Tyr Tyr Ser Asn Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

```
<210> SEQ ID NO 136
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Pro Gln Thr Pro Pro Trp Glu Val Lys Phe Asn Trp Tyr
        35                  40                  45

Val Asp Gly Val Glu Val His Asn Ala Lys Thr Lys Pro Arg Glu Glu
    50                  55                  60

Glu Tyr Tyr Ser Asn Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 137
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Phe Arg Gly Pro Trp Glu Val Lys Phe Asn Trp Tyr
        35                  40                  45

Val Asp Gly Val Glu Val His Asn Ala Lys Thr Lys Pro Arg Glu Glu
    50                  55                  60

Glu Tyr Tyr His Asp Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 138
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Pro Gln Thr Val Pro Trp Glu Val Lys Phe Asn Trp Tyr
        35                  40                  45

Val Asp Gly Val Glu Val His Asn Ala Lys Thr Lys Pro Arg Glu Glu
    50                  55                  60

Glu Tyr Tyr Ser Asn Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

```
Lys Ser Leu Ser Leu Ser Pro Gly Lys
    210                 215

<210> SEQ ID NO 139
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Val Pro Pro Arg Met Val Lys Phe Asn Trp Tyr
        35                  40                  45

Val Asp Gly Val Glu Val His Asn Ala Lys Thr Lys Ser Leu Thr Ser
    50                  55                  60

Gln His Asn Ser Thr Val Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 140
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Val Pro Pro Trp Met Val Lys Phe Asn Trp Tyr
        35                  40                  45

Val Asp Gly Val Glu Val His Asn Ala Lys Thr Lys Ser Leu Thr Ser
```

```
                    50                  55                  60
Gln His Asn Ser Thr Val Arg Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 141
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser Asp Met Trp Glu Tyr Val Lys Phe Asn Trp Tyr
            35                  40                  45

Val Asp Gly Val Glu Val His Asn Ala Lys Thr Lys Pro Trp Val Lys
 50                  55                  60

Gln Leu Asn Ser Thr Trp Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 142
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Asp Asp Trp Thr Trp Val Lys Phe Asn Trp Tyr
        35                  40                  45

Val Asp Gly Val Glu Val His Asn Ala Lys Thr Lys Pro Trp Ile Ala
    50                  55                  60

Gln Pro Asn Ser Thr Trp Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 143
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

Val Val Asp Val Ser Asp Asp Trp Glu Trp Val Lys Phe Asn Trp Tyr
         35                  40                  45

Val Asp Gly Val Glu Val His Asn Ala Lys Thr Lys Pro Trp Lys Leu
 50                  55                  60

Gln Leu Asn Ser Thr Trp Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
             100                 105                 110

Pro Arg Glu Pro Gln Val Tyr Thr Leu Pro Pro Ser Arg Asp Glu Leu
         115                 120                 125

Thr Lys Asn Gln Val Ser Leu Thr Cys Leu Val Lys Gly Phe Tyr Pro
     130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 144
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Trp Val Trp Phe Tyr Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Ser Val Val Asn Ile
                 85                  90                  95

Ala Leu Trp Trp Ser Ile Glu Lys Thr Ile Ser Lys Ala Lys Gly Gln
             100                 105                 110

Pro Arg Glu Pro Gln Val Tyr Thr Leu Pro Pro Ser Arg Asp Glu Leu
         115                 120                 125

Thr Lys Asn Gln Val Ser Leu Thr Cys Leu Val Lys Gly Phe Tyr Pro
     130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu

```
                    165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 145
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Val Val Gly Phe Arg Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Arg Val Ser Asn Ser
                85                  90                  95

Ala Leu Thr Trp Lys Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 146
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Ala Pro Glu Leu Leu Gly Gly Pro Ser Val Phe Leu Phe Pro Pro Lys
1               5                   10                  15
```

Pro Lys Asp Thr Leu Met Ile Ser Arg Thr Pro Glu Val Thr Cys Val
            20                  25                  30

Val Val Asp Val Ser His Glu Asp Pro Val Val Gly Phe Arg Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Arg Val Ser Asn Ser
            85                  90                  95

Ala Leu Ser Trp Arg Ile Glu Lys Thr Ile Ser Lys Ala Lys Gly Gln
        100                 105                 110

Pro Arg Glu Pro Gln Val Tyr Thr Leu Pro Pro Ser Arg Asp Glu Leu
    115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
    195                 200                 205

Lys Ser Leu Ser Leu Ser Pro Gly Lys
        210                 215

<210> SEQ ID NO 147
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Ile Val Gly Phe Arg Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Arg Val Ser Asn Ser
            85                  90                  95

Ala Leu Arg Trp Arg Ile Glu Lys Thr Ile Ser Lys Ala Lys Gly Gln
        100                 105                 110

Pro Arg Glu Pro Gln Val Tyr Thr Leu Pro Pro Ser Arg Asp Glu Leu
    115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 148
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Ala Val Gly Phe Glu Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Gln Val Phe Asn Trp
            85                  90                  95

Ala Leu Asp Trp Val Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 149
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 149

Arg Pro Arg Asn Ala Leu Leu Leu Ala Asp Asp Gly Gly Phe Glu
1               5                   10                  15

Ser Gly Ala Tyr Asn Asn Ser Ala Ile Ala Thr Pro His Leu Asp Ala
            20                  25                  30

Leu Ala Arg Arg Ser Leu Leu Phe Arg Asn Ala Phe Thr Ser Val Ser
        35                  40                  45

Ser Cys Ser Pro Ser Arg Ala Ser Leu Leu Thr Gly Leu Pro Gln His
50                  55                  60

Gln Asn Gly Met Tyr Gly Leu His Gln Asp Val His His Phe Asn Ser
65                  70                  75                  80

Phe Asp Lys Val Arg Ser Leu Pro Leu Leu Leu Ser Gln Ala Gly Val
                85                  90                  95

Arg Thr Gly Ile Ile Gly Lys Lys His Val Gly Pro Glu Thr Val Tyr
            100                 105                 110

Pro Phe Asp Phe Ala Tyr Thr Glu Glu Asn Gly Ser Val Leu Gln Val
        115                 120                 125

Gly Arg Asn Ile Thr Arg Ile Lys Leu Leu Val Arg Lys Phe Leu Gln
130                 135                 140

Thr Gln Asp Asp Arg Pro Phe Leu Tyr Val Ala Phe His Asp Pro
145                 150                 155                 160

His Arg Cys Gly His Ser Gln Pro Gln Tyr Gly Thr Phe Cys Glu Lys
                165                 170                 175

Phe Gly Asn Gly Glu Ser Gly Met Gly Arg Ile Pro Asp Trp Thr Pro
            180                 185                 190

Gln Ala Tyr Asp Pro Leu Asp Val Leu Val Pro Tyr Phe Val Pro Asn
        195                 200                 205

Thr Pro Ala Ala Arg Ala Asp Leu Ala Ala Gln Tyr Thr Thr Val Gly
210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
                245                 250                 255

Pro Phe Pro Ser Gly Arg Thr Asn Leu Tyr Trp Pro Gly Thr Ala Glu
            260                 265                 270

Pro Leu Leu Val Ser Ser Pro Glu His Pro Lys Arg Trp Gly Gln Val
        275                 280                 285

Ser Glu Ala Tyr Val Ser Leu Leu Asp Leu Thr Pro Thr Ile Leu Asp
290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
                325                 330                 335

Leu Trp Ala Thr Val Phe Gly Ser Gln Ser His His Glu Val Thr Met
            340                 345                 350

Ser Tyr Pro Met Arg Ser Val Gln His Arg His Phe Arg Leu Val His
        355                 360                 365

Asn Leu Asn Phe Lys Met Pro Phe Pro Ile Asp Gln Asp Phe Tyr Val
370                 375                 380

Ser Pro Thr Phe Gln Asp Leu Leu Asn Arg Thr Thr Ala Gly Gln Pro
385                 390                 395                 400

Thr Gly Trp Tyr Lys Asp Leu Arg His Tyr Tyr Arg Ala Arg Trp
                405                 410                 415
```

```
Glu Leu Tyr Asp Arg Ser Arg Asp Pro His Glu Thr Gln Asn Leu Ala
            420                 425                 430

Thr Asp Pro Arg Phe Ala Gln Leu Leu Glu Met Leu Arg Asp Gln Leu
        435                 440                 445

Ala Lys Trp Gln Trp Glu Thr His Asp Pro Trp Val Cys Ala Pro Asp
    450                 455                 460

Gly Val Leu Glu Glu Lys Leu Ser Pro Gln Cys Gln Pro Leu His Asn
465                 470                 475                 480

Glu Leu Gly Gly Gly Ser Asp Lys Thr His Thr Cys Pro Pro Cys
                485                 490                 495

Pro Ala Pro Glu Ala Ala Gly Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Ser Arg Asp Glu
    610                 615                 620

Leu Thr Lys Asn Gln Val Ser Leu Ser Cys Ala Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Val Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly Lys
705                 710

<210> SEQ ID NO 150
<211> LENGTH: 704
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 150

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Ser Arg Pro
210                 215                 220

Arg Asn Ala Leu Leu Leu Ala Asp Asp Gly Gly Phe Glu Ser Gly
225                 230                 235                 240

Ala Tyr Asn Asn Ser Ala Ile Ala Thr Pro His Leu Asp Ala Leu Ala
                245                 250                 255

Arg Arg Ser Leu Leu Phe Arg Asn Ala Phe Thr Ser Val Ser Ser Cys
            260                 265                 270

Ser Pro Ser Arg Ala Ser Leu Leu Thr Gly Leu Pro Gln His Gln Asn
        275                 280                 285

Gly Met Tyr Gly Leu His Gln Asp Val His Phe Asn Ser Phe Asp
290                 295                 300

Lys Val Arg Ser Leu Pro Leu Leu Leu Ser Gln Ala Gly Val Arg Thr
305                 310                 315                 320

Gly Ile Ile Gly Lys Lys His Val Gly Pro Glu Thr Val Tyr Pro Phe
                325                 330                 335

Asp Phe Ala Tyr Thr Glu Glu Asn Gly Ser Val Leu Gln Val Gly Arg
            340                 345                 350

Asn Ile Thr Arg Ile Lys Leu Leu Val Arg Lys Phe Leu Gln Thr Gln
        355                 360                 365

Asp Asp Arg Pro Phe Phe Leu Tyr Val Ala Phe His Asp Pro His Arg
370                 375                 380

Cys Gly His Ser Gln Pro Gln Tyr Gly Thr Phe Cys Glu Lys Phe Gly
385                 390                 395                 400

Asn Gly Glu Ser Gly Met Gly Arg Ile Pro Asp Trp Thr Pro Gln Ala
                405                 410                 415

Tyr Asp Pro Leu Asp Val Leu Val Pro Tyr Phe Val Pro Asn Thr Pro
            420                 425                 430

Ala Ala Arg Ala Asp Leu Ala Ala Gln Tyr Thr Thr Val Gly Arg Met
        435                 440                 445

Asp Gln Gly Val Gly Leu Val Leu Gln Glu Leu Arg Asp Ala Gly Val
450                 455                 460

Leu Asn Asp Thr Leu Val Ile Phe Thr Ser Asp Asn Gly Ile Pro Phe

```
                465                 470                 475                 480
        Pro Ser Gly Arg Thr Asn Leu Tyr Trp Pro Gly Thr Ala Glu Pro Leu
                        485                 490                 495

Leu Val Ser Ser Pro Glu His Pro Lys Arg Trp Gly Gln Val Ser Glu
                    500                 505                 510

Ala Tyr Val Ser Leu Leu Asp Leu Thr Pro Thr Ile Leu Asp Trp Phe
                    515                 520                 525

Ser Ile Pro Tyr Pro Ser Tyr Ala Ile Phe Gly Ser Lys Thr Ile His
                530                 535                 540

Leu Thr Gly Arg Ser Leu Leu Pro Ala Leu Glu Ala Glu Pro Leu Trp
        545                 550                 555                 560

Ala Thr Val Phe Gly Ser Gln Ser His His Glu Val Thr Met Ser Tyr
                        565                 570                 575

Pro Met Arg Ser Val Gln His Arg His Phe Arg Leu Val His Asn Leu
                    580                 585                 590

Asn Phe Lys Met Pro Phe Pro Ile Asp Gln Asp Phe Tyr Val Ser Pro
                    595                 600                 605

Thr Phe Gln Asp Leu Leu Asn Arg Thr Thr Ala Gly Gln Pro Thr Gly
                610                 615                 620

Trp Tyr Lys Asp Leu Arg His Tyr Tyr Arg Ala Arg Trp Glu Leu
        625                 630                 635                 640

Tyr Asp Arg Ser Arg Asp Pro His Glu Thr Gln Asn Leu Ala Thr Asp
                        645                 650                 655

Pro Arg Phe Ala Gln Leu Leu Glu Met Leu Arg Asp Gln Leu Ala Lys
                    660                 665                 670

Trp Gln Trp Glu Thr His Asp Pro Trp Val Cys Ala Pro Asp Gly Val
                    675                 680                 685

Leu Glu Glu Lys Leu Ser Pro Gln Cys Gln Pro Leu His Asn Glu Leu
                690                 695                 700
```

<210> SEQ ID NO 151
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151

```
        Ala Pro Glu Ala Ala Gly Gly Pro Ser Val Phe Leu Phe Pro Pro Lys
        1               5                   10                  15

Pro Lys Asp Thr Leu Met Ile Ser Arg Thr Pro Glu Val Thr Cys Val
                    20                  25                  30

Val Val Asp Val Ser His Glu Asp Pro Glu Val Lys Phe Asn Trp Tyr
                35                  40                  45

Val Asp Gly Val Glu Val His Asn Ala Lys Thr Lys Pro Arg Glu Glu
                50                  55                  60

Gln Tyr Asn Ser Thr Tyr Arg Val Val Ser Val Leu Thr Val Leu His
        65                  70                  75                  80

Gln Asp Trp Leu Asn Gly Lys Glu Tyr Lys Cys Lys Val Ser Asn Lys
                        85                  90                  95

Ala Leu Pro Ala Pro Ile Glu Lys Thr Ile Ser Lys Ala Lys Gly Gln
                    100                 105                 110

Pro Arg Glu Pro Gln Val Tyr Thr Leu Pro Pro Ser Arg Asp Glu Leu
                    115                 120                 125
```

```
Thr Lys Asn Gln Val Ser Leu Trp Cys Leu Val Lys Gly Phe Tyr Pro
    130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 152
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

Arg Pro Arg Asn Ala Leu Leu Leu Ala Asp Asp Gly Gly Phe Glu
1               5                   10                  15

Ser Gly Ala Tyr Asn Asn Ser Ala Ile Ala Thr Pro His Leu Asp Ala
                20                  25                  30

Leu Ala Arg Arg Ser Leu Leu Phe Arg Asn Ala Phe Thr Ser Val Ser
                35                  40                  45

Ser Cys Ser Pro Ser Arg Ala Ser Leu Leu Thr Gly Leu Pro Gln His
    50                  55                  60

Gln Asn Gly Met Tyr Gly Leu His Gln Asp Val His His Phe Asn Ser
65                  70                  75                  80

Phe Asp Lys Val Arg Ser Leu Pro Leu Leu Ser Gln Ala Gly Val
                85                  90                  95

Arg Thr Gly Ile Ile Gly Lys Lys His Val Gly Pro Glu Thr Val Tyr
                100                 105                 110

Pro Phe Asp Phe Ala Tyr Thr Glu Glu Asn Gly Ser Val Leu Gln Val
                115                 120                 125

Gly Arg Asn Ile Thr Arg Ile Lys Leu Leu Val Arg Lys Phe Leu Gln
                130                 135                 140

Thr Gln Asp Asp Arg Pro Phe Phe Leu Tyr Val Ala Phe His Asp Pro
145                 150                 155                 160

His Arg Cys Gly His Ser Gln Pro Gln Tyr Gly Thr Phe Cys Glu Lys
                165                 170                 175

Phe Gly Asn Gly Glu Ser Gly Met Gly Arg Ile Pro Asp Trp Thr Pro
                180                 185                 190

Gln Ala Tyr Asp Pro Leu Asp Val Leu Val Pro Tyr Phe Val Pro Asn
                195                 200                 205

Thr Pro Ala Ala Arg Ala Asp Leu Ala Ala Gln Tyr Thr Thr Val Gly
                210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
                245                 250                 255
```

```
Pro Phe Pro Ser Gly Arg Thr Asn Leu Tyr Trp Pro Gly Thr Ala Glu
            260                 265                 270

Pro Leu Leu Val Ser Ser Pro Glu His Pro Lys Arg Trp Gly Gln Val
            275                 280                 285

Ser Glu Ala Tyr Val Ser Leu Leu Asp Leu Thr Pro Thr Ile Leu Asp
            290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
                325                 330                 335

Leu Trp Ala Thr Val Phe Gly Ser Gln Ser His His Glu Val Thr Met
            340                 345                 350

Ser Tyr Pro Met Arg Ser Val Gln His Arg His Phe Arg Leu Val His
            355                 360                 365

Asn Leu Asn Phe Lys Met Pro Phe Pro Ile Asp Gln Asp Phe Tyr Val
            370                 375                 380

Ser Pro Thr Phe Gln Asp Leu Leu Asn Arg Thr Thr Ala Gly Gln Pro
385                 390                 395                 400

Thr Gly Trp Tyr Lys Asp Leu Arg His Tyr Tyr Arg Ala Arg Trp
                405                 410                 415

Glu Leu Tyr Asp Arg Ser Arg Asp Pro His Glu Thr Gln Asn Leu Ala
            420                 425                 430

Thr Asp Pro Arg Phe Ala Gln Leu Leu Glu Met Leu Arg Asp Gln Leu
            435                 440                 445

Ala Lys Trp Gln Trp Glu Thr His Asp Pro Trp Val Cys Ala Pro Asp
450                 455                 460

Gly Val Leu Glu Glu Lys Leu Ser Pro Gln Cys Gln Pro Leu His Asn
465                 470                 475                 480

Glu Leu Gly Gly Gly Ser Asp Lys Thr His Thr Cys Pro Pro Cys
                485                 490                 495

Pro Ala Pro Glu Ala Ala Gly Gly Pro Ser Val Phe Leu Phe Pro Pro
            500                 505                 510

Lys Pro Lys Asp Thr Leu Met Ile Ser Arg Thr Pro Glu Val Thr Cys
            515                 520                 525

Val Val Val Asp Val Ser His Glu Asp Pro Glu Val Lys Phe Asn Trp
530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
            595                 600                 605

Gln Pro Arg Glu Pro Gln Val Tyr Thr Leu Pro Pro Ser Arg Asp Glu
            610                 615                 620

Leu Thr Lys Asn Gln Val Ser Leu Trp Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
```

```
              675                 680                 685
Val Phe Ser Cys Ser Val Met His Glu Ala Leu His Asn His Tyr Thr
        690                 695                 700

Gln Lys Ser Leu Ser Leu Ser Pro Gly Lys
705                 710
```

<210> SEQ ID NO 153
<211> LENGTH: 704
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 153

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Ser Arg Pro
    210                 215                 220

Arg Asn Ala Leu Leu Leu Ala Asp Asp Gly Gly Phe Glu Ser Gly
225                 230                 235                 240

Ala Tyr Asn Asn Ser Ala Ile Ala Thr Pro His Leu Asp Ala Leu Ala
                245                 250                 255

Arg Arg Ser Leu Leu Phe Arg Asn Ala Phe Thr Ser Val Ser Ser Cys
            260                 265                 270

Ser Pro Ser Arg Ala Ser Leu Leu Thr Gly Leu Pro Gln His Gln Asn
        275                 280                 285

Gly Met Tyr Gly Leu His Gln Asp Val His His Phe Asn Ser Phe Asp
    290                 295                 300

Lys Val Arg Ser Leu Pro Leu Leu Leu Ser Gln Ala Gly Val Arg Thr
305                 310                 315                 320
```

```
Gly Ile Ile Gly Lys Lys His Val Gly Pro Glu Thr Val Tyr Pro Phe
            325                 330                 335

Asp Phe Ala Tyr Thr Glu Glu Asn Gly Ser Val Leu Gln Val Gly Arg
            340                 345                 350

Asn Ile Thr Arg Ile Lys Leu Leu Val Arg Lys Phe Leu Gln Thr Gln
            355                 360                 365

Asp Asp Arg Pro Phe Phe Leu Tyr Val Ala Phe His Asp Pro His Arg
            370                 375                 380

Cys Gly His Ser Gln Pro Gln Tyr Gly Thr Phe Cys Glu Lys Phe Gly
385                 390                 395                 400

Asn Gly Glu Ser Gly Met Gly Arg Ile Pro Asp Trp Thr Pro Gln Ala
            405                 410                 415

Tyr Asp Pro Leu Asp Val Leu Pro Tyr Phe Val Pro Asn Thr Pro
            420                 425                 430

Ala Ala Arg Ala Asp Leu Ala Ala Gln Tyr Thr Thr Val Gly Arg Met
            435                 440                 445

Asp Gln Gly Val Gly Leu Val Leu Gln Glu Leu Arg Asp Ala Gly Val
            450                 455                 460

Leu Asn Asp Thr Leu Val Ile Phe Thr Ser Asp Asn Gly Ile Pro Phe
465                 470                 475                 480

Pro Ser Gly Arg Thr Asn Leu Tyr Trp Pro Gly Thr Ala Glu Pro Leu
            485                 490                 495

Leu Val Ser Ser Pro Glu His Pro Lys Arg Trp Gly Gln Val Ser Glu
            500                 505                 510

Ala Tyr Val Ser Leu Leu Asp Leu Thr Pro Thr Ile Leu Asp Trp Phe
            515                 520                 525

Ser Ile Pro Tyr Pro Ser Tyr Ala Ile Phe Gly Ser Lys Thr Ile His
            530                 535                 540

Leu Thr Gly Arg Ser Leu Leu Pro Ala Leu Glu Ala Glu Pro Leu Trp
545                 550                 555                 560

Ala Thr Val Phe Gly Ser Gln Ser His His Glu Val Thr Met Ser Tyr
            565                 570                 575

Pro Met Arg Ser Val Gln His Arg His Phe Arg Leu Val His Asn Leu
            580                 585                 590

Asn Phe Lys Met Pro Phe Pro Ile Asp Gln Asp Phe Tyr Val Ser Pro
            595                 600                 605

Thr Phe Gln Asp Leu Leu Asn Arg Thr Thr Ala Gly Gln Pro Thr Gly
            610                 615                 620

Trp Tyr Lys Asp Leu Arg His Tyr Tyr Tyr Arg Ala Arg Trp Glu Leu
625                 630                 635                 640

Tyr Asp Arg Ser Arg Asp Pro His Glu Thr Gln Asn Leu Ala Thr Asp
            645                 650                 655

Pro Arg Phe Ala Gln Leu Leu Glu Met Leu Arg Asp Gln Leu Ala Lys
            660                 665                 670

Trp Gln Trp Glu Thr His Asp Pro Trp Val Cys Ala Pro Asp Gly Val
            675                 680                 685

Leu Glu Glu Lys Leu Ser Pro Gln Cys Gln Pro Leu His Asn Glu Leu
            690                 695                 700

<210> SEQ ID NO 154
<211> LENGTH: 714
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 154
```

Arg Pro Arg Asn Ala Leu Leu Leu Ala Asp Asp Gly Gly Phe Glu
1               5                   10                  15

Ser Gly Ala Tyr Asn Asn Ser Ala Ile Ala Thr Pro His Leu Asp Ala
            20                  25                  30

Leu Ala Arg Arg Ser Leu Leu Phe Arg Asn Ala Phe Thr Ser Val Ser
            35                  40                  45

Ser Cys Ser Pro Ser Arg Ala Ser Leu Leu Thr Gly Leu Pro Gln His
50                  55                  60

Gln Asn Gly Met Tyr Gly Leu His Gln Asp Val His His Phe Asn Ser
65                  70                  75                  80

Phe Asp Lys Val Arg Ser Leu Pro Leu Leu Ser Gln Ala Gly Val
                85                  90                  95

Arg Thr Gly Ile Ile Gly Lys Lys His Val Gly Pro Glu Thr Val Tyr
            100                 105                 110

Pro Phe Asp Phe Ala Tyr Thr Glu Glu Asn Gly Ser Val Leu Gln Val
            115                 120                 125

Gly Arg Asn Ile Thr Arg Ile Lys Leu Leu Val Arg Lys Phe Leu Gln
130                 135                 140

Thr Gln Asp Asp Arg Pro Phe Leu Tyr Val Ala Phe His Asp Pro
145                 150                 155                 160

His Arg Cys Gly His Ser Gln Pro Gln Tyr Gly Thr Phe Cys Glu Lys
                165                 170                 175

Phe Gly Asn Gly Glu Ser Gly Met Gly Arg Ile Pro Asp Trp Thr Pro
            180                 185                 190

Gln Ala Tyr Asp Pro Leu Asp Val Leu Val Pro Tyr Phe Val Pro Asn
            195                 200                 205

Thr Pro Ala Ala Arg Ala Asp Leu Ala Ala Gln Tyr Thr Thr Val Gly
            210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
                245                 250                 255

Pro Phe Pro Ser Gly Arg Thr Asn Leu Tyr Trp Pro Gly Thr Ala Glu
            260                 265                 270

Pro Leu Leu Val Ser Ser Pro Glu His Pro Lys Arg Trp Gly Gln Val
            275                 280                 285

Ser Glu Ala Tyr Val Ser Leu Leu Asp Leu Thr Pro Thr Ile Leu Asp
            290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
                325                 330                 335

Leu Trp Ala Thr Val Phe Gly Ser Gln Ser His His Glu Val Thr Met
            340                 345                 350

Ser Tyr Pro Met Arg Ser Val Gln His Arg His Phe Arg Leu Val His
            355                 360                 365

Asn Leu Asn Phe Lys Met Pro Phe Pro Ile Asp Gln Asp Phe Tyr Val
            370                 375                 380

Ser Pro Thr Phe Gln Asp Leu Leu Asn Arg Thr Thr Ala Gly Gln Pro

```
                385                 390                 395                 400
        Thr Gly Trp Tyr Lys Asp Leu Arg His Tyr Tyr Arg Ala Arg Trp
                        405                 410                 415

Glu Leu Tyr Asp Arg Ser Arg Asp Pro His Glu Thr Gln Asn Leu Ala
                        420                 425                 430

Thr Asp Pro Arg Phe Ala Gln Leu Leu Glu Met Leu Arg Asp Gln Leu
                        435                 440                 445

Ala Lys Trp Gln Trp Glu Thr His Asp Pro Trp Val Cys Ala Pro Asp
                        450                 455                 460

Gly Val Leu Glu Glu Lys Leu Ser Pro Gln Cys Gln Pro Leu His Asn
        465                 470                 475                 480

Glu Leu Gly Gly Gly Ser Asp Lys Thr His Thr Cys Pro Pro Cys
                            485                 490                 495

Pro Ala Pro Glu Ala Ala Gly Gly Pro Ser Val Phe Leu Phe Pro Pro
                        500                 505                 510

Lys Pro Lys Asp Thr Leu Met Ile Ser Arg Thr Pro Glu Val Thr Cys
                        515                 520                 525

Val Val Val Asp Val Ser His Glu Asp Pro Glu Val Lys Phe Asn Trp
                        530                 535                 540

Tyr Val Asp Gly Val Glu Val His Asn Ala Lys Thr Lys Pro Arg Glu
        545                 550                 555                 560

Glu Gln Tyr Asn Ser Thr Tyr Arg Val Val Ser Val Leu Thr Val Leu
                        565                 570                 575

His Gln Asp Trp Leu Asn Gly Lys Glu Tyr Lys Cys Lys Val Ser Asn
                        580                 585                 590

Lys Ala Leu Pro Ala Pro Ile Glu Lys Thr Ile Ser Lys Ala Lys Gly
                        595                 600                 605

Gln Pro Arg Glu Pro Gln Val Tyr Thr Leu Pro Pro Ser Arg Asp Glu
                        610                 615                 620

Leu Thr Lys Asn Gln Val Ser Leu Trp Cys Leu Val Lys Gly Phe Tyr
        625                 630                 635                 640

Pro Ser Asp Ile Ala Val Leu Trp Glu Ser Tyr Gly Thr Glu Trp Ser
                        645                 650                 655

Ser Tyr Lys Thr Thr Pro Pro Val Leu Asp Ser Asp Gly Ser Phe Phe
                        660                 665                 670

Leu Tyr Ser Lys Leu Thr Val Thr Lys Glu Glu Trp Gln Gln Gly Phe
                        675                 680                 685

Val Phe Ser Cys Ser Val Met His Glu Ala Leu His Asn His Tyr Thr
                        690                 695                 700

Gln Lys Ser Leu Ser Leu Ser Pro Gly Lys
        705                 710

<210> SEQ ID NO 155
<211> LENGTH: 704
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30
```

```
Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65              70                  75                      80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
        130                 135                 140

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Ser Arg Pro
    210                 215                 220

Arg Asn Ala Leu Leu Leu Ala Asp Asp Gly Gly Phe Glu Ser Gly
225                 230                 235                 240

Ala Tyr Asn Asn Ser Ala Ile Ala Thr Pro His Leu Asp Ala Leu Ala
                245                 250                 255

Arg Arg Ser Leu Leu Phe Arg Asn Ala Phe Thr Ser Val Ser Ser Cys
            260                 265                 270

Ser Pro Ser Arg Ala Ser Leu Leu Thr Gly Leu Pro Gln His Gln Asn
    275                 280                 285

Gly Met Tyr Gly Leu His Gln Asp Val His His Phe Asn Ser Phe Asp
    290                 295                 300

Lys Val Arg Ser Leu Pro Leu Leu Ser Gln Ala Gly Val Arg Thr
305                 310                 315                 320

Gly Ile Ile Gly Lys Lys His Val Gly Pro Glu Thr Val Tyr Pro Phe
                325                 330                 335

Asp Phe Ala Tyr Thr Glu Glu Asn Gly Ser Val Leu Gln Val Gly Arg
            340                 345                 350

Asn Ile Thr Arg Ile Lys Leu Leu Val Arg Lys Phe Leu Gln Thr Gln
            355                 360                 365

Asp Asp Arg Pro Phe Phe Leu Tyr Val Ala Phe His Asp Pro His Arg
    370                 375                 380

Cys Gly His Ser Gln Pro Gln Tyr Gly Thr Phe Cys Glu Lys Phe Gly
385                 390                 395                 400

Asn Gly Glu Ser Gly Met Gly Arg Ile Pro Asp Trp Thr Pro Gln Ala
            405                 410                 415

Tyr Asp Pro Leu Asp Val Leu Val Pro Tyr Phe Val Pro Asn Thr Pro
                420                 425                 430

Ala Ala Arg Ala Asp Leu Ala Ala Gln Tyr Thr Thr Val Gly Arg Met
            435                 440                 445
```

Asp Gln Gly Val Gly Leu Val Leu Gln Glu Leu Arg Asp Ala Gly Val
    450                 455                 460

Leu Asn Asp Thr Leu Val Ile Phe Thr Ser Asp Asn Gly Ile Pro Phe
465                 470                 475                 480

Pro Ser Gly Arg Thr Asn Leu Tyr Trp Pro Gly Thr Ala Glu Pro Leu
                485                 490                 495

Leu Val Ser Ser Pro Glu His Pro Lys Arg Trp Gly Gln Val Ser Glu
            500                 505                 510

Ala Tyr Val Ser Leu Leu Asp Leu Thr Pro Thr Ile Leu Asp Trp Phe
        515                 520                 525

Ser Ile Pro Tyr Pro Ser Tyr Ala Ile Phe Gly Ser Lys Thr Ile His
530                 535                 540

Leu Thr Gly Arg Ser Leu Leu Pro Ala Leu Glu Ala Glu Pro Leu Trp
545                 550                 555                 560

Ala Thr Val Phe Gly Ser Gln Ser His His Glu Val Thr Met Ser Tyr
                565                 570                 575

Pro Met Arg Ser Val Gln His Arg His Phe Arg Leu Val His Asn Leu
            580                 585                 590

Asn Phe Lys Met Pro Phe Pro Ile Asp Gln Asp Phe Tyr Val Ser Pro
        595                 600                 605

Thr Phe Gln Asp Leu Leu Asn Arg Thr Thr Ala Gly Gln Pro Thr Gly
610                 615                 620

Trp Tyr Lys Asp Leu Arg His Tyr Tyr Tyr Arg Ala Arg Trp Glu Leu
625                 630                 635                 640

Tyr Asp Arg Ser Arg Asp Pro His Glu Thr Gln Asn Leu Ala Thr Asp
                645                 650                 655

Pro Arg Phe Ala Gln Leu Leu Glu Met Leu Arg Asp Gln Leu Ala Lys
            660                 665                 670

Trp Gln Trp Glu Thr His Asp Pro Trp Val Cys Ala Pro Asp Gly Val
        675                 680                 685

Leu Glu Glu Lys Leu Ser Pro Gln Cys Gln Pro Leu His Asn Glu Leu
690                 695                 700

<210> SEQ ID NO 156
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln

```
            100                 105                 110
Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 157
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 157

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 158

```
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 158

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 159
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 160
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
```

<210> SEQ ID NO 161
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 162
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 162

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 163
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 163

```
Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 164
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 165
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
```

```
                35                  40                  45
Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 166
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166

Ala Pro Glu Ala Ala Gly Gly Pro Ser Val Phe Leu Phe Pro Pro Lys
1               5                  10                  15

Pro Lys Asp Thr Leu Tyr Ile Thr Arg Glu Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175
```

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 167
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Phe Gly Thr Glu Trp Ser Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 168
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Ala Pro Glu Leu Leu Gly Gly Pro Ser Val Phe Leu Phe Pro Pro Lys
1               5                   10                  15

```
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 169
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ala Asn
```

145             150             155             160

Tyr Lys Thr Thr Pro Pro Val Leu Asp Ser Asp Gly Ser Phe Phe Leu
            165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 170
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 171
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 172
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

```
Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 173
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 174
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 174

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 175
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 175

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
        180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 176
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
        180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 177
<211> LENGTH: 217
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 177

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 178
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 178

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys

```
                    85                  90                  95
Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 179
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Tyr Gly Thr Glu Trp Ala Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 180
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 180

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 181
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 181

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 182
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
```

```
                    195                 200                 205

Lys Ser Leu Ser Leu Ser Pro Gly Lys
    210                 215

<210> SEQ ID NO 183
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 184
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 184

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45
```

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 185
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 186
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 187
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 187

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val

```
            20                  25                  30
Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 188
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 188

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Val Asn
145                 150                 155                 160
```

```
Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 189
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 190
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190
```

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Trp Gln Gln Gly Phe Val
            180                 185                 190

Phe Ser Cys Ser Val Met His Glu Ala Leu His Asn His Tyr Thr Gln
                195                 200                 205

Lys Ser Leu Ser Leu Ser Pro Gly Lys
    210                 215

<210> SEQ ID NO 191
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 191

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
```

```
                130                 135                 140
Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
                210                 215

<210> SEQ ID NO 192
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 192

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
                35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
            130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
                210                 215

<210> SEQ ID NO 193
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 193

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 194
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 195
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 196
<211> LENGTH: 217
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 197
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 198
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 198

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215
```

```
<210> SEQ ID NO 199
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 200
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
```

```
                65                  70                  75                  80
Gln Asp Trp Leu Asn Gly Lys Glu Tyr Lys Cys Lys Val Ser Asn Lys
                    85                  90                  95

Ala Leu Gly Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 201
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                    85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205
```

```
Lys Ser Leu Ser Leu Ser Pro Gly Lys
    210                 215

<210> SEQ ID NO 202
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 203
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45
```

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Gly Ala Pro Ile Glu Lys Thr Ile Ser Lys Ala Lys Gly Gln
             100                 105                 110

Pro Arg Glu Pro Gln Val Tyr Thr Leu Pro Pro Ser Arg Asp Glu Leu
         115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 204
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
             100                 105                 110

Pro Arg Glu Pro Gln Val Tyr Thr Leu Pro Pro Ser Arg Asp Glu Leu
         115                 120                 125

Thr Lys Asn Gln Val Ser Leu Trp Cys Leu Val Lys Gly Phe Tyr Pro
130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val

```
                180                 185                 190
Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 205
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 206
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

```
Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
            130                 135                 140

Ser Asp Ile Ala Val Leu Trp Glu Ser Tyr Gly Thr Glu Trp Ala Ser
145                 150                 155                 160

Tyr Lys Thr Thr Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 207
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Ala Pro Glu Leu Leu Gly Gly Pro Ser Val Phe Leu Phe Pro Pro Lys
 1               5                  10                  15

Pro Lys Asp Thr Leu Tyr Ile Thr Arg Glu Pro Glu Val Thr Cys Val
             20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
            130                 135                 140

Ser Asp Ile Ala Val Leu Trp Glu Ser Tyr Gly Thr Glu Trp Ala Ser
145                 150                 155                 160
```

```
Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 208
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 208

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 209
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 209

```
Ala Pro Glu Ala Ala Gly Gly Pro Ser Val Phe Leu Phe Pro Pro Lys
```

```
              1               5                  10                 15
Pro Lys Asp Thr Leu Tyr Ile Thr Arg Glu Pro Glu Val Thr Cys Val
              20                 25                 30

Val Val Asp Val Ser His Glu Asp Pro Glu Val Lys Phe Asn Trp Tyr
              35                 40                 45

Val Asp Gly Val Glu Val His Asn Ala Lys Thr Lys Pro Arg Glu Glu
    50                 55                 60

Gln Tyr Asn Ser Thr Tyr Arg Val Val Ser Val Leu Thr Val Leu His
65                 70                 75                  80

Gln Asp Trp Leu Asn Gly Lys Glu Tyr Lys Cys Lys Val Ser Asn Lys
                85                 90                 95

Ala Leu Gly Ala Pro Ile Glu Lys Thr Ile Ser Lys Ala Lys Gly Gln
                100                105                110

Pro Arg Glu Pro Gln Val Tyr Thr Leu Pro Pro Ser Arg Asp Glu Leu
                115                120                125

Thr Lys Asn Gln Val Ser Leu Trp Cys Leu Val Lys Gly Phe Tyr Pro
                130                135                140

Ser Asp Ile Ala Val Leu Trp Glu Ser Tyr Gly Thr Glu Trp Ala Ser
145                150                155                160

Tyr Lys Thr Thr Pro Pro Val Leu Asp Ser Asp Gly Ser Phe Phe Leu
                165                170                175

Tyr Ser Lys Leu Thr Val Thr Lys Glu Glu Trp Gln Gln Gly Phe Val
                180                185                190

Phe Ser Cys Ser Val Met His Glu Ala Leu His Asn His Tyr Thr Gln
                195                200                205

Lys Ser Leu Ser Leu Ser Pro Gly Lys
                210                215

<210> SEQ ID NO 210
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 210

Ala Pro Glu Leu Leu Gly Gly Pro Ser Val Phe Leu Phe Pro Pro Lys
1               5                  10                 15

Pro Lys Asp Thr Leu Met Ile Ser Arg Thr Pro Glu Val Thr Cys Val
                20                 25                 30

Val Val Asp Val Ser His Glu Asp Pro Glu Val Lys Phe Asn Trp Tyr
                35                 40                 45

Val Asp Gly Val Glu Val His Asn Ala Lys Thr Lys Pro Arg Glu Glu
    50                 55                 60

Gln Tyr Asn Ser Thr Tyr Arg Val Val Ser Val Leu Thr Val Leu His
65                 70                 75                  80

Gln Asp Trp Leu Asn Gly Lys Glu Tyr Lys Cys Lys Val Ser Asn Lys
                85                 90                 95

Ala Leu Pro Ala Pro Ile Glu Lys Thr Ile Ser Lys Ala Lys Gly Gln
                100                105                110

Pro Arg Glu Pro Gln Val Tyr Thr Leu Pro Pro Ser Arg Asp Glu Leu
                115                120                125

Thr Lys Asn Gln Val Ser Leu Ser Cys Ala Val Lys Gly Phe Tyr Pro
                130                135                140
```

```
Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
            165                 170                 175

Val Ser Lys Leu Thr Val Thr Lys Glu Glu Trp Gln Gln Gly Phe Val
        180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 211
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 211

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
            165                 170                 175

Val Ser Lys Leu Thr Val Thr Lys Glu Glu Trp Gln Gln Gly Phe Val
        180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 212
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 212

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
210                 215
```

<210> SEQ ID NO 213
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 213

```
Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
```

```
                    115                 120                 125
Thr Lys Asn Gln Val Ser Leu Ser Cys Ala Val Lys Gly Phe Tyr Pro
            130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
                195                 200                 205

Lys Ser Leu Ser Leu Ser Pro Gly Lys
            210                 215

<210> SEQ ID NO 214
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 214

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 215
<211> LENGTH: 217
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 215

Ala Pro Glu Ala Ala Gly Gly Pro Ser Val Phe Leu Phe Pro Pro Lys
 1               5                  10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 216
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 216

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Thr Lys Glu Glu Trp Gln Gln Gly Phe Val
        180                 185                 190

Phe Ser Cys Ser Val Met His Glu Ala Leu His Asn His Tyr Thr Gln
    195                 200                 205

Lys Ser Leu Ser Leu Ser Pro Gly Lys
        210                 215

<210> SEQ ID NO 217
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 217

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Thr Lys Glu Glu Trp Gln Gln Gly Phe Val
        180                 185                 190

Phe Ser Cys Ser Val Met His Glu Ala Leu His Asn His Tyr Thr Gln
    195                 200                 205

Lys Ser Leu Ser Leu Ser Pro Gly Lys
        210                 215
```

```
<210> SEQ ID NO 218
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 218
```

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

```
<210> SEQ ID NO 219
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219
```

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 220
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 220

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

```
Lys Ser Leu Ser Leu Ser Pro Gly Lys
    210                 215
```

<210> SEQ ID NO 221
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 221

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 222
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
```

```
            50                  55                  60
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 223
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 223

```
Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190
```

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 224
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 224

Ala Pro Glu Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 225
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 225

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 226
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 226

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu

```
                     165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 227
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 227

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Gly Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 228
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 228

Asp Lys Thr His Thr Cys Pro Pro Cys Pro Ala Pro Glu Ala Ala Gly
1               5                   10                  15
```

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Leu
145                 150                 155                 160

Trp Glu Ser Tyr Gly Thr Glu Trp Ala Ser Tyr Lys Thr Thr Pro Pro
                165                 170                 175

Val Leu Asp Ser Asp Gly Ser Phe Phe Leu Tyr Ser Lys Leu Thr Val
            180                 185                 190

Thr Lys Glu Glu Trp Gln Gln Gly Phe Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 229
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 229

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

```
Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Tyr Gly Thr Glu Trp Ala Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Thr Lys Glu Glu Trp Gln Gln Gly Phe Val Phe Ser Cys Ser Val Met
                195                 200                 205

His Glu Ala Leu His Asn His Tyr Thr Gln Lys Ser Leu Ser Leu Ser
210                 215                 220

Pro Gly Lys
225

<210> SEQ ID NO 230
<211> LENGTH: 525
<212> TYPE: PRT
<213> ORGANISM: Homo sapiens

<400> SEQUENCE: 230

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270
```

```
Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525

<210> SEQ ID NO 231
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 231

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95
```

```
Tyr Phe Lys Glu Asn Gly Tyr Val Thr Met Ser Val Gly Lys Val Phe
                100                 105                 110
His Pro Gly Ile Ser Ser Asn His Thr Asp Asp Ser Pro Tyr Ser Trp
            115                 120                 125
Ser Phe Pro Pro Tyr His Pro Ser Ser Glu Lys Tyr Glu Asn Thr Lys
130                 135                 140
Thr Cys Arg Gly Pro Asp Gly Glu Leu His Ala Asn Leu Leu Cys Pro
145                 150                 155                 160
Val Asp Val Leu Asp Val Pro Glu Gly Thr Leu Pro Asp Lys Gln Ser
                165                 170                 175
Thr Glu Gln Ala Ile Gln Leu Leu Glu Lys Met Lys Thr Ser Ala Ser
            180                 185                 190
Pro Phe Phe Leu Ala Val Gly Tyr His Lys Pro His Ile Pro Phe Arg
        195                 200                 205
Tyr Pro Lys Glu Phe Gln Lys Leu Tyr Pro Leu Glu Asn Ile Thr Leu
    210                 215                 220
Ala Pro Asp Pro Glu Val Pro Asp Gly Leu Pro Pro Val Ala Tyr Asn
225                 230                 235                 240
Pro Trp Met Asp Ile Arg Gln Arg Glu Asp Val Gln Ala Leu Asn Ile
                245                 250                 255
Ser Val Pro Tyr Gly Pro Ile Pro Val Asp Phe Gln Arg Lys Ile Arg
            260                 265                 270
Gln Ser Tyr Phe Ala Ser Val Ser Tyr Leu Asp Thr Gln Val Gly Arg
        275                 280                 285
Leu Leu Ser Ala Leu Asp Asp Leu Gln Leu Ala Asn Ser Thr Ile Ile
    290                 295                 300
Ala Phe Thr Ser Asp His Gly Trp Ala Leu Gly Glu His Gly Glu Trp
305                 310                 315                 320
Ala Lys Tyr Ser Asn Phe Asp Val Ala Thr His Val Pro Leu Ile Phe
                325                 330                 335
Tyr Val Pro Gly Arg Thr Ala Ser Leu Pro Glu Ala Gly Glu Lys Leu
            340                 345                 350
Phe Pro Tyr Leu Asp Pro Phe Asp Ser Ala Ser Gln Leu Met Glu Pro
        355                 360                 365
Gly Arg Gln Ser Met Asp Leu Val Glu Leu Val Ser Leu Phe Pro Thr
    370                 375                 380
Leu Ala Gly Leu Ala Gly Leu Gln Val Pro Pro Arg Cys Pro Val Pro
385                 390                 395                 400
Ser Phe His Val Glu Leu Cys Arg Glu Gly Lys Asn Leu Leu Lys His
                405                 410                 415
Phe Arg Phe Arg Asp Leu Glu Glu Asp Pro Tyr Leu Pro Gly Asn Pro
            420                 425                 430
Arg Glu Leu Ile Ala Tyr Ser Gln Tyr Pro Arg Pro Ser Asp Ile Pro
        435                 440                 445
Gln Trp Asn Ser Asp Lys Pro Ser Leu Lys Asp Ile Lys Ile Met Gly
    450                 455                 460
Tyr Ser Ile Arg Thr Ile Asp Tyr Arg Tyr Thr Val Trp Val Gly Phe
465                 470                 475                 480
Asn Pro Asp Glu Phe Leu Ala Asn Phe Ser Asp Ile His Ala Gly Glu
                485                 490                 495
Leu Tyr Phe Val Asp Ser Asp Pro Leu Gln Asp His Asn Met Tyr Asn
            500                 505                 510
Asp Ser Gln Gly Gly Asp Leu Phe Gln Leu Leu Met Pro Gly Gly Gly
```

```
                515                 520                 525
Gly Ser Asp Lys Thr His Thr Cys Pro Pro Cys Pro Ala Pro Glu Ala
    530                 535                 540

Ala Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
    580                 585                 590

Glu Val His Asn Ala Lys Thr Lys Pro Arg Glu Glu Gln Tyr Asn Ser
    595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
                660                 665                 670

Val Ser Leu Ser Cys Ala Val Lys Gly Phe Tyr Pro Ser Asp Ile Ala
            675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
            740                 745                 750

Leu Ser Pro Gly Lys
        755

<210> SEQ ID NO 232
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 232

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
                100                 105                 110
```

```
His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
        130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
        515                 520                 525
```

```
Gly Ser Asp Lys Thr His Thr Cys Pro Pro Cys Pro Ala Pro Glu Leu
        530                 535                 540

Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
            580                 585                 590

Glu Val His Asn Ala Lys Thr Lys Pro Arg Glu Glu Gln Tyr Asn Ser
        595                 600                 605

Thr Tyr Arg Val Val Ser Val Leu Thr Val Leu His Gln Asp Trp Leu
610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
            660                 665                 670

Val Ser Leu Ser Cys Ala Val Lys Gly Phe Tyr Pro Ser Asp Ile Ala
        675                 680                 685

Val Glu Trp Glu Ser Asn Gly Gln Pro Glu Asn Asn Tyr Lys Thr Thr
690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
            740                 745                 750

Leu Ser Pro Gly Lys
            755

<210> SEQ ID NO 233
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 233

Ser Glu Thr Gln Ala Asn Ser Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
                100                 105                 110

His Pro Gly Ile Ser Ser Asn His Thr Asp Asp Ser Pro Tyr Ser Trp
```

```
            115                 120                 125
Ser Phe Pro Tyr His Pro Ser Ser Glu Lys Tyr Glu Asn Thr Lys
    130                 135                 140
Thr Cys Arg Gly Pro Asp Gly Glu Leu His Ala Asn Leu Leu Cys Pro
145                 150                 155                 160
Val Asp Val Leu Asp Val Pro Glu Gly Thr Leu Pro Asp Lys Gln Ser
                165                 170                 175
Thr Glu Gln Ala Ile Gln Leu Leu Glu Lys Met Lys Thr Ser Ala Ser
                180                 185                 190
Pro Phe Phe Leu Ala Val Gly Tyr His Lys Pro His Ile Pro Phe Arg
                195                 200                 205
Tyr Pro Lys Glu Phe Gln Lys Leu Tyr Pro Leu Glu Asn Ile Thr Leu
                210                 215                 220
Ala Pro Asp Pro Glu Val Pro Asp Gly Leu Pro Pro Val Ala Tyr Asn
225                 230                 235                 240
Pro Trp Met Asp Ile Arg Gln Arg Glu Asp Val Gln Ala Leu Asn Ile
                245                 250                 255
Ser Val Pro Tyr Gly Pro Ile Pro Val Asp Phe Gln Arg Lys Ile Arg
                260                 265                 270
Gln Ser Tyr Phe Ala Ser Val Ser Tyr Leu Asp Thr Gln Val Gly Arg
                275                 280                 285
Leu Leu Ser Ala Leu Asp Asp Leu Gln Leu Ala Asn Ser Thr Ile Ile
                290                 295                 300
Ala Phe Thr Ser Asp His Gly Trp Ala Leu Gly Glu His Gly Glu Trp
305                 310                 315                 320
Ala Lys Tyr Ser Asn Phe Asp Val Ala Thr His Val Pro Leu Ile Phe
                325                 330                 335
Tyr Val Pro Gly Arg Thr Ala Ser Leu Pro Glu Ala Gly Glu Lys Leu
                340                 345                 350
Phe Pro Tyr Leu Asp Pro Phe Asp Ser Ala Ser Gln Leu Met Glu Pro
                355                 360                 365
Gly Arg Gln Ser Met Asp Leu Val Glu Leu Val Ser Leu Phe Pro Thr
                370                 375                 380
Leu Ala Gly Leu Ala Gly Leu Gln Val Pro Pro Arg Cys Pro Val Pro
385                 390                 395                 400
Ser Phe His Val Glu Leu Cys Arg Glu Gly Lys Asn Leu Leu Lys His
                405                 410                 415
Phe Arg Phe Arg Asp Leu Glu Glu Asp Pro Tyr Leu Pro Gly Asn Pro
                420                 425                 430
Arg Glu Leu Ile Ala Tyr Ser Gln Tyr Pro Arg Pro Ser Asp Ile Pro
                435                 440                 445
Gln Trp Asn Ser Asp Lys Pro Ser Leu Lys Asp Ile Lys Ile Met Gly
                450                 455                 460
Tyr Ser Ile Arg Thr Ile Asp Tyr Arg Tyr Thr Val Trp Val Gly Phe
465                 470                 475                 480
Asn Pro Asp Glu Phe Leu Ala Asn Phe Ser Asp Ile His Ala Gly Glu
                485                 490                 495
Leu Tyr Phe Val Asp Ser Asp Pro Leu Gln Asp His Asn Met Tyr Asn
                500                 505                 510
Asp Ser Gln Gly Gly Asp Leu Phe Gln Leu Leu Met Pro Gly Gly Gly
                515                 520                 525
Gly Ser Asp Lys Thr His Thr Cys Pro Pro Cys Pro Ala Pro Glu Leu
                530                 535                 540
```

```
Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
            580                 585                 590

Glu Val His Asn Ala Lys Thr Lys Pro Arg Glu Glu Gln Tyr Asn Ser
        595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
            660                 665                 670

Val Ser Leu Trp Cys Leu Val Lys Gly Phe Tyr Pro Ser Asp Ile Ala
        675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Tyr Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
            740                 745                 750

Leu Ser Pro Gly Lys
            755

<210> SEQ ID NO 234
<211> LENGTH: 525
<212> TYPE: PRT
<213> ORGANISM: Homo sapiens
<220> FEATURE:
<221> NAME/KEY: MOD_RES
<222> LOCATION: (59)..(59)
<223> OTHER INFORMATION: Formylglycine

<400> SEQUENCE: 234

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Xaa Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125
```

```
Ser Phe Pro Pro Tyr His Pro Ser Ser Glu Lys Tyr Glu Asn Thr Lys
130                 135                 140
Thr Cys Arg Gly Pro Asp Gly Glu Leu His Ala Asn Leu Leu Cys Pro
145                 150                 155                 160
Val Asp Val Leu Asp Val Pro Glu Gly Thr Leu Pro Asp Lys Gln Ser
                165                 170                 175
Thr Glu Gln Ala Ile Gln Leu Leu Glu Lys Met Lys Thr Ser Ala Ser
                180                 185                 190
Pro Phe Phe Leu Ala Val Gly Tyr His Lys Pro His Ile Pro Phe Arg
        195                 200                 205
Tyr Pro Lys Glu Phe Gln Lys Leu Tyr Pro Leu Glu Asn Ile Thr Leu
210                 215                 220
Ala Pro Asp Pro Glu Val Pro Asp Gly Leu Pro Pro Val Ala Tyr Asn
225                 230                 235                 240
Pro Trp Met Asp Ile Arg Gln Arg Glu Asp Val Gln Ala Leu Asn Ile
                245                 250                 255
Ser Val Pro Tyr Gly Pro Ile Pro Val Asp Phe Gln Arg Lys Ile Arg
                260                 265                 270
Gln Ser Tyr Phe Ala Ser Val Ser Tyr Leu Asp Thr Gln Val Gly Arg
        275                 280                 285
Leu Leu Ser Ala Leu Asp Asp Leu Gln Leu Ala Asn Ser Thr Ile Ile
290                 295                 300
Ala Phe Thr Ser Asp His Gly Trp Ala Leu Gly Glu His Gly Glu Trp
305                 310                 315                 320
Ala Lys Tyr Ser Asn Phe Asp Val Ala Thr His Val Pro Leu Ile Phe
                325                 330                 335
Tyr Val Pro Gly Arg Thr Ala Ser Leu Pro Glu Ala Gly Glu Lys Leu
                340                 345                 350
Phe Pro Tyr Leu Asp Pro Phe Asp Ser Ala Ser Gln Leu Met Glu Pro
        355                 360                 365
Gly Arg Gln Ser Met Asp Leu Val Glu Leu Val Ser Leu Phe Pro Thr
370                 375                 380
Leu Ala Gly Leu Ala Gly Leu Gln Val Pro Pro Arg Cys Pro Val Pro
385                 390                 395                 400
Ser Phe His Val Glu Leu Cys Arg Glu Gly Lys Asn Leu Leu Lys His
                405                 410                 415
Phe Arg Phe Arg Asp Leu Glu Glu Asp Pro Tyr Leu Pro Gly Asn Pro
                420                 425                 430
Arg Glu Leu Ile Ala Tyr Ser Gln Tyr Pro Arg Pro Ser Asp Ile Pro
        435                 440                 445
Gln Trp Asn Ser Asp Lys Pro Ser Leu Lys Asp Ile Lys Ile Met Gly
450                 455                 460
Tyr Ser Ile Arg Thr Ile Asp Tyr Arg Tyr Thr Val Trp Val Gly Phe
465                 470                 475                 480
Asn Pro Asp Glu Phe Leu Ala Asn Phe Ser Asp Ile His Ala Gly Glu
                485                 490                 495
Leu Tyr Phe Val Asp Ser Asp Pro Leu Gln Asp His Asn Met Tyr Asn
                500                 505                 510
Asp Ser Gln Gly Gly Asp Leu Phe Gln Leu Leu Met Pro
        515                 520                 525

<210> SEQ ID NO 235
<211> LENGTH: 757
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (59)..(59)
<223> OTHER INFORMATION: Formylglycine

<400> SEQUENCE: 235

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Xaa Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
```

```
                355                 360                 365
Gly Arg Gln Ser Met Asp Leu Val Glu Leu Val Ser Leu Phe Pro Thr
370                 375                 380
Leu Ala Gly Leu Ala Gly Leu Gln Val Pro Pro Arg Cys Pro Val Pro
385                 390                 395                 400
Ser Phe His Val Glu Leu Cys Arg Glu Gly Lys Asn Leu Leu Lys His
                405                 410                 415
Phe Arg Phe Arg Asp Leu Glu Glu Asp Pro Tyr Leu Pro Gly Asn Pro
                420                 425                 430
Arg Glu Leu Ile Ala Tyr Ser Gln Tyr Pro Arg Pro Ser Asp Ile Pro
                435                 440                 445
Gln Trp Asn Ser Asp Lys Pro Ser Leu Lys Asp Ile Lys Ile Met Gly
                450                 455                 460
Tyr Ser Ile Arg Thr Ile Asp Tyr Arg Tyr Thr Val Trp Val Gly Phe
465                 470                 475                 480
Asn Pro Asp Glu Phe Leu Ala Asn Phe Ser Asp Ile His Ala Gly Glu
                485                 490                 495
Leu Tyr Phe Val Asp Ser Asp Pro Leu Gln Asp His Asn Met Tyr Asn
                500                 505                 510
Asp Ser Gln Gly Gly Asp Leu Phe Gln Leu Leu Met Pro Gly Gly Gly
                515                 520                 525
Gly Ser Asp Lys Thr His Thr Cys Pro Pro Cys Pro Ala Pro Glu Ala
530                 535                 540
Ala Gly Gly Pro Ser Val Phe Leu Phe Pro Pro Lys Pro Lys Asp Thr
545                 550                 555                 560
Leu Met Ile Ser Arg Thr Pro Glu Val Thr Cys Val Val Asp Val
                565                 570                 575
Ser His Glu Asp Pro Glu Val Lys Phe Asn Trp Tyr Val Asp Gly Val
                580                 585                 590
Glu Val His Asn Ala Lys Thr Lys Pro Arg Glu Glu Gln Tyr Asn Ser
                595                 600                 605
Thr Tyr Arg Val Val Ser Val Leu Thr Val Leu His Gln Asp Trp Leu
                610                 615                 620
Asn Gly Lys Glu Tyr Lys Cys Lys Val Ser Asn Lys Ala Leu Pro Ala
625                 630                 635                 640
Pro Ile Glu Lys Thr Ile Ser Lys Ala Lys Gly Gln Pro Arg Glu Pro
                645                 650                 655
Gln Val Tyr Thr Leu Pro Pro Ser Arg Asp Glu Leu Thr Lys Asn Gln
                660                 665                 670
Val Ser Leu Ser Cys Ala Val Lys Gly Phe Tyr Pro Ser Asp Ile Ala
                675                 680                 685
Val Glu Trp Glu Ser Asn Gly Gln Pro Glu Asn Asn Tyr Lys Thr Thr
                690                 695                 700
Pro Pro Val Leu Asp Ser Asp Gly Ser Phe Phe Leu Val Ser Lys Leu
705                 710                 715                 720
Thr Val Asp Lys Ser Arg Trp Gln Gln Gly Asn Val Phe Ser Cys Ser
                725                 730                 735
Val Met His Glu Ala Leu His Asn His Tyr Thr Gln Lys Ser Leu Ser
                740                 745                 750
Leu Ser Pro Gly Lys
            755

<210> SEQ ID NO 236
```

```
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (59)..(59)
<223> OTHER INFORMATION: Formylglycine

<400> SEQUENCE: 236
```

| | | | | | | | | | | | | | | | |
|---|---|---|---|---|---|---|---|---|---|---|---|---|---|---|---|
| Ser | Glu | Thr | Gln | Ala | Asn | Ser | Thr | Thr | Asp | Ala | Leu | Asn | Val | Leu | Leu |
| 1 | | | | 5 | | | | | 10 | | | | | 15 | |
| Ile | Ile | Val | Asp | Asp | Leu | Arg | Pro | Ser | Leu | Gly | Cys | Tyr | Gly | Asp | Lys |
| | | | 20 | | | | | 25 | | | | | 30 | | |
| Leu | Val | Arg | Ser | Pro | Asn | Ile | Asp | Gln | Leu | Ala | Ser | His | Ser | Leu | Leu |
| | | | 35 | | | | | 40 | | | | | 45 | | |
| Phe | Gln | Asn | Ala | Phe | Ala | Gln | Gln | Ala | Val | Xaa | Ala | Pro | Ser | Arg | Val |
| 50 | | | | | 55 | | | | | 60 | | | | | |
| Ser | Phe | Leu | Thr | Gly | Arg | Arg | Pro | Asp | Thr | Thr | Arg | Leu | Tyr | Asp | Phe |
| 65 | | | | | 70 | | | | | 75 | | | | | 80 |
| Asn | Ser | Tyr | Trp | Arg | Val | His | Ala | Gly | Asn | Phe | Ser | Thr | Ile | Pro | Gln |
| | | | | 85 | | | | | 90 | | | | | 95 | |
| Tyr | Phe | Lys | Glu | Asn | Gly | Tyr | Val | Thr | Met | Ser | Val | Gly | Lys | Val | Phe |
| | | | 100 | | | | | 105 | | | | | 110 | | |
| His | Pro | Gly | Ile | Ser | Ser | Asn | His | Thr | Asp | Asp | Ser | Pro | Tyr | Ser | Trp |
| | | 115 | | | | | 120 | | | | | 125 | | | |
| Ser | Phe | Pro | Pro | Tyr | His | Pro | Ser | Ser | Glu | Lys | Tyr | Glu | Asn | Thr | Lys |
| 130 | | | | | 135 | | | | | 140 | | | | | |
| Thr | Cys | Arg | Gly | Pro | Asp | Gly | Glu | Leu | His | Ala | Asn | Leu | Leu | Cys | Pro |
| 145 | | | | | 150 | | | | | 155 | | | | | 160 |
| Val | Asp | Val | Leu | Asp | Val | Pro | Glu | Gly | Thr | Leu | Pro | Asp | Lys | Gln | Ser |
| | | | | 165 | | | | | 170 | | | | | 175 | |
| Thr | Glu | Gln | Ala | Ile | Gln | Leu | Leu | Glu | Lys | Met | Lys | Thr | Ser | Ala | Ser |
| | | | 180 | | | | | 185 | | | | | 190 | | |
| Pro | Phe | Phe | Leu | Ala | Val | Gly | Tyr | His | Lys | Pro | His | Ile | Pro | Phe | Arg |
| | | 195 | | | | | 200 | | | | | 205 | | | |
| Tyr | Pro | Lys | Glu | Phe | Gln | Lys | Leu | Tyr | Pro | Leu | Glu | Asn | Ile | Thr | Leu |
| 210 | | | | | 215 | | | | | 220 | | | | | |
| Ala | Pro | Asp | Pro | Glu | Val | Pro | Asp | Gly | Leu | Pro | Pro | Val | Ala | Tyr | Asn |
| 225 | | | | | 230 | | | | | 235 | | | | | 240 |
| Pro | Trp | Met | Asp | Ile | Arg | Gln | Arg | Glu | Asp | Val | Gln | Ala | Leu | Asn | Ile |
| | | | | 245 | | | | | 250 | | | | | 255 | |
| Ser | Val | Pro | Tyr | Gly | Pro | Ile | Pro | Val | Asp | Phe | Gln | Arg | Lys | Ile | Arg |
| | | | 260 | | | | | 265 | | | | | 270 | | |
| Gln | Ser | Tyr | Phe | Ala | Ser | Val | Ser | Tyr | Leu | Asp | Thr | Gln | Val | Gly | Arg |
| | | | | 275 | | | | | 280 | | | | | 285 | |
| Leu | Leu | Ser | Ala | Leu | Asp | Asp | Leu | Gln | Leu | Ala | Asn | Ser | Thr | Ile | Ile |
| | | | 290 | | | | | 295 | | | | | 300 | | |
| Ala | Phe | Thr | Ser | Asp | His | Gly | Trp | Ala | Leu | Gly | Glu | His | Gly | Glu | Trp |
| 305 | | | | | 310 | | | | | 315 | | | | | 320 |
| Ala | Lys | Tyr | Ser | Asn | Phe | Asp | Val | Ala | Thr | His | Val | Pro | Leu | Ile | Phe |
| | | | | 325 | | | | | 330 | | | | | 335 | |
| Tyr | Val | Pro | Gly | Arg | Thr | Ala | Ser | Leu | Pro | Glu | Ala | Gly | Glu | Lys | Leu |
| | | | 340 | | | | | 345 | | | | | 350 | | |

```
Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
        515                 520                 525

Gly Ser Asp Lys Thr His Thr Cys Pro Pro Cys Pro Ala Pro Glu Leu
    530                 535                 540

Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
            580                 585                 590

Glu Val His Asn Ala Lys Thr Lys Pro Arg Glu Glu Gln Tyr Asn Ser
        595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
            660                 665                 670

Val Ser Leu Ser Cys Ala Val Lys Gly Phe Tyr Pro Ser Asp Ile Ala
        675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
            740                 745                 750

Leu Ser Pro Gly Lys
            755
```

<210> SEQ ID NO 237
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (59)..(59)
<223> OTHER INFORMATION: Formylglycine

<400> SEQUENCE: 237

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Xaa Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335
```

```
Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
                435                 440                 445

Gln Trp Asn Ser Asp Lys Pro Ser Leu Lys Asp Ile Lys Ile Met Gly
            450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
                515                 520                 525

Gly Ser Asp Lys Thr His Thr Cys Pro Pro Cys Pro Ala Pro Glu Leu
530                 535                 540

Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
            565                 570                 575

Ser His Glu Asp Pro Glu Val Lys Phe Asn Trp Tyr Val Asp Gly Val
                580                 585                 590

Glu Val His Asn Ala Lys Thr Lys Pro Arg Glu Glu Gln Tyr Asn Ser
            595                 600                 605

Thr Tyr Arg Val Val Ser Val Leu Thr Val Leu His Gln Asp Trp Leu
610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
            645                 650                 655

Gln Val Tyr Thr Leu Pro Pro Ser Arg Asp Glu Leu Thr Lys Asn Gln
                660                 665                 670

Val Ser Leu Trp Cys Leu Val Lys Gly Phe Tyr Pro Ser Asp Ile Ala
            675                 680                 685

Val Glu Trp Glu Ser Asn Gly Gln Pro Glu Asn Tyr Lys Thr Thr
            690                 695                 700

Pro Pro Val Leu Asp Ser Asp Gly Ser Phe Phe Leu Tyr Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
            740                 745                 750

Leu Ser Pro Gly Lys
```

<210> SEQ ID NO 238
<211> LENGTH: 181
<212> TYPE: PRT
<213> ORGANISM: Homo sapiens

<400> SEQUENCE: 238

Asn Ser Val Ile Ile Val Asp Lys Asn Gly Arg Leu Val Tyr Leu Val
1               5                   10                  15

Glu Asn Pro Gly Gly Tyr Val Ala Tyr Ser Lys Ala Ala Thr Val Thr
            20                  25                  30

Gly Lys Leu Val His Ala Asn Phe Gly Thr Lys Lys Asp Phe Glu Asp
        35                  40                  45

Leu Tyr Thr Pro Val Asn Gly Ser Ile Val Ile Val Arg Ala Gly Lys
    50                  55                  60

Ile Thr Phe Ala Glu Lys Val Ala Asn Ala Glu Ser Leu Asn Ala Ile
65                  70                  75                  80

Gly Val Leu Ile Tyr Met Asp Gln Thr Lys Phe Pro Ile Val Asn Ala
                85                  90                  95

Glu Leu Ser Phe Phe Gly His Ala His Leu Gly Thr Gly Asp Pro Tyr
            100                 105                 110

Thr Pro Gly Phe Pro Ser Phe Asn His Thr Gln Phe Pro Pro Ser Arg
        115                 120                 125

Ser Ser Gly Leu Pro Asn Ile Pro Val Gln Thr Ile Ser Arg Ala Ala
    130                 135                 140

Ala Glu Lys Leu Phe Gly Asn Met Glu Gly Asp Cys Pro Ser Asp Trp
145                 150                 155                 160

Lys Thr Asp Ser Thr Cys Arg Met Val Thr Ser Glu Ser Lys Asn Val
                165                 170                 175

Lys Leu Thr Val Ser
            180

<210> SEQ ID NO 239
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Gly Gly Gly Gly Ser
1               5

<210> SEQ ID NO 240
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Gly Gly Gly Gly Ser Gly Gly Gly Gly Ser
1               5                   10

<210> SEQ ID NO 241
<211> LENGTH: 6

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 241

His His His His His His
1               5

<210> SEQ ID NO 242
<211> LENGTH: 7
<212> TYPE: PRT
<213> ORGANISM: Unknown
<220> FEATURE:
<221> NAME/KEY: source
<223> OTHER INFORMATION: /note="Description of Unknown:
      motif sequence"
<220> FEATURE:
<221> NAME/KEY: MOD_RES
<222> LOCATION: (2)..(2)
<223> OTHER INFORMATION: Any amino acid

<400> SEQUENCE: 242

Tyr Xaa Thr Glu Trp Ser Ser
1               5
```

FUSION PROTEINS COMPRISING ENZYME REPLACEMENT THERAPY ENZYMES

CROSS-REFERENCE TO RELATED APPLICATIONS

This application is a continuation of International Application No. PCT/US2018/053747, filed Oct. 1, 2018, which claims priority to U.S. Provisional Application No. 62/566,898, filed on Oct. 2, 2017, U.S. Provisional Application No. 62/583,276, filed on Nov. 8, 2017, U.S. Provisional Application No. 62/626,365, filed on Feb. 5, 2018, U.S. Provisional Patent No. 62/678,183, filed on May 30, 2018, and U.S. Provisional Application No. 62/721,396, filed on Aug. 22, 2018, the disclosures of which are incorporated herein by reference in their entirety for all purposes.

SEQUENCE LISTING

The instant application contains a Sequence Listing which has been submitted electronically in ASCII format and is hereby incorporated by reference in its entirety. Said ASCII copy, created on Sep. 28, 2018, is named 102342-000350PC-1103949_SL.txt and is 580,464 bytes in size.

BACKGROUND

Lysosomal storage disorders (LSDs) are relatively rare inherited metabolic diseases that result from defects in lysosomal function. LSDs are typically caused by the deficiency of a single enzyme that participates in the breakdown of metabolic products in the lysosome. The buildup of the product resulting from lack of the enzymatic activity affects various organ systems and can lead to severe symptoms and premature death. The majority of LSDs also have a significant neurological component, which ranges from progressive neurodegeneration and severe cognitive impairment to epileptic, behavioral, and psychiatric disorders. A recombinant form of an enzyme that is deficient in an LSD can be used to treat the disorder, but such therapies may have little effect on the brain due to difficulties in delivering the recombinant enzyme across the blood-brain barrier (BBB).

SUMMARY

Provided herein are fusion proteins comprising enzyme replacement therapy (ERT) enzymes and methods of use thereof for treating lysosomal storage disorders (LSDs).

In some aspects, provided herein is a protein comprising:
(a) a first Fc polypeptide that is linked to an ERT enzyme, an ERT enzyme variant, or a catalytically active fragment thereof; and
(b) a second Fc polypeptide that forms an Fc dimer with the first Fc polypeptide.

In some embodiments, the first Fc polypeptide and/or the second Fc polypeptide does not include an immunoglobulin heavy and/or light chain variable region sequence or an antigen-binding portion thereof.

In some embodiments, the ERT enzyme is iduronate 2-sulfatase (IDS), an IDS variant, or a catalytically active fragment thereof. In some embodiments, the ERT enzyme comprises an amino acid sequence having at least 80%, 85%, 90%, or 95% identity to the amino acid sequence of any one of SEQ ID NOS:91, 92, 114, 230, and 234. In some embodiments, the ERT enzyme comprises the amino acid sequence of any one of SEQ ID NOS:91, 92, 114, 230, and 234.

In some embodiments, the ERT enzyme is N-sulfoglucosamine sulfohydrolase (SGSH), an SGSH variant, or a catalytically active fragment thereof. In some embodiments, the ERT enzyme comprises an amino acid sequence having at least 80%, 85%, 90%, or 95% identity to the amino acid sequence of any one of SEQ ID NOS:119 and 120. In some embodiments, the ERT enzyme comprises the amino acid sequence of any one of SEQ ID NOS:119 and 120.

In some embodiments, the ERT enzyme is acid sphingomyelinase (ASM), an ASM variant, or a catalytically active fragment thereof. In some embodiments, the ERT enzyme comprises an amino acid sequence having at least 80%, 85%, 90%, or 95% identity to the amino acid sequence of any one of SEQ ID NOS:121, 122, and 123. In some embodiments, the ERT enzyme comprises the amino acid sequence of any one of SEQ ID NOS:121, 122, and 123.

In some embodiments, the ERT enzyme is β-glucocerebrosidase (GBA), a GBA variant, or a catalytically active fragment thereof. In some embodiments, the ERT enzyme comprises an amino acid sequence having at least 80%, 85%, 90%, or 95% identity to the amino acid sequence of any one of SEQ ID NOS:93 and 94. In some embodiments, the ERT enzyme comprises the amino acid sequence of any one of SEQ ID NOS:93 and 94.

In some embodiments, the first Fc polypeptide is a fusion polypeptide that is linked to the ERT enzyme, the ERT enzyme variant, or the catalytically active fragment thereof by a peptide bond or by a polypeptide linker. In some embodiments, the polypeptide linker is a flexible polypeptide linker. In some embodiments, the flexible polypeptide linker is a glycine-rich linker. In some embodiments, the glycine-rich linker is $G_4S$ (SEQ ID NO:239) or $(G_4S)_2$ (SEQ ID NO:240). In some embodiments, the first Fc polypeptide is not linked to the ERT enzyme, the ERT enzyme variant, or the catalytically active fragment thereof by a chemical cross-linking agent, e.g., the fusion polypeptide does not include a non-peptide bond or a non-polypeptide linker.

In certain embodiments, the fusion polypeptide comprises from N- to C-terminus: the ERT enzyme, the ERT enzyme variant, or the catalytically active fragment thereof; the polypeptide linker; and the first Fc polypeptide.

In some embodiments, the second Fc polypeptide is linked to an ERT enzyme, an ERT enzyme variant, or a catalytically active fragment thereof. In some embodiments, the second Fc polypeptide is a fusion polypeptide that is linked to the ERT enzyme, the ERT enzyme variant, or the catalytically active fragment thereof by a peptide bond or by a polypeptide linker. In some embodiments, the polypeptide linker is a flexible polypeptide linker. In some embodiments, the flexible polypeptide linker is a glycine-rich linker. In some embodiments, the glycine-rich linker is $G_4S$ (SEQ ID NO:239) or $(G_4S)_2$ (SEQ ID NO:240). In some embodiments, the second Fc polypeptide is not linked to the ERT enzyme, the ERT enzyme variant, or the catalytically active fragment thereof by a chemical cross-linking agent, e.g., the fusion polypeptide does not include a non-peptide bond or a non-polypeptide linker.

In some embodiments, the N-terminus of the first Fc polypeptide and/or the N-terminus of the second Fc polypeptide is linked to the ERT enzyme. In some embodiments, the N-terminus of the first Fc polypeptide is linked to one ERT enzyme and the N-terminus of the second Fc polypeptide is linked to the other ERT enzyme.

In some embodiments, the C-terminus of the first Fc polypeptide and/or the C-terminus of the second Fc polypeptide is linked to the ERT enzyme. In some embodiments, the C-terminus of the first Fc polypeptide is linked to one ERT enzyme and the C-terminus of the second Fc polypeptide is linked to the other ERT enzyme.

In some embodiments, the N-terminus of the first Fc polypeptide is linked to one ERT enzyme and the C-terminus of the second Fc polypeptide is linked to the other ERT enzyme. In some embodiments, the C-terminus of the first Fc polypeptide is linked to one ERT enzyme and the N-terminus of the second Fc polypeptide is linked to the other ERT enzyme.

In some embodiments, the protein comprises a single ERT enzyme, and the N-terminus or the C-terminus of the first Fc polypeptide is linked to the ERT enzyme. In some embodiments, the protein comprises two ERT enzymes (e.g., exactly two ERT enzymes). In some embodiments, the protein comprises exactly one or exactly two ERT enzymes, enzyme variants, or catalytically active fragments thereof.

In some embodiments, the first Fc polypeptide is a modified Fc polypeptide and/or the second Fc polypeptide is a modified Fc polypeptide.

In some embodiments, the first Fc polypeptide and the second Fc polypeptide each contain modifications that promote heterodimerization. In some embodiments, the Fc dimer is an Fc heterodimer. In some embodiments, one of the Fc polypeptides has a T366W substitution and the other Fc polypeptide has T366S, L368A, and Y407V substitutions, according to EU numbering. In some embodiments, the first Fc polypeptide contains the T366S, L368A, and Y407V substitutions and the second Fc polypeptide contains the T366W substitution. In some embodiments, the first Fc polypeptide is linked to the ERT enzyme IDS and comprises the amino acid sequence of any one of SEQ ID NOS:117, 232, and 236. In some embodiments, the first Fc polypeptide contains the T366W substitution and the second Fc polypeptide contains the T366S, L368A, and Y407V substitutions. In some embodiments, the first Fc polypeptide is linked to the ERT enzyme IDS and comprises the amino acid sequence of any one of SEQ ID NOS:118, 233, and 237.

In some embodiments, the first Fc polypeptide and/or the second Fc polypeptide comprises a native FcRn binding site. In some embodiments, the first Fc polypeptide and the second Fc polypeptide do not have effector function. In some embodiments, the first Fc polypeptide and/or the second Fc polypeptide includes a modification that reduces effector function. In some embodiments, the modification that reduces effector function is the substitutions of Ala at position 234 and Ala at position 235, according to EU numbering. In some embodiments, the modification that reduces effector function further comprises a substitution of Gly at position 329, according to EU numbering. In some embodiments, the first Fc polypeptide is linked to the ERT enzyme IDS and comprises the amino acid sequence of any one of SEQ ID NOS:115, 231, and 235. In some embodiments, the first Fc polypeptide is linked to the ERT enzyme SGSH and comprises the amino acid sequence of any one of SEQ ID NOS:149, 150, 152, and 153.

In some embodiments, the first Fc polypeptide and/or the second Fc polypeptide comprises amino acid changes relative to the native Fc sequence that extend serum half-life. In some embodiments, the amino acid changes comprise substitutions of Tyr at position 252, Thr at position 254, and Glu at position 256, according to EU numbering. Alternatively, in other embodiments, the amino acid changes comprise substitutions of Leu at position 428 and Ser at position 434, according to EU numbering. Alternatively, in further embodiments, the amino acid changes comprise a substitution of Ser or Ala at position 434, according to EU numbering.

In some embodiments, the first Fc polypeptide and/or the second Fc polypeptide specifically binds to a transferrin receptor (TfR).

In some embodiments, the first Fc polypeptide and/or the second Fc polypeptide comprises at least two substitutions at positions selected from the group consisting of 384, 386, 387, 388, 389, 390, 413, 416, and 421, according to EU numbering. In some embodiments, the first Fc polypeptide and/or the second Fc polypeptide comprises at least three, four, five, six, seven, eight, or nine substitutions at the positions.

In some embodiments, the first Fc polypeptide and/or the second Fc polypeptide further comprises one, two, three, or four substitutions at positions comprising 380, 391, 392, and 415, according to EU numbering. In some embodiments, the first Fc polypeptide and/or the second Fc polypeptide further comprises one, two, or three substitutions at positions comprising 414, 424, and 426, according to EU numbering.

In some embodiments, the first Fc polypeptide and/or the second Fc polypeptide comprises Trp at position 388. In some embodiments, the first Fc polypeptide and/or the second Fc polypeptide comprises an aromatic amino acid at position 421. In some embodiments, the aromatic amino acid at position 421 is Trp or Phe.

In some embodiments, the first Fc polypeptide and/or the second Fc polypeptide comprises at least one position selected from the following: position 380 is Trp, Leu, or Glu; position 384 is Tyr or Phe; position 386 is Thr; position 387 is Glu; position 388 is Trp; position 389 is Ser, Ala, Val, or Asn; position 390 is Ser or Asn; position 413 is Thr or Ser; position 415 is Glu or Ser; position 416 is Glu; and position 421 is Phe.

In some embodiments, the first Fc polypeptide and/or the second Fc polypeptide comprises 2, 3, 4, 5, 6, 7, 8, 9, 10, or 11 positions selected from the following: position 380 is Trp, Leu, or Glu; position 384 is Tyr or Phe; position 386 is Thr; position 387 is Glu; position 388 is Trp; position 389 is Ser, Ala, Val, or Asn; position 390 is Ser or Asn; position 413 is Thr or Ser; position 415 is Glu or Ser; position 416 is Glu; and position 421 is Phe.

In some embodiments, the first Fc polypeptide and/or the second Fc polypeptide comprises 11 positions as follows: position 380 is Trp, Leu, or Glu; position 384 is Tyr or Phe; position 386 is Thr; position 387 is Glu; position 388 is Trp; position 389 is Ser, Ala, Val, or Asn; position 390 is Ser or Asn; position 413 is Thr or Ser; position 415 is Glu or Ser; position 416 is Glu; and position 421 is Phe.

In some embodiments, the first Fc polypeptide and/or the second Fc polypeptide has a CH3 domain with at least 85% identity, at least 90% identity, or at least 95% identity to amino acids 111-217 of any one of SEQ ID NOS:34-38, 58, and 60-90, 151, and 156-229. In some embodiments, the first Fc polypeptide and/or the second Fc polypeptide comprises the amino acid sequence of any one of SEQ ID NOS:156-229. In some embodiments, the residues at least 5, 6, 7, 8, 9, 10, 11, 12, 13, 14, 15, or 16 of the positions corresponding to EU index positions 380, 384, 386, 387, 388, 389, 390, 391, 392, 413, 414, 415, 416, 421, 424 and 426 of any one of SEQ ID NOS:34-38, 58, and 60-90, 151, and 156-229 are not deleted or substituted.

In some embodiments, the first Fc polypeptide and/or the second Fc polypeptide comprises the amino acid sequence of SEQ ID NO:157. In some embodiments, the first Fc polypeptide and/or the second Fc polypeptide comprises the amino acid sequence of SEQ ID NO:169. In some embodiments, the first Fc polypeptide and/or the second Fc polypeptide comprises the amino acid sequence of SEQ ID NO:181. In some embodiments, the first Fc polypeptide and/or the second Fc polypeptide comprises the amino acid sequence of SEQ ID NO:193. In some embodiments, the first Fc polypeptide and/or the second Fc polypeptide comprises the amino acid sequence of SEQ ID NO:205. In some embodiments, the first Fc polypeptide and/or the second Fc polypeptide comprises the amino acid sequence of SEQ ID NO:217.

In some embodiments, the first Fc polypeptide comprises the amino acid sequence of SEQ ID NO:115, and the second Fc polypeptide comprises the amino acid sequence of any one of SEQ ID NOS:205 and 228 (e.g., SEQ ID NO:228). In other embodiments, the first Fc polypeptide comprises the amino acid sequence of SEQ ID NO:115, and the second Fc polypeptide comprises the amino acid sequence of any one of SEQ ID NOS:169 and 229 (e.g., SEQ ID NO:229).

In some embodiments, the first Fc polypeptide comprises the amino acid sequence of SEQ ID NO:231, and the second Fc polypeptide comprises the amino acid sequence of any one of SEQ ID NOS:205 and 228 (e.g., SEQ ID NO:228). In other embodiments, the first Fc polypeptide comprises the amino acid sequence of SEQ ID NO:231, and the second Fc polypeptide comprises the amino acid sequence of any one of SEQ ID NOS:169 and 229 (e.g., SEQ ID NO:229).

In some embodiments, the first Fc polypeptide comprises the amino acid sequence of SEQ ID NO:235, and the second Fc polypeptide comprises the amino acid sequence of any one of SEQ ID NOS:205 and 228 (e.g., SEQ ID NO:228). In other embodiments, the first Fc polypeptide comprises the amino acid sequence of SEQ ID NO:235, and the second Fc polypeptide comprises the amino acid sequence of any one of SEQ ID NOS:169 and 229 (e.g., SEQ ID NO:229).

In some embodiments, the first Fc polypeptide and/or the second Fc polypeptide binds to the apical domain of TfR. In some embodiments, the binding of the protein to TfR does not substantially inhibit binding of transferrin to TfR.

In some embodiments, the first Fc polypeptide and/or the second Fc polypeptide has an amino acid sequence identity of at least 75%, or at least 80%, 85%, 90%, 92%, or 95%, as compared to the corresponding wild-type Fc polypeptide. In some embodiments, the corresponding wild-type Fc polypeptide is a human IgG1, IgG2, IgG3, or IgG4 Fc polypeptide.

In some embodiments, uptake of the ERT enzyme into the brain (e.g., using an appropriate animal model such as those described herein) is greater than the uptake of the ERT enzyme in the absence of the first Fc polypeptide and/or the second Fc polypeptide or the uptake of the ERT enzyme without the modifications to the first Fc polypeptide and/or the second Fc polypeptide that result in TfR binding. In some embodiments, uptake of the ERT enzyme into the brain is at least 2, 3, 4, 5, 6, 7, 8, 9, 10, 15, 20, 25, 30, 35, 40, 45, 50, 55, 60, 65, 70, 75, 80, 85, 90, 95, or 100-fold greater as compared to the uptake of the ERT enzyme in the absence of the first Fc polypeptide and/or the second Fc polypeptide or as compared to the uptake of the ERT enzyme without the modifications to the first Fc polypeptide and/or the second Fc polypeptide that result in TfR binding.

In some embodiments, the first Fc polypeptide is not modified to bind to a blood-brain barrier (BBB) receptor and the second Fc polypeptide is modified to specifically bind to TfR. In some embodiments, the first Fc polypeptide is modified to specifically bind to TfR and the second Fc polypeptide is not modified to bind to a BBB receptor.

In some embodiments, the protein does not include an immunoglobulin heavy and/or light chain variable region sequence or an antigen-binding portion thereof.

In some aspects, provided herein is a polypeptide comprising an Fc polypeptide that is linked to an ERT enzyme, an ERT enzyme variant, or a catalytically active fragment thereof, wherein the Fc polypeptide contains one or more modifications that promote its heterodimerization to another Fc polypeptide.

In some embodiments, the ERT enzyme is IDS, an IDS variant, or a catalytically active fragment thereof. In some embodiments, the ERT enzyme comprises an amino acid sequence having at least 80%, 85%, 90%, or 95% identity to the amino acid sequence of any one of SEQ ID NOS:91, 92, 114, 230, and 234. In some embodiments, the ERT enzyme comprises the amino acid sequence of any one of SEQ ID NOS:91, 92, 114, 230, and 234.

In some embodiments, the ERT enzyme is SGSH, an SGSH variant, or a catalytically active fragment thereof. In some embodiments, the ERT enzyme comprises an amino acid sequence having at least 80%, 85%, 90%, or 95% identity to the amino acid sequence of any one of SEQ ID NOS:119 and 120. In some embodiments, the ERT enzyme comprises the amino acid sequence of any one of SEQ ID NOS:119 and 120.

In some embodiments, the ERT enzyme is ASM, an ASM variant, or a catalytically active fragment thereof. In some embodiments, the ERT enzyme comprises an amino acid sequence having at least 80%, 85%, 90%, or 95% identity to the amino acid sequence of any one of SEQ ID NOS:121, 122, and 123. In some embodiments, the ERT enzyme comprises the amino acid sequence of any one of SEQ ID NOS:121, 122, and 123.

In some embodiments, the ERT enzyme is GBA, a GBA variant, or a catalytically active fragment thereof. In some embodiments, the ERT enzyme comprises an amino acid sequence having at least 80%, 85%, 90%, or 95% identity to the amino acid sequence of any one of SEQ ID NOS:93 and 94. In some embodiments, the ERT enzyme comprises the amino acid sequence of any one of SEQ ID NOS:93 and 94.

In some embodiments, the Fc polypeptide is a fusion polypeptide that is linked to the ERT enzyme, the ERT enzyme variant, or the catalytically active fragment thereof by a peptide bond or by a polypeptide linker. In some embodiments, the polypeptide linker is a flexible polypeptide linker. In some embodiments, the flexible polypeptide linker is a glycine-rich linker. In some embodiments, the glycine-rich linker is $G_4S$ (SEQ ID NO:239) or $(G_4S)_2$ (SEQ ID NO:240). In some embodiments, the Fc polypeptide is not linked to the ERT enzyme, the ERT enzyme variant, or the catalytically active fragment thereof by a chemical cross-linking agent, e.g., the fusion polypeptide does not include a non-peptide bond or a non-polypeptide linker.

In certain embodiments, the fusion polypeptide comprises from N- to C-terminus: the ERT enzyme, the ERT enzyme variant, or the catalytically active fragment thereof; the polypeptide linker; and the first Fc polypeptide.

In some embodiments, the Fc polypeptide contains T366S, L368A, and Y407V substitutions, according to EU numbering. In some embodiments, the polypeptide comprises the amino acid sequence of any one of SEQ ID NOS:115, 117, 231, 232, 235, and 236. In some embodiments, the polypeptide comprises the amino acid sequence of any one of SEQ ID NOS:149 and 150. In some embodiments, the Fc polypeptide contains a T366W substitution. In some embodiments, the polypeptide comprises the amino acid sequence of any one of SEQ ID NOS:118, 233, and 237. In some embodiments, the polypeptide comprises the amino acid sequence of any one of SEQ ID NOS:152-155. In some embodiments, the polypeptide further comprises the other Fc polypeptide. In some embodiments, the other Fc polypeptide contains a T366W substitution or contains T366S, L368A, and Y407V substitutions and forms an Fc dimer with the ERT enzyme-Fc fusion polypeptide.

In some embodiments, the Fc polypeptide comprises a native FcRn binding site. In some embodiments, the Fc polypeptide does not have effector function. In some embodiments, the Fc polypeptide includes a modification that reduces effector function. In some embodiments, the modification that reduces effector function is the substitutions of Ala at position 234 and Ala at position 235, according to EU numbering. In some embodiments, the modification that reduces effector function further comprises a substitution of Gly at position 329, according to EU numbering.

In some embodiments, the Fc polypeptide comprises amino acid changes relative to the native Fc sequence that extend serum half-life. In some embodiments, the amino acid changes comprise substitutions of Tyr at position 252, Thr at position 254, and Glu at position 256, according to EU numbering.

In some embodiments, the Fc polypeptide specifically binds to TfR.

In some embodiments, the Fc polypeptide comprises at least two substitutions at positions selected from the group consisting of 384, 386, 387, 388, 389, 390, 413, 416, and 421, according to EU numbering. In some embodiments, the Fc polypeptide comprises at least three, four, five, six, seven, eight, or nine substitutions at the positions.

In some embodiments, the Fc polypeptide further comprises one, two, three, or four substitutions at positions comprising 380, 391, 392, and 415, according to EU numbering. In some embodiments, the Fc polypeptide further comprises one, two, or three substitutions at positions comprising 414, 424, and 426, according to EU numbering.

In some embodiments, the Fc polypeptide comprises Trp at position 388. In some embodiments, the Fc polypeptide comprises an aromatic amino acid at position 421. In some embodiments, the aromatic amino acid at position 421 is Trp or Phe.

In some embodiments, the Fc polypeptide comprises at least one position selected from the following: position 380 is Trp, Leu, or Glu; position 384 is Tyr or Phe; position 386 is Thr; position 387 is Glu; position 388 is Trp; position 389 is Ser, Ala, Val, or Asn; position 390 is Ser or Asn; position 413 is Thr or Ser; position 415 is Glu or Ser; position 416 is Glu; and position 421 is Phe.

In some embodiments, the Fc polypeptide comprises 2, 3, 4, 5, 6, 7, 8, 9, 10, or 11 positions selected from the following: position 380 is Trp, Leu, or Glu; position 384 is Tyr or Phe; position 386 is Thr; position 387 is Glu; position 388 is Trp; position 389 is Ser, Ala, Val, or Asn; position 390 is Ser or Asn; position 413 is Thr or Ser; position 415 is Glu or Ser; position 416 is Glu; and position 421 is Phe.

In some embodiments, the Fc polypeptide comprises 11 positions as follows: position 380 is Trp, Leu, or Glu; position 384 is Tyr or Phe; position 386 is Thr; position 387 is Glu; position 388 is Trp; position 389 is Ser, Ala, Val, or Asn; position 390 is Ser or Asn; position 413 is Thr or Ser; position 415 is Glu or Ser; position 416 is Glu; and position 421 is Phe.

In some embodiments, the Fc polypeptide has a CH3 domain with at least 85% identity, at least 90% identity, or at least 95% identity to amino acids 111-217 of any one of SEQ ID NOS:34-38, 58, and 60-90. In some embodiments, the residues at least 5, 6, 7, 8, 9, 10, 11, 12, 13, 14, 15, or 16 of the positions corresponding to EU index positions 380, 384, 386, 387, 388, 389, 390, 391, 392, 413, 414, 415, 416, 421, 424 and 426 of any one of SEQ ID NOS:34-38, 58, and 60-90 are not deleted or substituted.

In some embodiments, the Fc polypeptide binds to the apical domain of TfR. In some embodiments, the binding of the protein to TfR does not substantially inhibit binding of transferrin to TfR.

In some embodiments, the Fc polypeptide has an amino acid sequence identity of at least 75%, or at least 80%, 85%, 90%, 92%, or 95%, as compared to the corresponding wild-type Fc polypeptide. In some embodiments, the corresponding wild-type Fc polypeptide is a human IgG1, IgG2, IgG3, or IgG4 Fc polypeptide.

In some embodiments, the Fc polypeptide does not include an immunoglobulin heavy and/or light chain variable region sequence or an antigen-binding portion thereof.

In some embodiments, provided herein is a polynucleotide comprising a nucleic acid sequence encoding a polypeptide comprising an Fc polypeptide that is linked to an ERT enzyme, an ERT enzyme variant, or a catalytically active fragment thereof, wherein the Fc polypeptide contains one or more modifications that promote its heterodimerization to another Fc polypeptide. In some embodiments, provided herein is a vector comprising the polynucleotide. In some embodiments, provided herein is a host cell comprising the polynucleotide or the vector. In some embodiments, the host cell further comprises a polynucleotide comprising a nucleic acid sequence encoding the other Fc polypeptide. In some embodiments, provided herein is a method for producing the polypeptide described herein, comprising culturing a host cell under conditions in which the polypeptide encoded by the polynucleotide is expressed.

In some aspects, provided herein is a protein comprising:
(a) a first polypeptide chain that comprises a modified Fc polypeptide that specifically binds to TfR;
(b) a second polypeptide chain that comprises an Fc polypeptide, wherein the first and second polypeptide chains form an Fc dimer; and
(c) an ERT enzyme, an ERT enzyme variant, or a catalytically active fragment thereof, that is linked to the modified Fc polypeptide of (a) or to the Fc polypeptide of (b).

In some embodiments, the ERT enzyme is IDS, an IDS variant, or a catalytically active fragment thereof. In some embodiments, the ERT enzyme comprises an amino acid sequence having at least 80%, 85%, 90%, or 95% identity to the amino acid sequence of any one of SEQ ID NOS:91, 92, 114, 230, and 234. In some embodiments, the ERT enzyme comprises the amino acid sequence of any one of SEQ ID NOS:91, 92, 114, 230, and 234.

In some embodiments, the ERT enzyme is SGSH, an SGSH variant, or a catalytically active fragment thereof. In some embodiments, the ERT enzyme comprises an amino acid sequence having at least 80%, 85%, 90%, or 95% identity to the amino acid sequence of any one of SEQ ID NOS:119 and 120. In some embodiments, the ERT enzyme comprises the amino acid sequence of any one of SEQ ID NOS:119 and 120.

In some embodiments, the ERT enzyme is ASM, an ASM variant, or a catalytically active fragment thereof. In some embodiments, the ERT enzyme comprises an amino acid sequence having at least 80%, 85%, 90%, or 95% identity to the amino acid sequence of any one of SEQ ID NOS:121, 122, and 123. In some embodiments, the ERT enzyme comprises the amino acid sequence of any one of SEQ ID NOS:121, 122, and 123.

In some embodiments, the ERT enzyme is GBA, a GBA variant, or a catalytically active fragment thereof. In some embodiments, the ERT enzyme comprises an amino acid sequence having at least 80%, 85%, 90%, or 95% identity to the amino acid sequence of any one of SEQ ID NOS:93 and 94. In some embodiments, the ERT enzyme comprises the amino acid sequence of any one of SEQ ID NOS:93 and 94.

In some embodiments, the ERT enzyme is linked to the modified Fc polypeptide of (a). In some embodiments, the ERT enzyme is linked to the Fc polypeptide of (b). In some embodiments, the Fc polypeptide of (b) is not modified to bind to a BBB receptor. In some embodiments, the Fc polypeptide of (b) is a modified Fc polypeptide that specifically binds to TfR.

In some embodiments, the ERT enzyme is linked (e.g., fused) to the modified Fc polypeptide of (a) or to the Fc polypeptide of (b) by a peptide bond or by a polypeptide linker to form a fusion polypeptide. In some embodiments, the polypeptide linker is a flexible polypeptide linker. In some embodiments, the flexible polypeptide linker is a glycine-rich linker. In some embodiments, the glycine-rich linker is $G_4S$ (SEQ ID NO:239) or $(G_4S)_2$ (SEQ ID NO:240). In some embodiments, the ERT enzyme is not linked to the modified Fc polypeptide of (a) or to the Fc polypeptide of (b) by a chemical cross-linking agent, e.g., the fusion polypeptide does not include a non-peptide bond or a non-polypeptide linker.

In some embodiments, the ERT enzyme is linked to the N-terminus of the modified Fc polypeptide of (a) or to the N-terminus of the Fc polypeptide of (b). In some embodiments, the ERT enzyme is linked to the C-terminus of the modified Fc polypeptide of (a) or to the C-terminus of the Fc polypeptide of (b).

In some embodiments, the protein comprises two ERT enzymes. In some embodiments, one ERT enzyme is linked to the modified Fc polypeptide of (a) and the other ERT enzyme is linked to the Fc polypeptide of (b). In some embodiments, the ERT enzymes are both linked to the N-terminus or are both linked to the C-terminus of the respective Fc polypeptides. In some embodiments, one ERT enzyme is linked to the N-terminus of the modified Fc polypeptide of (a) and the other ERT enzyme is linked to the C-terminus of the Fc polypeptide of (b). In some embodiments, one ERT enzyme is linked to the C-terminus of the modified Fc polypeptide of (a) and the other ERT enzyme is linked to the N-terminus of the Fc polypeptide of (b).

In some embodiments, the Fc polypeptides of (a) and (b) each contain modifications that promote heterodimerization. In some embodiments, one of the Fc polypeptides has a T366W substitution and the other Fc polypeptide has T366S, L368A, and Y407V substitutions, according to EU numbering. In some embodiments, the modified Fc polypeptide of (a) contains the T366W substitution and the Fc polypeptide of (b) contains the T366S, L368A, and Y407V substitutions. In some embodiments, the Fc polypeptide of (b) is linked to the ERT enzyme IDS and comprises the amino acid sequence of any one of SEQ ID NOS:117, 232, and 236. In some embodiments, the modified Fc polypeptide of (a) contains the T366S, L368A, and Y407V substitutions and the Fc polypeptide of (b) contains the T366W substitution. In some embodiments, the Fc polypeptide of (b) is linked to the ERT enzyme IDS and comprises the amino acid sequence of any one of SEQ ID NOS:118, 233, and 237.

In some embodiments, the modified Fc polypeptide of (a) and/or the Fc polypeptide of (b) comprises a native FcRn binding site. In some embodiments, the modified Fc polypeptide of (a) and the Fc polypeptide of (b) do not have effector function. In some embodiments, the modified Fc polypeptide of (a) and/or the Fc polypeptide of (b) includes a modification that reduces effector function. In some embodiments, the modification that reduces effector function is the substitutions of Ala at position 234 and Ala at position 235, according to EU numbering. In some embodiments, the modification that reduces effector function further comprises a substitution of Gly at position 329, according to EU numbering. In some embodiments, the Fc polypeptide of (b) is linked to the ERT enzyme IDS and comprises the amino acid sequence of any one of SEQ ID NOS:115, 231, and 235. In some embodiments, the Fc polypeptide of (b) is linked to the ERT enzyme SGSH and comprises the amino acid sequence of any one of SEQ ID NOS:149, 150, 152, and 153.

In some embodiments, the modified Fc polypeptide of (a) and/or the Fc polypeptide of (b) comprises amino acid changes relative to the native Fc sequence that extend serum half-life. In some embodiments, the amino acid changes comprise substitutions of Tyr at position 252, Thr at position 254, and Glu at position 256, according to EU numbering.

In some embodiments, the modified Fc polypeptide comprises at least two substitutions at positions selected from the group consisting of 384, 386, 387, 388, 389, 390, 413, 416, and 421, according to EU numbering. In some embodiments, the modified Fc polypeptide comprises at least three, four, five, six, seven, eight, or nine substitutions at the positions.

In some embodiments, the modified Fc polypeptide further comprises one, two, three, or four substitutions at positions comprising 380, 391, 392, and 415, according to EU numbering. In some embodiments, the modified Fc polypeptide further comprises one, two, or three substitutions at positions comprising 414, 424, and 426, according to EU numbering.

In some embodiments, the modified Fc polypeptide comprises Trp at position 388. In some embodiments, the modified Fc polypeptide comprises an aromatic amino acid at position 421. In some embodiments, the aromatic amino acid at position 421 is Trp or Phe.

In some embodiments, the modified Fc polypeptide comprises at least one position selected from the following: position 380 is Trp, Leu, or Glu; position 384 is Tyr or Phe; position 386 is Thr; position 387 is Glu; position 388 is Trp; position 389 is Ser, Ala, Val, or Asn; position 390 is Ser or Asn; position 413 is Thr or Ser; position 415 is Glu or Ser; position 416 is Glu; and position 421 is Phe.

In some embodiments, the modified Fc polypeptide comprises 2, 3, 4, 5, 6, 7, 8, 9, 10, or 11 positions selected from the following: position 380 is Trp, Leu, or Glu; position 384 is Tyr or Phe; position 386 is Thr; position 387 is Glu; position 388 is Trp; position 389 is Ser, Ala, Val, or Asn; position 390 is Ser or Asn; position 413 is Thr or Ser; position 415 is Glu or Ser; position 416 is Glu; and position 421 is Phe.

In some embodiments, the modified Fc polypeptide comprises 11 positions as follows: position 380 is Trp, Leu, or Glu; position 384 is Tyr or Phe; position 386 is Thr; position 387 is Glu; position 388 is Trp; position 389 is Ser, Ala, Val, or Asn; position 390 is Ser or Asn; position 413 is Thr or Ser; position 415 is Glu or Ser; position 416 is Glu; and position 421 is Phe.

In some embodiments, the modified Fc polypeptide has a CH3 domain with at least 85% identity, at least 90% identity, or at least 95% identity to amino acids 111-217 of any one of SEQ ID NOS:34-38, 58, and 60-90, 151, and 156-229. In some embodiments, the modified Fc polypeptide comprises the amino acid sequence of any one of SEQ ID NOS:156-229. In some embodiments, the residues at least 5, 6, 7, 8, 9, 10, 11, 12, 13, 14, 15, or 16 of the positions corresponding to EU index positions 380, 384, 386, 387, 388, 389, 390, 391, 392, 413, 414, 415, 416, 421, 424 and 426 of any one of SEQ ID NOS:34-38, 58, and 60-90, 151, and 156-229 are not deleted or substituted.

In some embodiments, the modified Fc polypeptide comprises the amino acid sequence of SEQ ID NO:157. In some embodiments, the modified Fc polypeptide comprises the amino acid sequence of SEQ ID NO:169. In some embodiments, the modified Fc polypeptide comprises the amino acid sequence of SEQ ID NO:181. In some embodiments, the modified Fc polypeptide comprises the amino acid sequence of SEQ ID NO:193. In some embodiments, the modified Fc polypeptide comprises the amino acid sequence of SEQ ID NO:205. In some embodiments, the modified Fc polypeptide comprises the amino acid sequence of SEQ ID NO:217.

In some embodiments, the first polypeptide chain comprises the amino acid sequence of any one of SEQ ID NOS:205 and 228 (e.g., SEQ ID NO:228) and the second polypeptide chain comprises the amino acid sequence of SEQ ID NO:115. In other embodiments, the first polypeptide chain comprises the amino acid sequence of any one of SEQ ID NOS:169 and 229 (e.g., SEQ ID NO:229) and the second polypeptide chain comprises the amino acid sequence of SEQ ID NO:115.

In some embodiments, the first polypeptide chain comprises the amino acid sequence of any one of SEQ ID NOS:205 and 228 (e.g., SEQ ID NO:228) and the second polypeptide chain comprises the amino acid sequence of SEQ ID NO:231. In other embodiments, the first polypeptide chain comprises the amino acid sequence of any one of SEQ ID NOS:169 and 229 (e.g., SEQ ID NO:229) and the second polypeptide chain comprises the amino acid sequence of SEQ ID NO:231.

In some embodiments, the first polypeptide chain comprises the amino acid sequence of any one of SEQ ID NOS:205 and 228 (e.g., SEQ ID NO:228) and the second polypeptide chain comprises the amino acid sequence of SEQ ID NO:235. In other embodiments, the first polypeptide chain comprises the amino acid sequence of any one of SEQ ID NOS:169 and 229 (e.g., SEQ ID NO:229) and the second polypeptide chain comprises the amino acid sequence of SEQ ID NO:235.

In some embodiments, the modified Fc polypeptide binds to the apical domain of TfR. In some embodiments, the binding of the protein to TfR does not substantially inhibit binding of transferrin to TfR.

In some embodiments, the modified Fc polypeptide has an amino acid sequence identity of at least 75%, or at least 80%, 85%, 90%, 92%, or 95%, as compared to the corresponding wild-type Fc polypeptide. In some embodiments, the corresponding wild-type Fc polypeptide is a human IgG1, IgG2, IgG3, or IgG4 Fc polypeptide.

In some embodiments, uptake of the ERT enzyme into the brain (e.g., using an appropriate animal model such as those described herein) is greater than the uptake of the ERT enzyme in the absence of the Fc polypeptide or the uptake of the ERT enzyme without the modifications to the Fc polypeptide that result in TfR binding. In some embodiments, uptake of the ERT enzyme into the brain is at least 2, 3, 4, 5, 6, 7, 8, 9, 10, 15, 20, 25, 30, 35, 40, 45, 50, 55, 60, 65, 70, 75, 80, 85, 90, 95, or 100-fold greater as compared to the uptake of the ERT enzyme in the absence of the Fc polypeptide or as compared to the uptake of the ERT enzyme without the modifications to the Fc polypeptide that result in TfR binding.

In some aspects, provided herein is a method of treating an LSD, the method comprising administering a protein or polypeptide as described above to a patient in need thereof. In some embodiments, the method decreases the accumulation of a toxic metabolic product in the patient, e.g., a toxic metabolic product in the patient's brain and/or cerebrospinal fluid (CSF) is decreased.

In related aspects, provided herein is a method of decreasing the accumulation of a toxic metabolic product in a patient having an LSD, the method comprising administering a protein or polypeptide as described above to the patient. In some embodiments, the method decreases the accumulation of a toxic metabolic product in the patient's brain and/or CSF.

In some embodiments, the LSD is Hunter syndrome, and the ERT enzyme is IDS. In some embodiments, the toxic metabolic product comprises heparan sulfate-derived disaccharides and/or dermatan sulfate-derived disaccharides.

In some embodiments, the LSD is Sanfilippo syndrome A, and the ERT enzyme is SGSH. In some embodiments, the toxic metabolic product comprises heparan sulfate-derived oligosaccharides (e.g., hexasaccharides).

In some embodiments, the LSD is Niemann-Pick disease, and the ERT enzyme is ASM. In some embodiments, the toxic metabolic product comprises sphingomyelin.

In some embodiments, the LSD is Gaucher's disease or Parkinson's disease, and the ERT enzyme is GBA. In some embodiments, the toxic metabolic product comprises glucosylceramide.

In some embodiments, the total amount of a toxic metabolic product is reduced by at least about 5%, 10%, 15%, 20%, 25%, 30%, 35%, 40%, 45%, 50%, 55%, 60%, 65%, 70%, 75%, 80%, 85%, 90%, or 95% as compared to the total amount of the toxic metabolic product in the absence of the protein or polypeptide. Illustrative assays for measuring ERT enzyme activity and substrate accumulation are described herein.

In some aspects, provided herein is a pharmaceutical composition comprising a protein or polypeptide as described above and a pharmaceutically acceptable carrier.

In some aspects, provided herein is a method of monitoring substrate accumulation to assess IDS activity, the method comprising:
  (a) disrupting cells in a cell or tissue sample or microvesicles in a fluid sample from a subject administered a protein or polypeptide as described above to break open microvesicles to obtain a glycosaminoglycan (GAG) solution to be analyzed;
  (b) digesting the GAG solution with at least one heparinase (e.g., heparinase I, heparinase II, and heparinase III) and chondroitinase B to obtain GAG-derived disaccharides;
  (c) analyzing the GAG-derived disaccharides by mass spectrometry (e.g., LC-MS/MS); and
  (d) determining the levels of heparan sulfate- and/or dermatan sulfate-derived disaccharides, wherein decreased levels of heparan sulfate- and/or dermatan sulfate-derived disaccharides compared to a control that lacks IDS activity is indicative of increased IDS activity in the sample compared to the control.

In some embodiments, the step of disrupting cells or microvesicles comprises at least one freeze-thaw cycle and/or at least one sonication step. In some embodiments, the cells are from a tissue sample and the method comprises at least three, four, or five freeze-thaw cycles. In some embodiments, the subject is a mouse deficient in IDS activity. In some embodiments, the subject is a non-human primate. In some embodiments, the subject is a human patient having Hunter syndrome.

In some embodiments, the levels of heparan sulfate- and/or dermatan sulfate-derived disaccharides are reduced by at least about 5%, 10%, 15%, 20%, 25%, 30%, 35%, 40%, 45%, 50%, 55%, 60%, 65%, 70%, 75%, 80%, 85%, 90%, or 95% as compared to the levels of heparan sulfate- and/or dermatan sulfate-derived disaccharides in a control that lacks IDS activity. In some embodiments, the control is a cell or tissue sample of the same cell of tissue type obtained from the subject prior to administration of the protein or polypeptide. In some embodiments, the control is a cell or tissue sample of the same cell of tissue type known to be deficient in IDS activity. In some embodiments, the protein or polypeptide increases IDS activity in the sample by at least 2, 3, 4, 5, 6, 7, 8, 9, 10, 15, 20, 25, 30, 35, 40, 45, 50, 55, 60, 65, 70, 75, 80, 85, 90, 95, or 100-fold as compared to the IDS activity in the control.

In other aspects, provided herein is a method of monitoring substrate accumulation to assess SGSH activity, the method comprising:
  (a) disrupting cells in a cell or tissue sample or microvesicles in a fluid sample from a subject administered a protein or polypeptide as described above to break open microvesicles to obtain a glycosaminoglycan (GAG) solution to be analyzed;
  (b) digesting the GAG solution with at least one heparinase to obtain GAG-derived disaccharides;
  (c) analyzing the GAG-derived disaccharides by mass spectrometry (e.g., LC-MS/MS); and
  (d) determining the levels of heparan sulfate-derived disaccharides, wherein decreased levels of heparan sulfate-derived disaccharides compared to a control that lacks SGSH activity is indicative of increased SGSH activity in the sample compared to the control.

In some embodiments, the step of disrupting cells or microvesicles comprises at least one freeze-thaw cycle and/or at least one sonication step. In some embodiments, the cells are from a tissue sample and the method comprises at least three, four, or five freeze-thaw cycles. In some embodiments, the subject is a mouse deficient in SGSH activity. In some embodiments, the subject is a non-human primate. In some embodiments, the subject is a human patient having Sanfilippo syndrome A.

In some embodiments, the levels of heparan sulfate- derived disaccharides are reduced by at least about 5%, 10%, 15%, 20%, 25%, 30%, 35%, 40%, 45%, 50%, 55%, 60%, 65%, 70%, 75%, 80%, 85%, 90%, or 95% as compared to the levels of heparan sulfate-derived disaccharides in a control that lacks SGSH activity. In some embodiments, the control is a cell or tissue sample of the same cell of tissue type obtained from the subject prior to administration of the protein or polypeptide. In some embodiments, the control is a cell or tissue sample of the same cell of tissue type known to be deficient in SGSH activity. In some embodiments, the protein or polypeptide increases SGSH activity in the sample by at least 2, 3, 4, 5, 6, 7, 8, 9, 10, 15, 20, 25, 30, 35, 40, 45, 50, 55, 60, 65, 70, 75, 80, 85, 90, 95, or 100-fold as compared to the SGSH activity in the control.

In other aspects, provided herein is a method for transporting an agent across the BBB of a mammal, the method comprising exposing the BBB to a protein that binds to a TfR with an affinity of from about 50 nM to about 250 nM, wherein the protein is linked to the agent and transports the linked agent across the BBB. In some embodiments, the maximum concentration ($C_{max}$) of the agent in the brain of the mammal is improved. In some embodiments, the agent is useful for treating an LSD.

In still other aspects, provided herein is a method for treating an LSD, the method comprising administering to a mammal a protein that binds to a TfR with an affinity of from about 50 nM to about 250 nM, wherein the protein is linked to an agent for treating the LSD, thereby exposing the brain of the mammal to the agent. In some embodiments, the protein improves the $C_{max}$ of the agent in the brain as compared to the agent linked to a reference protein that binds to the TfR with a weaker affinity. In some embodiments, the reference protein binds to the TfR with an affinity of about 600 nM, or weaker.

In some embodiments, the TfR is a primate TfR. In some embodiments, the primate TfR is a human TfR. In some embodiments, the protein binds to the TfR apical domain.

In some embodiments, the protein binds to the TfR with an affinity of from about 100 nM to about 200 nM. In some embodiments, the protein binds to the TfR with an affinity of from about 110 nM to about 150 nM.

In some embodiments, the therapeutically effective concentration of the agent is a concentration that treats one or more symptoms of an LSD in the mammal. In some embodiments, the agent is a protein replacement therapeutic. In some embodiments, the agent or protein replacement therapeutic is an enzyme.

In some embodiments, the enzyme decreases the accumulation of a toxic metabolic product in the brain of the mammal having the LSD to a greater extent when linked to the protein as compared to when the enzyme is linked to the reference protein. In some embodiments, the enzyme is IDS and the LSD is Hunter syndrome. In some embodiments, the toxic metabolic product comprises heparin sulfate-derived disaccharides and/or dermatan sulfate-derived disaccharides. In some embodiments, the enzyme is SGSH and the LSD is Sanfilippo syndrome A. In some embodiments, the enzyme is ASM and the LSD is Niemann-Pick disease. In some embodiments, the enzyme is GBA and the LSD is Gaucher's disease.

In some embodiments, the agent comprises an antibody variable region. In some embodiments, the agent comprises an antibody fragment. In some embodiments, the agent comprises a Fab or scFv.

In some embodiments, the protein is a modified Fc polypeptide that contains a non-native binding site capable of binding TfR. In some embodiments, the protein comprises an antibody variable region that specifically binds TfR. In some embodiments, the protein comprises an antibody fragment. In some embodiments, the protein comprises a Fab or scFv.

In some embodiments, the protein linked to the agent is administered as part of a pharmaceutically acceptable carrier.

BRIEF DESCRIPTION OF THE DRAWINGS

FIG. 1 shows the purification and analysis of an IDS-Fc fusion protein comprising an Fc polypeptide linked to an iduronate-2-sulfatase (IDS) enzyme and a modified Fc polypeptide that binds to transferrin receptor (TfR).

FIGS. 5C-5D: "ETV:IDS"=ETV:IDS 35.23.2; Graphs display mean values across experimental replicates ±SEM.

FIG. 10C shows levels of disaccharides D0S0, D0A0, and D0a4 ("Total sGAG levels") in brain, CSF, and peripheral tissues of IDS KO×TfR$^{ms/hu}$ KI mice were measured after a single dose or multiple doses of ETV:IDS or IDS and compared to vehicle treatment and wild-type mice; n=8 per IDS KO×TfR$^{ms/hu}$ KI groups and n=5 for wild-type group. Graphs display mean±SEM and p values: one-way ANOVA with Dunnett multiple comparison test;  p<0.01, * p<0.001, and **** p<0.0001.

FIG. 11 shows the purification and analysis of an ASM-Fc fusion protein comprising an Fc region linked to two acid sphingomyelinase (ASM) enzymes.

DETAILED DESCRIPTION

I. Introduction

Figure 2:
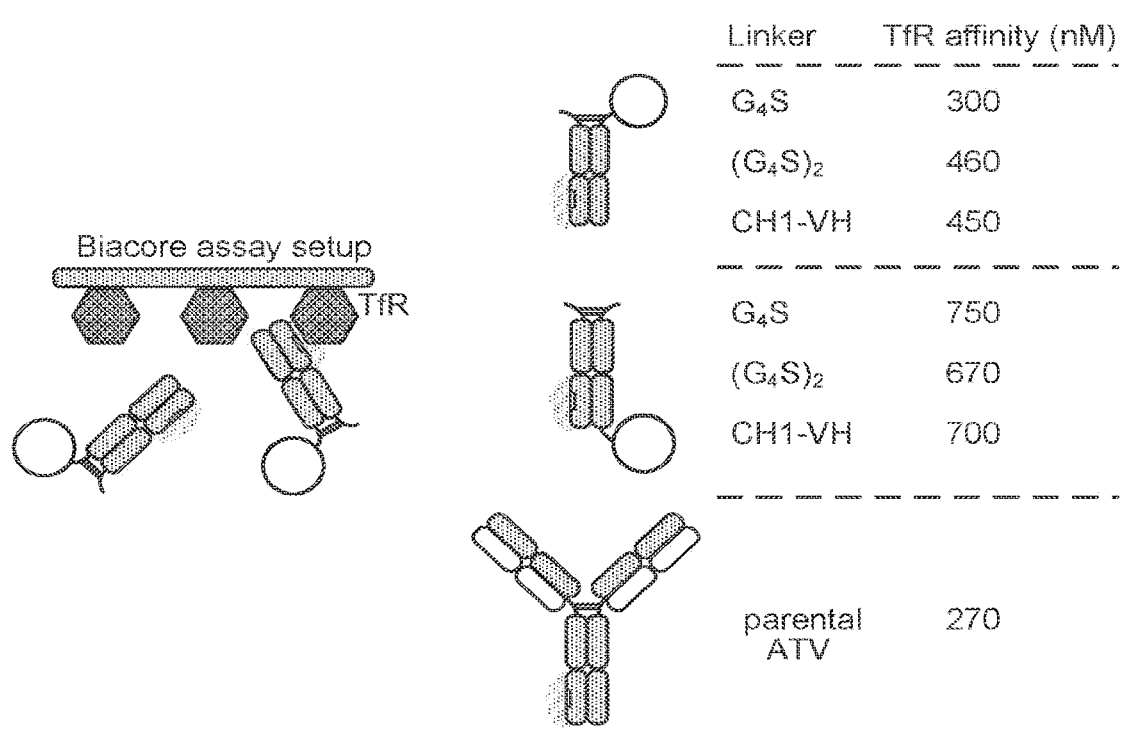
FIG. 2 shows the results of a binding affinity assay for IDS-Fc fusion proteins analyzed in FIG. 1 demonstrating that the fusion proteins bind to TfR.

We have developed fusion proteins that include an enzyme replacement therapy (ERT) enzyme linked to an Fc polypeptide. These proteins can be used to treat lysosomal storage disorders (LSDs). In some cases, the protein includes a dimeric Fc polypeptide, where one of the Fc polypeptide monomers is linked to the ERT enzyme. The Fc polypeptides can increase enzyme half-life and, in some cases, can be modified to confer additional functional properties onto the protein. Also described herein are fusion proteins that facilitate delivery of an ERT enzyme across the blood-brain barrier (BBB). These proteins comprise an Fc polypeptide and a modified Fc polypeptide that form a dimer, and an ERT enzyme linked to the Fc region and/or the modified Fc region. The modified Fc region can specifically bind to a BBB receptor such as a transferrin receptor (TfR). In some embodiments, the ERT enzyme is iduronate 2-sulfatase (IDS), or a catalytically active variant or fragment of a wild-type IDS, e.g., a wild-type human IDS. In other embodiments, the ERT enzyme is N-sulfoglucosamine sulfohydrolase (SGSH), acid sphingomyelinase (ASM), β-glucocerbrosidase (GBA), or a catalytically active variant or fragment of a wild-type SGSH, ASM, or GBA, e.g., a wild-type human SGSH, ASM, or GBA.

We have also developed a method for transporting therapeutic agents that are linked to TfR-binding polypeptides and proteins across the BBB for the treatment of disease. We discovered that the desired TfR binding affinity for transporting a therapeutic agent across the BBB depends on the target of the therapeutic agent, as well as the mechanism of action that drives efficacy in treating the disease. In particular, we discovered that using polypeptides and proteins that have stronger TfR affinities results in greater $C_{max}$ but faster clearance.

For some therapies, such as protein replacement therapies that can be used to treat, e.g., LSDs, which include the use of ERT enzymes such as IDS (e.g., for the treatment of Hunter syndrome), as well as others, achieving a high brain $C_{max}$ of the therapeutic is desired over the dosing window, as higher extracellular concentrations will in turn drive increased intracellular protein concentrations. Once delivered into cells, the intracellular half-life of the delivered protein is sustained for a longer period of time compared to plasma residence time. In addition, having a high $C_{max}$ may be beneficial for enzyme replacement, as the high enzyme concentration can drive an increased rate of substrate turnover by the enzyme. For improving brain $C_{max}$, using polypeptides and proteins that have a TfR affinity range of 50-250 nM is particularly useful.

II. Definitions

As used herein, the singular forms "a," "an," and "the" include plural referents unless the content clearly dictates otherwise. Thus, for example, reference to "a polypeptide" may include two or more such molecules, and the like.

As used herein, the terms "about" and "approximately," when used to modify an amount specified in a numeric value or range, indicate that the numeric value as well as reasonable deviations from the value known to the skilled person in the art, for example ±20%, ±10%, or ±5%, are within the intended meaning of the recited value.

An "enzyme replacement therapy enzyme" or "ERT enzyme" refers to an enzyme that is deficient in a lysosomal storage disorder. An "ERT enzyme variant" refers to a functional variant, including allelic and splice variants, of a wild-type ERT enzyme or a fragment thereof, where the ERT enzyme variant has at least 50%, at least 55%, at least 60%, at least 65%, at least 70%, at least 75%, at least 80%, at least 85%, at least 90%, or at least 95% of the activity of the corresponding wild-type ERT enzyme or fragment thereof, e.g., when assayed under identical conditions. A "catalytically active fragment" of an ERT enzyme refers to a portion of a full-length ERT enzyme or a variant thereof, where the catalytically active fragment has at least 50%, at least 55%, at least 60%, at least 65%, at least 70%, at least 75%, at least 80%, at least 85%, at least 90%, or at least 95% of the activity of the corresponding full-length ERT enzyme or variant thereof, e.g., when assayed under identical conditions.

An "iduronate sulfatase," "iduronate-2-sulfatase," or "IDS" as used herein refers to iduronate 2-sulfatase (EC 3.1.6.13), which is an enzyme involved in the lysosomal degradation of the glycosaminoglycans heparan sulfate and dermatan sulfate. Deficiency of IDS is associated with Mucopolysaccharidosis II, also known as Hunter syndrome. The term "IDS" as used herein as a component of a protein that comprises an Fc polypeptide is catalytically active and encompasses functional variants, including allelic and splice variants, of a wild-type IDS or a fragment thereof. The sequence of human IDS isoform I, which is the human sequence designated as the canonical sequence, is available under UniProt entry P22304 and is encoded by the human IDS gene at Xq28. The full-length sequence is provided as SEQ ID NO:91. A "mature" IDS sequence as used herein refers to a form of a polypeptide chain that lacks the signal and propeptide sequences of the naturally occurring full-length polypeptide chain. The amino acid sequence of a mature human IDS polypeptide is provided as SEQ ID NO:92, which corresponds to amino acids 34-550 of the full-length human sequence. A "truncated" IDS sequence as used herein refers to a catalytically active fragment of the naturally occurring full-length polypeptide chain. The amino acid sequence of an exemplary truncated human IDS polypeptide is provided as SEQ ID NO:114, which corresponds to amino acids 26-550 of the full-length human sequence. The structure of human IDS has been well-characterized. An illustrative structure is available under PDB accession code 5FQL. The structure is also described in *Nat. Comm.* 8:15786 doi: 10.1038/ncomms15786, 2017. Non-human primate IDS sequences have also been described, including chimpanzee (UniProt entry K7BKV4) and rhesus macaque (UniProt entry H9FTX2). A mouse IDS sequence is available under Uniprot entry Q08890. An IDS variant has at least 50%, at least 55%, at least 60%, at least 65%, at least 70%, at least 75%, at least 80%, at least 85%, at least 90%, or at least 95% of the activity of the corresponding wild-type IDS or fragment thereof, e.g., when assayed under identical conditions. A catalytically active IDS fragment has at least 50%, at least 55%, at least 60%, at least 65%, at least 70%, at least 75%, at least 80%, at least 85%, at least 90%, or at least 95% of the activity of the corresponding full-length IDS or variant thereof, e.g., when assayed under identical conditions.

A "sulfoglucosamine sulfohydrolase," "N-sulfoglucosamine sulfohydrolase," or "SGSH" as used herein refers to N-sulfoglucosamine sulfohydrolase (EC 3.10.1.1), which is an enzyme involved in the lysosomal degradation of heparan sulfate. Mutations in this gene are associated with Sanfilippo syndrome A, one type of the lysosomal storage disorder mucopolysaccaridosis III, which results from impaired degradation of heparan sulfate. The term "SGSH" as used herein as a component of a protein that comprises an Fc polypeptide is catalytically active and encompasses functional variants, including allelic and splice variants, of a wild-type SGSH or a fragment thereof. The sequence of human SGSH is available under UniProt entry P51688 and is encoded by the human SGSH gene at 17q25.3. The full-length sequence is provided as SEQ ID NO:119. A "mature" SGSH sequence as used herein refers to a form of a polypeptide chain that lacks the signal sequence of the naturally occurring full-length polypeptide chain. The amino acid sequence of a mature human SGSH polypeptide is provided as SEQ ID NO:120, which corresponds to amino acids 21-502 of the full-length human sequence. A "truncated" SGSH sequence as used herein refers to a catalytically active fragment of the naturally occurring full-length polypeptide chain. The structure of human SGSH has been well-characterized. An illustrative structure is available under PDB accession code 4MHX. Non-human primate SGSH sequences have also been described, including chimpanzee (UniProt entry K7C218). A mouse SGSH sequence is available under Uniprot entry Q9EQ08. An SGSH variant has at least 50%, at least 55%, at least 60%, at least 65%, at least 70%, at least 75%, at least 80%, at least 85%, at least 90%, or at least 95% of the activity of the corresponding wild-type SGSH or fragment thereof, e.g., when assayed under identical conditions. A catalytically active SGSH fragment has at least 50%, at least 55%, at least 60%, at least 65%, at least 70%, at least 75%, at least 80%, at least 85%, at least 90%, or at least 95% of the activity of the corresponding full-length SGSH or variant thereof, e.g., when assayed under identical conditions.

An "acid sphingomyelinase," "sphingomyelin phosphodiesterase," or "ASM" as used herein refers to sphingomyelin phosphodiesterase 1 (EC 3.1.4.12), which is a lysosomal enzyme that converts sphingomyelin to ceramide. Diseases associated with ASM deficiency include Niemann-Pick disease (e.g., Type A or Type B). The term "ASM" as used herein as a component of a protein that comprises an Fc polypeptide is catalytically active and encompasses functional variants, including allelic and splice variants, of a wild-type ASM or a fragment thereof. The sequence of human ASM isoform 1, which is the human sequence designated as the canonical sequence, is available under UniProt entry P17405 and is encoded by the human SMPD1 gene at 11p15.4. The full-length sequence is provided as SEQ ID NO:121. A "mature" ASM sequence as used herein refers to a form of a polypeptide chain that lacks the signal sequence of the naturally occurring full-length polypeptide chain. The amino acid sequence of a mature human ASM polypeptide is provided as SEQ ID NO:122, which corresponds to amino acids 47-629 of the full-length human sequence. A "truncated" ASM sequence as used herein refers to a catalytically active fragment of the naturally occurring full-length polypeptide chain. The amino acid sequence of an exemplary truncated human ASM polypeptide is provided as SEQ ID NO:123, which corresponds to amino acids 47-620 of the full-length human sequence. The structure of human ASM has been well-characterized. An illustrative structure is available under PDB accession code 5I81. Non-human primate ASM sequences have also been described, including chimpanzee (UniProt entry H2Q319). A mouse ASM sequence is available under Uniprot entry Q04519. An ASM variant has at least 50%, at least 55%, at least 60%, at least 65%, at least 70%, at least 75%, at least 80%, at least 85%, at least 90%, or at least 95% of the activity of the corresponding wild-type ASM or fragment thereof, e.g., when assayed under identical conditions. A catalytically active ASM fragment has at least 50%, at least 55%, at least 60%, at least 65%, at least 70%, at least 75%, at least 80%, at least 85%, at least 90%, or at least 95% of the activity of the corresponding full-length ASM or variant thereof, e.g., when assayed under identical conditions.

A "β-glucocerebrosidase" or "GBA" is also known as glucosylceramidase (EC 3.2.1.45). The term as used herein refers to a lysosomal enzyme that has glucosylceramidase activity and catalyzes the breakdown of glucosylceramide to ceramide and glucose. Deficiency of GBA is associated with Gaucher's disease and Parkinson's disease. The term "GBA" as used herein as a component of a protein that comprises an Fc polypeptide is catalytically active and encompasses functional variants, including allelic and splice variants, of a wild-type GBA, or a fragment thereof. The sequence of human GBA, long isoform, which is designated as the canonical sequence, is available under UniProt entry P04062-1 and is encoded by the human GBA gene at 1q22. The full-length sequence is provided as SEQ ID NO:93. A "mature" GBA sequence as used herein refers to a form of a polypeptide chain that lacks the signal and propeptide sequences of the naturally occurring full-length polypeptide chain. The amino acid sequence of a mature human GBA polypeptide is provided as SEQ ID NO:94, which corresponds to amino acids 40-536 of the full-length human sequence. A "truncated" GBA sequence as used herein refers to a catalytically active fragment of the naturally occurring full-length polypeptide chain. The structure of human GBA has been well-characterized. Nearly 20 crystal structures of GBA are available. Non-human primate GBA sequences have also been described, including chimpanzee (UniProt entry Q9BDTO) and orangutan (UniProt entry Q5R8E3). A mouse GBA sequence is available under UniProt entry P17439. A GBA variant has at least 50%, at least 55%, at least 60%, at least 65%, at least 70%, at least 75%, at least 80%, at least 85%, at least 90%, or at least 95% of the activity of the corresponding wild-type GBA or fragment thereof, e.g., when assayed under identical conditions. A catalytically active GBA fragment has at least 50%, at least 55%, at least 60%, at least 65%, at least 70%, at least 75%, at least 80%, at least 85%, at least 90%, or at least 95% of the activity of the corresponding full-length GBA or variant thereof, e.g., when assayed under identical conditions.

A "transferrin receptor" or "TfR" as used herein refers to transferrin receptor protein 1. The human transferrin receptor 1 polypeptide sequence is set forth in SEQ ID NO:96. Transferrin receptor protein 1 sequences from other species are also known (e.g., chimpanzee, accession number XP_003310238.1; rhesus monkey, NP_001244232.1; dog, NP_001003111.1; cattle, NP_001193506.1; mouse, NP_035768.1; rat, NP_073203.1; and chicken, NP_990587.1). The term "transferrin receptor" also encompasses allelic variants of exemplary reference sequences, e.g., human sequences, that are encoded by a gene at a transferrin receptor protein 1 chromosomal locus. Full-length transferrin receptor protein includes a short N-terminal intracellular region, a transmembrane region, and a large extracellular domain. The extracellular domain is characterized by three domains: a protease-like domain, a helical domain, and an apical domain. The apical domain sequence of human transferrin receptor 1 is set forth in SEQ ID NO:238.

A "fusion protein" or "[ERT enzyme]-Fc fusion protein" as used herein refers to a dimeric protein comprising a first Fc polypeptide that is linked (e.g., fused) to an ERT enzyme, an ERT enzyme variant, or a catalytically active fragment thereof (i.e., an "[ERT]-Fc fusion polypeptide"); and a second Fc polypeptide that forms an Fc dimer with the first Fc polypeptide. The second Fc polypeptide may also be linked (e.g., fused) to an ERT enzyme, an ERT enzyme variant, or a catalytically active fragment thereof. The first Fc polypeptide and/or the second Fc polypeptide may be linked to the ERT enzyme, ERT enzyme variant, or catalytically active fragment thereof by a peptide bond or by a polypeptide linker. The first Fc polypeptide and/or the second Fc polypeptide may be a modified Fc polypeptide that contains one or more modifications that promote its heterodimerization to the other Fc polypeptide. The first Fc polypeptide and/or the second Fc polypeptide may be a modified Fc polypeptide that contains one or more modifications that confer binding to a transferrin receptor. The first Fc polypeptide and/or the second Fc polypeptide may be a modified Fc polypeptide that contains one or more modifications that reduce effector function. The first Fc polypeptide and/or the second Fc polypeptide may be a modified Fc polypeptide that contains one or more modifications that extend serum half-life.

A "fusion polypeptide" or "[ERT enzyme]-Fc fusion polypeptide" as used herein refers to an Fc polypeptide that is linked (e.g., fused) to an ERT enzyme, an ERT enzyme variant, or a catalytically active fragment thereof. The Fc polypeptide may be linked to the ERT enzyme, ERT enzyme variant, or catalytically active fragment thereof by a peptide bond or by a polypeptide linker. The Fc polypeptide may be a modified Fc polypeptide that contains one or more modifications that promote its heterodimerization to another Fc polypeptide. The Fc polypeptide may be a modified Fc polypeptide that contains one or more modifications that confer binding to a transferrin receptor. The Fc polypeptide may be a modified Fc polypeptide that contains one or more modifications that reduce effector function. The Fc polypeptide may be a modified Fc polypeptide that contains one or more modifications that extend serum half-life.

As used herein, the term "Fc polypeptide" refers to the C-terminal region of a naturally occurring immunoglobulin heavy chain polypeptide that is characterized by an Ig fold as a structural domain. An Fc polypeptide contains constant region sequences including at least the CH2 domain and/or the CH3 domain and may contain at least part of the hinge region. In general, an Fc polypeptide does not contain a variable region.

A "modified Fc polypeptide" refers to an Fc polypeptide that has at least one mutation, e.g., a substitution, deletion or insertion, as compared to a wild-type immunoglobulin heavy chain Fc polypeptide sequence, but retains the overall Ig fold or structure of the native Fc polypeptide.

The term "FcRn" refers to the neonatal Fc receptor. Binding of Fc polypeptides to FcRn reduces clearance and increases serum half-life of the Fc polypeptide. The human FcRn protein is a heterodimer that is composed of a protein of about 50 kDa in size that is similar to a major histocompatibility (MHC) class I protein and a β2-microglobulin of about 15 kDa in size.

As used herein, an "FcRn binding site" refers to the region of an Fc polypeptide that binds to FcRn. In human IgG, the FcRn binding site, as numbered using the EU index, includes T250, L251, M252, I253, S254, R255, T256, T307, E380, M428, H433, N434, H435, and Y436. These positions correspond to positions 20 to 26, 77, 150, 198, and 203 to 206 of SEQ ID NO:1.

As used herein, a "native FcRn binding site" refers to a region of an Fc polypeptide that binds to FcRn and that has the same amino acid sequence as the region of a naturally occurring Fc polypeptide that binds to FcRn.

The terms "CH3 domain" and "CH2 domain" as used herein refer to immunoglobulin constant region domain polypeptides. For purposes of this application, a CH3 domain polypeptide refers to the segment of amino acids from about position 341 to about position 447 as numbered according to EU, and a CH2 domain polypeptide refers to the segment of amino acids from about position 231 to about position 340 as numbered according to the EU numbering scheme and does not include hinge region sequences. CH2 and CH3 domain polypeptides may also be numbered by the IMGT (ImMunoGeneTics) numbering scheme in which the CH2 domain numbering is 1-110 and the CH3 domain numbering is 1-107, according to the IMGT Scientific chart numbering (IMGT website). CH2 and CH3 domains are part of the Fc region of an immunoglobulin. An Fc region refers to the segment of amino acids from about position 231 to about position 447 as numbered according to the EU numbering scheme, but as used herein, can include at least a part of a hinge region of an antibody. An illustrative hinge region sequence is the human IgG1 hinge sequence EPKSCDKTHTCPPCP (SEQ ID NO:95).

The terms "wild-type," "native," and "naturally occurring" with respect to a CH3 or CH2 domain are used herein to refer to a domain that has a sequence that occurs in nature.

As used herein, the term "mutant" with respect to a mutant polypeptide or mutant polynucleotide is used interchangeably with "variant." A variant with respect to a given wild-type CH3 or CH2 domain reference sequence can include naturally occurring allelic variants. A "non-naturally" occurring CH3 or CH2 domain refers to a variant or mutant domain that is not present in a cell in nature and that is produced by genetic modification, e.g., using genetic engineering technology or mutagenesis techniques, of a native CH3 domain or CH2 domain polynucleotide or polypeptide. A "variant" includes any domain comprising at least one amino acid mutation with respect to wild-type. Mutations may include substitutions, insertions, and deletions.

The term "amino acid" refers to naturally occurring and synthetic amino acids, as well as amino acid analogs and amino acid mimetics that function in a manner similar to the naturally occurring amino acids.

Naturally occurring amino acids are those encoded by the genetic code, as well as those amino acids that are later modified, e.g., hydroxyproline, γ-carboxyglutamate and 0-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid.

Naturally occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission.

The terms "polypeptide" and "peptide" are used interchangeably herein to refer to a polymer of amino acid residues in a single chain. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

The term "protein" as used herein refers to either a polypeptide or a dimer (i.e, two) or multimer (i.e., three or more) of single chain polypeptides. The single chain polypeptides of a protein may be joined by a covalent bond, e.g., a disulfide bond, or non-covalent interactions.

The term "conservative substitution," "conservative mutation," or "conservatively modified variant" refers to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys. Examples of categories of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH$_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences, refer to two or more sequences or subsequences that are the same or have a specified percentage of amino acid residues, e.g., at least 60% identity, at least 65%, at least 70%, at least 75%, at least 80%, at least 85%, at least 90%, or at least 95% or greater, that are identical over a specified region when compared and aligned for maximum correspondence over a comparison window, or designated region, as measured using a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, an amino acid residue in a modified Fc polypeptide "corresponds to" an amino acid in SEQ ID NO:1, when the residue aligns with the amino acid in SEQ ID NO:1 when optimally aligned to SEQ ID NO: 1. The polypeptide that is aligned to the reference sequence need not be the same length as the reference sequence.

A "binding affinity" as used herein refers to the strength of the non-covalent interaction between two molecules, e.g., a single binding site on a polypeptide and a target, e.g., transferrin receptor, to which it binds. Thus, for example, the term may refer to 1:1 interactions between a polypeptide and its target, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and BioLayer interferometry (e.g., using the ForteBio® Octet® platform). As used herein, "binding affinity" includes not only formal binding affinities, such as those reflecting 1:1 interactions between a polypeptide and its target, but also apparent affinities for which $K_D$'s are calculated that may reflect avid binding.

As used herein, the term "specifically binds" or "selectively binds" to a target, e.g., TfR, when referring to an engineered TfR-binding polypeptide, TfR-binding peptide, or TfR-binding antibody as described herein, refers to a binding reaction whereby the engineered TfR-binding polypeptide, TfR-binding peptide, or TfR-binding antibody binds to the target with greater affinity, greater avidity, and/or greater duration than it binds to a structurally different target. In typical embodiments, the engineered TfR-binding polypeptide, TfR-binding peptide, or TfR-binding antibody has at least 5-fold, 10-fold, 50-fold, 100-fold, 1,000-fold, 10,000-fold, or greater affinity for a specific target, e.g., TfR, compared to an unrelated target when assayed under the same affinity assay conditions. The term "specific binding," "specifically binds to," or "is specific for" a particular target (e.g., TfR), as used herein, can be exhibited, for example, by a molecule having an equilibrium dissociation constant $K_D$ for the target to which it binds of, e.g., $10^{-4}$ M or smaller, e.g., $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In some embodiments, an engineered TfR-binding polypeptide, TfR-binding peptide, or TfR-binding antibody specifically binds to an epitope on TfR that is conserved among species, (e.g., structurally conserved among species), e.g., conserved between non-human primate and human species (e.g., structurally conserved between non-human primate and human species). In some embodiments, an engineered TfR-binding polypeptide, TfR-binding peptide, or TfR-binding antibody may bind exclusively to a human TfR.

The term "variable region" or "variable domain" refers to a domain in an antibody heavy chain or light chain that is derived from a germline Variable (V) gene, Diversity (D) gene, or Joining (J) gene (and not derived from a Constant (Cμ and Cδ) gene segment), and that gives an antibody its specificity for binding to an antigen. Typically, an antibody variable region comprises four conserved "framework" regions interspersed with three hypervariable "complementarity determining regions."

The terms "antigen-binding portion" and "antigen-binding fragment" are used interchangeably herein and refer to one or more fragments of an antibody that retains the ability to specifically bind to an antigen via its variable region. Examples of antigen-binding fragments include, but are not limited to, a Fab fragment (a monovalent fragment consisting of the VL, VH, CL, and CH1 domains), a F(ab')2 fragment (a bivalent fragment comprising two Fab fragments linked by a disulfide bridge at the hinge region), a single chain Fv (scFv), a disulfide-linked Fv (dsFv), complementarity determining regions (CDRs), a VL (light chain variable region), and a VH (heavy chain variable region).

The terms "treatment," "treating," and the like are used herein to generally mean obtaining a desired pharmacologic and/or physiologic effect. "Treating" or "treatment" may refer to any indicia of success in the treatment or amelioration of a lysosomal storage disorder, e.g., Hunter syndrome, Sanfilippo syndrome A, Niemann-Pick disease, Gaucher's disease, or Parkinson's disease, including any objective or subjective parameter such as abatement, remission, improvement in patient survival, increase in survival time or rate, diminishing of symptoms or making the disorder more tolerable to the patient, slowing in the rate of degeneration or decline, or improving a patient's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

The term "subject," "individual," and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the patient is a human.

The term "pharmaceutically acceptable excipient" refers to a non-active pharmaceutical ingredient that is biologically or pharmacologically compatible for use in humans or animals, such as but not limited to a buffer, carrier, or preservative.

As used herein, a "therapeutic amount," "therapeutically effective amount," or "therapeutically effective concentration" of an agent is an amount or concentration of the agent that treats signs or symptoms of a disease (e.g., an LSD) in the subject (e.g., mammal).

The term "administer" refers to a method of delivering agents, compounds, or compositions to the desired site of biological action. These methods include, but are not limited to, topical delivery, parenteral delivery, intravenous delivery, intradermal delivery, intramuscular delivery, intrathecal delivery, colonic delivery, rectal delivery, or intraperitoneal delivery. In one embodiment, the polypeptides described herein are administered intravenously.

III. Enzyme Replacement Therapy (ERT) Enzymes

Lysosomal storage disorders (LSDs) are inherited metabolic diseases characterized by the accumulation of undigested or partially digested macromolecules, which ultimately results in cellular dysfunction and clinical abnormalities. Classically, LSDs have been defined as deficiencies in lysosomal function generally classified by the accumulated substrate and include sphingolipidoses, oligosaccharidoses, mucolipidoses, mucopolysaccharidoses, lipoprotein storage disorders, neuronal ceroid lipofuscinoses, and others. The classification of these disorders has recently been expanded to include other deficiencies or defects in proteins that result in accumulation of macromolecules, such as proteins necessary for normal post-translational modification of lysosomal enzymes, or proteins important for proper lysosomal trafficking.

In some aspects, a fusion protein described herein comprises: (i) an Fc polypeptide, which may contain modifications (e.g., one or more modifications that promote heterodimerization) or may be a wild-type Fc polypeptide; and an ERT enzyme; and (ii) an Fc polypeptide, which may contain modifications (e.g., one or more modifications that promote heterodimerization) or may be a wild-type Fc polypeptide; and optionally an ERT enzyme. In some embodiments, one or both Fc polypeptides may contain modifications that result in binding to a blood-brain barrier (BBB) receptor, e.g., a transferrin receptor (TfR). The ERT enzyme may be any enzyme that is deficient in an LSD. An ERT enzyme incorporated into the fusion protein is catalytically active, i.e., it retains the enzymatic activity that is deficient in the LSD. In some embodiments, the ERT enzyme is iduronate 2-sulfatase (IDS), which is deficient in Hunter syndrome. In some embodiments, the ERT enzyme is N-sulfoglucosamine sulfohydrolase (SGSH), which is deficient in Sanfilippo syndrome. In some embodiments, the ERT enzyme is acid sphingomyelinase (ASM), which is deficient in Niemann-Pick disease. In some embodiments, the ERT enzyme is β-glucocerebrosidase (GBA), which is deficient in Gaucher's disease and Parkinson's disease.

In some embodiments, a fusion protein comprising an ERT enzyme and optionally a modified Fc polypeptide that binds to a BBB receptor, e.g., a TfR-binding Fc polypeptide, comprises a catalytically active fragment or variant of a wild-type IDS. In some embodiments, the IDS enzyme is a variant or a catalytically active fragment of an IDS protein that comprises the amino acid sequence of any one of SEQ ID NOS:91, 92, 114, 230, and 234. In some embodiments, a catalytically active variant or fragment of an IDS enzyme has at least 50%, at least 55%, at least 60%, at least 65%, at least 70%, at least 75%, at least 80%, at least 85%, at least 90%, at least 95%, or greater of the activity of the wild-type IDS enzyme.

In some embodiments, a fusion protein comprising an ERT enzyme and optionally a modified Fc polypeptide that binds to a BBB receptor, e.g., a TfR-binding Fc polypeptide, comprises a catalytically active fragment or variant of a wild-type SGSH. In some embodiments, the SGSH enzyme is a variant or a catalytically active fragment of an SGSH protein that comprises the amino acid sequence of any one of SEQ ID NOS:119 and 120. In some embodiments, a catalytically active variant or fragment of an SGSH enzyme has at least 50%, at least 55%, at least 60%, at least 65%, at least 70%, at least 75%, at least 80%, at least 85%, at least 90%, at least 95%, or greater of the activity of the wild-type SGSH enzyme.

In some embodiments, a fusion protein comprising an ERT enzyme and optionally a modified Fc polypeptide that binds to a BBB receptor, e.g., a TfR-binding Fc polypeptide, comprises a catalytically active fragment or variant of a wild-type ASM. In some embodiments, the ASM enzyme is a variant or a catalytically active fragment of an ASM protein that comprises the amino acid sequence of any one of SEQ ID NOS:121, 122, and 123. In some embodiments, a catalytically active variant or fragment of an ASM enzyme has at least 50%, at least 55%, at least 60%, at least 65%, at least 70%, at least 75%, at least 80%, at least 85%, at least 90%, at least 95%, or greater of the activity of the wild-type ASM enzyme.

In some embodiments, a fusion protein comprising an ERT enzyme and optionally a modified Fc polypeptide that binds to a BBB receptor, e.g., a TfR-binding Fc polypeptide, comprises a catalytically active fragment or variant of a wild-type GBA. In some embodiments, the GBA enzyme is a variant or a catalytically active fragment of a GBA protein that comprises the amino acid sequence of any one of SEQ ID NOS:93 and 94. In some embodiments, a catalytically active variant or fragment of a GBA enzyme has at least 50%, at least 55%, at least 60%, at least 65%, at least 70%, at least 75%, at least 80%, at least 85%, at least 90%, at least 95%, or greater of the activity of the wild-type GBA enzyme.

In some embodiments, an ERT enzyme, e.g., IDS, SGSH, ASM, or GBA, or a catalytically active variant or fragment thereof, that is present in a fusion protein described herein, retains at least 25% of its activity compared to its activity when not joined to an Fc polypeptide or a TfR-binding Fc polypeptide. In some embodiments, an ERT enzyme, or a catalytically active variant or fragment thereof, retains at least 10%, or at least 15%, 20%, 25%, 30%, 35%, 40%, 45%, 50%, 55%, 60%, 65%, 70%, 75%, 80%, 85%, 90%, or 95%, of its activity compared to its activity when not joined to an Fc polypeptide or a TfR-binding Fc polypeptide. In some embodiments, an ERT enzyme, or a catalytically active variant or fragment thereof, retains at least 80%, 85%, 90%, or 95% of its activity compared to its activity when not joined to an Fc polypeptide or a TfR-binding Fc polypeptide. In some embodiments, fusion to an Fc polypeptide does not decrease the activity of the ERT enzyme, e.g., IDS, SGSH, ASM, or GBA, or catalytically active variant or fragment thereof. In some embodiments, fusion to a TfR-binding Fc polypeptide does not decrease the activity of the ERT enzyme.

IV. FC Polypeptide Modifications for Blood-Brain Barrier (BBB) Receptor Binding In some aspects, provided herein are fusion proteins that are capable of being transported across the blood-brain barrier (BBB). Such a protein comprises a modified Fc polypeptide that binds to a BBB receptor. BBB receptors are expressed on BBB endothelia, as well as other cell and tissue types. In some embodiments, the BBB receptor is transferrin receptor (TfR).

Amino acid residues designated in various Fc modifications, including those introduced in a modified Fc polypeptide that binds to a BBB receptor, e.g., TfR, are numbered herein using EU index numbering. Any Fc polypeptide, e.g., an IgG1, IgG2, IgG3, or IgG4 Fc polypeptide, may have modifications, e.g., amino acid substitutions, in one or more positions as described herein.

A modified (e.g., enhancing heterodimerization and/or BBB receptor-binding) Fc polypeptide present in a fusion protein described herein can have at least 70% identity, at least 75% identity, at least 80% identity, at least 85% identity, at least 90% identity, or at least 95% identity to a native Fc region sequence or a fragment thereof, e.g., a fragment of at least 50 amino acids or at least 100 amino acids, or greater in length. In some embodiments, the native Fc amino acid sequence is the Fc region sequence of SEQ ID NO:1. In some embodiments, the modified Fc polypeptide has at least 70% identity, at least 75% identity, at least 80% identity, at least 85% identity, at least 90% identity, or at least 95% identity to amino acids 1-110 of SEQ ID NO:1, or to amino acids 111-217 of SEQ ID NO:1, or a fragment thereof, e.g., a fragment of at least 50 amino acids or at least 100 amino acids, or greater in length.

In some embodiments, a modified (e.g., enhancing heterodimerization and/or BBB receptor-binding) Fc polypeptide comprises at least 50 amino acids, or at least 60, 65, 70, 75, 80, 85, 90, or 95 or more, or at least 100 amino acids, or more, that correspond to a native Fc region amino acid sequence. In some embodiments, the modified Fc polypeptide comprises at least 25 contiguous amino acids, or at least 30, 35, 40, or 45 contiguous amino acids, or 50 contiguous amino acids, or at least 60, 65, 70, 75, 80 85, 90, or 95 or more contiguous amino acids, or 100 or more contiguous amino acids, that correspond to a native Fc region amino acid sequence, such as SEQ ID NO:1.

In some embodiments, the domain that is modified for BBB receptor-binding activity is a human Ig CH3 domain, such as an IgG1 CH3 domain. The CH3 domain can be of any IgG subtype, i.e., from IgG1, IgG2, IgG3, or IgG4. In the context of IgG1 antibodies, a CH3 domain refers to the segment of amino acids from about position 341 to about position 447 as numbered according to the EU numbering scheme.

In some embodiments, the domain that is modified for BBB receptor-binding activity is a human Ig CH2 domain, such as an IgG CH2 domain. The CH2 domain can be of any IgG subtype, i.e., from IgG1, IgG2, IgG3, or IgG4. In the context of IgG1 antibodies, a CH2 domain refers to the segment of amino acids from about position 231 to about position 340 as numbered according to the EU numbering scheme.

In some embodiments, a modified (e.g., BBB receptor-binding) Fc polypeptide present in a fusion protein described herein comprises at least one, two, or three substitutions; and in some embodiments, at least four five, six, seven, eight, nine, or ten substitutions at amino acid positions comprising 266, 267, 268, 269, 270, 271, 295, 297, 298, and 299, according to the EU numbering scheme.

In some embodiments, a modified (e.g., BBB receptor-binding) Fc polypeptide present in a fusion protein described herein comprises at least one, two, or three substitutions; and in some embodiments, at least four, five, six, seven, eight, or nine substitutions at amino acid positions comprising 274, 276, 283, 285, 286, 287, 288, 289, and 290, according to the EU numbering scheme.

In some embodiments, a modified (e.g., BBB receptor-binding) Fc polypeptide present in a fusion protein described herein comprises at least one, two, or three substitutions; and in some embodiments, at least four, five, six, seven, eight, nine, or ten substitutions at amino acid positions comprising 268, 269, 270, 271, 272, 292, 293, 294, 296, and 300, according to the EU numbering scheme.

In some embodiments, a modified (e.g., BBB receptor-binding) Fc polypeptide present in a fusion protein described herein comprises at least one, two, or three substitutions; and in some embodiments, at least four, five, six, seven, eight, or nine substitutions at amino acid positions comprising 272, 274, 276, 322, 324, 326, 329, 330, and 331, according to the EU numbering scheme.

In some embodiments, a modified (e.g., BBB receptor-binding) Fc polypeptide present in a fusion protein described herein comprises at least one, two, or three substitutions; and in some embodiments, at least four, five, six, or seven substitutions at amino acid positions comprising 345, 346, 347, 349, 437, 438, 439, and 440, according to the EU numbering scheme.

In some embodiments, a modified (e.g., BBB receptor-binding) Fc polypeptide present in a fusion protein described herein comprises at least one, two, or three substitutions; and in some embodiments, at least four, five, six, seven, eight, or nine substitutions at amino acid positions 384, 386, 387, 388, 389, 390, 413, 416, and 421, according to the EU numbering scheme.

FcRn Binding Sites

In certain aspects, modified (e.g., BBB receptor-binding) Fc polypeptides, or Fc polypeptides present in a fusion protein described herein that do not specifically bind to a BBB receptor, can also comprise an FcRn binding site. In some embodiments, the FcRn binding site is within the Fc polypeptide or a fragment thereof.

In some embodiments, the FcRn binding site comprises a native FcRn binding site. In some embodiments, the FcRn binding site does not comprise amino acid changes relative to the amino acid sequence of a native FcRn binding site. In some embodiments, the native FcRn binding site is an IgG binding site, e.g., a human IgG binding site. In some embodiments, the FcRn binding site comprises a modification that alters FcRn binding.

In some embodiments, an FcRn binding site has one or more amino acid residues that are mutated, e.g., substituted, wherein the mutation(s) increase serum half-life or do not substantially reduce serum half-life (i.e., reduce serum half-life by no more than 25% compared to a counterpart modified Fc polypeptide having the wild-type residues at the mutated positions when assayed under the same conditions). In some embodiments, an FcRn binding site has one or more amino acid residues that are substituted at positions 250-256, 307, 380, 428, and 433-436, according to the EU numbering scheme.

In some embodiments, one or more residues at or near an FcRn binding site are mutated, relative to a native human IgG sequence, to extend serum half-life of the modified polypeptide. In some embodiments, mutations are introduced into one, two, or three of positions 252, 254, and 256. In some embodiments, the mutations are M252Y, S254T, and T256E. In some embodiments, a modified Fc polypeptide further comprises the mutations M252Y, S254T, and T256E. In some embodiments, a modified Fc polypeptide comprises a substitution at one, two, or all three of positions T307, E380, and N434, according to the EU numbering scheme. In some embodiments, the mutations are T307Q and N434A. In some embodiments, a modified Fc polypeptide comprises mutations T307A, E380A, and N434A. In some embodiments, a modified Fc polypeptide comprises substitutions at positions T250 and M428, according to the EU numbering scheme. In some embodiments, the modified Fc polypeptide comprises mutations T250Q and/or M428L. In some embodiments, a modified Fc polypeptide comprises substitutions at positions M428 and N434, according to the EU numbering scheme. In some embodiments, the modified Fc polypeptide comprises mutations M428L and N434S. In some embodiments, a modified Fc polypeptide comprises an N434S or N434A mutation.

V. Transferrin Receptor-Binding Fc Polypeptides

This section describes generation of modified Fc polypeptides described herein that bind to transferrin receptor (TfR) and are capable of being transported across the blood-brain barrier (BBB).

TfR-Binding Fc Polypeptides Comprising Mutations in the CH3 Domain

In some embodiments, a modified Fc polypeptide that specifically binds to TfR comprises substitutions in a CH3 domain. In some embodiments, a modified Fc polypeptide comprises a human Ig CH3 domain, such as an IgG CH3 domain, that is modified for TfR-binding activity. The CH3 domain can be of any IgG subtype, i.e., from IgG1, IgG2, IgG3, or IgG4. In the context of IgG antibodies, a CH3 domain refers to the segment of amino acids from about position 341 to about position 447 as numbered according to the EU numbering scheme.

In some embodiments, a modified Fc polypeptide that specifically binds to TfR binds to the apical domain of TfR and may bind to TfR without blocking or otherwise inhibiting binding of transferrin to TfR. In some embodiments, binding of transferrin to TfR is not substantially inhibited. In some embodiments, binding of transferrin to TfR is inhibited by less than about 50% (e.g., less than about 45%, 40%, 35%, 30%, 25%, 20%, 15%, 10%, or 5%). In some embodiments, binding of transferrin to TfR is inhibited by less than about 20% (e.g., less than about 19%, 18%, 17%, 16%, 15%, 14%, 13%, 12%, 11%, 10%, 9%, 8%, 7%, 6%, 5%, 4%, 3%, 2%, or 1%).

In some embodiments, a modified Fc polypeptide that specifically binds to TfR comprises at least two, three, four, five, six, seven, eight, or nine substitutions at positions 384, 386, 387, 388, 389, 390, 413, 416, and 421, according to the EU numbering scheme. Illustrative substitutions that may be introduced at these positions are shown in Tables 4 and 5. In some embodiments, the amino acid at position 388 and/or 421 is an aromatic amino acid, e.g., Trp, Phe, or Tyr. In some embodiments, the amino acid at position 388 is Trp. In some embodiments, the aromatic amino acid at position 421 is Trp or Phe.

In some embodiments, at least one position as follows is substituted: Leu, Tyr, Met, or Val at position 384; Leu, Thr, His, or Pro at position 386; Val, Pro, or an acidic amino acid at position 387; an aromatic amino acid, e.g., Trp at position 388; Val, Ser, or Ala at position 389; an acidic amino acid, Ala, Ser, Leu, Thr, or Pro at position 413; Thr or an acidic amino acid at position 416; or Trp, Tyr, His, or Phe at position 421. In some embodiments, the modified Fc polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set. Thus, for example, Ile may be present at position 384, 386, and/or position 413. In some embodiments, the acidic amino acid at position one, two, or each of positions 387, 413, and 416 is Glu. In other embodiments, the acidic amino acid at one, two or each of positions 387, 413, and 416 is Asp. In some embodiments, two, three, four, five, six, seven, or all eight of positions 384, 386, 387, 388, 389, 413, 416, and 421 have an amino acid substitution as specified in this paragraph.

In some embodiments, an Fc polypeptide that is modified as described in the preceding two paragraphs comprises a native Asn at position 390. In some embodiments, the modified Fc polypeptide comprises Gly, His, Gln, Leu, Lys, Val, Phe, Ser, Ala, or Asp at position 390. In some embodiments, the modified Fc polypeptide further comprises one, two, three, or four substitutions at positions comprising 380, 391, 392, and 415, according to the EU numbering scheme. In some embodiments, Trp, Tyr, Leu, or Gln may be present at position 380. In some embodiments, Ser, Thr, Gln, or Phe may be present at position 391. In some embodiments, Gln, Phe, or His may be present at position 392. In some embodiments, Glu may be present at position 415.

In certain embodiments, the modified Fc polypeptide comprises two, three, four, five, six, seven, eight, nine, ten, or eleven positions selected from the following: Trp, Leu, or Glu at position 380; Tyr or Phe at position 384; Thr at position 386; Glu at position 387; Trp at position 388; Ser, Ala, Val, or Asn at position 389; Ser or Asn at position 390; Thr or Ser at position 413; Glu or Ser at position 415; Glu at position 416; and/or Phe at position 421. In some embodiments, the modified Fc polypeptide comprises all eleven positions as follows: Trp, Leu, or Glu at position 380; Tyr or Phe at position 384; Thr at position 386; Glu at position 387; Trp at position 388; Ser, Ala, Val, or Asn at position 389; Ser or Asn at position 390; Thr or Ser at position 413; Glu or Ser at position 415; Glu at position 416; and/or Phe at position 421.

In certain embodiments, the modified Fc polypeptide comprises Leu or Met at position 384; Leu, His, or Pro at position 386; Val at position 387; Trp at position 388; Val or Ala at position 389; Pro at position 413; Thr at position 416; and/or Trp at position 421. In some embodiments, the modified Fc polypeptide further comprises Ser, Thr, Gln, or Phe at position 391. In some embodiments, the modified Fc polypeptide further comprises Trp, Tyr, Leu, or Gln at position 380 and/or Gln, Phe, or His at position 392. In some embodiments, Trp is present at position 380 and/or Gln is present at position 392. In some embodiments, the modified Fc polypeptide does not have a Trp at position 380.

In other embodiments, the modified Fc polypeptide comprises Tyr at position 384; Thr at position 386; Glu or Val and position 387; Trp at position 388; Ser at position 389; Ser or Thr at position 413; Glu at position 416; and/or Phe at position 421. In some embodiments, the modified Fc polypeptide comprises a native Asn at position 390. In certain embodiments, the modified Fc polypeptide further comprises Trp, Tyr, Leu, or Gln at position 380; and/or Glu at position 415. In some embodiments, the modified Fc polypeptide further comprises Trp at position 380 and/or Glu at position 415.

In additional embodiments, the modified Fc polypeptide further comprises one, two, or three substitutions at positions comprising 414, 424, and 426, according to the EU numbering scheme. In some embodiments, position 414 is Lys, Arg, Gly, or Pro; position 424 is Ser, Thr, Glu, or Lys; and/or position 426 is Ser, Trp, or Gly.

In some embodiments, the modified Fc polypeptide comprises one or more of the following substitutions: Trp at position 380; Thr at position 386; Trp at position 388; Val at position 389; Thr or Ser at position 413; Glu at position 415; and/or Phe at position 421, according to the EU numbering scheme.

In some embodiments, the modified Fc polypeptide has at least 70% identity, at least 75% identity, at least 80% identity, at least 85% identity, at least 90% identity, or at least 95% identity to amino acids 111-217 of any one of SEQ ID NOS:4-90, 97-100, and 105-108 (e.g., SEQ ID NOS:34-38, 58, and 60-90). In some embodiments, the modified Fc polypeptide has at least 70% identity, at least 75% identity, at least 80% identity, at least 85% identity, at least 90% identity, or at least 95% identity to any one of SEQ ID NOS:4-90, 97-100, and 105-108 (e.g., SEQ ID NOS:34-38, 58, and 60-90). In some embodiments, the modified Fc polypeptide comprises the amino acids at EU index positions 384-390 and/or 413-421 of any one of SEQ ID NOS:4-90, 97-100, and 105-108 (e.g., SEQ ID NOS:34-38, 58, and 60-90). In some embodiments, the modified Fc polypeptide comprises the amino acids at EU index positions 380-390 and/or 413-421 of any one of 4-90, 97-100, and 105-108 (e.g., SEQ ID NOS:34-38, 58, and 60-90). In some embodiments, the modified Fc polypeptide comprises the amino acids at EU index positions 380-392 and/or 413-426 of any one of SEQ ID NOS:4-90, 97-100, and 105-108 (e.g., SEQ ID NOS:34-38, 58, and 60-90).

In some embodiments, the modified Fc polypeptide has at least 75% identity, at least 80% identity, at least 85% identity, at least 90% identity, or at least 95% identity to any one of SEQ ID NOS:4-90, 97-100, and 105-108 (e.g., SEQ ID NOS:34-38, 58, and 60-90), and further comprises at least five, six, seven, eight, nine, ten, eleven, twelve, thirteen, fourteen, fifteen, or sixteen of the positions, numbered according to the EU index, as follows: Trp, Tyr, Leu, Gln, or Glu at position 380; Leu, Tyr, Met, or Val at position 384; Leu, Thr, His, or Pro at position 386; Val, Pro, or an acidic amino acid at position 387; an aromatic amino acid, e.g., Trp, at position 388; Val, Ser, or Ala at position 389; Ser or Asn at position 390; Ser, Thr, Gln, or Phe at position 391; Gln, Phe, or His at position 392; an acidic amino acid, Ala, Ser, Leu, Thr, or Pro at position 413; Lys, Arg, Gly or Pro at position 414; Glu or Ser at position 415; Thr or an acidic amino acid at position 416; Trp, Tyr, His or Phe at position 421; Ser, Thr, Glu or Lys at position 424; and Ser, Trp, or Gly at position 426.

In some embodiments, the modified Fc polypeptide comprises the amino acid sequence of any one of SEQ ID NOS:34-38, 58, and 60-90. In other embodiments, the modified Fc polypeptide comprises the amino acid sequence of any one of SEQ ID NOS:34-38, 58, and 60-90, but in which one, two, or three amino acids are substituted.

In some embodiments, the modified Fc polypeptide comprises additional mutations such as the mutations described in Section VI below, including, but not limited to, a knob mutation (e.g., T366W as numbered with reference to EU numbering), hole mutations (e.g., T366S, L368A, and Y407V as numbered with reference to EU numbering), mutations that modulate effector function (e.g., L234A, L235A, and/or P329G (e.g., L234A and L235A) as numbered with reference to EU numbering), and/or mutations that increase serum stability or serum half-life (e.g., (i) M252Y, S254T, and T256E as numbered with reference to EU numbering, or (ii) N434S with or without M428L as numbered according to the EU numbering scheme). By way of illustration, SEQ ID NOS:156-229 provide non-limiting examples of modified Fc polypeptides with mutations in the CH3 domain (e.g., clones CH3C.35.20.1, CH3C.35.23.2, CH3C.35.23.3, CH3C.35.23.4, CH3C.35.21.17.2, and CH3C.35.23) comprising one or more of these additional mutations.

In some embodiments, the modified Fc polypeptide comprises a knob mutation (e.g., T366W as numbered with reference to EU numbering) and has at least 85% identity, at least 90% identity, or at least 95% identity to the sequence of any one of SEQ ID NOS:156, 168, 180, 192, 204, and 216. In some embodiments, the modified Fc polypeptide comprises the sequence of any one of SEQ ID NOS:156, 168, 180, 192, 204, and 216.

In some embodiments, the modified Fc polypeptide comprises a knob mutation (e.g., T366W as numbered with reference to EU numbering) and mutations that modulate effector function (e.g., L234A, L235A, and/or P329G (e.g., L234A and L235A) as numbered with reference to EU numbering), and has at least 85% identity, at least 90% identity, or at least 95% identity to the sequence of any one of SEQ ID NOS:157, 158, 169, 170, 181, 182, 193, 194, 205, 206, 217, 218, 228, and 229. In some embodiments, the modified Fc polypeptide comprises the sequence of any one of SEQ ID NOS:157, 158, 169, 170, 181, 182, 193, 194, 205, 206, 217, and 218.

In some embodiments, the modified Fc polypeptide comprises a knob mutation (e.g., T366W as numbered with reference to EU numbering) and mutations that increase serum stability or serum half-life (e.g., (i) M252Y, S254T, and T256E as numbered with reference to EU numbering, or (ii) N434S with or without M428L as numbered according to the EU numbering scheme), and has at least 85% identity, at least 90% identity, or at least 95% identity to the sequence of any one of SEQ ID NOS:159, 171, 183, 195, 207, and 219. In some embodiments, the modified Fc polypeptide comprises the sequence of any one of SEQ ID NOS:159, 171, 183, 195, 207, and 219.

In some embodiments, the modified Fc polypeptide comprises a knob mutation (e.g., T366W as numbered with reference to EU numbering), mutations that modulate effector function (e.g., L234A, L235A, and/or P329G (e.g., L234A and L235A) as numbered with reference to EU numbering), and mutations that increase serum stability or serum half-life (e.g., (i) M252Y, S254T, and T256E as numbered with reference to EU numbering, or (ii) N434S with or without M428L as numbered according to the EU numbering scheme), and has at least 85% identity, at least 90% identity, or at least 95% identity to the sequence of any one of SEQ ID NOS:160, 161, 172, 173, 184, 185, 196, 197, 208, 209, 220, and 221. In some embodiments, the modified Fc polypeptide comprises the sequence of any one of SEQ ID NOS:160, 161, 172, 173, 184, 185, 196, 197, 208, 209, 220, and 221.

In some embodiments, the modified Fc polypeptide comprises hole mutations (e.g., T366S, L368A, and Y407V as numbered with reference to EU numbering) and has at least 85% identity, at least 90% identity, or at least 95% identity to the sequence of any one of SEQ ID NOS:162, 174, 186, 198, 210, and 222. In some embodiments, the modified Fc polypeptide comprises the sequence of any one of SEQ ID NOS:162, 174, 186, 198, 210, and 222.

In some embodiments, the modified Fc polypeptide comprises hole mutations (e.g., T366S, L368A, and Y407V as numbered with reference to EU numbering) and mutations that modulate effector function (e.g., L234A, L235A, and/or P329G (e.g., L234A and L235A) as numbered with reference to EU numbering), and has at least 85% identity, at least 90% identity, or at least 95% identity to the sequence of any one of SEQ ID NOS:163, 164, 175, 176, 187, 188, 199, 200, 211, 212, 223, and 224. In some embodiments, the modified Fc polypeptide comprises the sequence of any one of SEQ ID NOS:163, 164, 175, 176, 187, 188, 199, 200, 211, 212, 223, and 224.

In some embodiments, the modified Fc polypeptide comprises hole mutations (e.g., T366S, L368A, and Y407V as numbered with reference to EU numbering) and mutations that increase serum stability or serum half-life (e.g., (i) M252Y, S254T, and T256E as numbered with reference to EU numbering, or (ii) N434S with or without M428L as numbered according to the EU numbering scheme), and has at least 85% identity, at least 90% identity, or at least 95% identity to the sequence of any one of SEQ ID NOS:165, 177, 189, 201, 213, and 225. In some embodiments, the modified Fc polypeptide comprises the sequence of any one of SEQ ID NOS:165, 177, 189, 201, 213, and 225.

In some embodiments, the modified Fc polypeptide comprises hole mutations (e.g., T366S, L368A, and Y407V as numbered with reference to EU numbering), mutations that modulate effector function (e.g., L234A, L235A, and/or P329G (e.g., L234A and L235A) as numbered with reference to EU numbering), and mutations that increase serum stability or serum half-life (e.g., (i) M252Y, S254T, and T256E as numbered with reference to EU numbering, or (ii) N434S with or without M428L as numbered according to the EU numbering scheme), and has at least 85% identity, at least 90% identity, or at least 95% identity to the sequence of any one of SEQ ID NOS:166, 167, 178, 179, 190, 191, 202, 203, 214, 215, 226, and 227. In some embodiments, the modified Fc polypeptide comprises the sequence of any one of SEQ ID NOS:166, 167, 178, 179, 190, 191, 202, 203, 214, 215, 226, and 227.

In some embodiments, a modified Fc polypeptide that specifically binds to TfR comprises at least two, three, four, five, six, seven, or eight substitutions at positions 345, 346, 347, 349, 437, 438, 439, and 440, according to the EU numbering scheme. Illustrative modified Fc polypeptides are provided in SEQ ID NOS:124-128. In some embodiments, the modified Fc polypeptide comprises Gly at position 437; Phe at position 438; and/or Asp at position 440. In some embodiments, Glu is present at position 440. In certain embodiments, the modified Fc polypeptide comprises at least one substitution at a position as follows: Phe or Ile at position 345; Asp, Glu, Gly, Ala, or Lys at position 346; Tyr, Met, Leu, Ile, or Asp at position 347; Thr or Ala at position 349; Gly at position 437; Phe at position 438; His Tyr, Ser, or Phe at position 439; or Asp at position 440. In some embodiments, two, three, four, five, six, seven, or all eight of positions 345, 346, 347, 349, 437, 438, 439, and 440 and have a substitution as specified in this paragraph. In some embodiments, the modified Fc polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, the modified Fc polypeptide has at least 70% identity, at least 75% identity, at least 80% identity, at least 85% identity, at least 90% identity, or at least 95% identity to amino acids 111-217 of any one of SEQ ID NOS:124-128. In some embodiments, the modified Fc polypeptide has at least 70% identity, at least 75% identity, at least 80% identity, at least 85% identity, at least 90% identity, or at least 95% identity to SEQ ID NOS:124-128. In some embodiments, the modified Fc polypeptide comprises the amino acid sequence of any one of SEQ ID NOS:124-128. In other embodiments, the modified Fc polypeptide comprises the amino acid sequence of any one of SEQ ID NOS:124-128, but in which one, two, or three amino acids are substituted.

TfR-Binding Fc Polypeptides Comprising Mutations in the CH2 Domain

In some embodiments, a modified Fc polypeptide that specifically binds to TfR comprises substitutions in a CH2 domain. In some embodiments, a modified Fc polypeptide comprises a human Ig CH2 domain, such as an IgG CH2 domain, that is modified for TfR-binding activity. The CH2 domain can be of any IgG subtype, i.e., from IgG1, IgG2, IgG3, or IgG4. In the context of IgG antibodies, a CH2 domain refers to the segment of amino acids from about position 231 to about position 340 as numbered according to the EU numbering scheme.

In some embodiments, a modified Fc polypeptide that specifically binds to TfR binds to the apical domain of TfR and may bind to TfR without blocking or otherwise inhibiting binding of transferrin to TfR. In some embodiments, binding of transferrin to TfR is not substantially inhibited. In some embodiments, binding of transferrin to TfR is inhibited by less than about 50% (e.g., less than about 45%, 40%, 35%, 30%, 25%, 20%, 15%, 10%, or 5%). In some embodiments, binding of transferrin to TfR is inhibited by less than about 20% (e.g., less than about 19%, 18%, 17%, 16%, 15%, 14%, 13%, 12%, 11%, 10%, 9%, 8%, 7%, 6%, 5%, 4%, 3%, 2%, or 1%).

In some embodiments, a modified Fc polypeptide that specifically binds to TfR comprises at least two, three, four, five, six, seven, eight, or nine substitutions at positions 274, 276, 283, 285, 286, 287, 288, and 290, according to the EU numbering scheme. Illustrative modified Fc polypeptides are provided in SEQ ID NOS:129-133. In some embodiments, the modified Fc polypeptide comprises Glu at position 287 and/or Trp at position 288. In some embodiments, the modified Fc polypeptide comprises at least one substitution at a position as follows: Glu, Gly, Gln, Ser, Ala, Asn, Tyr, or Trp at position 274; Ile, Val, Asp, Glu, Thr, Ala, or Tyr at position 276; Asp, Pro, Met, Leu, Ala, Asn, or Phe at position 283; Arg, Ser, Ala, or Gly at position 285; Tyr, Trp, Arg, or Val at position 286; Glu at position 287; Trp or Tyr at position 288; Gln, Tyr, His, Ile, Phe, Val, or Asp at position 289; or Leu, Trp, Arg, Asn, Tyr, or Val at position 290. In some embodiments, two, three, four, five, six, seven, eight, or all nine of positions 274, 276, 283, 285, 286, 287, 288, and 290 have a substitution as specified in this paragraph. In some embodiments, the modified Fc polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, the modified Fc polypeptide comprises Glu, Gly, Gln, Ser, Ala, Asn, or Tyr at position 274; Ile, Val, Asp, Glu, Thr, Ala, or Tyr at position 276 Asp, Pro, Met, Leu, Ala, or Asn at position 283; Arg, Ser, or Ala at position 285; Tyr, Trp, Arg, or Val at position 286; Glu at position 287; Trp at position 288; Gln, Tyr, His, Ile, Phe, or Val at position 289; and/or Leu, Trp, Arg, Asn, or Tyr at position 290. In some embodiments, the modified Fc polypeptide comprises Arg at position 285; Tyr or Trp at position 286; Glu at position 287; Trp at position 288; and/or Arg or Trp at position 290.

In some embodiments, the modified Fc polypeptide has at least 70% identity, at least 75% identity, at least 80% identity, at least 85% identity, at least 90% identity, or at least 95% identity to amino acids 1-110 of any one of SEQ ID NOS:129-133. In some embodiments, the modified Fc polypeptide has at least 70% identity, at least 75% identity, at least 80% identity, at least 85% identity, at least 90% identity, or at least 95% identity to SEQ ID NOS:129-133. In some embodiments, the modified Fc polypeptide comprises the amino acid sequence of any one of SEQ ID NOS:129-133. In other embodiments, the modified Fc polypeptide comprises the amino acid sequence of any one of SEQ ID NOS:129-133, but in which one, two, or three amino acids are substituted.

In some embodiments, a modified Fc polypeptide that specifically binds to TfR comprises at least two, three, four, five, six, seven, eight, nine, or ten substitutions at positions 266, 267, 268, 269, 270, 271, 295, 297, 298, and 299, according to the EU numbering scheme. Illustrative modified Fc polypeptides are provided in SEQ ID NOS:134-138. In some embodiments, the modified Fc polypeptide comprises Pro at position 270, Glu at position 295, and/or Tyr at position 297. In some embodiments, the modified Fc polypeptide comprises at least one substitution at a position as follows: Pro, Phe, Ala, Met, or Asp at position 266; Gln, Pro, Arg, Lys, Ala, Ile, Leu, Glu, Asp, or Tyr at position 267; Thr, Ser, Gly, Met, Val, Phe, Trp, or Leu at position 268; Pro, Val, Ala, Thr, or Asp at position 269; Pro, Val, or Phe at position 270; Trp, Gln, Thr, or Glu at position 271; Glu, Val, Thr, Leu, or Trp at position 295; Tyr, His, Val, or Asp at position 297; Thr, His, Gln, Arg, Asn, or Val at position 298; or Tyr, Asn, Asp, Ser, or Pro at position 299. In some embodiments, two, three, four, five, six, seven, eight, nine, or all ten of positions 266, 267, 268, 269, 270, 271, 295, 297, 298, and 299 have a substitution as specified in this paragraph. In some embodiments, a modified Fc polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, the modified Fc polypeptide comprises Pro, Phe, or Ala at position 266; Gln, Pro, Arg, Lys, Ala, or Ile at position 267; Thr, Ser, Gly, Met, Val, Phe, or Trp at position 268; Pro, Val, or Ala at position 269; Pro at position 270; Trp or Gln at position 271; Glu at position 295; Tyr at position 297; Thr, His, or Gln at position 298; and/or Tyr, Asn, Asp, or Ser at position 299.

In some embodiments, the modified Fc polypeptide comprises Met at position 266; Leu or Glu at position 267; Trp at position 268; Pro at position 269; Val at position 270; Thr at position 271; Val or Thr at position 295; His at position 197; His, Arg, or Asn at position 198; and/or Pro at position 299.

In some embodiments, the modified Fc polypeptide comprises Asp at position 266; Asp at position 267; Leu at position 268; Thr at position 269; Phe at position 270; Gln at position 271; Val or Leu at position 295; Val at position 297; Thr at position 298; and/or Pro at position 299.

In some embodiments, the modified Fc polypeptide has at least 70% identity, at least 75% identity, at least 80% identity, at least 85% identity, at least 90% identity, or at least 95% identity to amino acids 1-110 of any one of SEQ ID NOS:134-138. In some embodiments, the modified Fc polypeptide has at least 70% identity, at least 75% identity, at least 80% identity, at least 85% identity, at least 90% identity, or at least 95% identity to SEQ ID NOS:134-138.

In some embodiments, the modified Fc polypeptide comprises the amino acid sequence of any one of SEQ ID NOS:134-138. In other embodiments, the modified Fc polypeptide comprises the amino acid sequence of any one of SEQ ID NOS:134-138, but in which one, two, or three amino acids are substituted.

In some embodiments, a modified Fc polypeptide that specifically binds to TfR comprises at least two, three, four, five, six, seven, eight, nine, or ten substitutions at positions 268, 269, 270, 271, 272, 292, 293, 294, and 300, according to the EU numbering scheme. Illustrative modified Fc polypeptides are provided in SEQ ID NOS:139-143. In some embodiments, the modified Fc polypeptide comprises at least one substitution at a position as follows: Val or Asp at position 268; Pro, Met, or Asp at position 269; Pro or Trp at position 270; Arg, Trp, Glu, or Thr at position 271; Met, Tyr, or Trp at position 272; Leu or Trp at position 292; Thr, Val, Ile, or Lys at position 293; Ser, Lys, Ala, or Leu at position 294; His, Leu, or Pro at position 296; or Val or Trp at position 300. In some embodiments, two, three, four, five, six, seven, eight, nine, or all ten of positions 268, 269, 270, 271, 272, 292, 293, 294, and 300 have a substitution as specified in this paragraph. In some embodiments, the modified Fc polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, the modified Fc polypeptide comprises Val at position 268; Pro at position 269; Pro at position 270; Arg or Trp at position 271; Met at position 272; Leu at position 292; Thr at position 293; Ser at position 294; His at position 296; and/or Val at position 300.

In some embodiments, the modified Fc polypeptide comprises Asp at position 268; Met or Asp at position 269; Trp at position 270; Glu or Thr at position 271; Tyr or Trp at position 272; Trp at position 292; Val, Ile, or Lys at position 293; Lys, Ala, or Leu at position 294; Leu or Pro at position 296; and/or Trp at position 300.

In some embodiments, the modified Fc polypeptide has at least 70% identity, at least 75% identity, at least 80% identity, at least 85% identity, at least 90% identity, or at least 95% identity to amino acids 1-110 of any one of SEQ ID NOS:139-143. In some embodiments, the modified Fc polypeptide has at least 70% identity, at least 75% identity, at least 80% identity, at least 85% identity, at least 90% identity, or at least 95% identity to SEQ ID NOS:139-143. In some embodiments, the modified Fc polypeptide comprises the amino acid sequence of any one of SEQ ID NOS:139-143. In other embodiments, the modified Fc polypeptide comprises the amino acid sequence of any one of SEQ ID NOS:139-143, but in which one, two, or three amino acids are substituted.

In some embodiments, a modified Fc polypeptide that specifically binds to TfR has at least two, three, four, five, six, seven, eight, nine, or ten substitutions at positions 272, 274, 276, 322, 324, 326, 329, 330, and 331, according to the EU numbering scheme. Illustrative modified Fc polypeptides are provided in SEQ ID NOS:144-148. In some embodiments, the modified Fc polypeptide comprises Trp at position 330. In some embodiments, the modified Fc polypeptide comprises at least one substitution at a position as follows: Trp, Val, Ile, or Ala at position 272; Trp or Gly at position 274; Tyr, Arg, or Glu at position 276; Ser, Arg, or Gln at position 322; Val, Ser, or Phe at position 324; Ile, Ser, or Trp at position 326; Trp, Thr, Ser, Arg, or Asp at position 329; Trp at position 330; or Ser, Lys, Arg, or Val at position 331. In some embodiments, two, three, four, five, six, seven, eight, or all nine of positions 272, 274, 276, 322, 324, 326, 329, 330, and 331 have a substitution as specified in this paragraph. In some embodiments, the modified Fc polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

In some embodiments, the modified Fc polypeptide comprises two, three, four, five, six, seven, eight, or nine positions selected from the following: position 272 is Trp, Val, Ile, or Ala; position 274 is Trp or Gly; position 276 is Tyr, Arg, or Glu; position 322 is Ser, Arg, or Gln; position 324 is Val, Ser, or Phe; position 326 is Ile, Ser, or Trp; position 329 is Trp, Thr, Ser, Arg, or Asp; position 330 is Trp; and position 331 is Ser, Lys, Arg, or Val. In some embodiments, the modified Fc polypeptide comprises Val or Ile at position 272; Gly at position 274; Arg at position 276; Arg at position 322; Ser at position 324; Ser at position 326; Thr, Ser, or Arg at position 329; Trp at position 330; and/or Lys or Arg at position 331.

In some embodiments, the modified Fc polypeptide has at least 70% identity, at least 75% identity, at least 80% identity, at least 85% identity, at least 90% identity, or at least 95% identity to amino acids 1-110 of any one of SEQ ID NOS:144-148. In some embodiments, the modified Fc polypeptide has at least 70% identity, at least 75% identity, at least 80% identity, at least 85% identity, at least 90% identity, or at least 95% identity to SEQ ID NOS:144-148. In some embodiments, the modified Fc polypeptide comprises the amino acid sequence of any one of SEQ ID NOS:144-148. In other embodiments, the modified Fc polypeptide comprises the amino acid sequence of any one of SEQ ID NOS:144-148, but in which one, two, or three amino acids are substituted.

VI. Additional Fc Polypeptide Mutations

In some aspects, a fusion protein described herein comprises two Fc polypeptides that may each comprise independently selected modifications or may be a wild-type Fc polypeptide, e.g., a human IgG1 Fc polypeptide. In some embodiments, one or both Fc polypeptides contains one or more modifications that confer binding to a blood-brain barrier (BBB) receptor, e.g., transferrin receptor (TfR). Non-limiting examples of other mutations that can be introduced into one or both Fc polypeptides include, e.g., mutations to increase serum stability or serum half-life, to modulate effector function, to influence glycosylation, to reduce immunogenicity in humans, and/or to provide for knob and hole heterodimerization of the Fc polypeptides.

In some embodiments, the Fc polypeptides present in the fusion protein independently have an amino acid sequence identity of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% to a corresponding wild-type Fc polypeptide (e.g., a human IgG1, IgG2, IgG3, or IgG4 Fc polypeptide).

In some embodiments, the Fc polypeptides present in the fusion protein include knob and hole mutations to promote heterodimer formation and hinder homodimer formation. Generally, the modifications introduce a protuberance ("knob") at the interface of a first polypeptide and a corresponding cavity ("hole") in the interface of a second polypeptide, such that the protuberance can be positioned in the cavity so as to promote heterodimer formation and thus hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). In some embodiments, such additional mutations are at a position in the Fc polypeptide that does not have a negative effect on binding of the polypeptide to a BBB receptor, e.g., TfR.

In one illustrative embodiment of a knob and hole approach for dimerization, position 366 (numbered according to the EU numbering scheme) of one of the Fc polypeptides present in the fusion protein comprises a tryptophan in place of a native threonine. The other Fc polypeptide in the dimer has a valine at position 407 (numbered according to the EU numbering scheme) in place of the native tyrosine. The other Fc polypeptide may further comprise a substitution in which the native threonine at position 366 (numbered according to the EU numbering scheme) is substituted with a serine and a native leucine at position 368 (numbered according to the EU numbering scheme) is substituted with an alanine. Thus, one of the Fc polypeptides of a fusion protein described herein has the T366W knob mutation and the other Fc polypeptide has the Y407V mutation, which is typically accompanied by the T366S and L368A hole mutations.

In some embodiments, modifications to enhance serum half-life may be introduced. For example, in some embodiments, one or both Fc polypeptides present in a fusion protein described herein may comprise a tyrosine at position 252, a threonine at position 254, and a glutamic acid at position 256, as numbered according to the EU numbering scheme. Thus, one or both Fc polypeptides may have M252Y, S254T, and T256E substitutions. Alternatively, one or both Fc polypeptides may have M428L and N434S substitutions, as numbered according to the EU numbering scheme. Alternatively, one or both Fc polypeptides may have an N434S or N434A substitution.

In some embodiments, one or both Fc polypeptides present in a fusion protein described herein may comprise modifications that reduce effector function, i.e., having a reduced ability to induce certain biological functions upon binding to an Fc receptor expressed on an effector cell that mediates the effector function. Examples of antibody effector functions include, but are not limited to, C1q binding and complement dependent cytotoxicity (CDC), Fc receptor binding, antibody-dependent cell-mediated cytotoxicity (ADCC), antibody-dependent cell-mediated phagocytosis (ADCP), down-regulation of cell surface receptors (e.g., B cell receptor), and B-cell activation. Effector functions may vary with the antibody class. For example, native human IgG1 and IgG3 antibodies can elicit ADCC and CDC activities upon binding to an appropriate Fc receptor present on an immune system cell; and native human IgG1, IgG2, IgG3, and IgG4 can elicit ADCP functions upon binding to the appropriate Fc receptor present on an immune cell.

In some embodiments, one or both Fc polypeptides present in a fusion protein described herein may also be engineered to contain other modifications for heterodimerization, e.g., electrostatic engineering of contact residues within a CH3-CH3 interface that are naturally charged or hydrophobic patch modifications.

In some embodiments, one or both Fc polypeptides present in a fusion protein described herein may include additional modifications that modulate effector function.

In some embodiments, one or both Fc polypeptides present in a fusion protein described herein may comprise modifications that reduce or eliminate effector function. Illustrative Fc polypeptide mutations that reduce effector function include, but are not limited to, substitutions in a CH2 domain, e.g., at positions 234 and 235, according to the EU numbering scheme. For example, in some embodiments, one or both Fc polypeptides can comprise alanine residues at positions 234 and 235. Thus, one or both Fc polypeptides may have L234A and L235A (LALA) substitutions.

Additional Fc polypeptide mutations that modulate an effector function include, but are not limited to, the following: position 329 may have a mutation in which proline is substituted with a glycine or arginine or an amino acid residue large enough to destroy the Fc/Fcγ receptor interface that is formed between proline 329 of the Fc and tryptophan residues Trp 87 and Trp 110 of FcγRIII Additional illustrative substitutions include S228P, E233P, L235E, N297A, N297D, and P331S, according to the EU numbering scheme. Multiple substitutions may also be present, e.g., L234A and L235A of a human IgG1 Fc region; L234A, L235A, and P329G of a human IgG1 Fc region; S228P and L235E of a human IgG4 Fc region; L234A and G237A of a human IgG1 Fc region; L234A, L235A, and G237A of a human IgG1 Fc region; V234A and G237A of a human IgG2 Fc region; L235A, G237A, and E318A of a human IgG4 Fc region; and S228P and L236E of a human IgG4 Fc region, according to the EU numbering scheme. In some embodiments, one or both Fc polypeptides may have one or more amino acid substitutions that modulate ADCC, e.g., substitutions at positions 298, 333, and/or 334, according to the EU numbering scheme.

Illustrative Fc Polypeptides Comprising Additional Mutations

By way of non-limiting example, one or both Fc polypeptides present in a fusion protein described herein may comprise additional mutations including a knob mutation (e.g., T366W as numbered according to the EU numbering scheme), hole mutations (e.g., T366S, L368A, and Y407V as numbered according to the EU numbering scheme), mutations that modulate effector function (e.g., L234A, L235A, and/or P329G (e.g., L234A and L235A) as numbered according to the EU numbering scheme), and/or mutations that increase serum stability or serum half-life (e.g., (i) M252Y, S254T, and T256E as numbered with reference to EU numbering, or (ii) N434S with or without M428L as numbered according to the EU numbering scheme).

In some embodiments, an Fc polypeptide may have a knob mutation (e.g., T366W as numbered according to the EU numbering scheme) and at least 85% identity, at least 90% identity, or at least 95% identity to the sequence of any one of SEQ ID NOS:1, 4-90, and 124-148. In some embodiments, an Fc polypeptide having the sequence of any one of SEQ ID NOS:1, 4-90, and 124-148 may be modified to have a knob mutation.

In some embodiments, an Fc polypeptide may have a knob mutation (e.g., T366W as numbered according to the EU numbering scheme), mutations that modulate effector function (e.g., L234A, L235A, and/or P329G (e.g., L234A and L235A) as numbered according to the EU numbering scheme), and at least 85% identity, at least 90% identity, or at least 95% identity to the sequence of any one of SEQ ID NOS:1, 4-90, and 124-148. In some embodiments, an Fc polypeptide having the sequence of any one of SEQ ID NOS:1, 4-90, and 124-148 may be modified to have a knob mutation and mutations that modulate effector function.

In some embodiments, an Fc polypeptide may have a knob mutation (e.g., T366W as numbered according to the EU numbering scheme), mutations that increase serum stability or serum half-life (e.g., (i) M252Y, S254T, and T256E as numbered with reference to EU numbering, or (ii) N434S with or without M428L as numbered according to the EU numbering scheme), and at least 85% identity, at least 90% identity, or at least 95% identity to the sequence of any one of SEQ ID NOS:1, 4-90, and 124-148. In some embodiments, an Fc polypeptide having the sequence of any one of SEQ ID NOS:1, 4-90, and 124-148 may be modified to have a knob mutation and mutations that increase serum stability or serum half-life.

In some embodiments, an Fc polypeptide may have a knob mutation (e.g., T366W as numbered according to the EU numbering scheme), mutations that modulate effector function (e.g., L234A, L235A, and/or P329G (e.g., L234A and L235A) as numbered according to the EU numbering scheme), mutations that increase serum stability or serum half-life (e.g., (i) M252Y, S254T, and T256E as numbered with reference to EU numbering, or (ii) N434S with or without M428L as numbered according to the EU numbering scheme), and at least 85% identity, at least 90% identity, or at least 95% identity to the sequence of any one of SEQ ID NOS:1, 4-90, and 124-148. In some embodiments, an Fc polypeptide having the sequence of any one of SEQ ID NOS:1, 4-90, and 124-148 may be modified to have a knob mutation, mutations that modulate effector function, and mutations that increase serum stability or serum half-life.

In some embodiments, an Fc polypeptide may have hole mutations (e.g., T366S, L368A, and Y407V as numbered according to the EU numbering scheme) and at least 85% identity, at least 90% identity, or at least 95% identity to the sequence of any one of SEQ ID NOS:1, 4-90, and 124-148. In some embodiments, an Fc polypeptide having the sequence of any one of SEQ ID NOS:1, 4-90, and 124-148 may be modified to have hole mutations.

In some embodiments, an Fc polypeptide may have hole mutations (e.g., T366S, L368A, and Y407V as numbered according to the EU numbering scheme), mutations that modulate effector function (e.g., L234A, L235A, and/or P329G (e.g., L234A and L235A) as numbered according to the EU numbering scheme), and at least 85% identity, at least 90% identity, or at least 95% identity to the sequence of any one of SEQ ID NOS:1, 4-90, and 124-148. In some embodiments, an Fc polypeptide having the sequence of any one of SEQ ID NOS:1, 4-90, and 124-148 may be modified to have hole mutations and mutations that modulate effector function.

In some embodiments, an Fc polypeptide may have hole mutations (e.g., T366S, L368A, and Y407V as numbered according to the EU numbering scheme), mutations that increase serum or serum half-life (e.g., (i) M252Y, S254T, and T256E as numbered with reference to EU numbering, or (ii) N434S with or without M428L as numbered according to the EU numbering scheme), and at least 85% identity, at least 90% identity, or at least 95% identity to the sequence of any one of SEQ ID NOS:1, 4-90, and 124-148. In some embodiments, an Fc polypeptide having sequence of any one of SEQ ID NOS:1, 4-90, and 124-148 may be modified to have hole mutations and mutations that increase serum stability or serum half-life.

In some embodiments, an Fc polypeptide may have hole mutations (e.g., T366S, L368A, and Y407V as numbered according to the EU numbering scheme), mutations that modulate effector function (e.g., L234A, L235A, and/or P329G (e.g., L234A and L235A) as numbered according to the EU numbering scheme), mutations that increase serum stability or serum half-life (e.g., (i) M252Y, S254T, and T256E as numbered with reference to EU numbering, or (ii) N434S with or without M428L as numbered according to the EU numbering scheme), and at least 85% identity, at least 90% identity, or at least 95% identity to the sequence of any one of SEQ ID NOS:1, 4-90, and 124-148. In some embodiments, an Fc polypeptide having the sequence of any one of SEQ ID NOS:1, 4-90, and 124-148 may be modified to have hole mutations, mutations that modulate effector function, and mutations that increase serum stability or serum half-life.

VII. Illustrative Fusion Proteins Comprising an ERT Enzyme

In some aspects, a fusion protein described herein comprises a first Fc polypeptide that is linked to an enzyme replacement therapy (ERT) enzyme, an ERT enzyme variant, or a catalytically active fragment thereof; and a second Fc polypeptide that forms an Fc dimer with the first Fc polypeptide. In some embodiments, the first Fc polypeptide and/or the second Fc polypeptide does not include an immunoglobulin heavy and/or light chain variable region sequence or an antigen-binding portion thereof. In some embodiments, the ERT enzyme is IDS, SGSH, ASM, or GBA. In some embodiments, the first Fc polypeptide is a modified Fc polypeptide and/or the second Fc polypeptide is a modified Fc polypeptide. In some embodiments, the second Fc polypeptide is a modified Fc polypeptide. In some embodiments, the modified Fc polypeptide contains one or more modifications that promote its heterodimerization to the other Fc polypeptide. In some embodiments, the modified Fc polypeptide contains one or more modifications that reduce effector function. In some embodiments, the modified Fc polypeptide contains one or more modifications that extend serum half-life. In some embodiments, the modified Fc polypeptide contains one or more modifications that confer binding to a blood-brain barrier (BBB) receptor, e.g., transferrin receptor (TfR).

In other aspects, a fusion protein described herein comprises a first polypeptide chain that comprises a modified Fc polypeptide that specifically binds to a BBB receptor, e.g., TfR, and a second polypeptide chain that comprises an Fc polypeptide which dimerizes with the modified Fc polypeptide to form an Fc dimer. An ERT enzyme may be linked to either the first or the second polypeptide chain. In some embodiments, the ERT enzyme is IDS, SGSH, ASM, or GBA. In some embodiments, the ERT enzyme is linked to the second polypeptide chain. In some embodiments, the protein comprises two ERT enzymes, each linked to one of the polypeptide chains. In some embodiments, the Fc polypeptide may be a BBB receptor-binding polypeptide that specifically binds to the same BBB receptor as the modified Fc polypeptide in the first polypeptide chain. In some embodiments, the Fc polypeptide does not specifically bind to a BBB receptor.

In some embodiments, a fusion protein described herein comprises a first polypeptide chain comprising a modified Fc polypeptide that specifically binds to TfR and a second polypeptide chain that comprises an Fc polypeptide, wherein the modified Fc polypeptide and the Fc polypeptide dimerize to from an Fc dimer. In some embodiments, the ERT enzyme is IDS, SGSH, ASM, or GBA. In some embodiments, the ERT enzyme is linked to the first polypeptide chain. In some embodiments, the ERT enzyme is linked to the second polypeptide chain. In some embodiments, the Fc polypeptide does not specifically bind to a BBB receptor, e.g., TfR.

In some embodiments, a fusion protein described herein comprises a first polypeptide chain that comprises a modified Fc polypeptide that binds to TfR and comprises a T366W (knob) substitution; and a second polypeptide chain that comprises an Fc polypeptide comprising T366S, L368A, and Y407V (hole) substitutions. In some embodiments, the modified Fc polypeptide and/or the Fc polypeptide further comprises L234A and L235A (LALA) substitutions. In some embodiments, the modified Fc polypeptide and/or the Fc polypeptide further comprises M252Y, S254T, and T256E (YTE) substitutions. In some embodiments, the modified Fc polypeptide and/or the Fc polypeptide further comprises L234A and L235A (LALA) substitutions and M252Y, S254T, and T256E (YTE) substitutions. In some embodiments, the modified Fc polypeptide and/or the Fc polypeptide comprises human IgG1 wild-type residues at positions 234, 235, 252, 254, 256, and 366.

In some embodiments, the modified Fc polypeptide comprises the knob, LALA, and YTE mutations as specified for any one of SEQ ID NOS:97-100, 151, 156-161, 168-173, 180-185, 192-197, 204-209, and 216-221, and has at least 85% identity, at least 90% identity, or at least 95% identity to the respective sequence; or comprises the sequence of any one of SEQ ID NOS:97-100, 151, 156-161, 168-173, 180-185, 192-197, 204-209, and 216-221. In some embodiments, the Fc polypeptide comprises the hole, LALA, and YTE mutations as specified for any one of SEQ ID NOS:101-104 and has at least 85% identity, at least 90% identity, or at least 95% identity to the respective sequence; or comprises the sequence of any one of SEQ ID NOS:101-104. In some embodiments, the modified Fc polypeptide comprises any one of SEQ ID NOS:97-100, 151, 156-161, 168-173, 180-185, 192-197, 204-209, and 216-221, and the Fc polypeptide comprises any one of SEQ ID NOS:101-104. In some embodiments, the N-terminus of the modified Fc polypeptide and/or the Fc polypeptide includes a portion of an IgG1 hinge region (e.g., DKTHTCPPCP; SEQ ID NO:113). In some embodiments, the modified Fc polypeptide has at least 85%, at least 90%, or at least 95% identity to any one of SEQ ID NOS:116, 228, and 229, or comprises the sequence of any one of SEQ ID NOS:116, 228, and 229.

In some embodiments, a fusion protein described herein comprises a first polypeptide chain that comprises a modified Fc polypeptide that binds to TfR and comprises T366S, L368A, and Y407V (hole) substitutions; and a second polypeptide chain that comprises an Fc polypeptide comprising a T366W (knob) substitution. In some embodiments, the modified Fc polypeptide and/or the Fc polypeptide further comprises L234A and L235A (LALA) substitutions. In some embodiments, the modified Fc polypeptide and/or the Fc polypeptide further comprises M252Y, S254T, and T256E (YTE) substitutions. In some embodiments, the modified Fc polypeptide and/or the Fc polypeptide further comprises L234A and L235A (LALA) substitutions and M252Y, S254T, and T256E (YTE) substitutions. In some embodiments, the modified Fc polypeptide and/or the Fc polypeptide comprises human IgG1 wild-type residues at positions 234, 235, 252, 254, 256, and 366.

In some embodiments, the modified Fc polypeptide comprises the hole, LALA, and YTE mutations as specified for any one of SEQ ID NOS:105-108, 162-167, 174-179, 186-191, 198-203, 210-215, and 222-227, and has at least 85% identity, at least 90% identity, or at least 95% identity to the respective sequence; or comprises the sequence of any one of SEQ ID NOS:105-108, 162-167, 174-179, 186-191, 198-203, 210-215, and 222-227. In some embodiments, the Fc polypeptide comprises the knob, LALA, and YTE mutations as specified for any one of SEQ ID NOS:109-112 and has at least 85% identity, at least 90% identity, or at least 95% identity to the respective sequence; or comprises the sequence of any one of SEQ ID NOS:109-112. In some embodiments, the modified Fc polypeptide comprises any one of SEQ ID NOS:105-108, 162-167, 174-179, 186-191, 198-203, 210-215, and 222-227, and the Fc polypeptide comprises any one of SEQ ID NOS:109-112. In some embodiments, the N-terminus of the modified Fc polypeptide and/or the Fc polypeptide includes a portion of an IgG1 hinge region (e.g., DKTHTCPPCP; SEQ ID NO:113).

In some embodiments, an ERT enzyme, e.g., IDS, SGSH, ASM, or GBA, present in a fusion protein described herein is linked to a polypeptide chain that comprises an Fc polypeptide having at least 85%, at least 90%, or at least 95% identity to any one of SEQ ID NOS:101-104, or comprises the sequence of any one of SEQ ID NOS:101-104 (e.g., as a fusion polypeptide). In some embodiments, the ERT enzyme, e.g., IDS, SGSH, ASM, or GBA, is linked to the Fc polypeptide by a linker, such as a flexible linker, and/or a hinge region or portion thereof (e.g., DKTHTCPPCP; SEQ ID NO:113). In some embodiments, the ERT enzyme comprises an IDS sequence having at least 85%, at least 90%, or at least 95% identity to any one of SEQ ID NOS:114, 230, and 234, or comprises the sequence of any one of SEQ ID NOS:114, 230, and 234. In some embodiments, the IDS sequence linked to the Fc polypeptide has at least 85%, at least 90%, or at least 95% identity to any one of SEQ ID NOS:115, 117, 231, 232, 235, and 236, or comprises the sequence of any one of SEQ ID NOS:115, 117, 231, 232, 235, and 236. In some embodiments, the ERT enzyme comprises an SGSH sequence having at least 85%, at least 90%, or at least 95% identity to SEQ ID NO:120, or comprises the sequence of SEQ ID NO:120. In some embodiments, the SGSH sequence linked to the Fc polypeptide has at least 85%, at least 90%, or at least 95% identity to any one of SEQ ID NOS:149 and 150, or comprises the sequence of any one of SEQ ID NOS:149 and 150. In some embodiments, the fusion protein comprises a modified Fc polypeptide having at least 85%, at least 90%, or at least 95% identity to any one of SEQ ID NOS:97-100, 151, 156-161, 168-173, 180-185, 192-197, 204-209, and 216-221, or comprises the sequence of any one of SEQ ID NOS:97-100, 151, 156-161, 168-173, 180-185, 192-197, 204-209, and 216-221. In some embodiments, the N-terminus of the Fc polypeptide and/or the modified Fc polypeptide includes a portion of an IgG1 hinge region (e.g., DKTHTCPPCP; SEQ ID NO:113). In some embodiments, the modified Fc polypeptide has at least 85%, at least 90%, or at least 95% identity to any one of SEQ ID NOS:116, 228, and 229, or comprises the sequence of any one of SEQ ID NOS:116, 228, and 229.

In some embodiments, the fusion protein comprises an IDS-Fc fusion polypeptide comprising the sequence of SEQ ID NO:115, and a modified Fc polypeptide comprising the sequence of any one of SEQ ID NOS:205 and 228. In other embodiments, the fusion protein comprises an IDS-Fc fusion polypeptide comprising the sequence of SEQ ID NO:115, and a modified Fc polypeptide comprising the sequence of any one of SEQ ID NOS:169 and 229.

In some embodiments, the fusion protein comprises an IDS-Fc fusion polypeptide comprising the sequence of SEQ ID NO:231, and a modified Fc polypeptide comprising the sequence of any one of SEQ ID NOS:205 and 228. In other embodiments, the fusion protein comprises an IDS-Fc fusion polypeptide comprising the sequence of SEQ ID NO:231, and a modified Fc polypeptide comprising the sequence of any one of SEQ ID NOS:169 and 229.

In some embodiments, the fusion protein comprises an IDS-Fc fusion polypeptide comprising the sequence of SEQ ID NO:235, and a modified Fc polypeptide comprising the sequence of any one of SEQ ID NOS:205 and 228. In other embodiments, the fusion protein comprises an IDS-Fc fusion polypeptide comprising the sequence of SEQ ID NO:235, and a modified Fc polypeptide comprising the sequence of any one of SEQ ID NOS:169 and 229.

In some embodiments, an ERT enzyme, e.g., IDS, SGSH, ASM, or GBA, present in a fusion protein described herein is linked to a polypeptide chain that comprises an Fc polypeptide having at least 85%, at least 90%, or at least 95% identity to any one of SEQ ID NOS:109-112, or comprises the sequence of any one of SEQ ID NOS:109-112 (e.g., as a fusion polypeptide). In some embodiments, the ERT enzyme, e.g., IDS SGSH, ASM, or GBA, is linked to the Fc polypeptide by a linker, such as a flexible linker, and/or a hinge region or portion thereof (e.g., DKTHTCPPCP; SEQ ID NO:113). In some embodiments, the ERT enzyme comprises an IDS sequence having at least 85%, at least 90%, or at least 95% identity to any one of SEQ ID NOS:114, 230, and 234, or comprises the sequence of any one of SEQ ID NOS:114, 230, and 234. In some embodiments, the IDS sequence linked to the Fc polypeptide has at least 85%, at least 90%, or at least 95% identity to any one of SEQ ID NOS:118, 233, and 237, or comprises the sequence of any one of SEQ ID NOS:118, 233, and 237. In some embodiments, the ERT enzyme comprises an SGSH sequence having at least 85%, at least 90%, or at least 95% identity to SEQ ID NO:120, or comprises the sequence of SEQ ID NO:120. In some embodiments, the SGSH sequence linked to the Fc polypeptide has at least 85%, at least 90%, or at least 95% identity to any one of SEQ ID NOS:152 and 153, or comprises the sequence of any one of SEQ ID NOS:152 and 153. In some embodiments, the fusion protein comprises a modified Fc polypeptide having at least 85%, at least 90%, or at least 95% identity to any one of SEQ ID NOS:105-108, 162-167, 174-179, 186-191, 198-203, 210-215, and 222-227, or comprises the sequence of any one of SEQ ID NOS:105-108, 162-167, 174-179, 186-191, 198-203, 210-215, and 222-227. In some embodiments, the N-terminus of the Fc polypeptide and/or the modified Fc polypeptide includes a portion of an IgG1 hinge region (e.g., DKTHTCPPCP; SEQ ID NO:113).

In some embodiments, an ERT enzyme, e.g., IDS, SGSH, ASM, or GBA, present in a fusion protein described herein is linked to a polypeptide chain that comprises a modified Fc polypeptide having at least 85%, at least 90%, or at least 95% identity to any one of SEQ ID NOS:97-100, 151, 156-161, 168-173, 180-185, 192-197, 204-209, and 216-221, or comprises the sequence of any one of SEQ ID NOS:97-100, 151, 156-161, 168-173, 180-185, 192-197, 204-209, and 216-221 (e.g., as a fusion polypeptide). In some embodiments, the ERT enzyme, e.g., IDS, SGSH, ASM, or GBA, is linked to the modified Fc polypeptide by a linker, such as a flexible linker, and/or a hinge region or portion thereof (e.g., DKTHTCPPCP; SEQ ID NO:113). In some embodiments, the ERT enzyme comprises an IDS sequence having at least 85%, at least 90%, or at least 95% identity to any one of SEQ ID NOS:114, 230, and 234, or comprises the sequence of any one of SEQ ID NOS:114, 230, and 234. In some embodiments, the ERT enzyme comprises an SGSH sequence having at least 85%, at least 90%, or at least 95% identity to SEQ ID NO:120, or comprises the sequence of SEQ ID NO:120. In some embodiments, the SGSH sequence linked to the modified Fc polypeptide has at least 85%, at least 90%, or at least 95% identity to any one of SEQ ID NOS:154 and 155, or comprises the sequence of any one of SEQ ID NOS:154 and 155. In some embodiments, the fusion protein comprises an Fc polypeptide having at least 85%, at least 90%, or at least 95% identity to any one of SEQ ID NOS:101-104, 149 and 150, or comprises the sequence of any one of SEQ ID NOS:101-104, 149 and 150. In some embodiments, the N-terminus of the modified Fc polypeptide and/or the Fc polypeptide includes a portion of an IgG1 hinge region (e.g., DKTHTCPPCP; SEQ ID NO:113).

In some embodiments, an ERT enzyme, e.g., IDS, SGSH, ASM, or GBA, present in a fusion protein described herein is linked to a polypeptide chain that comprises a modified Fc polypeptide having at least 85%, at least 90%, or at least 95% identity to any one of SEQ ID NOS:105-108, 162-167, 174-179, 186-191, 198-203, 210-215, and 222-227, or comprises the sequence of any one of SEQ ID NOS:105-108, 162-167, 174-179, 186-191, 198-203, 210-215, and 222-227 (e.g., as a fusion polypeptide). In some embodiments, the ERT enzyme, e.g., IDS, SGSH, ASM, or GBA, is linked to the modified Fc polypeptide by a linker, such as a flexible linker, and/or a hinge region or portion thereof (e.g., DKTHTCPPCP; SEQ ID NO:113). In some embodiments, the ERT enzyme comprises an IDS sequence having at least 85%, at least 90%, or at least 95% identity to any one of SEQ ID NOS:114, 230, and 234, or comprises the sequence of any one of SEQ ID NOS:114, 230, and 234. In some embodiments, the ERT enzyme comprises an SGSH sequence having at least 85%, at least 90%, or at least 95% identity to SEQ ID NO:120, or comprises the sequence of SEQ ID NO:120. In some embodiments, the fusion protein comprises an Fc polypeptide having at least 85%, at least 90%, or at least 95% identity to any one of SEQ ID NOS:109-112, or comprises the sequence of any one of SEQ ID NOS:109-112. In some embodiments, the fusion protein comprises an SGSH sequence linked to an Fc polypeptide having at least 85%, at least 90%, or at least 95% identity to any one of SEQ ID NOS:152 and 153, or comprising the sequence of any one of SEQ ID NOS:152 and 153. In some embodiments, the N-terminus of the modified Fc polypeptide and/or the Fc polypeptide includes a portion of an IgG1 hinge region (e.g., DKTHTCPPCP; SEQ ID NO:113).

VIII. Measuring Binding Kinetics, Affinity, Brain Concentration, and Brain Exposure Fusion proteins and other compositions described herein may have a broad range of binding affinities. For example, in some embodiments, a protein has an affinity for a blood-brain barrier (BBB) receptor, e.g., transferrin receptor (TfR), ranging anywhere from 1 pM to 10 μM. In some embodiments, the affinity for TfR ranges from 1 nM to 5 µM, or from 10 nM to 1 µM. In some embodiments, the affinity for TfR ranges from about 50 nM to about 250 nM.

In some embodiments, the affinity of a TfR-binding polypeptide may be measured in a monovalent format. In other embodiments, affinity may be measured in a bivalent format, e.g., as a dimer comprising a polypeptide-Fab fusion protein.

Methods for analyzing binding affinity, binding kinetics, and cross-reactivity to analyze binding to a BBB receptor, e.g., TfR, are known in the art. These methods include, but are not limited to, solid-phase binding assays (e.g., ELISA assay), immunoprecipitation, surface plasmon resonance (e.g., Biacore™ (GE Healthcare, Piscataway, N.J.)), kinetic exclusion assays (e.g., KinExA®), flow cytometry, fluorescence-activated cell sorting (FACS), BioLayer interferometry (e.g., Octet® (FortéBio, Inc., Menlo Park, Calif.)), and Western blot analysis. In some embodiments, ELISA is used to determine binding affinity and/or cross-reactivity. Methods for performing ELISA assays are known in the art and are also described in the Examples section below. In some embodiments, surface plasmon resonance (SPR) is used to determine binding affinity, binding kinetics, and/or cross-reactivity. In some embodiments, kinetic exclusion assays are used to determine binding affinity, binding kinetics, and/or cross-reactivity. In some embodiments, BioLayer interferometry assays are used to determine binding affinity, binding kinetics, and/or cross-reactivity.

A non-limiting example of a method for determining binding affinity (e.g., for TfR) is described in Example 13 below, in which a Biacore™ instrument was used to determine affinity by surface plasmon resonance (SPR). In this method, an engineered TfR-binding polypeptide, a TfR-binding peptide, or a TfR-binding antibody of interest is captured on a sensor chip and serial dilutions of TfR are injected onto the sensor chip at a specified flow rate (e.g., 30 µL/min) and temperature (e.g., room temperature). Samples are analyzed using specified association and dissociation times (e.g., 45 and 180 seconds, respectively), followed by sensor chip regeneration. Binding responses are corrected by subtracting the measured response from a control (e.g., using an irrelevant IgG at similar density) and then steady-state affinities can be determined by using software to fit the equilibrium response against concentration.

The concentration of an engineered TfR-binding polypeptide, a TfR-binding peptide, a TfR-binding antibody, or an agent (e.g., linked to the engineered TfR-binding polypeptide, TfR-binding peptide, or TfR-binding antibody) in the brain and/or plasma can be measured, for example, using a human transferrin receptor (hTfR) knock-in mouse model. Such a model can be used, for example, to measure and/or compare maximum brain concentration ($C_{max}$) and/or brain exposure, e.g., to determine whether $C_{max}$ is increased and/or brain exposure is prolonged. The creation of a human apical TfR (TfR$^{ms/hu}$) mouse knock-in model is described below in Example 12. To create a suitable model, a CRISPR/Cas9 system can be used to generate a mouse that expresses a human Tfrc apical domain within a murine Tfrc gene (e.g., in which in vivo expression is under the control of an endogenous promoter). In particular, Cas9, single guide RNAs and donor DNA (e.g., a human apical domain coding sequence that has been codon optimized for expression in mouse) can be introduced into mouse embryos (e.g., by pronuclear injection). The embryos can then be transferred to pseudo pregnant females. A founder male from the progeny of the female that received the embryos can be bred to wild-type females to generate F1 heterozygous mice. Homozygous mice can then be subsequently generated from breeding of F1 generation heterozygous mice.

For evaluation of brain and/or plasma concentration or exposure of the engineered TfR-binding polypeptide, TfR-binding peptide, TfR-binding antibody, or agent (e.g., linked to the engineered TfR-binding polypeptide, TfR-binding peptide, or TfR-binding antibody), the engineered TfR-binding polypeptide, TfR-binding peptide, TfR-binding antibody (e.g., linked to the agent) can be administered to the mouse model (e.g., TfR$^{ms/hu}$). Plasma samples can be obtained from the mouse after a suitable period of time, followed by perfusion of the vascular system with a suitable solution. Following perfusion, brains (or portions thereof) can be extracted and homogenized and lysed. Concentrations of the agent in the plasma and/or brain lysate can then be determined using standard methods that will be known to one of ordinary skill in the art. As a non-limiting example, an ELISA-based assay such as one described in Example 3 below can be used to measure concentrations. Briefly, the concentration of an agent, engineered TfR-binding polypeptide, TfR-binding peptide, or TfR-binding antibody (e.g., in plasma or lysate) can be quantified using a sandwich ELISA. A capture antibody (e.g., an anti-Fc capture antibody) can be coated onto a plate (e.g., a 384-well MaxiSorp™ plate) at a desired concentration (e.g., about 3 µg/mL). The plate is blocked (e.g., with 5% BSA) and then incubated with plasma that has been diluted (e.g., 1:1,000 or 1:10,000). Next, a detection antibody is added at a desired concentration (e.g., about 0.5 µg/mL) followed by a secondary antibody such as an anti-goat-HRP antibody. The plates are then developed (e.g., using TMB substrate), stopped (e.g., with sulfuric acid), and the absorbance at an appropriate wavelength (e.g., 450 nm) measured on a plate reader (e.g., a BioTek plate reader). Standard curves can be generated using an appropriate (e.g., 4-fold) dilution series and fit using an algorithm such as a four-parameter logistic regression.

By administering a range of doses to the knock-in mouse model, a standard curve can be generated. By administering to the knock-in mouse model an agent linked to different engineered TfR-binding polypeptides, TfR-binding peptides, or TfR-binding antibodies (e.g., having different TfR affinities), or an agent linked to a reference polypeptide or protein (e.g., that has a weaker affinity for TfR than the polypeptide or protein of interest), comparisons can be made regarding the effects of the engineered TfR-binding polypeptides, TfR-binding peptides, or TfR-binding antibodies on brain exposure to the agent and/or $C_{max}$ values of the agent in the brain.

IX. ERT Enzymes Linked to Fc Polypeptides

In some embodiments, a fusion protein described herein comprises two Fc polypeptides as described herein and one or both of the Fc polypeptides may further comprise a partial or full hinge region. The hinge region can be from any immunoglobulin subclass or isotype. An illustrative immunoglobulin hinge is an IgG hinge region, such as an IgG1 hinge region, e.g., human IgG1 hinge amino acid sequence EPKSCDKTHTCPPCP (SEQ ID NO:95) or a portion thereof (e.g., DKTHTCPPCP; SEQ ID NO:113). In some embodiments, the hinge region is at the N-terminal region of the Fc polypeptide.

In some embodiments, an Fc polypeptide is joined to the ERT enzyme by a linker, e.g., a peptide linker. In some embodiments, the Fc polypeptide is joined to the ERT enzyme by a peptide bond or by a peptide linker, e.g., is a fusion polypeptide. The peptide linker may be configured such that it allows for the rotation of the ERT enzyme relative to the Fc polypeptide to which it is joined; and/or is resistant to digestion by proteases. Peptide linkers may contain natural amino acids, unnatural amino acids, or a combination thereof. In some embodiments, the peptide linker may be a flexible linker, e.g., containing amino acids such as Gly, Asn, Ser, Thr, Ala, and the like. Such linkers are designed using known parameters and may be of any length and contain any number of repeat units of any length (e.g., repeat units of Gly and Ser residues). For example, the linker may have repeats, such as two, three, four, five, or more Gly4-Ser (SEQ ID NO:239) repeats or a single Gly4-Ser (SEQ ID NO:239). In some embodiments, the peptide linker may include a protease cleavage site, e.g., that is cleavable by an enzyme present in the central nervous system.

In some embodiments, the ERT enzyme is joined to the N-terminus of the Fc polypeptide, e.g., by a Gly4-Ser linker (SEQ ID NO:239) or a (Gly4-Ser)$_2$ linker (SEQ ID NO:240). In some embodiments, the Fc polypeptide may comprise a hinge sequence or partial hinge sequence at the N-terminus that is joined to the linker or directly joined to the ERT enzyme.

In some embodiments, the ERT enzyme is joined to the C-terminus of the Fc polypeptide, e.g., by a Gly4-Ser linker (SEQ ID NO:239) or a (Gly4-Ser)$_2$ linker (SEQ ID NO:240). In some embodiments, the C-terminus of the Fc polypeptide is directly joined to the ERT enzyme.

In some embodiments, the ERT enzyme is joined to the Fc polypeptide by a chemical cross-linking agent. Such conjugates can be generated using well-known chemical cross-linking reagents and protocols. For example, there are a large number of chemical cross-linking agents that are known to those skilled in the art and useful for cross-linking the polypeptide with an agent of interest. For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including N-hydroxysuccinimide (NHS) or its water soluble analog N-hydroxysulfosuccinimide (sulfo-NHS), succinimidyl 4-(N-maleimidomethyl)cyclohexane-1-carboxylate (SM-CC), m-maleimidobenzoyl-N-hydroxysuccinimide ester (MBS); N-succinimidyl (4-iodoacetyl) aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-a-methyl-a-(2-pyridyldithio)-toluene (SMPT), N-succinimidyl 3-(2-pyridyldithio)propionate (SPDP), and succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exist a number of other cross-linking agents including homobifunctional and photoreactive cross-linkers. Disuccinimidyl subcrate (DSS), bismaleimidohexane (BMH) and dimethylpimelimidate. 2HCl (DMP) are examples of useful homobifunctional cross-linking agents, and bis[B-(4-azidosalicylamido)ethyl] disulfide (BASED) and N-succinimidyl-6(4'-azido-2'-nitrophenylamino)hexanoate (SANPAH) are examples of useful photoreactive cross-linkers.

X. Evaluation of Protein Activity

Activity of fusion proteins described herein that comprise an ERT enzyme such as, e.g., IDS, SGSH, ASM, or GBA, can be assessed using various assays, including assays that measure activity in vitro using an artificial substrate, such as those described in the Examples section. An illustrative protocol for measuring IDS activity in vitro is provided in Example 2. An illustrative protocol for measuring ASM activity in vitro is provided in Example 5. Illustrative protocols for measuring SGSH activity in vitro are provided in Examples 7 and 8.

In some aspects, IDS activity is assessed by assaying a sample, such as a cell sample, tissue sample, or fluid sample (e.g., CSF or urine), for the amount of the glycosaminoglycans (GAGs) heparan and dermatan sulfate, which accumulate as a result of IDS deficiency. The amount of heparan and dermatan sulfate is determined by digesting GAGs present in a sample with heparinase and chondroitinase. The resulting disaccharides can then be assayed by mass spectrometry (e.g., LC-MS/MS). Samples with high levels of heparan and dermatan sulfate accumulation will have increased amounts of heparan and dermatan sulfate-derived disaccharides. Thus, the level of disaccharides is inversely proportional to IDS enzymatic activity.

The mass spectrometry (e.g., LC-MS/MS) assay can be performed on any sample in which GAGs accumulate, including cell samples, tissue samples, and fluid samples. Such samples can be evaluated to monitor the activity of an IDS-containing protein described herein, e.g., that is administered to cells in vitro, or in some embodiments, administered to a subject in vivo. The subject may be an animal, such as a rodent, e.g., a mouse, or a non-human primate. In some embodiments, the subject is a human patient, such as a patient having Hunter syndrome that is undergoing treatment with an IDS therapy, wherein the assay is used to monitor IDS activity in the patient. In some embodiments, the human patient is undergoing treatment with a fusion protein described herein.

For cellular samples, such as cells or tissue samples, the assay comprises disrupting the cells and breaking open microvesicles. Disruption of cells or breaking open microvesicles may be achieved by using freeze-thawing and/or sonication to obtain an extract (e.g., a cellular extract) comprising GAGs. The GAGs are then subject to treatment with heparinases (e.g., any described herein) and chondroitinase, which break down heparan sulfate and dermatan sulfate GAGs. Following digestion, a supernatant containing the GAG disaccharides is obtained and the disaccharide products are analyzed by mass spectrometry (e.g., LC-MS/MS). An illustrative protocol is provided in Example 2.

In some embodiments, a cell sample to be assayed for IDS activity is washed and frozen. Cell pellets are sonicated in a disaccharide digestion buffer. A desired amount of total protein from the sonicated sample is then added to digestion buffer comprising heparinase I, heparinase II, heparinase III, and chondroitinase B, the latter of which is specific for dermatan sulfate. Following digestion, e.g., about 3 hours at 30° C., the enzymes are deactivated with EDTA and boiling. Sample are then centrifuged, e.g., at 16,000×G, and the supernatant transferred to a centrifugal filter and centrifuged at about 14,000×G. Disaccharides are then resuspended in a mixture of assay buffer: acetonitrile at a 1:1 v/v ratio and further analyzed by liquid chromatography coupled to electrospray mass spectrometry, e.g., as described in Example 2. GAG-derived disaccharide products can be identified based on a retention time compared to those of commercially available reference standards. Illustrative heparan sulfate-derived disaccharides include D0S0 and D2S0 (nomenclature according to Lawrence et al., *Nat. Methods,* 5:291-292 (2008)).

In other aspects, SGSH activity is assessed by assaying a sample, such as a cell sample or tissue sample, for the amount of heparan sulfate glycosaminoglycans (GAGs), which accumulate as a result of SGSH deficiency. The amount of heparan sulfate is determined by digesting GAGs present in a sample with heparinase (e.g., any described herein). The resulting disaccharides can then be assayed by mass spectrometry (e.g., LC-MS/MS). Samples with high levels of heparan sulfate accumulation will have increased amounts of heparan sulfate-derived disaccharides. Thus, the level of disaccharides is inversely proportional to SGSH enzymatic activity.

The mass spectrometry (e.g., LC-MS/MS) assay can be performed on any sample in which GAGs accumulate, including cell samples, tissue samples, and fluid samples. Such samples can be evaluated to monitor the activity of an SGSH-containing protein described herein, e.g., that is administered to cells in vitro, or in some embodiments, administered to a subject in vivo. The subject may be an animal, such as a rodent, e.g., a mouse, or a non-human primate. In some embodiments, the subject is a human patient, such as a patient having Sanfilippo syndrome A that is undergoing treatment with an SGSH therapy, wherein the assay is used to monitor SGSH activity in the patient. In some embodiments, the human patient is undergoing treatment with a fusion protein described herein.

For cellular samples, such as cells or tissue samples, the assay comprises disrupting the cells and/or breaking open microvesicles. Disruption of cells or breaking open microvesicles may be achieved by using freeze-thawing and/or sonication to obtain an extract (e.g., a cellular extract) comprising GAGs. The GAGs are then subject to treatment with heparinases (e.g., any described herein), which break down heparan sulfate GAGs. Following digestion, a supernatant containing the GAG disaccharides is obtained and the disaccharide products are analyzed by mass spectrometry (e.g., LC-MS/MS). An illustrative protocol is provided in Example 7.

In some embodiments, a cell sample to be assayed for SGSH activity is washed and frozen. Cell pellets are sonicated in a disaccharide digestion buffer. A desired amount of total protein from the sonicated sample is then added to digestion buffer comprising heparinase I, heparinase II, and/or heparinase III. Following digestion, e.g., about 3 hours at 30° C., the enzymes are deactivated with EDTA and boiling. Sample are then centrifuged, e.g., at 16,000×G, and the supernatant transferred to a centrifugal filter and centrifuged at about 14,000×G. Disaccharides are then resuspended in a mixture of assay buffer:acetonitrile at a 1:1 v/v ratio and further analyzed by liquid chromatography coupled to electrospray mass spectrometry, e.g., as described in Example 7. GAG-derived disaccharide products can be identified based on a retention time compared to those of commercially available reference standards. Illustrative heparan sulfate-derived disaccharides include D0S0 and D2S0 (nomenclature according to Lawrence et al., *Nat. Methods,* 5:291-292 (2008)).

In some embodiments, a tissue sample is evaluated. A tissue sample can be evaluated using an assay as described above, except multiple free-thaw cycles, e.g., 2, 3, 4, 5, or more, are typically included before the sonication step to ensure that microvesicles are broken open.

Samples that can be evaluated by the assays described herein include brain, liver, kidney, lung, spleen, plasma, serum, cerebrospinal fluid (CSF), and urine. In some embodiments, CSF samples from a patient receiving an enzyme-Fc fusion protein (e.g., an IDS-Fc or SGSH-Fc fusion protein) described herein may be evaluated.

XI. Nucleic Acids, Vectors, and Host Cells

Polypeptide chains contained in the fusion proteins as described herein are typically prepared using recombinant methods. Accordingly, in some aspects, the present disclosure provides isolated nucleic acids comprising a nucleic acid sequence encoding any of the polypeptide chains comprising Fc polypeptides as described herein, and host cells into which the nucleic acids are introduced that are used to replicate the polypeptide-encoding nucleic acids and/or to express the polypeptides. In some embodiments, the host cell is eukaryotic, e.g., a human cell.

In another aspect, polynucleotides are provided that comprise a nucleotide sequence that encodes the polypeptide chains described herein. The polynucleotides may be single-stranded or double-stranded. In some embodiments, the polynucleotide is DNA. In particular embodiments, the polynucleotide is cDNA. In some embodiments, the polynucleotide is RNA.

In some embodiments, the polynucleotide is included within a nucleic acid construct. In some embodiments, the construct is a replicable vector. In some embodiments, the vector is selected from a plasmid, a viral vector, a phagemid, a yeast chromosomal vector, and a non-episomal mammalian vector.

In some embodiments, the polynucleotide is operably linked to one or more regulatory nucleotide sequences in an expression construct. In one series of embodiments, the nucleic acid expression constructs are adapted for use as a surface expression library. In some embodiments, the library is adapted for surface expression in yeast. In some embodiments, the library is adapted for surface expression in phage. In another series of embodiments, the nucleic acid expression constructs are adapted for expression of the polypeptide in a system that permits isolation of the polypeptide in milligram or gram quantities. In some embodiments, the system is a mammalian cell expression system. In some embodiments, the system is a yeast cell expression system.

Expression vehicles for production of a recombinant polypeptide include plasmids and other vectors. For instance, suitable vectors include plasmids of the following types: pBR322-derived plasmids, pEMBL-derived plasmids, pEX-derived plasmids, pBTac-derived plasmids, and pUC-derived plasmids for expression in prokaryotic cells, such as *E. coli*. The pcDNAI/amp, pcDNAI/neo, pRc/CMV, pSV2gpt, pSV2neo, pSV2-dhfr, pTk2, pRSVneo, pMSG, pSVT7, pko-neo, and pHyg-derived vectors are examples of mammalian expression vectors suitable for transfection of eukaryotic cells. Alternatively, derivatives of viruses such as the bovine papilloma virus (BPV-1), or Epstein-Barr virus (pHEBo, pREP-derived, and p205) can be used for transient expression of polypeptides in eukaryotic cells. In some embodiments, it may be desirable to express the recombinant polypeptide by the use of a baculovirus expression system. Examples of such baculovirus expression systems include pVL-derived vectors (such as pVL1392, pVL1393, and pVL941), pAcUW-derived vectors (such as pAcUW1), and pBlueBac-derived vectors. Additional expression systems include adenoviral, adeno-associated virus, and other viral expression systems.

Vectors may be transformed into any suitable host cell. In some embodiments, the host cells, e.g., bacteria or yeast cells, may be adapted for use as a surface expression library. In some cells, the vectors are expressed in host cells to express relatively large quantities of the polypeptide. Such host cells include mammalian cells, yeast cells, insect cells, and prokaryotic cells. In some embodiments, the cells are mammalian cells, such as Chinese Hamster Ovary (CHO) cell, baby hamster kidney (BHK) cell, NS0 cell, Y0 cell, HEK293 cell, COS cell, Vero cell, or HeLa cell.

A host cell transfected with an expression vector encoding one or more Fc polypeptide chains as described herein can be cultured under appropriate conditions to allow expression of the one or more polypeptides to occur. The polypeptides may be secreted and isolated from a mixture of cells and medium containing the polypeptides. Alternatively, the polypeptides may be retained in the cytoplasm or in a membrane fraction and the cells harvested, lysed, and the polypeptide isolated using a desired method.

XII. Therapeutic Methods

A fusion protein or an agent (e.g., a therapeutic agent) linked to an engineered TfR-binding polypeptide, TfR-binding peptide, or TfR-binding antibody described herein may be used therapeutically to treat an LSD. In some embodiments, a patient having Hunter syndrome is treated with a fusion protein or an agent linked to an engineered TfR-binding polypeptide, TfR-binding peptide, or TfR-binding antibody that comprises IDS. In some embodiments, a patient having Sanfilippo syndrome A is treated with a fusion protein or an agent linked to an engineered TfR-binding polypeptide, TfR-binding peptide, or TfR-binding antibody that comprises SGSH. In some embodiments, a patient having Niemann-Pick disease is treated with a fusion protein or an agent linked to an engineered TfR-binding polypeptide, TfR-binding peptide, or TfR-binding antibody that comprises ASM. In some embodiments, a patient having Gaucher disease or Parkinson's disease is treated with a fusion protein or an agent linked to an engineered TfR-binding polypeptide, TfR-binding peptide, or TfR-binding antibody that comprises GBA.

A fusion protein described herein that comprises an ERT enzyme, e.g., IDS, SGSH, ASM, or GBA, is administered to a subject at a therapeutically effective amount or dose. Illustrative dosages include a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. In some embodiments, the protein has an enzymatic activity of at least about 500 units (U)/mg, about 1,000 U/mg, or at least about 1,500, 2,000, 2,500, 3,000, 3,500, 4,000, 4,500, 5,000, 6,000, 7,000, 8,000, 9,000, or 10,000 U/mg. In some embodiments, the enzymatic activity is at least about 11,000 U/mg, or at least about 12,000, 13,000, 14,000, 15,000, 16,000, 17,000, 18,000, 19,000, 20,000, 25,000, 30,000, 35,000, 40,000, 45000, or 50,000 U/mg; or anywhere in a range of about 500 U/mg to about 50,000 U/mg. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In some embodiments, a patient initially is given a low dose, which is then increased to an efficacious dosage tolerable to the patient. Determination of an effective amount is well within the capability of those skilled in the art.

In various embodiments, a fusion protein described herein is administered parenterally. In some embodiments, the protein is administered intravenously. Intravenous administration can be by infusion, e.g., over a period of from about 10 to about 30 minutes, or over a period of at least 1 hour, 2 hours, or 3 hours. In some embodiments, the protein is administered as an intravenous bolus. Combinations of infusion and bolus administration may also be used.

In some parenteral embodiments, a fusion protein or agent (e.g., therapeutic agent) linked to an engineered TfR-binding polypeptide, TfR-binding peptide, or TfR-binding antibody is administered intraperitoneally, subcutaneously, intradermally, or intramuscularly. In some embodiments, the protein or agent linked to an engineered TfR-binding polypeptide, TfR-binding peptide, or TfR-binding antibody is administered intradermally or intramuscularly. In some embodiments, the protein or agent linked to an engineered TfR-binding polypeptide, TfR-binding peptide, or TfR-binding antibody is administered intrathecally, such as by epidural administration, or intracerebroventricularly.

In other embodiments, a fusion protein or an agent (e.g., therapeutic agent) linked to an engineered TfR-binding polypeptide, TfR-binding peptide, or TfR-binding antibody may be administered orally, by pulmonary administration, intranasal administration, intraocular administration, or by topical administration. Pulmonary administration can also be employed, e.g., by use of an inhaler or nebulizer, and formulation with an aerosolizing agent.

XIII. Methods for Protein Replacement

In other aspects, provided herein is a method for transporting an agent (e.g., an agent that is useful for treating a lysosomal storage disorder (LSD)) across the blood-brain barrier (BBB) of a mammal. In some embodiments, the method comprises exposing the BBB to a polypeptide or protein that binds (e.g., specifically binds) to a transferrin receptor (TfR) with an affinity of from about 50 nM to about 250 nM. In some embodiments, the polypeptide or protein is linked to the agent and transports the linked agent across the BBB. In some embodiments, the maximum concentration ($C_{max}$) of the agent in the brain of the mammal is improved (e.g., increased).

In other aspects, provided herein is a method for treating an LSD. In some embodiments, the method comprises administering to a mammal a polypeptide or protein that binds (e.g., specifically binds) to a TfR with an affinity of from about 50 nM to about 250 nM. In some embodiments, the polypeptide or protein is linked to an agent for treating the LSD, thereby exposing the brain of the mammal to the agent.

In some embodiments, the polypeptide or protein binds (e.g., specifically binds) to a TfR with an affinity of about 50, 60, 70, 80, 90, 100, 110, 120, 130, 140, 150, 160, 170, 180, 190, 200, 210, 220, 230, 240, or 250 nM. In some embodiments, the polypeptide or protein binds to a TfR with an affinity of from about 100 nM to about 200 nM or from about 110 nM to about 150 nM.

In some embodiments, the polypeptide or protein (e.g., linked to the agent) improves (e.g., increases) $C_{max}$ of the agent in the brain as compared to the agent linked to a reference polypeptide or protein that binds (e.g., specifically binds) to a TfR with a weaker affinity.

In some embodiments, $C_{max}$ of the agent in the brain is improved (e.g., increased) by at least about 1.1-fold, 1.2-fold, 1.3-fold, 1.4-fold, 1.5-fold, 1.6-fold, 1.7-fold, 1.8-fold, 1.9-fold, 2-fold, 2.2-fold, 2.4-fold, 2.6-fold, 2.8-fold, 3-fold, 4-fold, 5-fold, or more, as compared to the agent that is linked to a reference polypeptide or protein (e.g., that binds to a TfR with a weaker affinity).

In some embodiments, the brain of the mammal is exposed to the agent at a therapeutically effective concentration (e.g., a concentration that is sufficient to treat one or more signs or symptoms of an LSD) for a shorter duration as compared to the agent that is linked to the reference polypeptide or protein. In some embodiments, brain exposure duration is shortened by at least about 5%, 10%, 25%, 40%, 50%, 60%, 75%, 85%, 90%, 95%, or 98%.

In some embodiments, brain exposure is quantified by plotting brain exposure (e.g., concentration of the agent in the brain) as a function of time and calculating the area under the curve (AUC). Decreased AUC can represent decreased or shortened brain exposure. In some embodiments, duration of brain exposure to the agent (e.g., at a therapeutically effective concentration) is shortened.

In some embodiments, the reference polypeptide or protein binds (e.g., specifically binds) to the TfR with an affinity that is, or is weaker than, about 250 nM, 300 nM, 350 nM, 400 nM, 450 nM, 500 nM, 550 nM, or 600 nM. In some embodiments, the reference polypeptide or protein binds to the TfR with an affinity that is, or is weaker than, about 600 nM.

In some embodiments, the mammal is a primate (e.g., a human). In some embodiments, the human is a patient in need of treatment for an LSD. In some embodiments, the patient has one or more signs or symptoms of an LSD.

In some embodiments, the polypeptide or protein binds (e.g., specifically binds) to a primate TfR. In some embodiments, the primate TfR is a human TfR. In some embodiments, the polypeptide or protein binds to a TfR apical domain.

In some embodiments, the agent (e.g., therapeutic agent) is linked to an engineered TfR-binding polypeptide. In some embodiments, the engineered TfR-binding polypeptide comprises CH3 or CH2 domains that have modifications that allow the polypeptide to specifically bind to TfR. Non-limiting examples of suitable engineered TfR-binding polypeptides are described herein. In some embodiments, the agent is linked to an engineered TfR-binding polypeptide that is described in Table 4 or Table 5. In some embodiments, the agent is linked to an engineered TfR-binding polypeptide selected from the group consisting of CH3C.35.20.2, CH3C.35.23.2, CH3C.35.23.5, CH3C.35.21.17, and CH3C.35.21.17.2.

In some embodiments, the agent (e.g., therapeutic agent) is linked to a TfR-binding peptide. In some embodiments, the TfR-binding peptide is a short peptide, being about 5, 6, 7, 8, 9, 10, 11, 12, 13, 14, 15, 16, 17, 18, 19, or 20 amino acids in length. Methods for generating, screening, and identifying suitable peptides (i.e., that bind to a TfR with an affinity within the desired range) are known in the art. For example, a phage display strategy in which alternating rounds of negative and positive selection are employed can be used to identify suitable peptides. This strategy is described, e.g., in Lee et al., *Eur. J. Biochem.*, 268:2004-2012 (2001), which is hereby incorporated in its entirety for all purposes.

In some embodiments, the agent (e.g., therapeutic agent) is linked to a TfR-binding antibody. Non-limiting examples of suitable TfR-binding antibodies include OX26 anti-TfR antibodies (i.e., having affinities of about 76 nM, 108 nM, and 174 nM) that are disclosed in Thom et al., *Mol. Pharm.*, 15(4):1420-1431 (2018). In some embodiments, the agent is linked to a protein that comprises an antibody variable region that specifically binds to TfR. In some instances, the protein comprises a Fab or an scFv.

In some embodiments, the agent (e.g., therapeutic agent) is a protein (e.g., an enzyme). In some embodiments, the agent is a protein replacement therapeutic. In some embodiments, the agent is a protein or enzyme that is deficient (e.g., underexpressed or absent) in a cell or tissue (e.g., a neural cell or tissue) in the mammal. In some embodiments, the agent is a protein or enzyme that is endogenous to, or expressed in, a normal healthy cell or tissue (e.g., a neural cell or tissue) in the mammal, but is deficient (e.g., in the corresponding cell or tissue) in the mammal that is being treated for the LSD.

In some embodiments, the protein replacement therapeutic is an enzyme. Any number of agents (e.g., protein replacement therapeutics such as enzymes) can be linked to polypeptides or proteins (e.g., that bind to TfR) for the treatment of various LSDs. In some embodiments, the agent is an enzyme that decreases the accumulation of a toxic metabolic product in the brain of the mammal having the LSD to a greater extent when linked to the polypeptide or protein, as compared to when the enzyme is linked to the reference polypeptide or protein. In some embodiments, the enzyme is iduronate 2-sulfatase (IDS) and the LSD is Hunter syndrome. In some instances, the toxic metabolic product comprises heparin sulfate-derived disaccharides and/or dermatan sulfate-derived disaccharides. In some embodiments, the enzyme is N-sulfoglucosamine sulfohydrolase (SGSH) and the LSD is Sanfilippo syndrome. In some embodiments, the enzyme is acid sphingomyelinase (ASM) and the LSD is Niemann-Pick disease. In some embodiments, the enzyme is β-glucocerebrosidase (GBA) and the LSd Gaucher's disease.

In some embodiments, the agent (e.g., therapeutic agent) comprises an antibody variable region. In some embodiments, the agent comprises an antibody fragment. In some embodiments, the agent comprises a Fab or an scFv. In some embodiments, the agent does not comprise an antibody variable region. In some instances, the agent does not comprise an anti-beta secretase 1 (BACE1) Fab.

Additional Embodiments and Linkers

A polypeptide (e.g., a modified CH3 or CH2 domain polypeptide as described further herein) may be joined to another domain of an Fc region. In some embodiments, a modified CH3 domain polypeptide is joined to a CH2 domain, which may be a naturally occurring CH2 domain or a variant CH2 domain, typically at the C-terminal end of the CH2 domain. In some embodiments, a modified CH2 domain polypeptide is joined to a CH3 domain, which may be a naturally occurring CH3 domain or a CH3 variant domain, typically at the N-terminal end of the CH3 domain. In some embodiments, the polypeptide comprising a modified CH2 domain joined to a CH3 domain, or the polypeptide comprising the modified CH3 domain joined to a CH2 domain, further comprises a partial or full hinge region of an antibody, thus resulting in a format in which the modified CH3 domain polypeptide or modified CH2 domain polypeptide is part of an Fc region having a partial or full hinge region. The hinge region can be from any immunoglobulin subclass or isotype. An illustrative immunoglobulin hinge is an IgG hinge region, such as an IgG1 hinge region, e.g., human IgG1 hinge amino acid sequence EPKSCDKTHTCPPCP (SEQ ID NO:95).

In some embodiments, an engineered TfR-binding polypeptide, TfR-binding peptide, or TfR-binding antibody is fused to a peptide or protein that is useful for protein purification, e.g., polyhistidine, epitope tags, e.g., FLAG, c-Myc, hemagglutinin tags and the like, glutathione S transferase (GST), thioredoxin, protein A, protein G, or maltose binding protein (MBP). In some cases, the peptide or protein to which the engineered TfR-binding polypeptide, TfR-binding peptide, or TfR-binding antibody is fused may comprise a protease cleavage site, such as a cleavage site for Factor Xa or Thrombin.

In methods of the present disclosure, an agent (e.g., therapeutic agent) is linked to a polypeptide or protein (e.g., an engineered TfR-binding polypeptide, a TfR-binding peptide, or a TfR-binding antibody). The linker may be any linker suitable for joining an agent to the polypeptide or protein. In some embodiments, the linkage is enzymatically cleavable. In certain embodiments, the linkage is cleavable by an enzyme present in the central nervous system.

In some embodiments, the linker is a peptide linker. The peptide linker may be configured such that it allows for the rotation of the agent (e.g., therapeutic agent) and the polypeptide or protein relative to each other; and/or is resistant to digestion by proteases. In some embodiments, the linker may be a flexible linker, e.g., containing amino acids such as Gly, Asn, Ser, Thr, Ala, and the like. Such linkers are designed using known parameters. For example, the linker may have repeats, such as Gly-Ser repeats.

In various embodiments, linking of the agent (e.g., therapeutic agent) to the polypeptide or protein (e.g., engineered TfR-binding polypeptide, TfR-binding peptide, or TfR-binding antibody) can be achieved using well-known chemical cross-linking reagents and protocols. For example, there are a large number of chemical cross-linking agents that are known to those skilled in the art and useful for cross-linking the polypeptide or protein with an agent of interest. For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers.

The agent (e.g., therapeutic agent) may be linked to the N-terminal or C-terminal region of the polypeptide or protein, or attached to any region of the polypeptide or protein (e.g., engineered TfR-binding polypeptide, TfR-binding peptide, or TfR-binding antibody), so long as the agent does not interfere with binding of the polypeptide or protein to a transferrin receptor.

XIV. Pharmaceutical Compositions and Kits

In other aspects, pharmaceutical compositions and kits comprising a fusion protein described herein are provided.
Pharmaceutical Compositions Guidance for preparing formulations for use in the present disclosure can be found in any number of handbooks for pharmaceutical preparation and formulation that are known to those of skill in the art.

In some embodiments, a pharmaceutical composition comprises a fusion protein as described herein and further comprises one or more pharmaceutically acceptable carriers and/or excipients. A pharmaceutically acceptable carrier includes any solvents, dispersion media, or coatings that are physiologically compatible and that do not interfere with or otherwise inhibit the activity of the active agent.

In some embodiments, the carrier is suitable for intravenous, intrathecal, ocular, intracerebroventricular, intramuscular, oral, intraperitoneal, transdermal, topical, or subcutaneous administration. Pharmaceutically acceptable carriers can contain one or more physiologically acceptable compounds that act, for example, to stabilize the composition or to increase or decrease the absorption of the polypeptide. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are also available in the art.

The pharmaceutical compositions described herein can be manufactured, e.g., by means of conventional mixing, dissolving, granulating, dragee-making, emulsifying, encapsulating, entrapping, or lyophilizing processes. The following methods and excipients are exemplary.

For oral administration, a fusion protein as described herein can be formulated by combining it with pharmaceutically acceptable carriers that are well known in the art. Such carriers enable the fusion protein to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the fusion protein with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone. If desired, disintegrating agents can be added, such as a cross-linked polyvinyl pyrrolidone, agar, or alginic acid or a salt thereof such as sodium alginate.

As disclosed above, a fusion protein as described herein can be formulated for parenteral administration by injection, e.g., by bolus injection or continuous infusion. For injection, the fusion protein can be formulated into preparations by dissolving, suspending, or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives. In some embodiments, the fusion protein can be formulated in aqueous solutions, such as physiologically compatible buffers, non-limiting examples of which include Hanks's solution, Ringer's solution, and physiological saline buffer. Formulations for injection can be presented in unit dosage form, e.g., in ampules or in multi-dose containers, with an added preservative. The compositions can take such forms as suspensions, solutions, or emulsions in oily or aqueous vehicles, and can contain formulatory agents such as suspending, stabilizing, and/or dispersing agents.

In some embodiments, a fusion protein as described herein is prepared for delivery in a sustained-release, controlled release, extended-release, timed-release, or delayed-release formulation, for example, in semi-permeable matrices of solid hydrophobic polymers containing the active agent. Various types of sustained-release materials have been established and are well known by those skilled in the art. Extended-release formulations include film-coated tablets, multiparticulate or pellet systems, matrix technologies using hydrophilic or lipophilic materials and wax-based tablets with pore-forming excipients. Usually, sustained release formulations can be prepared using naturally-occurring or synthetic polymers, for instance, polymeric vinyl pyrrolidones, such as polyvinyl pyrrolidone; carboxyvinyl hydrophilic polymers; hydrophobic and/or hydrophilic hydrocolloids, such as methylcellulose, ethylcellulose, hydroxypropyl cellulose, and hydroxypropylmethyl cellulose; and carboxypolymethylene.

Typically, a pharmaceutical composition for use in in vivo administration is sterile. Sterilization can be accomplished according to methods known in the art, e.g., heat sterilization, steam sterilization, sterile filtration, or irradiation.

Dosages and desired drug concentration of pharmaceutical compositions described herein may vary depending on the particular use envisioned. Suitable dosages are also described in Section XII above.

Kits

In some embodiments, a kit for use in treating an LSD, e.g., Hunter syndrome, Sanfilippo syndrome A, Niemann-Pick disease, Gaucher's disease, or Parkinson's disease, comprising a fusion protein as described herein is provided.

In some embodiments, the kit further comprises one or more additional therapeutic agents. For example, in some embodiments, the kit comprises a fusion protein as described herein and further comprises one or more additional therapeutic agents for use in the treatment of neurological symptoms of an LSD. In some embodiments, the kit further comprises instructional materials containing directions (i.e., protocols) for the practice of the methods described herein (e.g., instructions for using the kit for administering a fusion protein comprising the ERT enzyme across the blood-brain barrier). While the instructional materials typically comprise written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD-ROM), and the like. Such media may include addresses to internet sites that provide such instructional materials.

XV. Examples

The present disclosure will be described in greater detail by way of specific examples. The following examples are offered for illustrative purposes only, and are not intended to limit the disclosure in any manner. Those of skill in the art will readily recognize a variety of noncritical parameters which can be changed or modified to yield essentially the same results. Efforts have been made to ensure accuracy with respect to numbers used (e.g., amounts, temperatures, etc.), but some experimental error and deviation may be present. The practice of the present disclosure will employ, unless otherwise indicated, conventional methods of protein chemistry, biochemistry, recombinant DNA techniques and pharmacology, within the skill of the art. Such techniques are explained fully in the literature. Additionally, it should be apparent to one of skill in the art that the methods for engineering as applied to certain libraries can also be applied to other libraries described herein.

Example 1. Construction of Fusion Proteins Comprising Iduronate 2-Sulfatase (IDS)

Design and Cloning

IDS-Fc fusion proteins were designed that contain (i) a fusion polypeptide where a mature, human IDS enzyme is fused to a human IgG1 fragment that includes the Fc region (an "IDS-Fc fusion polypeptide"), and (ii) a modified human IgG1 fragment which contains mutations in the Fc region that confer transferrin receptor (TfR) binding (a "modified Fc polypeptide"). In particular, IDS-Fc fusion polypeptides were created in which IDS fragments were fused to either the N- or C-terminus of the human IgG1 Fc region. In some cases, a linker was placed between the IDS and IgG1 fragments to alleviate any steric hindrance between the two fragments. In all constructs, the signal peptide from the kappa chain V-III, amino acids 1-20 (UniProtKB ID—P01661) was inserted upstream of the fusion to facilitate secretion, and IDS was truncated to consist of amino acids S26-P550 (UniProtKB ID—P22304). The fragment of the human IgG1 Fc region used corresponds to amino acids D104-K330 of the sequence in UniProtKB ID P01857 (positions 221-447, EU numbering, which includes 10 amino acids of the hinge (positions 221-230)). In some embodiments, a second Fc polypeptide derived from human IgG1 residues D104-K330 but lacking the IDS fusion was co-transfected with the IDS-Fc fusion polypeptide in order to generate heterodimeric fusion proteins with one IDS enzyme (a "monozyme"). In some constructs, the IgG1 fragments contained additional mutations to facilitate heterodimerization of the two Fc regions. Control IDS-Fc fusion proteins that lack the mutations that confer TfR binding were designed and constructed analogously, with the difference being that these proteins lacked the mutations that confer TfR binding. As an additional control, we generated IDS (amino acids S26-P550) with a C-terminal hexahistidine tag (SEQ ID NO:241) to facilitate detection and purification.

The TfR-binding IDS-Fc fusion proteins used in the examples are dimers formed by an IDS-Fc fusion polypeptide and a modified Fc polypeptide that binds to TfR. For dimers where the IDS enzyme is linked to the N-terminus of the Fc region, the IDS-Fc fusion polypeptide may have the sequence of any one of SEQ ID NOS:115, 231, and 235. In these sequences, the IDS sequence is underlined and contains a cysteine at position 59 (double underlined) modified to formylglycine. The IDS was joined to the Fc polypeptide by a GGGGS linker (SEQ ID NO:239). A portion of an IgG1 hinge region (DKTHTCPPCP; SEQ ID NO:113) was included at the N-terminus of the Fc polypeptide. The CH2 domain sequence starts at position 541 of SEQ ID NOS:115, 231, and 235.

The IDS-Fc fusion protein ETV:IDS 35.21 used in the examples is a dimer formed by an IDS-Fc fusion polypeptide having the sequence of any one of SEQ ID NOS:115, 231, and 235 and a modified Fc polypeptide that binds to TfR having the sequence of SEQ ID NO:116. The first 10 amino acids are a portion of an IgG1 hinge region. The CH2 domain sequence starts at position 11 of SEQ ID NO:116.

The IDS-Fc fusion protein ETV:IDS 35.21.17.2 used in the examples is a dimer formed by an IDS-Fc fusion polypeptide having the sequence of any one of SEQ ID NOS:115, 231, and 235 and a modified Fc polypeptide that binds to TfR having the sequence of SEQ ID NO:228. The first 10 amino acids are a portion of an IgG1 hinge region. The CH2 domain sequence starts at position 11 of SEQ ID NO:228.

The IDS-Fc fusion protein ETV:IDS 35.23.2 used in the examples is a dimer formed by an IDS-Fc fusion polypeptide having the sequence of any one of SEQ ID NOS:115, 231, and 235 and a modified Fc polypeptide that binds to TfR having the sequence of SEQ ID NO:229. The first 10 amino acids are a portion of an IgG1 hinge region. The CH2 domain sequence starts at position 11 of SEQ ID NO:229.

The IDS-Fc fusion protein ETV:IDS 35.21.17 used in the examples is a dimer formed by an IDS-Fc fusion polypeptide having the sequence of any one of SEQ ID NOS:115, 231, and 235 and a modified Fc polypeptide that binds to TfR having the sequence of SEQ ID NO:151. The N-terminus of the modified Fc polypeptide may include a portion of an IgG1 hinge region (e.g., SEQ ID NO:113).

Recombinant Protein Expression and Purification

To express recombinant IDS enzyme fused to an Fc region, ExpiCHO cells (Thermo Fisher Scientific) were transfected with relevant DNA constructs using Expifectamine™ CHO transfection kit according to manufacturer's instructions (Thermo Fisher Scientific). Cells were grown in ExpiCHO™ Expression Medium at 37° C., 6% $CO_2$ and 120 rpm in an orbital shaker (Infors HT Multitron). In brief, logarithmic growing ExpiCHO™ cells were transfected at $6 \times 10^6$ cells/ml density with 0.8 µg of DNA plasmid per mL of culture volume. After transfection, cells were returned to 37° C. and transfected cultures were supplemented with feed as indicated 18-22 hrs post transfection. Transfected cell culture supernatants were harvested 120 hrs post transfection by centrifugation at 3,500 rpm from 20 mins. Clarified supernatants were filtered (0.22 µM membrane) and stored at 4° C. Expression of an epitope-tagged IDS enzyme (used as a control) was carried out as described above with minor modifications. In brief, an IDS enzyme harboring a C-terminal hexahistidine tag (SEQ ID NO:241) was expressed in ExpiCHO cells.

IDS-Fc fusion proteins with (or without) engineered Fc regions conferring TfR binding were purified from cell culture supernatants using Protein A affinity chromatography. Supernatants were loaded onto a HiTrap Mab Select SuRe Protein A affinity column (GE Healthcare Life Sciences using an Akta Pure System). The column was then washed with >20 column volumes (CVs) of PBS. Bound proteins were eluted using 100 mM citrate/NaOH buffer pH 3.0 containing 150 mM NaCl. Immediately after elution, fractions were neutralized using 1 M arginine-670 mM succinate buffer pH 5.0 (at a 1:5 dilution). Homogeneity of IDS-Fc fusion proteins in eluted fractions was assessed by reducing and non-reducing SDS-PAGE.

To purify hexahistadine-tagged (SEQ ID NO:241) IDS enzyme, transfected supernatants were exhaustively dialyzed against 15 L of 20 mM HEPES pH 7.4 containing 100 mM NaCl overnight. Dialyzed supernatants were bound to a HisTrap column (GE Healthcare Life Sciences using an Akta Pure System). After binding, the column was washed with 20 CV of PBS. Bound proteins were eluted using PBS containing 500 mM imidazole. Homogeneity of IDS enzyme in eluted fractions was assessed by reducing and non-reducing SDS-PAGE. Pooled fractions containing IDS enzyme were diluted 1:10 in 50 mM Tris pH 7.5 and further purified using Q Sepharose High Performance (GE Healthcare). After binding, the column was washed with 10 CV of 50 mM Tris pH 7.5. Bound proteins were eluted using a linear gradient to 50 mM Tris pH 7.5 and 0.5 M NaCl and collected in 1 CV fractions. Fraction purity was assessed by non-reducing SDS-PAGE. As shown in FIG. 1, purification yielded homogeneous IDS-Fc fusion proteins and hexahistidine-tagged (SEQ ID NO:241) IDS enzyme.

Example 2. Characterization of IDS Fusion Proteins

IDS-Fc Fusion Proteins with Engineered TfR Binding Site Bind to Human TfR

To determine whether IDS-Fc fusion proteins with engineered TfR binding affects the ability of the modified Fc domain to interact with human TfR, the affinity of this protein for human TfR was assessed using a Biacore™ surface plasmon resonance assay. Biacore™ Series S CM5 sensor chips were immobilized with anti-human Fab (human Fab capture kit from GE Healthcare). 5 µg/mL of the IDS-Fc fusion proteins were captured for 1 minute on each flow cell and serial 3-fold dilutions of human apical domain TfR were injected at a flow rate of 30 µL/min. Each sample was analyzed with a 3-minute association and a 3-minute dissociation. After each injection, the chip was regenerated using 10 mM glycine-HCl (pH 2.1). Binding response was corrected by subtracting the RU from a flow cell capturing an irrelevant IgG at similar density. Steady-state affinities were obtained by fitting the response at equilibrium against the concentration using Biacore™ T200 Evaluation Software v3.1. As shown in FIG. 2, Biacore™ analysis established that the IDS-Fc fusion proteins with a TfR-binding site engineered into the Fc region binds to human TfR. Biacore™ analysis also established that the IDS-Fc fusion protein ETV:IDS 35.21 binds to human TfR with an affinity of ~200 nM.

IDS-Fc Fusion Proteins with Engineered TfR Binding Site are Active In Vitro, in Cells, and In Vivo The in vitro and cellular activity of engineered TfR-binding IDS-Fc fusion proteins were assessed to demonstrate that IDS maintains its enzymatic activity when fused to the human IgG fragment. In vitro activity was measured with a two-step fluorometric enzymatic assay using an artificial substrate. Specifically, 20 µL of 1 mM 4-Methylumbelliferyl a-L-idopyranosiduronic acid 2-sulphate disodium salt substrate (Carbosynth Limited, # EM03201) was diluted in the assay buffer (100 mM sodium acetate, 10 mM lead acetate, 0.05% Triton X-100, pH 5.0) and mixed with 10 µL of 0.2 nM IDS. The first reaction was incubated for 4 hr at 37° C. and terminated with 60 µL of 0.2 M phosphate-citrate buffer, pH 5.0. The second reaction was then carried out in the presence of 15 µg cell lysate from HEK 293T cells transiently transfected with human α-iduronidase (IDUA), incubated for 16 hr at 37° C., and stopped with the addition of 100 µL of 0.5 M sodium carbonate buffer, pH 10.5. Fluorescence of the reaction solution was then measured (excitation at 365 nm and emission at 450 nm). A 4-Methylumbelliferone standard curve was fit by linear regression to calculate the amount of product and verified as less than 10% of total substrate cleavage. Specific activity (nmol product/min/nmol IDS) was calculated by dividing the amount of product by the reaction time and molar amount of IDS.

Figure 3:
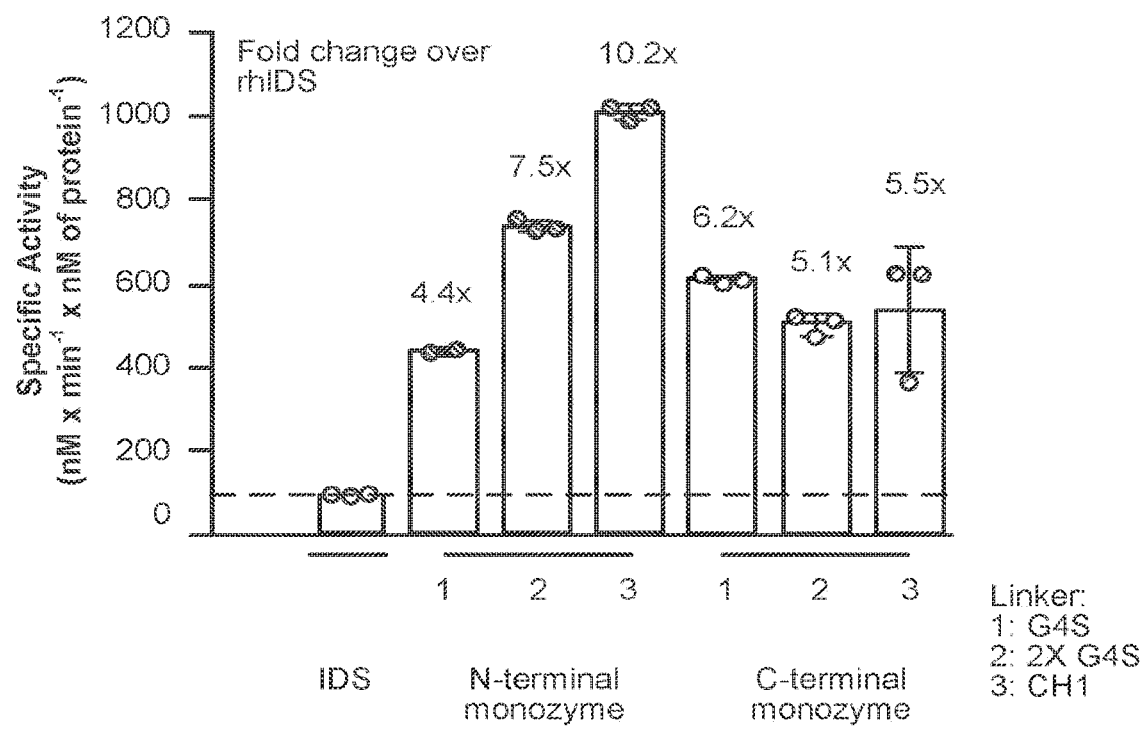
FIG. 3 provides data demonstrating in vitro IDS activity of IDS-Fc fusion proteins analyzed in FIG. 1.

The in vitro enzymatic activity assay demonstrated that IDS-Fc fusion proteins were active and indicated that the fusion of an Fc region to IDS does not interfere with enzymatic activity (FIG. 3).

IDS knockout (KO) cells were generated using CRISPR/CAS9 to provide a cellular system to test the cellular activity of the engineered IDS-Fc fusion proteins. HEK 293T cells (ATCC) were transfected with CRISPR/CAS9 pCas-Guide- EF1a-GFP vector (Origene) containing guide sequences targeted to the second half of exon 1 in human IDS. Single cell clones were analyzed for the presence of indels within the genomic sequence of IDS following Guide-it Mutation Detection Kit (Clontech) per manufacturer instructions. To identify IDS KO cells, indel positive clone cell lysates were analyzed using the in vitro IDS enzyme assay described above. Briefly, the in vitro activity assay was performed using 12.5, 25, 50 and 100 cell lysate in lead acetate assay buffer pH 5.0 (100 mM sodium acetate, 10 mM lead acetate, 0.02% NaAzide) as previously described (Vozyni et al., *J. Inherit. Metab. Dis.*, 24:675-80 (2001)). The reaction was started by combining 10 µL normalized cell lysate (in water) with 1 mM substrate in 20 µL lead acetate buffer. The first reaction was incubated for 4 hr at 37° C. and terminated with 60 µL of 0.2 M phosphate-citrate buffer, pH 5.0. The second reaction was then carried out with the addition of 10 µg/10 µL cell lysate from HEK 293T cells transiently transfected with human α-iduronidase (IDUA) and allowed to proceed for 24 hr at 37° C., and stopped with the addition of 100 µL of 0.5 M sodium carbonate buffer, pH 10.3. Fluorescence of the reaction solution was then measured (excitation at 365 nm and emission at 450 nm). IDS activity in HEK 293T CRISPR clones was compared to recombinant IDS used as an assay standard, HEK wild-type (WT) lysates, and HEK cell lysates over-expressing IDS. Clones with enzyme activity levels comparable to background signal were sequence verified after mini-Topo (ThermoFisher) cloning and confirmed as KO clones. Subsequent cell assays use three unique and verified IDS KO clones and three independent batches of WT HEK 293T cells.

To test the cellular activity of naked IDS enzyme or IDS-Fc fusion proteins, an LC-MS/MS-based glycomic assay was developed that allows monitoring of the amount of substrate accumulation (heparan sulfate and dermatan sulfate) as an indicator of IDS activity. Substrate accumulation was measured in IDS KO cells before and after addition of IDS or IDS-Fc fusion proteins to the cell culture media. Briefly, cells were washed three times with PBS, pelleted, and frozen. Cell pellets were sonicated in disaccharide digestion buffer (111 mM $NH_4OAc$, 11 mM $CaOAc$, pH 7.0). Protein concentration was measured using BCA assay (Pierce). Total protein (100 µg) was added to 100 µL digestion buffer with 2 mM DTT, 1.25 mIU Heparinase I (Galen), 1.25 mIU Heparinase II (Galen), 1.25 mIU Heparinase III (Galen), and 6.25 mIU Chondroitinase B (Galen). Heparan sulfate and dermatan sulfate digestion was complete after three hours at 30° C., after which 20 ng of internal standard (4UA-2S-G1cNCOEt-65 HD009 [Galen]) was added to each sample. The enzymes were deactivated by the addition of 6 µL of 250 mM EDTA and samples were boiled at 95° C. for 10 minutes. Samples were then centrifuged at 16,000×G for 5 minutes at room temperature. Supernatant was transferred to an Amicon Ultra 30 KD centrifugal filter (Millipore) and centrifuged at 14,000×G for 15 minutes. Disaccharides were concentrated in the flow through and were resuspended in a mixture of [1:1, v/v] assay buffer: acetonitrile which was then transferred to mass-spectrometry vials for further analysis.

Analysis of disaccharides generated by enzymatic digestion of heparan and dermatan sulfate was performed by liquid chromatography (Shimadzu Nexera X2 system, Shimadzu Scientific Instrument, Columbia, Md., USA) coupled to electrospray mass spectrometry (Sciex 6500+ QTRAP, Sciex, Framingham, Mass., USA). For each analysis, 10 µL of sample was injected on an ACQUITY UPLC BEH Amide 1.7 µm, 2.1×150 mm column (Waters Corporation, Milford, Mass., USA) using a flow rate of 0.4 mL/min with column temperature at 50° C. Mobile phase A consisted of water with 10 mM ammonium formate and 0.1% formic acid. Mobile phase B consisted of acetonitrile with 0.1% formic acid. The gradient was programmed as follows: 0.0-1.0 min at 85% B, 1.0-5.0 min from 85% B to 50% B, 5.0-6.0 min 50% B to 85% B, 6-8.0 min hold at 85% B. Electrospray ionization was performed in the negative-ion mode applying the following settings: curtain gas at 30; collision gas was set at medium; ion spray voltage at −4500; temperature at 450; ion source gas 1 at 50; ion source gas 2 at 60. Data acquisition was performed using Analyst 1.6.3 (Sciex) in multiple reaction monitoring mode (MRM), with dwell time 25 (msec). Collision energy at −30; declustering potential at −80; entrance potential at −10; collision cell exit potential at −10. GAGs were detected as [M−H]− using the following MRM transitions: D0A0 at m/z 378.1>87.0; D0a0 at m/z 378.1>175.0; D0S0 at m/z 416.1>138.0; D0a4 at m/z 458.1>300.0; D0A6,D2A0, D0a6, D2a0 at m/z 458.1>97.0; D0S6, D2S0 at m/z 496.0>416.1; D2a4, D2a6, D0a10, D2A6 at m/z 538.0>458.0; D0S6 at m/z 575.95>97.0 4UA-2S-G1cNCOEt-6S at m/z 472.0 (fragment ion) >97.0 was used as internal standard (I.S.). GAGs were identified based on their retention times and MRM transitions match to commercially available reference standards (Iduron Ltd, Manchester, UK). Quantification was performed using MultiQuant 3.0.2 (Sciex) by the area ratio to I.S. GAGs were normalized to total protein amount. Protein concentration was measured using BCA assay (Pierce).

Figure 4:
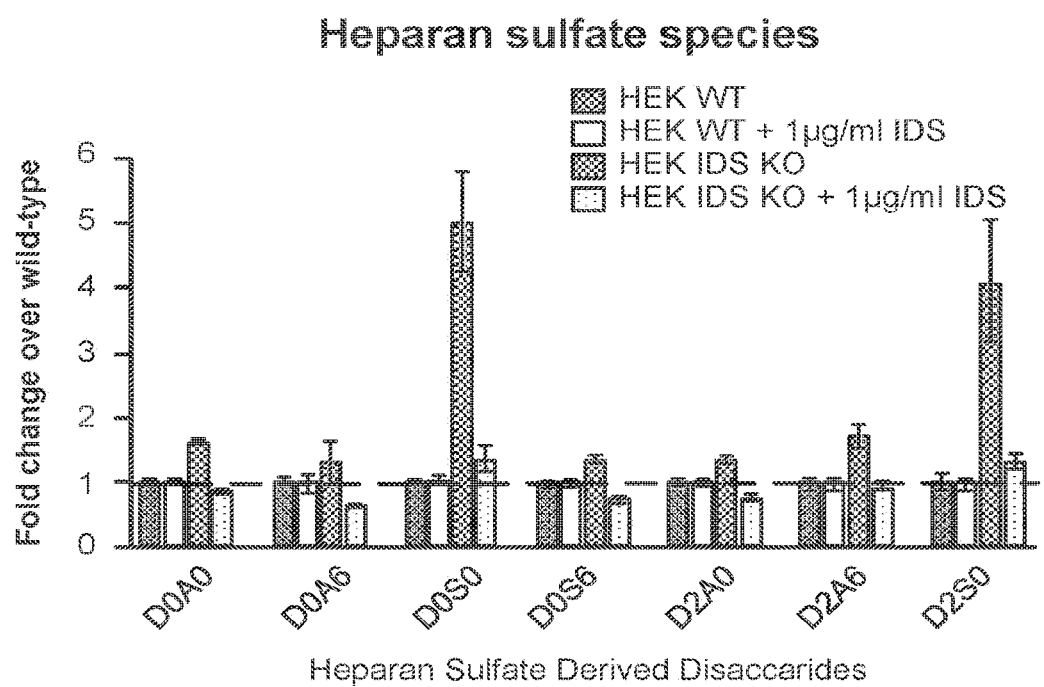
FIG. 4 provides data demonstrating that knockout cells that lack IDS have increased levels of heparan sulfate-derived disaccharides as assessed using an LC-MS/MS assay, and expression of IDS in the IDS knockout (KO) cells rescues the knockout phenotype.

Significant substrate accumulation, as reflected by the amount of disaccharides observed after digestion of heparan sulfate and dermatan sulfate, was seen in IDS KO cells compared to control cell lines, an effect that could be rescued with addition of recombinant IDS to the cells (FIG. 4). This validated that the LC-MS/MS-based assay can be used to assess the cellular activity of IDS and IDS-Fc fusion proteins.

Figure 5A:
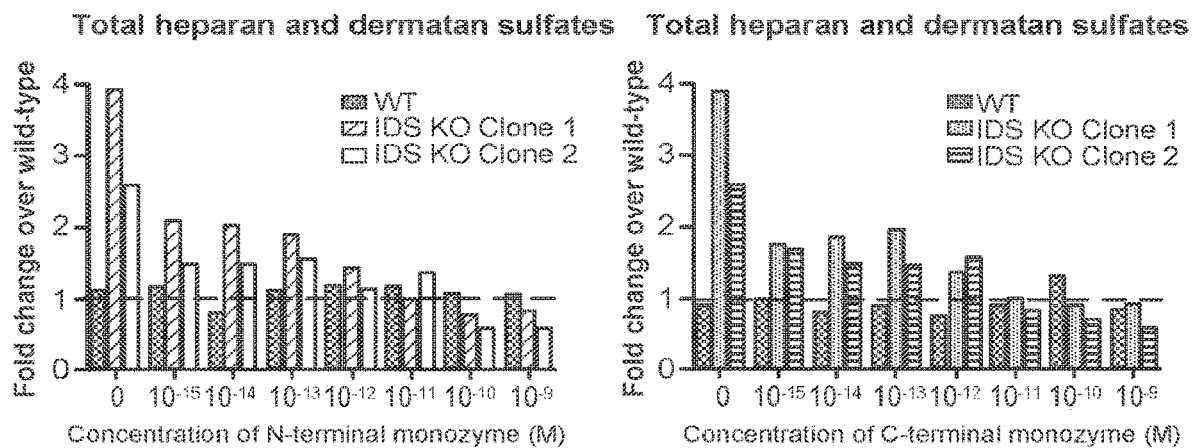
FIG. 5A shows that IDS-Fc fusion proteins as either an N-terminal monozyme or a C-terminal monozyme comprising the same TfR-binding Fc polypeptide (i.e., CH3C.35.21.17) reverse heparan sulfate and dermatan sulfate accumulation in IDS KO cells.
Figure 5B:
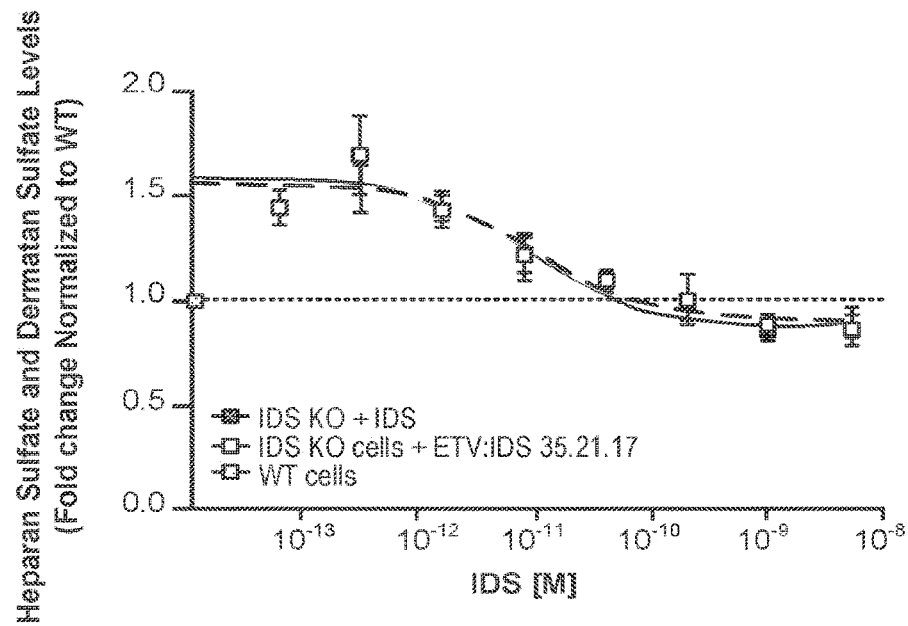
FIG. 5B shows that the N-terminal monozyme ("ETV:IDS 35.21.17") has comparable cellular efficacy to IDS.

Using this assay, it was established that treatment of cells with IDS-Fc fusion proteins as either an N-terminal monozyme (i.e., ETV:IDS 35.21.17) or a C-terminal monozyme comprising the same TfR-binding Fc polypeptide (i.e., CH3C.35.21.17) reduced the levels of heparan and dermatan sulfate-derived disaccharides back to that seen in wild-type cells (FIG. 5A). In addition, the activity of the N-terminal monozyme was comparable to IDS (FIG. 5B). Together, these data demonstrate that IDS-Fc fusion proteins maintain enzymatic activity and can reduce substrate accumulation in IDS KO cells.

Figure 5D:
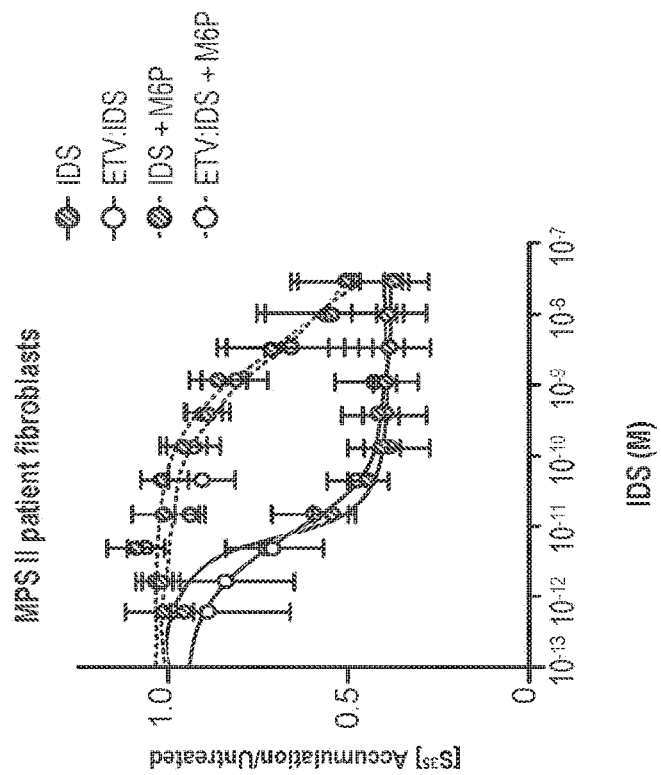
FIG. 5D shows assessment of M6PR-dependent clearance of $S^{35}$-labeled proteins in MPS II patient fibroblasts treated with increasing doses of IDS-Fc fusion protein ("ETV:IDS") or IDS in the presence or absence of 5 mM M6P; n=3.
Figure 5C:
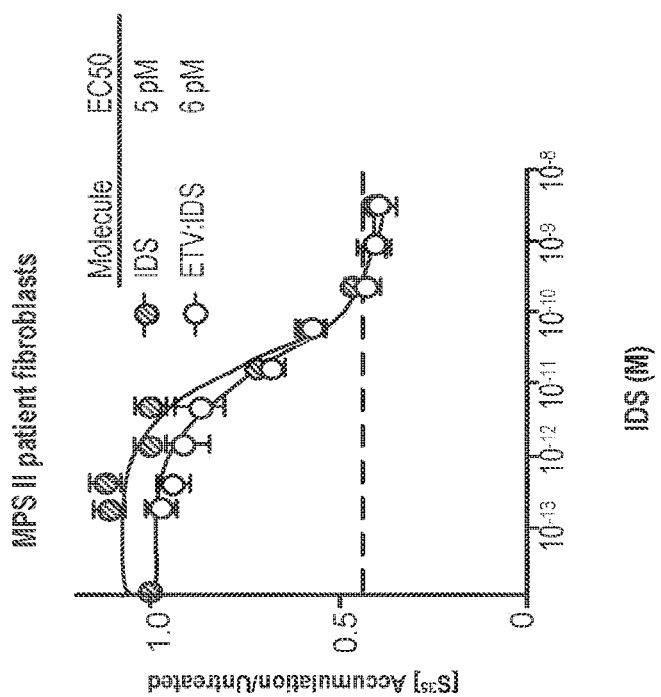
FIG. 5C shows dose-dependent reduction of accumulated $S^{35}$-sulfate labeled proteins in MPS II patient fibroblasts treated with IDS-Fc fusion protein ("ETV:IDS") or IDS; n=8.

The cellular activity of IDS-Fc fusion proteins was also examined in fibroblasts from MPS II patients and healthy controls using a $^{35}S$ pulse-chase assay, in which $^{35}S$ is integrated into newly-synthesized GAGs, as previously described (Lu et al., *Bioconjugate Chemistry*, 21:151-156 (2010)). MPS II patient fibroblasts lack detectable IDS activity, leading to an approximate 10-fold accumulation of substrate and 2.5-fold accumulation of $^{35}S$ signal (FIG. 5C). Similar to the IDS KO cells, IDS-Fc fusion proteins such as ETV:IDS 35.23.2 were highly efficacious in MPS II patient-derived cells, displaying a low picomolar cellular $EC_{50}$ for reducing the accumulation of $S^{35}$-labeled proteins (FIG. 5C). Furthermore, cellular activity of IDS-Fc fusion proteins such as ETV:IDS 35.23.2 was demonstrated to be M6PR-dependent, as an excess of M6P inhibited the clearance of $^{35}S$-labeled proteins in treated MPS II patient fibroblasts (FIG. 5D). Collectively, these data demonstrate that the M6PR-dependent trafficking and cellular activity of IDS can be maintained in the IDS-Fc fusion protein format.

To measure heparan and dermatan sulfate-derived disaccharides in vivo, the LC-MS/MS-based glycomics assay was adapted for analysis from tissues and fluids. Briefly, all tissues and fluids were collected and then immediately frozen and stored at −80° C. Samples were subjected to 5 freeze-thaw cycles and processed as described above for cell analysis. Significant accumulation of heparan sulfate and dermatan sulfate-derived disaccharides was seen in all tissues and fluids analyzed from male IDS KO mice compared to male wild-type littermate controls (Table 1). This assay is used for efficacy studies of the fusion proteins in vivo. IDS KO mice were obtained from The Jackson Laboratories (JAX strain 024744).

TABLE 1

Glycomic analysis of tissue and fluids from IDS KO mice.

| Sample Type | Fold change (over WT) | Amount of total HS and DS-derived disaccharides (ng/100 ug protein) | |
| --- | --- | --- | --- |
| | | WT | IDS KO |
| Liver | 86.3 | 6.3 (+/−0.4) | 543.6 (+/−14.7) |
| Kidney | 14.1 | 29.3 (+/−0.9) | 413.4 (+/−6.1) |
| Lung | 9.0 | 40.3 (+/−6.9) | 362.6 (+/−37.0) |
| Brain | 8.8 | 5.8 (+/−0.5) | 51.3 (+/−2.5) |
| Spleen | 7.4 | 19.5 (+/−5.8) | 145.2 (+/−5.3) |
| Plasma | 49.1 | 0.4 (+/−0.03) | 20.0 (+/−5.1) |
| Serum | 43.1 | 0.5 (+/−0.03) | 23.5 (+/−4.8) |
| CSF | 20.1 | 0.04 (+/−0.007) | 0.78 (+/−0.05) |
| Urine | 13.8 | 38.83* (+/−1.4) | 537.3* (+/−92.9) |

Figure 6:
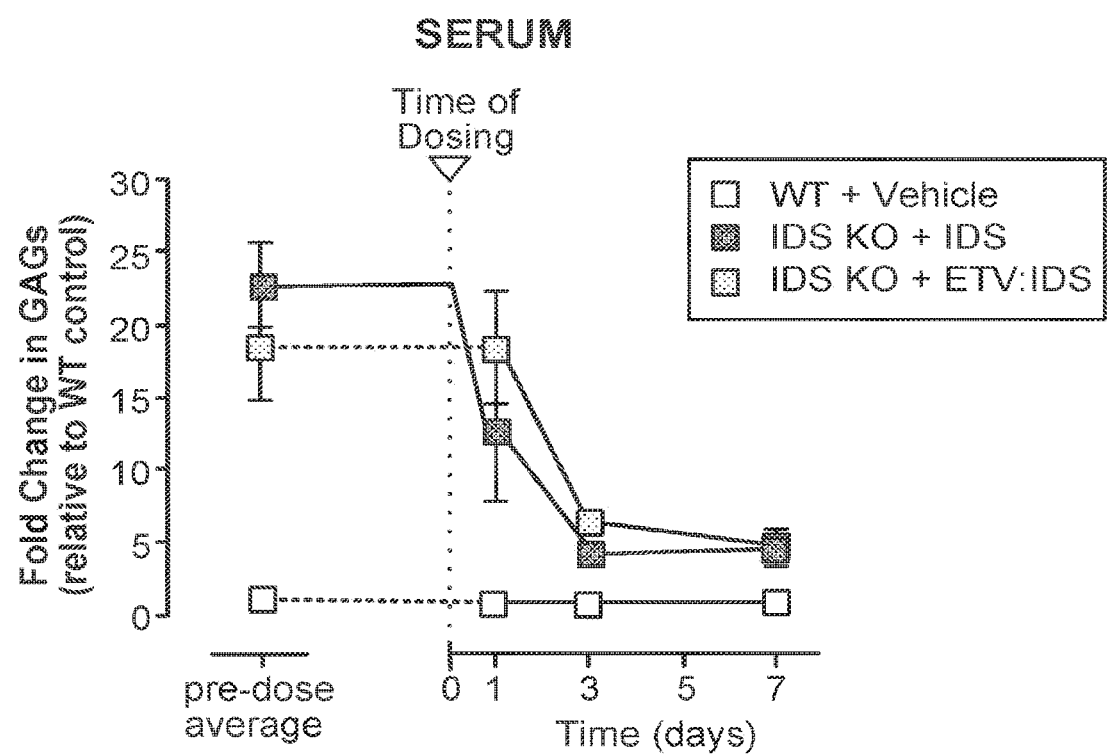
FIG. 6 provides data illustrating heparan and dermatan sulfate levels in serum from wild-type (WT) mice dosed with vehicle or IDS KO mice dosed with IDS or an IDS-Fc fusion protein ("ETV:IDS") in mice over time. "ETV:IDS"=ETV:IDS 35.21.
Figure 7:
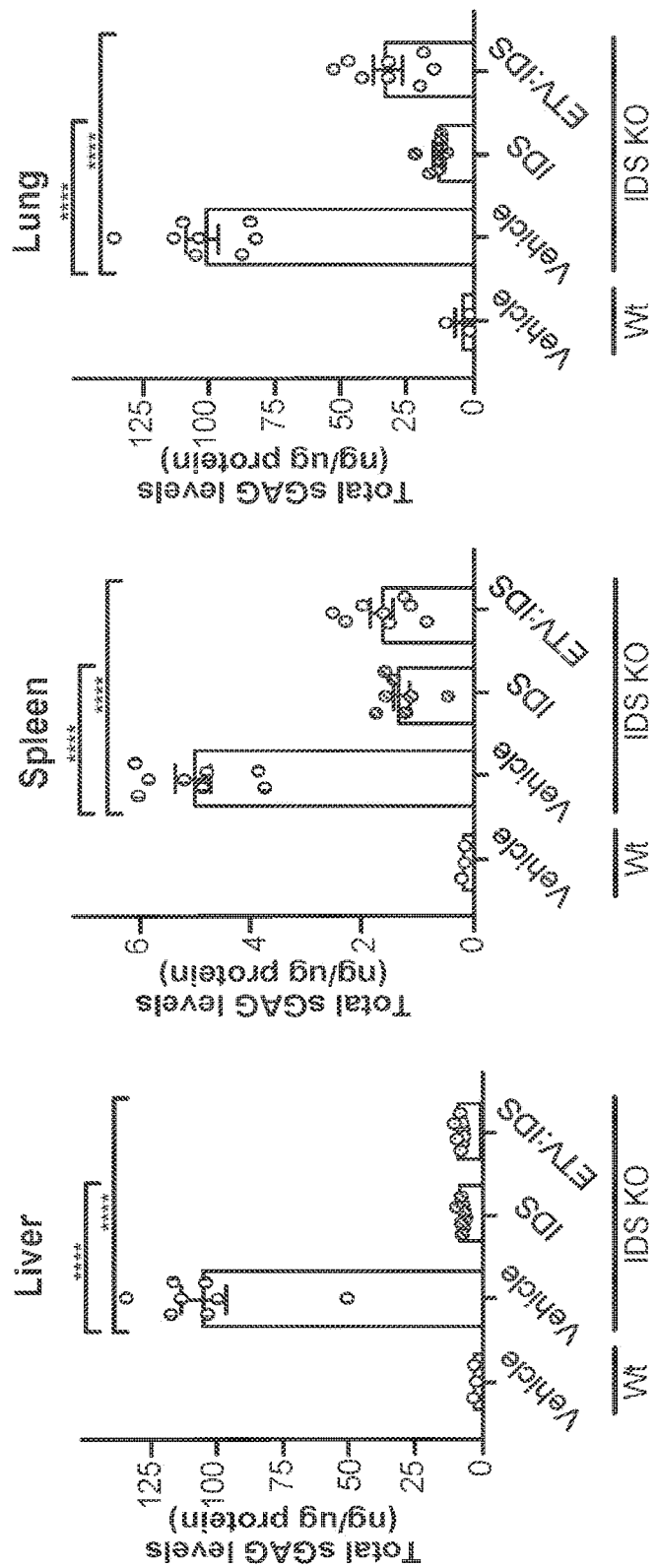
FIG. 7 provides data illustrating that the collective levels of disaccharides D0S0, D0A0, and D0a4 (referred to as "Total sGAG levels") in peripheral tissues from IDS KO mice were assessed seven days post-administration of a single intravenous injection of 40 mg/kg IDS-Fc fusion protein ("ETV:IDS") or 5.3 mg/kg IDS and compared to vehicle-treated IDS KO and wild-type mice; n=8 for IDS KO groups and n=3 for wild-type groups. Data shown as mean±SEM with p values: one-way ANOVA with Dunnett multiple comparison test;  p<0.01 and ** p<0.0001. "ETV:IDS"=ETV:IDS 35.21.

Using this method, the levels of heparan and dermatan sulfate-derived disaccharides were assessed in serum from wild-type (WT) mice dosed with vehicle and IDS KO mice dosed with IDS or an IDS-Fc fusion protein (i.e., ETV:IDS 35.21). Baseline measurements prior to dosing demonstrated significant accumulation of heparan and dermatan sulfate-derived disaccharides in serum from IDS KO mice compared to WT mice. After dosing with the IDS-Fc fusion protein, the levels of heparan and dermatan sulfate-derived disaccharides were significantly reduced in IDS KO serum, showing a comparable reduction as that seen in serum from IDS KO mice dosed with IDS (FIG. 6). These data demonstrate that the IDS-Fc fusion protein is active in vivo and can reduce substrate accumulation in IDS KO mice. Based on these data, the distribution and pharmacodynamic (PD) response was assessed in tissues of IDS KO mice seven days after a single dose of the IDS-Fc fusion protein. IDS KO mice were intravenously administered 40 mg/kg of IDS-Fc fusion protein or 5.3 mg/kg of IDS (25% molar equivalent dose) as a positive control, and GAG levels were assessed. Distribution of both molecules in peripheral tissues was confirmed at two hours post-dose. Significant substrate reduction was observed in the liver, spleen, and lung of IDS KO mice seven days after dosing with the IDS-Fc fusion protein (FIG. 7).

Figure 8:
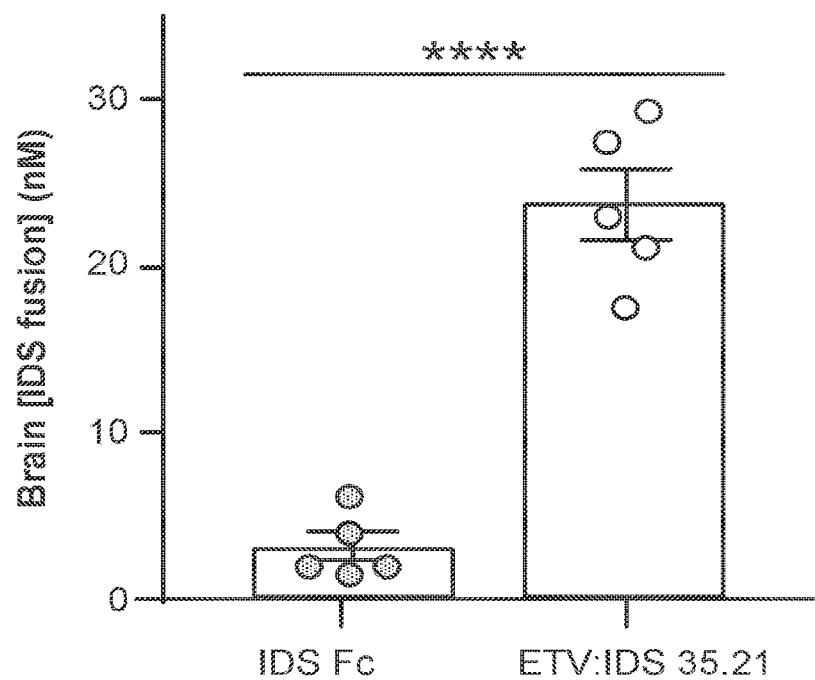
FIG. 8 provides data illustrating the concentration of IDS-Fc fusion proteins in the brains of human TfR knock-in (TfR$^{ms/hu}$ KI) mice after peripheral administration of the IDS-Fc fusion protein ETV:IDS 35.21 or a control IDS-Fc fusion protein lacking the mutations that confer TfR binding ("IDS:Fc").
Figure 9A:
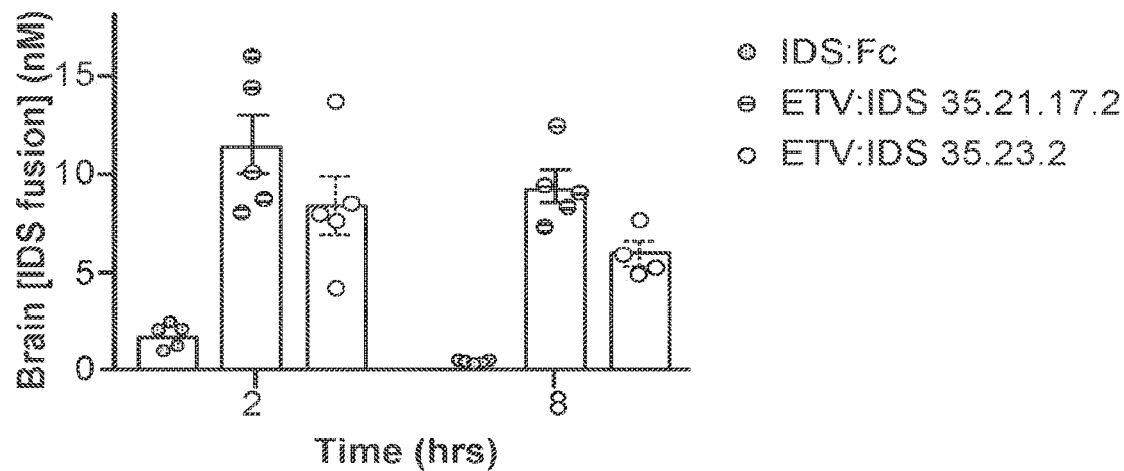
FIG. 9A provides data illustrating the concentration of IDS-Fc fusion proteins in the brains of TfR$^{ms/hu}$ KI mice after peripheral administration of the IDS-Fc fusion protein ETV:IDS 35.21.17.2 or ETV:IDS 35.23.2, or a control IDS-Fc fusion protein lacking the mutations that confer TfR binding ("IDS:Fc").
Figure 9B:
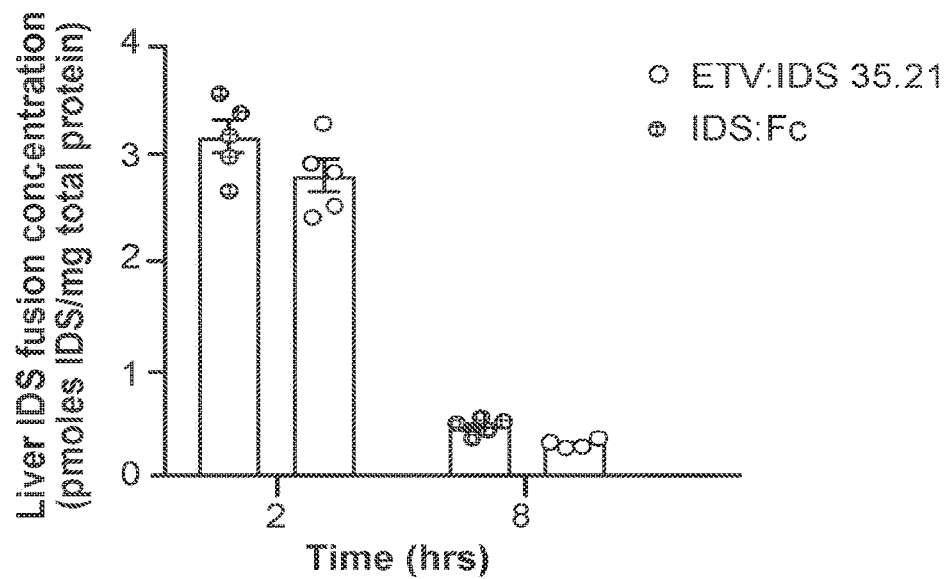
FIG. 9B provides data illustrating the liver concentration of the IDS-Fc fusion protein ETV:IDS 35.21 or IDS:Fc in TfR$^{ms/hu}$ KI mice following a single intravenous injection of 50 mg/kg dose; n=4-5. Graphs display mean±SEM.

To determine whether TfR-binding IDS-Fc fusion proteins showed improved brain delivery compared to a control IDS-Fc fusion protein, human TfR knock-in (TfR$^{ms/hu}$ KI) mice were dosed with 50 mg/kg of the TfR-binding IDS-Fc fusion protein ETV:IDS 35.21 or a control IDS-Fc fusion protein lacking the mutations that confer TfR binding ("IDS: Fc"), and the concentration of the IDS-Fc fusion protein in brain was measured using a sandwich ELISA-based assay described in Example 3 below at 4 hours post-dose. TfR$^{ms/hu}$ KI mice were generated as described in International Patent Publication No. WO 2018/152285 using CRISPR/Cas9 technology to express human Tfrc apical domain within the murine Tfrc gene; the resulting chimeric TfR was expressed in vivo under the control of the endogenous promoter. Significantly higher levels of the IDS-Fc fusion protein ETV:IDS 35.21 were detected in brain compared to the control IDS-Fc fusion protein, with an average brain concentration of 23.7 nM for ETV:IDS 35.21 (FIG. 8). The brain uptake of two additional TfR-binding IDS-Fc fusion proteins, ETV:IDS 35.21.17.2 and ETV:IDS 35.23.2, was assessed using the TfR$^{ms/hu}$ KI mice. TfR$^{ms/hu}$ KI mice were dosed with 50 mg/kg of ETV:IDS 35.21.17.2, ETV:IDS 35.23.2, or the control IDS-Fc fusion protein ("IDS:Fc"), and the concentration of the IDS-Fc fusion protein in brain was measured using the sandwich ELISA-based assay at 2 hours and 8 hours post-dose. Administration of the TfR-binding IDS-Fc fusion proteins led to a 5-fold increase in brain uptake relative to the control IDS-Fc fusion protein at 2 hours and a 10-20 fold increase in brain concentration at 8 hours post-dose (FIG. 9A). Serum PK and accumulation of the intact fusion protein in the liver was equivalent for both ETV:IDS 35.21 and IDS:Fc (FIG. 9B), indicating that the IDS moiety largely determines the distribution phase of the plasma clearance. Brain levels of TfR-binding IDS-Fc fusion proteins remained elevated for eight hours, decreasing slightly with peripheral clearance. Together, these data demonstrate that the interaction of the TfR-binding IDS-Fc fusion proteins with TfR generally maintains peripheral distribution while significantly improving brain exposure.

Intravenous Administration of ETV:IDS Reduces GAGs in the Brain

To examine whether the improved brain exposure observed with the TfR-binding IDS-Fc fusion proteins described above and prepared in accordance with Example 1 (referred to herein as ETV:IDS) produced a corresponding reduction of accumulated substrates in the brain, a mouse model deficient for IDS that harbors the human TfR apical domain knocked into the murine TfR was generated (referred to herein as IDS KO×TfR$^{ms/hu}$ KI mice). Briefly, TfR$^{ms/hu}$ KI male mice were bred to female IDS heterozygous mice to generate IDS KO mice in a TfR$^{ms/hu}$ KI homozygous background. All mice used in this study were males and housed under a 12 hour light-dark cycle with ad libitum access to food (LabDiet IL irradiated 6F) and water.

IDS KO×TfR$^{ms/hu}$ KI mice were intravenously administered either single or four weekly activity-equivalent doses of ETV:IDS or IDS (747 nmol product/min/kg or 40 mg/kg and 14.2 mg/kg, respectively), and pharmacokinetic and pharmacodynamic responses were assessed. In particular, the effect of peripheral administration of ETV:IDS on brain and tissue GAG in IDS KO×TfR$^{ms/hu}$ KI mice was determined using 2-month-old IDS KO×TfR$^{ms/hu}$ KI mice injected intravenously (i.v.) with saline, IDS (14.2 mg/kg body weight), or ETV:IDS (40 mg/kg body weight) either once (n=8) or once every week for 4 weeks (n=8). 2-month-old littermate TfR$^{ms/hu}$ KI mice, injected i.v. with saline either once (n=5) or once every week for 4 weeks (n=5), were used as controls. For animals dosed with IDS or ETV:IDS, in-life serum samples were collected by submandibular bleed at various time points. All animals were sacrificed either 7 days post single dose or 7 days following last 4 week dose. Urine, serum, CSF, liver, kidney, spleen, lung, heart and right hemibrain were dissected and flash-frozen on dry ice.

Figure 10A:
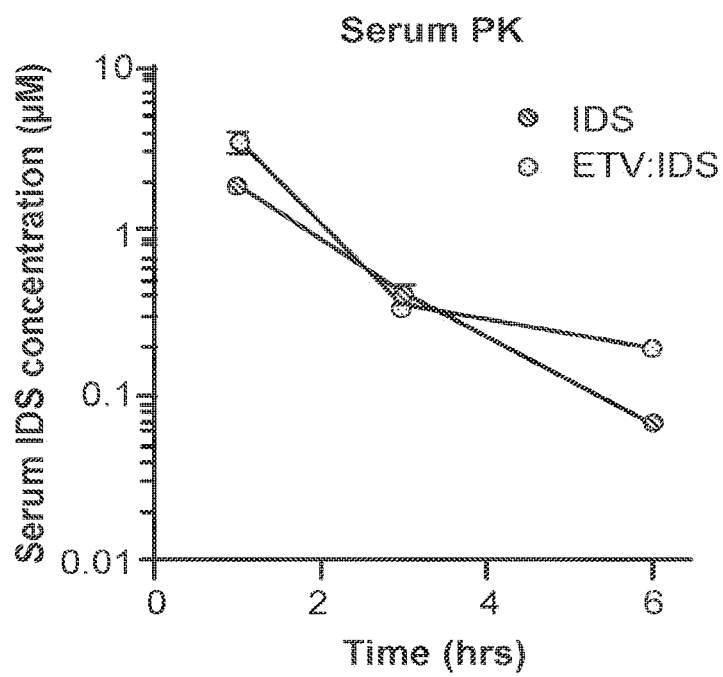
FIGS. 10A-10C show that ETV:IDS reduces GAGs in the brain and peripheral tissues of IDS KO×TfR$^{ms/hu}$ KI mice. IDS KO×TfR$^{ms/hu}$ KI mice were administered a single intravenous injection of 40 mg/kg ETV:IDS or 14.2 mg/kg IDS or four weekly doses as described in Example 2. The concentration of IDS in serum (FIG. 10A) and tissues (FIG. 10B) was measured in IDS KO×TfR$^{ms/hu}$ KI mice following a single dose. Tissue PK is shown 2 h post-dose; n=4. Graphs display mean±SEM and p values: unpaired t-test analysis.
Figure 10B:
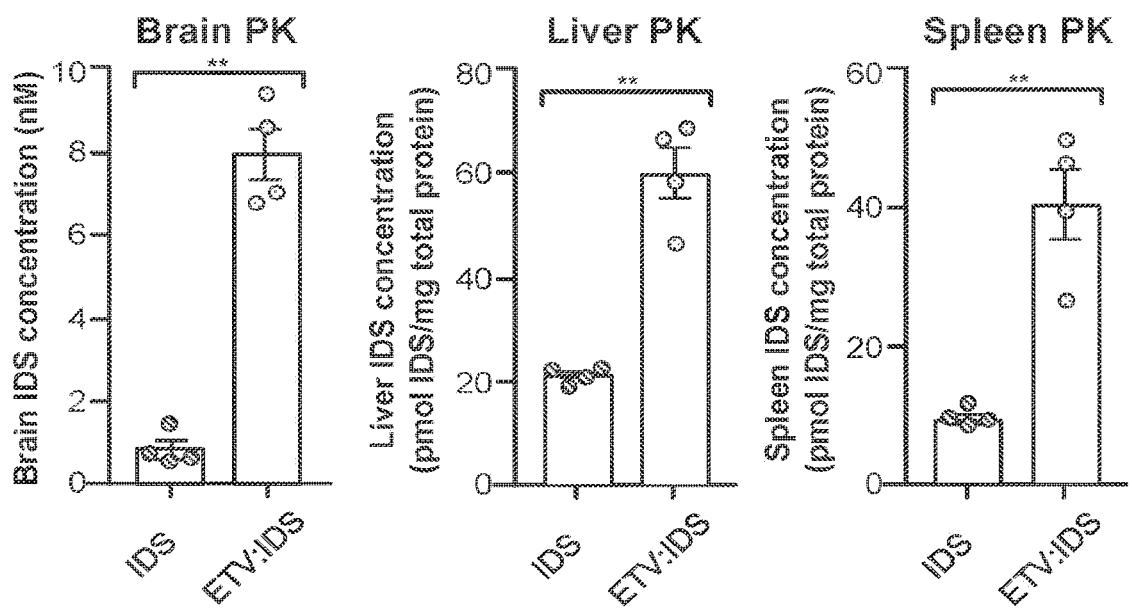

Following a single dose, ETV:IDS exhibited a similar serum clearance profile as IDS, as assessed using an ELISA-based assay described in Example 3 below for detecting the concentration of IDS, providing additional support that the enzyme largely dictates peripheral clearance (FIG. 10A). Brain levels of ETV:IDS were significantly increased compared to IDS two hours post-dose, with a mean concentration of 8.4 and 1.6 nM, respectively, and liver and spleen levels of ETV:IDS were significantly elevated compared to IDS (FIG. 10B).

Figure 10C:
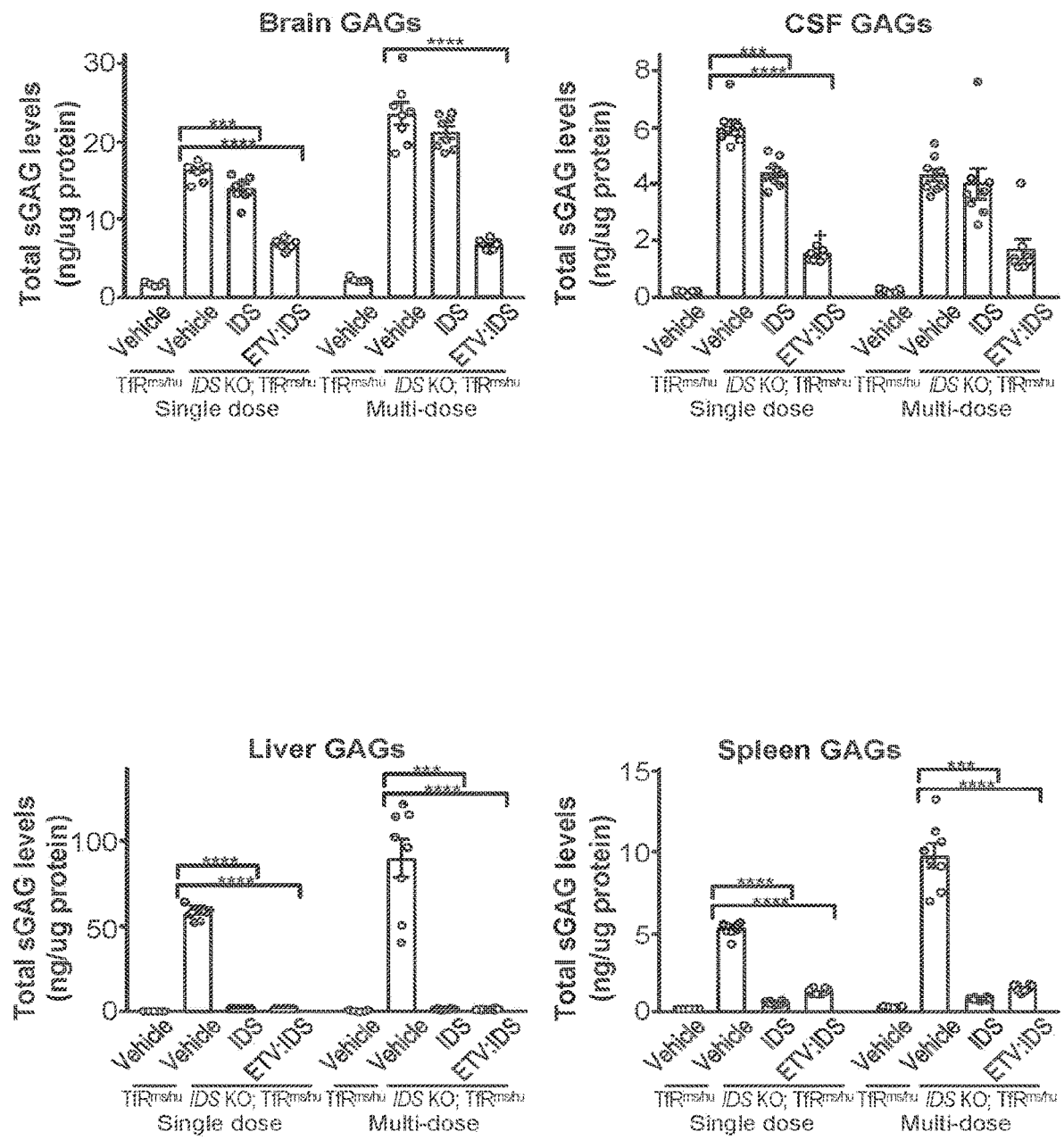

To determine whether ETV:IDS reduces substrate levels in the brain, GAG levels were assessed as described in Example 2 in IDS KO×TfR$^{ms/hu}$ KI mice after a single dose or four, weekly doses of enzyme. IDS marginally decreased brain GAG levels at early time points but was ineffective at significantly lowering GAGs after four weeks of treatment (FIG. 10C). ETV:IDS, however, reduced brain GAG levels by approximately 58% following a single dose and 71% following four weeks of treatment (FIG. 10C). This led to a concomitant reduction of CSF GAGs by approximately 75% after a single dose which was sustained after four weeks of dosing (FIG. 10C). Both molecules effectively lowered GAG levels in liver and spleen after one week, and the response was sustained with repeat dosing (FIG. 10C), demonstrating that TfR binding does not negatively impact pharmacodynamic responses in these tissues. Together, these data demonstrate that ETV:IDS significantly increases brain exposure of enzyme and robustly reduces substrate accumulation in both the periphery and CNS.

Example 3. Pharmacokinetic Characterization of IDS Fusion Proteins

This example describes pharmacokinetic (PK) characterization of engineered IDS-Fc fusion proteins in mouse plasma.

To determine the plasma half-life and clearance of TfR-binding IDS-Fc fusion proteins, 7-8 week old male C57BL/6 mice were dosed with 10 mg/kg of two IDS-Fc fusion protein molecules (an N-terminal monozyme and a C-terminal monozyme) via tail vein injection. The concentration of IDS-Fc fusion proteins remaining in plasma over a 24-hour period was measured using an ELISA-based assay. Briefly, the concentration of IDS-Fc fusion proteins in mouse plasma was quantified using a sandwich ELISA. An anti-Fc capture antibody (Abcam # ab124055) was coated onto a 384-well MaxiSorp™ plate (Thermo Scientific #464718) at 3 µg/mL. The plate was blocked with 5% BSA and then incubated with plasma diluted either 1:1,000 or 1:10,000. Next, a polyclonal anti-IDS detection antibody (R&D Systems # AF2449) was added at 0.5 µg/mL followed by an anti-goat-HRP antibody. The plates were developed using TMB substrate, stopped with sulfuric acid, and the absorbance at 450 nm measured on a BioTek plate reader. The standard curves were the individual constructs from 200-0.1 ng/mL in a 4-fold dilution series and were fit using a four-parameter logistic regression.

Using this assay, it was established that the terminal plasma half-life of IDS-Fc fusion proteins was 7.7-10 hrs (Table 2). No unanticipated PK liabilities were seen with IDS-Fc fusion proteins in vivo.

TABLE 2

Pharmacokinetics of IDS-Fc fusion proteins in mice over 24 hours.

| ETV:IDS Description | Dose (mg/kg) | CL (ml/h/kg) | CL (ml/d/kg) | Terminal $t_{1/2}$ (hrs) |
|---|---|---|---|---|
| N-terminal monozyme | 10 | 22.0 | 528 | 10 |
| C-terminal monozyme | 10 | 42.6 | 1020 | 7.7 |

Example 4. Construction of Fusion Proteins Comprising Acid Sphingomyelinase (ASM)

Design and Cloning

ASM-Fc fusion proteins were designed as dimers of a fusion polypeptide where a mature, human ASM enzyme is fused to a human IgG1 fragment that includes the Fc region (an "ASM-Fc fusion polypeptide"). In some embodiments, an ASM-Fc fusion polypeptide comprises a modified Fc region containing mutations that confer transferrin receptor (TfR) binding. In particular, ASM-Fc fusion polypeptides were created in which ASM fragments were fused to the N-terminus of the human IgG1 Fc region. In some cases, a linker was placed between the ASM and IgG1 fragments to alleviate any steric hindrance between the two fragments. In all constructs, the native ASM signal sequence, amino acids 1-46 (UniProtKB ID—P17405), was removed and replaced with a secretion signal from the kappa chain V-III, amino acids 1-20 (UniProtKB ID—P01661), to improve secretion of ASM. Additionally, in the fusion proteins, ASM was truncated at its C-terminus, ending at amino acid Q620, to prevent any unwanted cleavage between ASM and the human IgG1 Fc region. A fragment of the human IgG1 Fc region (UniProtKB ID—P01857) was then placed in frame with the C-terminus of ASM beginning at amino acid E99, with the cysteine at position 103 being mutated to serine. In some embodiments, the IgG1 fragments contained additional mutations to facilitate heterodimerization of the two Fc regions. Additionally, ASM-Fc fusion proteins were generated containing one or two molecules of ASM. As a control, ASM-hexahistidine (SEQ ID NO:241) fusion proteins were designed consisting of ASM amino acids 1-628, truncated to remove the C-terminal cysteine and promote enzymatic activation, and a C-terminally fused hexahistidine tag (SEQ ID NO:241).

Recombinant Protein Expression and Purification

To express recombinant ASM enzyme fused to an Fc region, ExpiCHO-S cells (Thermo Fisher) were transfected at 6×10$^6$ cells/ml density with Expifectamine CHO/plasmid DNA complex according to manufacturer's instructions (Thermo Fisher Scientific). After transfection, cells were incubated at 32° C. with a humidified atmosphere of 6-8% CO$_2$ in an orbital shaker (Infors HT Multitron). On day one post-transfection, Expifectamine enhancer and Expifectamine feed were added to the culture. Media supernatant was harvested by centrifugation after 48-72 hour expression time. The clarified supernatant was supplemented with EDTA-free protease inhibitor (Roche) and was stored at −80° C.

For ASM-Fc fusion protein purification, clarified media supernatant was supplemented with 200 µM zinc acetate (Sigma Aldrich). The supernatant was loaded on HiTrap Mab Select SuRe Protein A affinity column (GE Healthcare Life Sciences) and washed with 200 mM arginine and 137 mM succinate buffer pH 5.0 (arginine-succinate buffer). The fusion proteins were eluted in 100 mM QB citrate buffer pH 3.0 supplemented with 200 µM zinc acetate. Immediately after elution, the arginine-succinate buffer was added to adjust the pH. Protein aggregates were separated from ASM-Fc fusion proteins by size exclusion chromatography (SEC) on Superdex 200 increase 10/300 GL column (GE Healthcare Life Sciences). The SEC mobile phase was kept in arginine-succinate pH 5.0 buffer supplemented with 200 µM zinc acetate. All chromatography steps were performed on using an Akta Pure System or Akta Avant system (GE Healthcare Life Sciences). Fraction purity was assessed by non-reducing SD S-PAGE. As shown in FIG. 11, purification yielded homogeneous ASM-Fc fusion proteins.

Example 5. Characterization of ASM Fusion Proteins

ASH-Fc Fusion Proteins are Active In Vitro and in Cells

Figure 12:
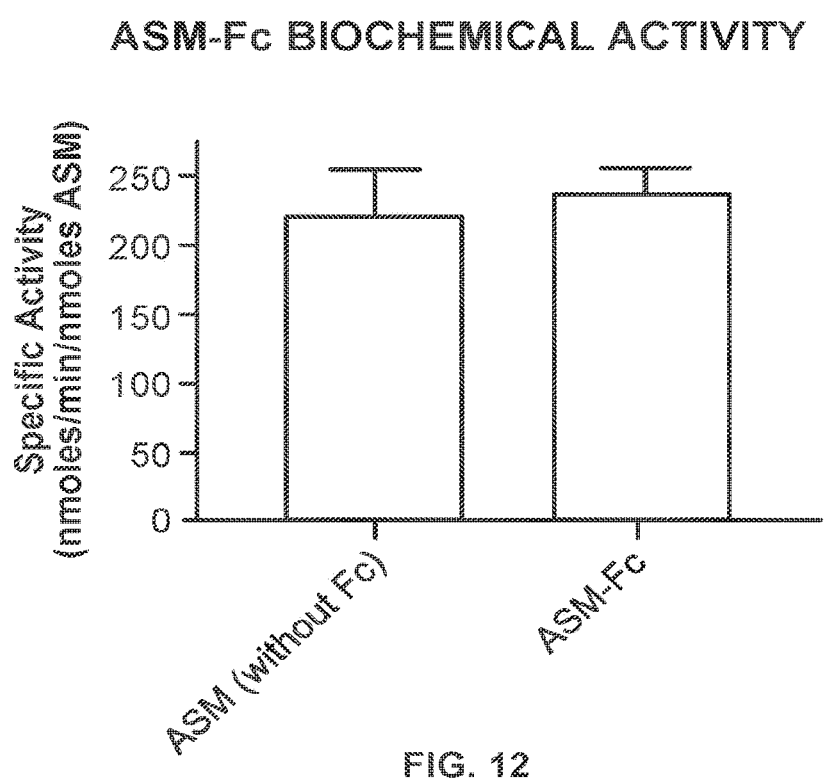
FIG. 12 provides data demonstrating in vitro ASM activity of an ASM-Fc fusion protein analyzed in FIG. 11.

To demonstrate that ASM maintains its enzymatic activity when fused to the human IgG heavy chain, the in vitro and cellular activity of ASM-Fc fusion proteins were assessed. In vitro activity of recombinant ASM enzyme or recombinant ASM-Fc fusion proteins were measured using a synthetic chromogenic analog of sphingomyelin. Specifically, 2.5 mM 2-(N-hexadecanoylamino)-4-nitrophenylphosphorylcholine (EMD Millipore) was mixed with 0.75 nM ASM in 100 mM sodium acetate buffer (pH 5.3; final concentrations in 100 µL reaction volume). The reaction was incubated for 16 hr at 37 and stopped with the addition of an equal volume of 0.2 M NaOH. Absorbance of the reaction solution was then measured at 410 nm. A p-nitrophenol standard curve was fit by linear regression to calculate the amount of product and verified as less than 10% of total substrate cleavage, Specific activity (nmol product/min/nmol ASM) was calculated by dividing the amount of product by the reaction time and molar amount of ASM. The in vitro enzymatic activity assay demonstrated that ASM-Fc fusion proteins are active and indicate that fusion of an Fc region to ASM does not interfere with its enzymatic activity (FIG. 12).

ASM KO cells were generated using CRISPR/CAS9 to provide a cellular system to test the cellular activity of ASM-Fc fusion proteins. HEK 293T cells (ATCC) were transfected with CRISPR/CAS9 pCas-Guide-EF1a-GFP vector (Origene) containing guide sequences targeted to the second half of exon 2 in human SMPD1. Single cell clones were analyzed for the presence of indels within the genomic sequence of ASM following Guide-it Mutation Detection Kit (Clontech) per manufacturer's instructions. Indel positive clone cell lysates were subjected to an in vitro ASM enzyme assay using the ASM chromogenic substrate 2-N-Hexadecanoylamino-4-nitrophenylphosphorylcholine (EMD Millipore). Briefly, the in vitro activity assay was performed using 12.5, 25, 50 and 100 µs cell lysate in 100 mM sodium acetate buffer (pH 5.3). The reaction was started by the addition of 2.5 mM substrate and stopped after 20 hours with addition of 0.2 M NaOH. ASM activity in HEK293T CRISPR clones was compared to recombinant ASM used as an assay standard, HEK wild-type (WT) lysates, and HEK cell lysates overexpressing ASM. Clones with enzyme activity levels comparable to background signal were sequence verified after mini-Topo (Thermo Fisher Scientific) cloning and confirmed as KO clones. Subsequent cell assays used three unique and verified ASM KO clones and three independent batches of WT HEK293T cells.

Figure 13:
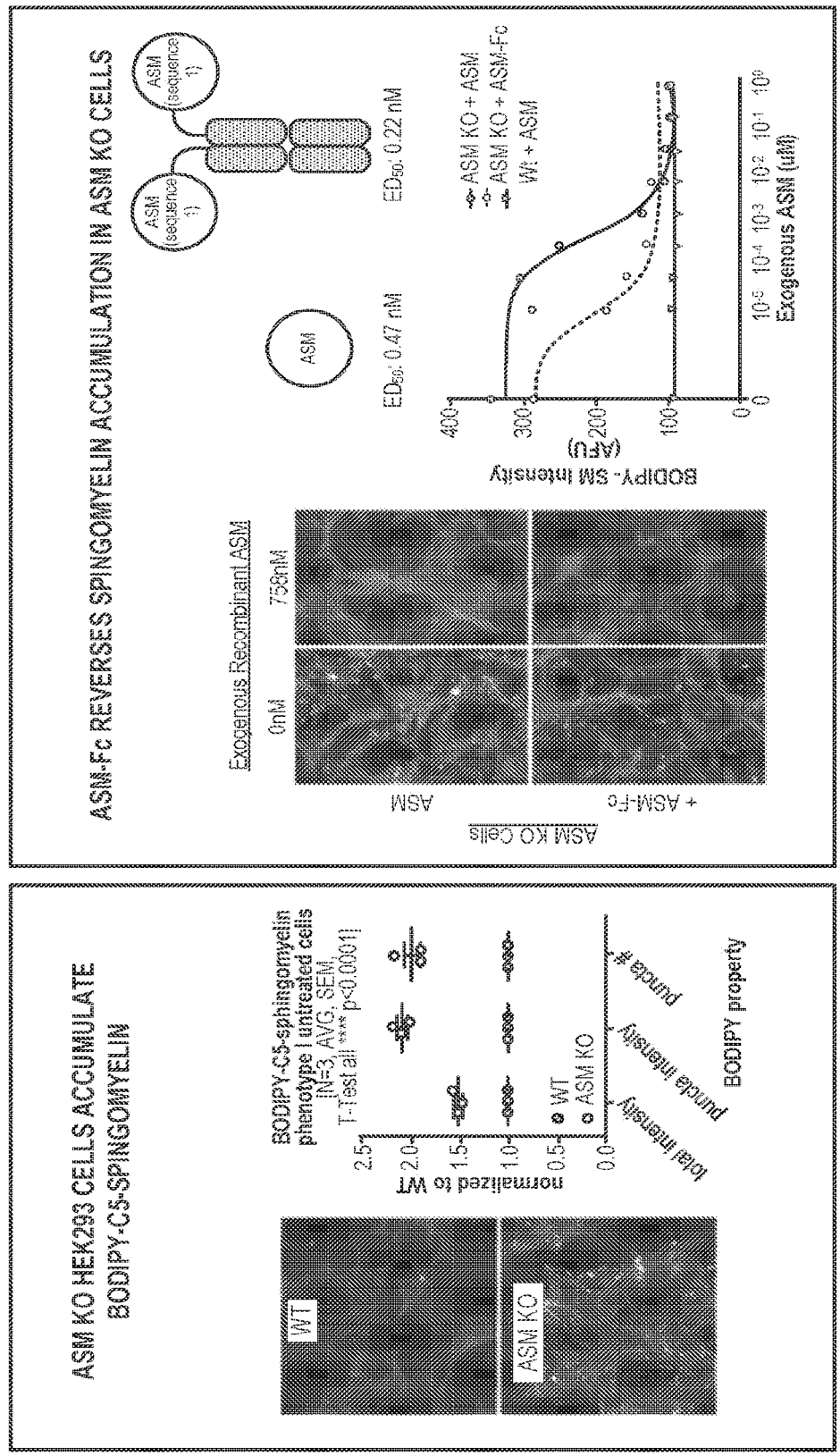
FIG. 13 provides data showing that an ASM-Fc fusion protein as analyzed in FIG. 11 reduces sphingomyelin accumulation in ASMKO cells using an imaging-based assay.

To test the cellular activity of naked ASM enzyme or ASM-Fc fusion proteins, two cellular assays were developed that allow monitoring of the amount of substrate accumulation (sphingomyelin) in ASM KO cells basally and after treatment with ASM or ASM-Fc fusions. First, an imaging-based assay was developed to monitor the amount of BODIPY-conjugated C5-sphingomyelin accumulation in ASMKO cells. Briefly, HEK293T WT and ASMKO cells were plated in DMEM supplement with 10% FBS (Gibco) at low density onto PDL-coated, 96-well plates (Perkin Elmer). Four hours post-plating, recombinant ASM enzyme, ASM-Fc fusion proteins, or control buffer were added to each well and incubated for 48 hours at 37° C. Media was removed, replaced with fresh media containing 1 µM BODIPY-C5-sphingomyelin (Thermo Fisher Scientific), and incubated at 37° C. for 16 hours. Cells were then washed with PBS, fixed with 4% paraformaldehyde, and stained with nuclear (DAPI, Thermo Fisher) and cytoplasmic (far red cell mask, Thermo Fisher Scientific) stains. Images were acquired on the Opera Phenix confocal microscope (Perkin Elmer) with a 63× objective with multiple fields per well and triplicate wells per condition. Image analysis was performed using Harmony software (Perkin Elmer) that detects and analyzes the average total intensity, puncta number, and puncta intensity of the BODIPY-C5-sphingomylein on a per cell basis. These per cell values were then averaged into a per well value that was used to analyze the effect of genotype and/or treatment on the accumulation of BODIPY-C5-sphingomyelin. Significant BODIPY-C5-sphingomyelin accumulation was seen in ASM KO cells compared to control cell lines, an effect that could be rescued with the addition of recombinant ASM enzyme and ASM-Fc fusion proteins (FIG. 13).

To further verify that ASM-Fc fusion proteins maintain their activity in cells, an LC-MS/MS-based assay was developed to monitor the accumulation of endogenous sphingomyelin in ASMKO cells. HEK293T WT and ASMKO cells were cultured and treated with enzyme as described above. At 68 hours post-plating, with or without ASM or ASM-Fc fusion protein treatment, cells were washed thoroughly with PBS, and lipids were extracted with a mixture of water:methanol [1:1, v/v] spiked with appropriate internal standards. Lipids were extracted using methyl-tert-butyl ether (MTBE), vortexed, and centrifuged at 10,000×g and 4° C. for 10 min. The upper MTBE fraction containing lipids was then evaporated to dryness under gentle nitrogen stream. Lipids were resuspended in a mixture of isopropanol:acetonitrile:water [2:1:1, v/v/v] and then transferred to mass-spectrometry vials for further analysis.

Figure 14:
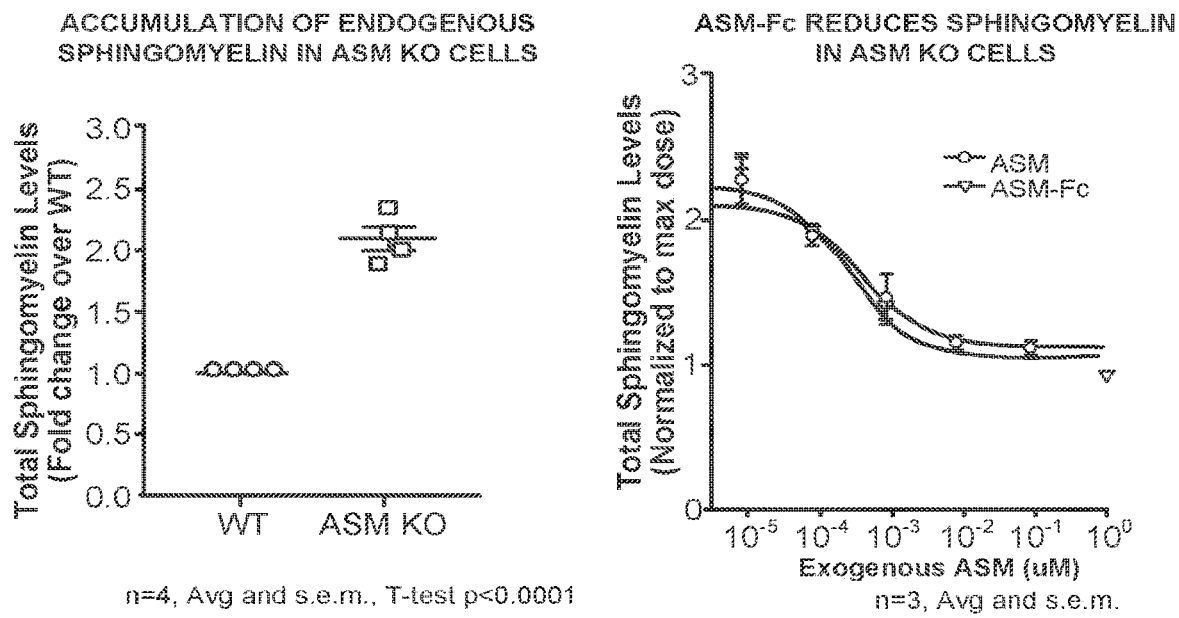
FIG. 14 provides data showing that an ASM-Fc fusion protein as analyzed in FIG. 11 reduces sphingomyelin accumulation in ASMKO cells using an LC-MS/MS-based assay.

Lipid analyses were performed by liquid chromatography (Shimadzu Nexera X2 system, Shimadzu Scientific Instrument, Columbia, Md., USA) coupled to electrospray mass spectrometry (Sciex 6500+ QTRAP, Sciex, Framingham, Mass., USA). For each analysis, 5 of sample was injected on a BEH C18 1.7 µm, 2.1×100 mm column (Waters Corporation, Milford, Mass., USA) using a flow rate of 0.25 mL/min at 55° C. Mobile phase A consisted of 60:40 acetonitrile/water (v/v) with 10 mM ammonium formate+ 0.1% formic acid. Mobile phase B consisted of 90:10 isopropanol/acetonitrile (v/v) with 10 mM ammonium formate+0.1% formic acid. The gradient was programmed as follows: 0.0-8.0 min from 45% B to 99% B, 8.0-10.0 min at 99% B, 10.0-10.1 min to 45% B, and 10.1-12.0 min at 45% B. Electrospray ionization was performed in the positive-ion mode applying the following settings: curtain gas at 20; collision gas was set at medium; ion spray voltage at 5200; temperature at 250; ion source gas 1 at 50; ion source gas 2 at 60. Data acquisition was performed using Analyst 1.6 (Sciex) in multiple reaction monitoring mode (MRM). Collision energy at 40; declustering potential at 80; entrance potential at 10; collision cell exit potential at 12.5. Ceramides (Cer) were detected as [M–H2O+H]$^+$ using the following MRM transitions: Cer d18:1/16:0 at m/z 538.5>264.3; Cer d18:1/18:0 at m/z 566.6>264.3; Cer d18:1/20:0 at m/z 594.6>264.3; Cer d18:1/22:0 at m/z 622.6>264.3; Cer d18:1/24:0 at m/z 650.6>264.3; Cer d18:1/24:1 at m/z 648.6>264.3; Cer d18:1/17:0 at m/z 552.4>264.3 was used as internal standard. Sphingomyelins (SM) were detected as [M+H]$^+$ using the following MRM transitions: SM d18:1/16:0 at m/z 703.7>184.1; SM d18:1/18:0 at m/z 731.7>184.1; SM d18:1/20:0 at m/z 759.7>184.1; SM d18:1/22:0 at m/z 787.7>184.1; SM d18:1/24:0 at m/z 815.7>184.1; SM d18:1/24:1 at m/z 813.7>184.1; SM d18:1/18:1 (d9) at m/z 738.7>184.1 was used as internal standard. Lipids were identified based on their retention times and MRM properties of commercially available reference standards (Avanti Polar Lipids, Birmingham, Ala., USA). Quantification was performed using MultiQuant 3.02 (Sciex). Lipids were normalized to total protein amount. Protein concentration was measured using BCA assay (Pierce). LC-MS/MS analysis demonstrated that ASM-Fc fusion proteins can reduce the levels of endogenous sphingomyelin in ASM KO cells back to that seen in wild-type cells (FIG. 14). Further, ASM-Fc fusion proteins were as potent as naked ASM enzyme in reducing sphingomyelin in both assays (Table 3).

TABLE 3

ASM-Fc fusion proteins show similar potency to ASM in cellular assays.

| Molecule | EC$_{50}$ (LC/MS-MS) | EC$_{50}$ (Imaging assay) |
|---|---|---|
| ASM | 0.32 nM | 0.47 nM |
| ASM-Fc | 0.25 nM | 0.22 nM |

Together, these data demonstrate that ASM-Fc fusion proteins retain their activity and can rescue substrate accumulation in ASM-deficient cells.

Example 6. Construction of Fusion Proteins Comprising N-Sulfoglucosamine Sulfohydrolase (SGSH)

Design and Cloning

SGSH-Fc fusion proteins were designed that contain (i) a fusion polypeptide where a mature, human SGSH enzyme is fused to a human IgG1 fragment that includes the Fc region (an "SGSH-Fc fusion polypeptide"), and (ii) a modified human IgG1 fragment which contains mutations in the Fc region that confer transferrin receptor (TfR) binding (a "modified Fc polypeptide"). In particular, SGSH-Fc fusion polypeptides were created in which SGSH fragments were fused to either the N- or C-terminus of the human IgG1 Fc region. In some cases, a linker was placed between the SGSH and IgG1 fragments to alleviate any steric hindrance between the two fragments. In all constructs, the signal peptide from the kappa chain V-III, amino acids 1-20 (UniProtKB ID—P01661) was inserted upstream of the fusion to facilitate secretion, and SGSH was truncated to consist of amino acids R21-L502 (UniProtKB ID—P51688). The fragment of the human IgG1 Fc region used corresponds to amino acids D104-K330 of the sequence in UniProtKB ID P01857 (positions 221-447, EU numbering, which includes 10 amino acids of the hinge (positions 221-230)). In some embodiments, a second Fc polypeptide derived from human IgG1 residues D104-K330 containing mutations in the Fc region conferring TfR binding but lacking the SGSH fusion was co-transfected with the SGSH-Fc fusion polypeptide in order to generate heterodimeric fusion proteins with one SGSH enzyme (a "monozyme"). In other embodiments, a second Fc polypeptide derived from human IgG1 residues D104-K330 containing mutations in the Fc region conferring TfR binding and fused to SGSH was co-transfected with the SGSH-Fc fusion polypeptide in order to generate heterodimeric fusion proteins with two SGSH enzymes (a "bizyme"). In some constructs, the IgG1 fragments contained additional mutations to facilitate heterodimerization of the two Fc regions. Control SGSH-Fc fusion proteins that lack the mutations that confer TfR binding were designed and constructed analogously. As an additional control, SGSH (amino acids R21-L502) was generated with a C-terminal hexahistidine tag (SEQ ID NO:241) to facilitate detection and purification.

The SGSH-Fc fusion proteins comprising TfR-binding used in the examples are dimers formed by an SGSH-Fc fusion polypeptide and a modified Fc polypeptide that binds to TfR, wherein the modified Fc polypeptide lacks the SGSH fusion (a "monozyme") or is fused to a second SGSH molecule (a "bizyme").

An SGSH-Fc fusion polypeptide comprising a mature human SGSH sequence fused to the N-terminus of an IgG1 Fc polypeptide sequence with hole and LALA mutations has the sequence of SEQ ID NO:149. The SGSH enzyme was joined to the Fc polypeptide by a GGGGS linker (SEQ ID NO:239) and the N-terminus of the Fc polypeptide included a portion of an IgG1 hinge region (DKTHTCPPCP; SEQ ID NO:113).

An SGSH-Fc fusion polypeptide comprising a mature human SGSH sequence fused to the C-terminus of an IgG1 Fc polypeptide sequence with hole and LALA mutations has the sequence of SEQ ID NO:150. The SGSH enzyme was joined to the Fc polypeptide by a GGGGS linker (SEQ ID NO:239) and the N-terminus of the Fc polypeptide may include a portion of an IgG1 hinge region (e.g., SEQ ID NO:113).

A modified Fc polypeptide that binds to TfR comprising the sequence of clone CH3C.35.21.17 (SEQ ID NO:58) with knob and LALA mutations has the sequence of SEQ ID NO:151. The N-terminus of the modified Fc polypeptide may include a portion of an IgG1 hinge region (e.g., SEQ ID NO:113).

An "N-terminal monozyme" containing a single SGSH molecule at the N-terminus of the Fc polypeptide was formed between SEQ ID NOS:149 and 151. A "C-terminal monozyme" containing a single SGSH molecule at the C-terminus of the Fc polypeptide was formed between SEQ ID NOS:150 and 151.

A modified Fc polypeptide that binds to TfR comprising a mature human SGSH sequence fused to the N-terminus of the sequence of clone CH3C.35.21.17 (SEQ ID NO:58) with knob and LALA mutations has the sequence of SEQ ID NO:154. The SGSH enzyme was joined to the modified Fc polypeptide by a GGGGS linker (SEQ ID NO:239) and the N-terminus of the modified Fc polypeptide included a portion of an IgG1 hinge region (SEQ ID NO:113).

An "N-terminal bizyme" containing a first SGSH molecule at the N-terminus of the Fc polypeptide and a second SGSH molecule at the N-terminus of the modified Fc polypeptide was formed between SEQ ID NOS:149 and 154.

Recombinant Protein Expression and Purification

To express recombinant SGSH enzyme fused to an Fc region, ExpiCHO cells (Thermo Fisher Scientific) were transfected with relevant DNA constructs using Expifectamine™ CHO transfection kit according to manufacturer's instructions (Thermo Fisher Scientific). Cells were grown in ExpiCHO™ Expression Medium at 37° C., 6% $CO_2$ and 120 rpm in an orbital shaker (Infors HT Multitron). In brief, logarithmic growing ExpiCHO™ cells were transfected at $6 \times 10^6$ cells/ml density with 0.8 μg of DNA plasmid per mL of culture volume. After transfection, cells were returned to 37° C. and transfected cultures were supplemented with feed as indicated 18-22 hrs post transfection. Transfected cell culture supernatants were harvested 120 hrs post transfection by centrifugation at 3,500 rpm from 20 mins. Clarified supernatants were filtered (0.22 μM membrane) and stored at 4° C. Expression of an epitope-tagged SGSH enzyme (used as a control) was carried out as described above with minor modifications. In brief, an SGSH enzyme harboring a C-terminal hexahistidine tag (SEQ ID NO:241) was expressed in ExpiCHO cells.

SGSH-Fc fusion proteins with (or without) engineered Fc regions conferring TfR binding were purified from cell culture supernatants using Protein A affinity chromatography. Supernatants were loaded onto a HiTrap Mab Select SuRe Protein A affinity column (GE Healthcare Life Sciences using an Akta Pure System). The column was then washed with >20 column volumes (CVs) of PBS. Bound proteins were eluted using 100 mM citrate/NaOH buffer pH 3.0 containing 150 mM NaCl. Immediately after elution, fractions were neutralized using 1 M arginine-670 mM succinate buffer pH 5.0 (at a 1:5 dilution). Homogeneity of SGSH-Fc fusions in eluted fractions was assessed by reducing and non-reducing SDS-PAGE.

To purify hexahistidine-tagged (SEQ ID NO:241) SGSH, transfected supernatants were exhaustively dialyzed against 15 L of 20 mM HEPES pH 7.4 containing 100 mM NaCl overnight, and 20 mM imidazole was added to the dialyzed supernatants prior to purification. Dialyzed supernatants were bound to a HisTrap column (GE Healthcare Life Sciences using an Akta Pure System). After binding, the column was washed with 20 CV of PBS. Bound proteins were eluted using PBS containing 500 mM imidazole. Homogeneity of SGSH enzyme in eluted fractions was assessed by reducing and non-reducing SDS-PAGE. Pooled fractions containing SGSH can be diluted 1:10 in 50 mM Tris pH 7.5 and further purified using Q Sepharose High Performance (GE Healthcare). After binding, the column is washed with 10 CV of 50 mM Tris pH 7.5. Bound proteins are eluted using a linear gradient to 50 mM Tris pH 7.5 and 0.5 M NaCl and collected in 1 CV fractions. Fraction purity is assessed by non-reducing SDS-PAGE. Purification yields homogeneous SGSH-Fc fusion proteins and hexahistidine-tagged (SEQ ID NO:241) SGSH.

Example 7. Characterization of SGSH Fusion Proteins

SGSH-Fc Fusion Proteins with Engineered TfR Binding Site Bind to Human TfR

To determine whether SGSH-Fc fusion proteins with engineered TfR binding affects the ability of the modified Fc domain to interact with human TfR, the affinity of this protein for human TfR can be assessed using a Biacore™ surface plasmon resonance assay. Biacore™ Series S CM5 sensor chips are immobilized with anti-human Fab (human Fab capture kit from GE Healthcare). 5 μg/mL of the SGSH-Fc fusion proteins are captured for 1 minute on each flow cell and serial 3-fold dilutions of human apical domain TfR are injected at a flow rate of 30 μL/min. Each sample is analyzed with a 3-minute association and a 3-minute dissociation. After each injection, the chip is regenerated using 10 mM glycine-HCl (pH 2.1). Binding response is corrected by subtracting the RU from a flow cell capturing an irrelevant IgG at similar density. Steady-state affinities are obtained by fitting the response at equilibrium against the concentration using Biacore™ T200 Evaluation Software v3.1. Biacore™ analysis establishes that SGSH-Fc fusion proteins with a TfR-binding site engineered into the Fc region bind to human TfR.

SGSH-Fc Fusion Proteins with Engineered TfR Binding Site are Active In Vitro and in Cells The in vitro and cellular activity of engineered TfR-binding SGSH-Fc fusion proteins were assessed to demonstrate that SGSH maintains its enzymatic activity when fused to the human IgG fragment. The in vitro activity of recombinant SGSH was measured using a two-step fluorometric enzymatic assay using an artificial substrate. Specifically, 20 μL of 1 mM 4-Methylumbelliferyl 2-deoxy-2-sulfamino-a-D-glucopyranoside sodium salt substrate (Carbosynth Limited, # EM06602) diluted in the assay buffer (0.03 M sodium acetate, 0.12 M NaCl, pH 6.5) was mixed with 10 μL of 40 nM SGSH. The first reaction was incubated for 17 hr at 37° C. and then terminated with 10 μL of 0.2 M phosphate-citrate buffer, pH 6.7. Next, the second reaction was initiated by adding 10 μL (0.5 U) of yeast α-Glucosidase (Sigma, # G0660-750UN), incubated for 24 hr at 37° C., and stopped with the addition of 100 μL of 0.5 M sodium carbonate buffer, pH 10.3. Fluorescence of the reaction solution was then measured (excitation at 365 nm and emission at 450 nm). A 4-Methylumbelliferone standard curve was fit by linear regression to calculate the amount of product and verified as less than 10% of total substrate cleavage. Specific activity (fmol product/min/pmol SGSH) was calculated by dividing the amount of product by the reaction time and molar amount of SGSH.

Figure 15:
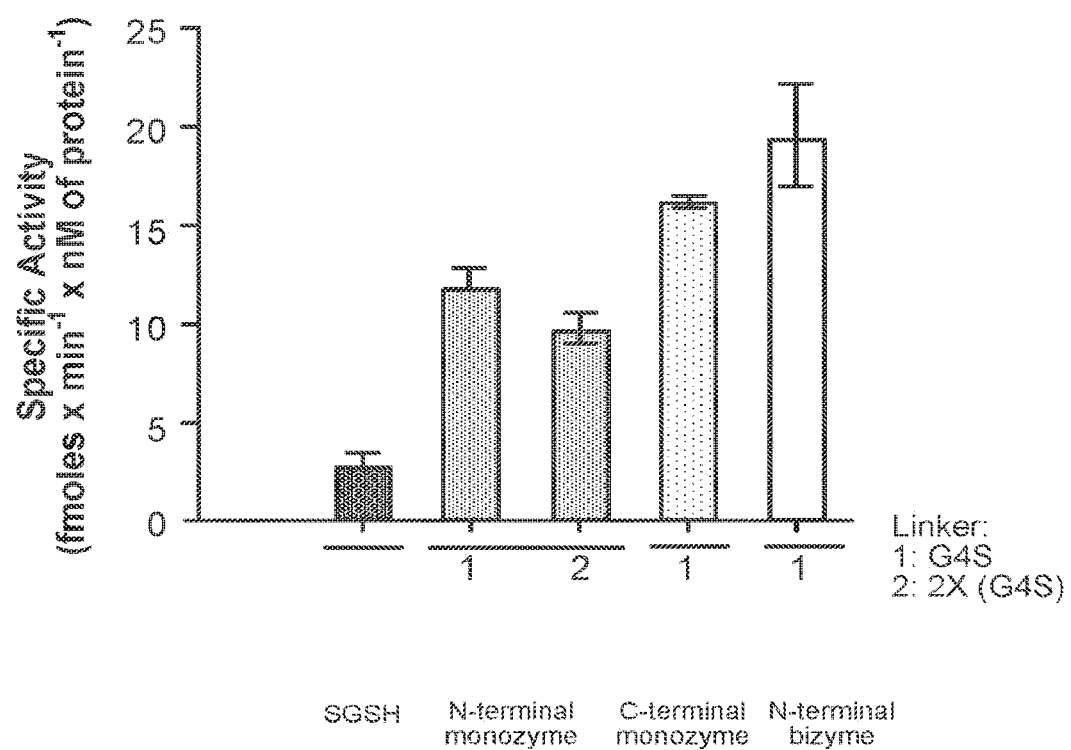
FIG. 15 provides data demonstrating in vitro N-sulfoglucosamine sulfohydrolase (SGSH) activity of SGSH-Fc fusion proteins described in Example 6.

The in vitro enzymatic activity assay demonstrated that SGSH-Fc fusion proteins were active and indicated that the fusion of an Fc region to SGSH does not interfere with enzymatic activity (FIG. 15).

SGSH knockout (KO) cells were generated using CRISPR/CAS9 to provide a cellular system to test the cellular activity of the engineered SGSH-Fc polypeptides. HEK 293T cells (ATCC) were transfected with CRISPR/CAS9 pCas-Guide-EF1a-GFP vector (Origene) containing guide sequences targeted to exon 2 upstream of the reactive cysteine site that generates the formylglycine in human SGSH. To identify SGSH KO cells, single cell clones were grown and cell lysates were subjected to the in vitro SGSH enzyme assay described above. Briefly, the in vitro activity assay was performed using 12.5, 25, 50 and 100 μs cell lysate in lead acetate assay buffer pH 5.0 (100 mM sodium acetate, 10 mM lead acetate). The reaction was started by combining 20 μL normalized cell lysate (in water) with 1 mM substrate in 10 IAL lead acetate buffer (3×) and incubated at 37° C. for seventeen hours. This first reaction was stopped by the addition of 70 μL 4× citrate phosphate buffer pH 6.7 plus 0.5 U NAGLU (Sigma). The reaction proceeded for 24 hours at 37° C. and was then stopped by the addition of 100 μL 0.5 M sodium carbonate pH 10.3. SGSH activity in HEK293T CRISPR clones was compared to recombinant SGSH (R&D) used as an assay standard, HEK wild-type (WT) lysates, and HEK cell lysates over-expressing SGSH. Clones with enzyme activity levels comparable to background signal were sequence verified after mini-Topo (ThermoFisher) cloning and confirmed as KO clones. Subsequent cell assays used three unique and verified SGSH KO clones and three independent batches of WT HEK293T cells.

To test the cellular activity of naked SGSH enzyme or SGSH-Fc fusion proteins, an LC-MS/MS-based glycomic assay was developed that allows monitoring of the amount of substrate accumulation (heparan sulfate) as an indicator of SGSH activity. Substrate accumulation was measured in SGSH KO cells and WT HEK293T cells. SGSH KO cells and WT HEK293T cells were cultured for 24 hours, and cells were washed three times with PBS, pelleted, and frozen. Cell pellets were sonicated in disaccharide digestion buffer (111 mM NH$_4$OAc, 11 mM CaOAc, pH 7.0). Protein concentration was measured using BCA assay (Pierce). Total protein (100 µg) was added to 100 µL digestion buffer with 2 mM DTT, 1.25 mIU Heparinase I (Galen), 1.25 mIU Heparinase II (Galen), and 1.25 mIU Heparinase III (Galen). Heparan sulfate digestion was complete after three hours at 30° C., after which 20 ng of internal standard (4UA-2S-G1cNCOEt-6S HD009 [Galen]) was added to each sample. The enzymes were deactivated by the addition of 6 µL of 250 mM EDTA, and samples were boiled at 95° C. for 10 minutes. Samples were then centrifuged 16,000×G for 5 minutes at room temperature. Supernatant was transferred to an Amicon Ultra 30 KD centrifugal filter (Millipore) and centrifuged at 14,000×G for 15 minutes. Disaccharides were concentrated in the flow through and were resuspended in a mixture of [1:1, v/v] assay buffer: acetonitrile which was then transferred to mass-spectrometry vials for further analysis.

GAG analyses were performed by liquid chromatography (Shimadzu Nexera X2 system, Shimadzu Scientific Instrument, Columbia, Md., USA) coupled to electrospray mass spectrometry (Sciex 6500+ QTRAP, Sciex, Framingham, Mass., USA). For each analysis, 10 µL of sample was injected on a ACQUITY UPLC BEH Amide 1.7 µm, 2.1× 150 mm column (Waters Corporation, Milford, Mass., USA) using a flow rate of 0.4 mL/min with column temperature at 50° C. Mobile phase A consisted of water with 10 mM ammonium formate and 0.1% formic acid. Mobile phase B consisted of acetonitrile with 0.1% formic acid. The gradient was programmed as follows: 0.0-1.0 min at 85% B, 1.0-5.0 min from 85% B to 50% B, 5.0-6.0 min 50% B to 85% B, 6-8.0 min hold at 85% B. Electrospray ionization was performed in the negative-ion mode applying the following settings: curtain gas at 30; collision gas was set at medium; ion spray voltage at −4500; temperature at 450; ion source gas 1 at 50; ion source gas 2 at 60. Data acquisition was performed using Analyst 1.6.3 (Sciex) in multiple reaction monitoring mode (MRM), with dwell time 25 (msec). Collision energy at −30; declustering potential at −80; entrance potential at −10; collision cell exit potential at −10. GAGs were detected as [M−H]− using the following MRM transitions: D0A0 at m/z 378.1>87.0; D0a0 at m/z 378.1>175.0; D0S0 at m/z 416.1>138.0; D0a4 at m/z 458.1>300.0; D0A6, D2A0, D0a6, D2a0 at m/z 458.1>97.0; D0S6, D2S0 at m/z 496.0>416.1; D2a4, D2a6, D0a10, D2A6 at m/z 538.0>458.0; D0S6 at m/z 575.95>97.0 4UA-2S-G1cNCOEt-6S at m/z 472.0 (fragment ion) >97.0 was used as internal standard (I. S.). GAGs were identified based on their retention times and MRM transitions match to commercially available reference standards (Iduron Ltd, Manchester, UK). Quantification was performed using MultiQuant 3.0.2 (Sciex) by the area ratio to I.S. GAGs were normalized to total protein amount. Protein concentration was measured using BCA assay (Pierce).

Figure 16:
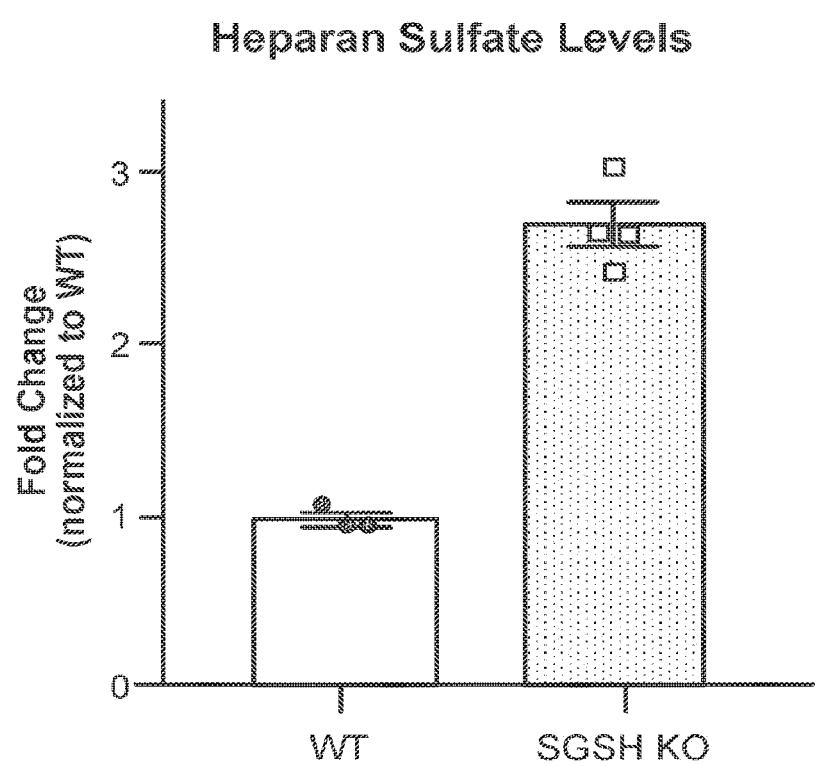
FIG. 16 provides data demonstrating that knockout (KO) cells that lack SGSH have increased levels of heparan sulfate-derived disaccharides as assessed using an LC-MS/MS assay. n=3-4 independent cell lines; data shown as mean±s.e.m.
Figure 17:
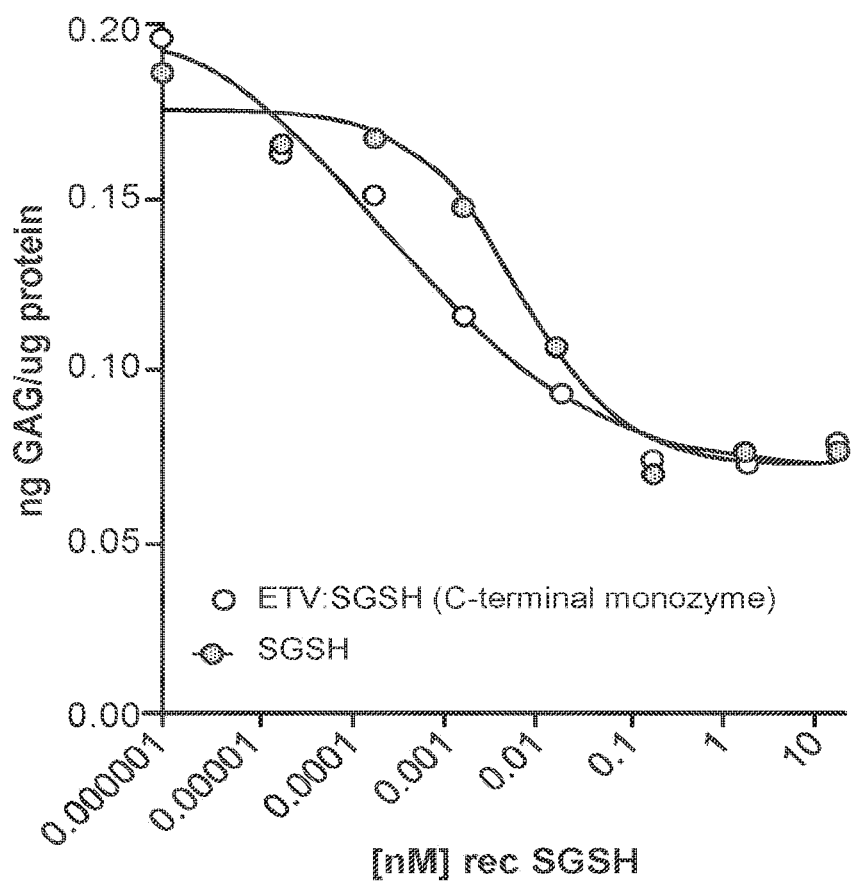
FIG. 17 provides data illustrating that a SGSH-Fc fusion protein analyzed in FIG. 15 reverses heparan sulfate accumulation in SGSH KO cells.
Figure 18:
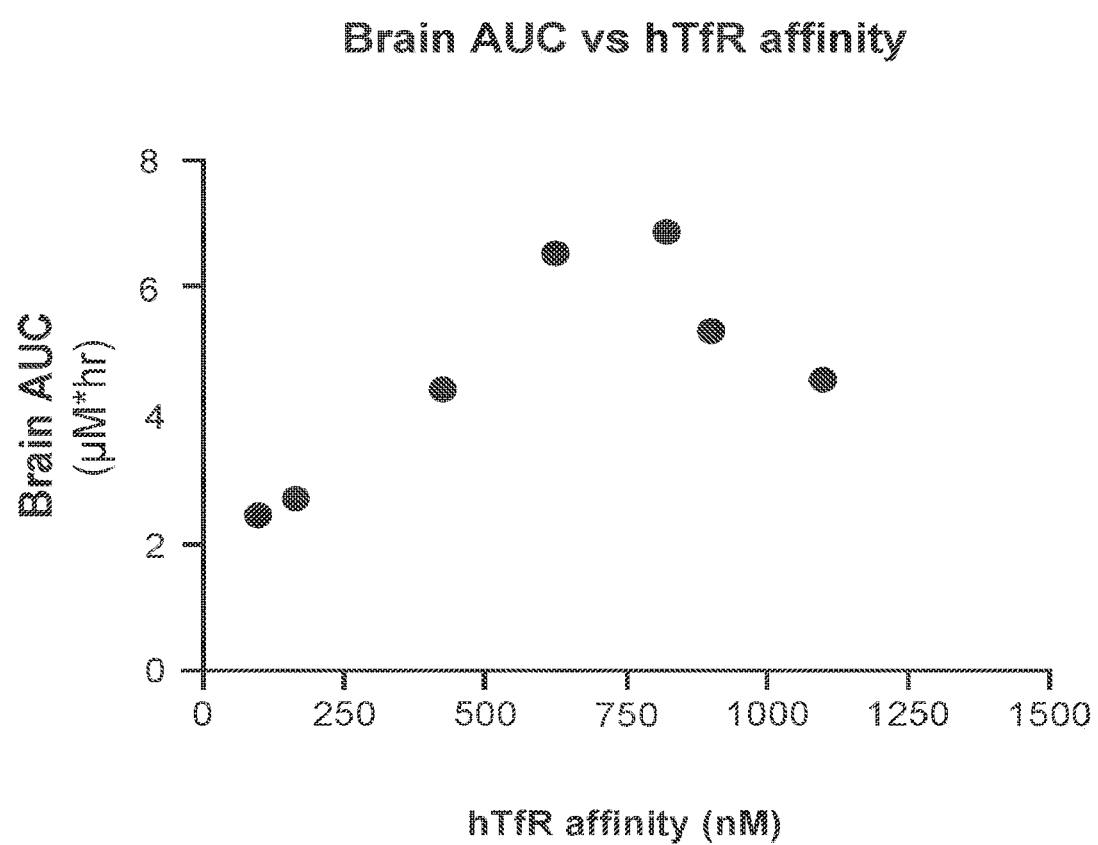
FIG. 18 shows the relationship between engineered TfR-binding polypeptide hTfR affinity and brain exposure over time in TfR$^{ms/hu}$ KI mice. Dots represent cumulative brain exposure over time (AUC) of different engineered TfR-binding polypeptide affinity variants following a single dose of 50 mg/kg in TfR$^{ms/hu}$ KI mice. Brain concentrations of polypeptide (as measured by huIgG1) were calculated at various days post-dose (ranges from 1-10 days). Data represents summary of three independent studies, n=4-5 mice per group for each study.
Figure 19:
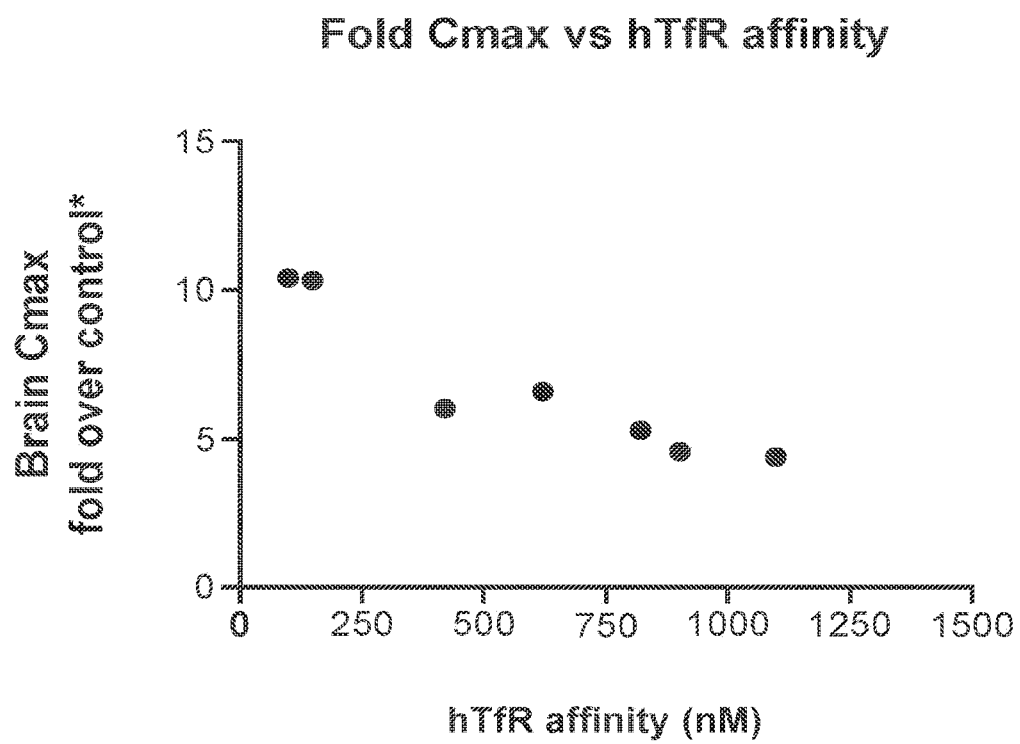
FIG. 19 shows the relationship between engineered TfR-binding polypeptide hTfR affinity and maximum brain concentration in TfR$^{ms/hu}$ KI mice. Dots represent maximum brain concentrations of different polypeptide affinity variants measured at 1 day post-dose after a single 50 mg/kg dose. Data represents summary of three independent studies, n=4-5 mice per group for each study.
Figure 20:
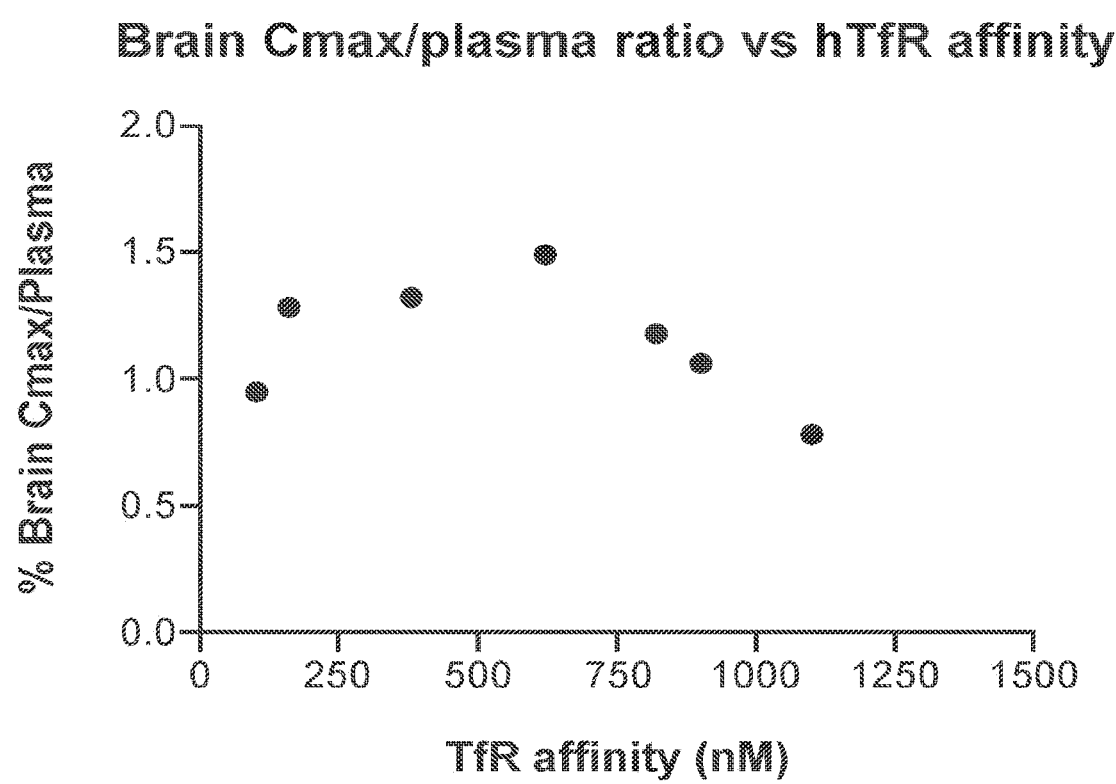
FIG. 20 shows the relationship between engineered TfR-binding polypeptide hTfR affinity and ratio of brain versus plasma concentration of polypeptide in TfR$^{ms/hu}$ KI mice. Dots represent ratio of maximum brain versus plasma concentration of different polypeptide affinity variants measured at 1 day post-dose after a single 50 mg/kg dose. Data represents summary of three independent studies, n=4-5 mice per group for each study.

Significant substrate accumulation, as reflected by the amount of disaccharides observed after digestion of heparan sulfate, was seen in SGSH KO cells compared to control cell lines (FIG. 16). Using the LC-MS/MS-based glycomic assay, it was established that treatment of cells with a TfR-binding SGSH-Fc fusion protein reduced the levels of heparan sulfate-derived disaccharides back to that seen in wild-type cells (FIG. 17). Together, these data demonstrate that SGSH-Fc fusion proteins maintain enzymatic activity and can reduce substrate accumulation in SGSH KO cells.

Example 8. In Vitro Assay for SGSH Activity

This example provides an alternative in vitro activity assay for SGSH-Fc fusion proteins. The assay is adapted from Karpova et al., *J. Inherit. Metab. Dis.,* 19:278-285 (1996).

The standard reaction mixtures consisted of 10-15 µg of protein and 20 µL MU-α-GlcN5 (5 or 10 mmol/L, respectively) in Michaelis' barbital sodium acetate buffer, pH 6.5 (29 mmol/L sodium barbital, 29 mmol/L sodium acetate, 0.68% (w/v) NaCl, 0.02% (w/v) sodium azide; adjusted to pH 6.5 with HCl) and the reaction mixtures were incubated for 17 h at 37° C. MU-α-GlcNS is available from Moscerdam Substrates. After the first incubation, 6 µl twice-concentrated McIlvain's phosphate/citrate buffer, pH 6.7, containing 0.02% sodium azide and 10 µl (0.1 U) yeast a-glucosidase (Sigma) in water were added and a second incubation of 24 h at 37° C. was carried out. Long incubations at 37° C. (17-24 h) were carried out in 96-well plates which were sealed airtight with broad sticky tape, limiting evaporation to <15%. Next, 200 µL 0.5 mol/L Na$_2$CO$_3$/NaHCO$_3$, pH 10.7, was added, and the fluorescence of the released 4-methylumbelliferone (MU) was measured on a Fluoroskan (Titertek) fluorimeter. Protein was determined as described previously (van Diggelen et al., *Clin. Chim. Acta.,* 187:131-139 (1990)).

Example 9. Modified Fc Polypeptides that Bind to TfR

This example describes modifications to Fc polypeptides to confer transferrin receptor (TfR) binding and transport across the blood-brain barrier (BBB).

Unless otherwise indicated, the positions of amino acid residues in this section are numbered based on EU index numbering for a human IgG1 wild-type Fc region.

Generation and Characterization of Fc Polypeptides Comprising Modifications at Positions 384, 386, 387, 388, 389, 390, 413, 416, and 421 (CH3C clones)

Yeast libraries containing Fc regions having modifications introduced into positions including amino acid positions 384, 386, 387, 388, 389, 390, 413, 416, and 421 were generated as described below. Illustrative clones that bind to TfR are shown in Tables 4 and 5.

After an additional two rounds of sorting, single clones were sequenced and four unique sequences were identified. These sequences had a conserved Trp at position 388, and all had an aromatic residue (i.e., Trp, Tyr, or His) at position 421. There was a great deal of diversity at other positions.

The four clones selected from the library were expressed as Fc fusions to Fab fragments in CHO or 293 cells, and purified by Protein A and size-exclusion chromatography, and then screened for binding to human TfR in the presence or absence of holo-Tf by ELISA. The clones all bound to human TfR and the binding was not affected by the addition of excess (5 µM) holo-Tf. Clones were also tested for binding to 293F cells, which endogenously express human TfR. The clones bound to 293F cells, although the overall binding was substantially weaker than the high-affinity positive control.

Next, it was tested whether clones could internalize in TfR-expressing cells using clone CH3C.3 as a test clone. Adherent HEK 293 cells were grown in 96-well plates to about 80% confluence, media was removed, and samples were added at 1 μM concentrations: clone CH3C.3, anti-TfR benchmark positive control antibody (Ab204), anti-BACE1 benchmark negative control antibody (Ab107), and human IgG isotype control (obtained from Jackson Immunoresearch). The cells were incubated at 37° C. and 8% $CO_2$ concentration for 30 minutes, then washed, permeabilized with 0.1% Triton™ X-100, and stained with anti-human-IgG-Alexa Fluor® 488 secondary antibody. After additional washing, the cells were imaged under a high content fluorescence microscope (i.e., an Opera Phenix™ system), and the number of puncta per cell was quantified. At 1 μM, clone CH3C.3 showed a similar propensity for internalization to the positive anti-TfR control, while the negative controls showed no internalization.

Further Engineering of Clones

Additional libraries were generated to improve the affinity of the initial hits against human TfR using a soft randomization approach, wherein DNA oligos were generated to introduce soft mutagenesis based on each of the original four hits. Additional clones were identified that bound TfR and were selected. The selected clones fell into two general sequence groups. Group 1 clones (i.e., clones CH3C.18, CH3C.21, CH3C.25, and CH3C.34) had a semi-conserved Leu at position 384, a Leu or His at position 386, a conserved and a semi-conserved Val at positions 387 and 389, respectively, and a semi-conserved P-T-W motif at positions 413, 416, and 421, respectively. Group 2 clones had a conserved Tyr at position 384, the motif TXWSX at positions 386-390, and the conserved motif S/T-E-F at positions 413, 416, and 421, respectively. Clones CH3C.18 and CH3C.35 were used in additional studies as representative members of each sequence group.

Epitope Mapping

To determine whether the engineered Fc regions bound to the apical domain of TfR, TfR apical domain was expressed on the surface of phage. To properly fold and display the apical domain, one of the loops had to be truncated and the sequence needed to be circularly permuted. Clones CH3C.18 and CH3C.35 were coated on ELISA plates and a phage ELISA protocol was followed. Briefly, after washing and blocking with 1% PBSA, dilutions of phage displaying were added and incubated at room temperature for 1 hour. The plates were subsequently washed and anti-M13-HRP was added, and after additional washing the plates were developed with TMB substrate and quenched with 2N $H_2SO_4$. Both clones CH3C.18 and CH3C.35 bound to the apical domain in this assay.

Paratope Mapping

To understand which residues in the Fc domain were most important for TfR binding, a series of mutant clone CH3C.18 and clone CH3C.35 Fc regions was created in which each mutant had a single position in the TfR binding register mutated back to wild-type. The resulting variants were expressed recombinantly as Fc-Fab fusions and tested for binding to human or cyno TfR. For clone CH3C.35, positions 388 and 421 were important for binding; reversion of either of these to wild-type completely ablated binding to human TfR.

Binding Characterization of Maturation Clones

Binding ELISAs were conducted with purified Fc-Fab fusion variants with human or cyno TfR coated on the plate, as described above. The variants from the clone CH3C.18 maturation library, clone CH3C.3.2-1, clone CH3C.3.2-5, and clone CH3C.3.2-19, bound human and cyno TfR with approximately equivalent EC50 values, whereas the parent clones CH3C.18 and CH3C.35 had greater than 10-fold better binding to human versus cyno TfR.

Next, it was tested whether the modified Fc polypeptides internalized in human and monkey cells. Using the protocol described above, internalization in human HEK 293 cells and rhesus LLC-MK2 cells was tested. The variants that similarly bound human and cyno TfR, clones CH3C.3.2-5 and CH3C.3.2-19, had significantly improved internalization in LLC-MK2 cells as compared with clone CH3C.35.

Additional Engineering of Clones

Additional engineering to further affinity mature clones CH3C.18 and CH3C.35 involved adding additional mutations to the positions that enhanced binding through direct interactions, second-shell interactions, or structure stabilization. This was achieved via generation and selection from an "NNK walk" or "NNK patch" library. The NNK walk library involved making one-by-one NNK mutations of residues that are near to the paratope. By looking at the structure of Fc bound to FcγRI (PDB ID: 4W40), 44 residues near the original modification positions were identified as candidates for interrogation. Specifically, the following residues were targeted for NNK mutagenesis: K248, R255, Q342, R344, E345, Q347, T359, K360, N361, Q362, S364, K370, E380, E382, S383, G385, Y391, K392, T393, D399, S400, D401, S403, K409, L410, T411, V412, K414, S415, Q418, Q419, G420, V422, F423, S424, S426, Q438, S440, S442, L443, S444, P4458, G446, and K447. The 44 single point NNK libraries were generated using Kunkel mutagenesis, and the products were pooled and introduced to yeast via electroporation, as described above for other yeast libraries.

The combination of these mini-libraries (each of which had one position mutated, resulting in 20 variants) generated a small library that was selected using yeast surface display for any positions that lead to higher affinity binding. Selections were performed as described above, using TfR apical domain proteins. After three rounds of sorting, clones from the enriched yeast library were sequenced, and several "hot-spot" positions were identified where certain point mutations significantly improved the binding to apical domain proteins. For clone CH3C.35, these mutations included E380 (mutated to Trp, Tyr, Leu, or Gln) and S415 (mutated to Glu). The sequences of the clone CH3C.35 single and combination mutants are set forth in SEQ ID NOS:27-38. For clone CH3C.18, these mutations included E380 (mutated to Trp, Tyr, or Leu) and K392 (mutated to Gln, Phe, or His). The sequences of the clone CH3C.18 single mutants are set forth in SEQ ID NOS:21-26.

Additional Maturation Libraries to Improve Clone CH3C.35 Affinity

An additional library to identify combinations of mutations from the NNK walk library, while adding several additional positions on the periphery of these, was generated as described for previous yeast libraries. In this library, the YxTEWSS (SEQ ID NO:242) and TxxExxxxF motifs were kept constant, and six positions were completely randomized: E380, K392, K414, S415, S424, and S426. Positions E380 and S415 were included because they were "hot spots" in the NNK walk library. Positions K392, S424, and S426 were included because they make up part of the core that may position the binding region, while K414 was selected due to its adjacency to position 415.

This library was sorted, as previously described, with the cyno TfR apical domain only. The enriched pool was sequenced after five rounds, and the sequences of the modified regions of the identified unique clones are set forth in SEQ ID NOS:42-59.

The next libraries were designed to further explore acceptable diversity in the main binding paratope. Each of the original positions (384, 386, 387, 388, 389, 390, 413, 416, and 421) plus the two hot spots (380 and 415) were individually randomized with NNK codons to generate a series of single-position saturation mutagenesis libraries on yeast. In addition, each position was individually reverted to the wild-type residue, and these individual clones were displayed on yeast. It was noted that positions 380, 389, 390, and 415 were the only positions that retained substantial binding to TfR upon reversion to the wild-type residue (some residual but greatly diminished binding was observed for reversion of 413 to wild-type).

The single-position NNK libraries were sorted for three rounds against the human TfR apical domain to collect the top ~5% of binders, and then at least 16 clones were sequenced from each library. The results indicate what amino acids at each position can be tolerated without significantly reducing binding to human TfR, in the context of clone CH3C.35. A summary is below:
Position 380: Trp, Leu, or Glu;
Position 384: Tyr or Phe;
Position 386: Thr only;
Position 387: Glu only;
Position 388: Trp only;
Position 389: Ser, Ala, or Val (although the wild type Asn residue seems to retain some binding, it did not appear following library sorting);
Position 390: Ser or Asn;
Position 413: Thr or Ser;
Position 415: Glu or Ser;
Position 416: Glu only; and
Position 421: Phe only.

The above residues, when substituted into clone CH3C.35 as single changes or in combinations, represent paratope diversity that retains binding to TfR apical domain. Clones having mutations at these positions include those shown in Table 5, and the sequences of the CH3 domains of these clones are set forth in SEQ ID NOS:34-38, 58, and 60-90.

Example 10. Additional Fc Positions that can be Modified to Confer TfR Binding Additional modified Fc polypeptides that bind to transferrin receptor (TfR) were generated having modifications at alternative sites in the Fc region, e.g., at the following positions:

positions 274, 276, 283, 285, 286, 287, 288, and 290 (CH2A2 clones);

positions 266, 267, 268, 269, 270, 271, 295, 297, 298, and 299 (CH2C clones);

positions 268, 269, 270, 271, 272, 292, 293, 294, and 300 (CH2D clones);

positions 272, 274, 276, 322, 324, 326, 329, 330, and 331 (CH2E3 clones); or positions 345, 346, 347, 349, 437, 438, 439, and 440 (CH3B clones).

Illustrative CH3B clones that bind to TfR are set forth in SEQ ID NOS:124-128. Illustrative CH2A2 clones that bind to TfR are set forth in SEQ ID NOS:129-133. Illustrative CH2C clones that bind to TfR are set forth in SEQ ID NOS:134-138. Illustrative CH2D clones that bind to TfR are set forth in SEQ ID NOS:139-143. Illustrative CH2E3 clones that bind to TfR are set forth in SEQ ID NOS:144-148.

Example 11. Methods

Generation of Phage-Display Libraries

A DNA template coding for the wild-type human Fc sequence was synthesized and incorporated into a phagemid vector. The phagemid vector contained an ompA or pelB leader sequence, the Fc insert fused to c-Myc and 6×His (SEQ ID NO:241) epitope tags, and an amber stop codon followed by M13 coat protein pIII.

Primers containing "NNK" tricodons at the desired positions for modifications were generated, where N is any DNA base (i.e., A, C, G, or T) and K is either G or T. Alternatively, primers for "soft" randomization were used, where a mix of bases corresponding to 70% wild-type base and 10% of each of the other three bases was used for each randomization position. Libraries were generated by performing PCR amplification of fragments of the Fc region corresponding to regions of randomization and then assembled using end primers containing SfiI restriction sites, then digested with SfiI and ligated into the phagemid vectors. Alternatively, the primers were used to conduct Kunkel mutagenesis. The ligated products or Kunkel products were transformed into electrocompetent *E. coli* cells of strain TG1 (obtained from Lucigen®). The *E. coli* cells were infected with M13K07 helper phage after recovery and grown overnight, after which library phage were precipitated with 5% PEG/NaCl, resuspended in 15% glycerol in PBS, and frozen until use. Typical library sizes ranged from about $10^9$ to about $10^{11}$ transformants. Fc-dimers were displayed on phage via pairing between pIII-fused Fc and soluble Fc not attached to pIII (the latter being generated due to the amber stop codon before pIII).

Generation of Yeast-Display Libraries

A DNA template coding for the wild-type human Fc sequence was synthesized and incorporated into a yeast display vector. For CH2 and CH3 libraries, the Fc polypeptides were displayed on the Aga2p cell wall protein. Both vectors contained prepro leader peptides with a Kex2 cleavage sequence, and a c-Myc epitope tag fused to the terminus of the Fc.

Yeast display libraries were assembled using methods similar to those described for the phage libraries, except that amplification of fragments was performed with primers containing homologous ends for the vector. Freshly prepared electrocompetent yeast (i.e., strain EBY100) were electroporated with linearized vector and assembled library inserts. Electroporation methods will be known to one of skill in the art. After recovery in selective SD-CAA media, the yeast were grown to confluence and split twice, then induced for protein expression by transferring to SG-CAA media. Typical library sizes ranged from about $10^7$ to about $10^9$ transformants. Fc-dimers were formed by pairing of adjacently displayed Fc monomers.

General Methods for Phage Selection

Phage methods were adapted from Phage Display: A Laboratory Manual (Barbas, 2001). Additional protocol details can be obtained from this reference.

Plate Sorting Methods

Antigen was coated on MaxiSorp® microtiter plates (typically 1-10 μg/mL) overnight at 4° C. The phage libraries were added into each well and incubated overnight for binding. Microtiter wells were washed extensively with PBS containing 0.05% Tween® 20 (PBST) and bound phage were eluted by incubating the wells with acid (typically 50 mM HCl with 500 mM KCl, or 100 mM glycine, pH 2.7) for 30 minutes. Eluted phage were neutralized with 1 M Tris (pH 8) and amplified using TG1 cells and M13/KO7 helper phage and grown overnight at 37° C. in 2YT media containing 50 µg/mL carbenacillin and 50 ug/mL Kanamycin. The titers of phage eluted from a target-containing well were compared to titers of phage recovered from a non-target-containing well to assess enrichment. Selection stringency was increased by subsequently decreasing the incubation time during binding and increasing washing time and number of washes.

Bead Sorting Methods

Antigen was biotinylated through free amines using NHS-PEG4-Biotin (obtained from Pierce™). For biotinylation reactions, a 3- to 5-fold molar excess of biotin reagent was used in PBS. Reactions were quenched with Tris followed by extensive dialysis in PBS. The biotinylated antigen was immobilized on streptavidin-coated magnetic beads, (i.e., M280-streptavidin beads obtained Thermo Fisher). The phage display libraries were incubated with the antigen-coated beads at room temperature for 1 hour. The unbound phage were then removed and beads were washed with PBST. The bound phage were eluted by incubating with 50 mM HCl containing 500 mM KCl (or 0.1 M glycine, pH 2.7) for 30 minutes, and then neutralized and propagated as described above for plate sorting.

After three to five rounds of panning, single clones were screened by either expressing Fc on phage or solubly in the E. coli periplasm. Such expression methods will be known to one of skill in the art. Individual phage supernatants or periplasmic extracts were exposed to blocked ELISA plates coated with antigen or a negative control and were subsequently detected using HRP-conjugated goat anti-Fc (obtained from Jackson Immunoresearch) for periplasmic extracts or anti-M13 (GE Healthcare) for phage, and then developed with TMB reagent (obtained from Thermo Fisher). Wells with OD450 values greater than around 5-fold over background were considered positive clones and sequenced, after which some clones were expressed either as a soluble Fc fragment or fused to Fab fragments General Methods for Yeast Selection Bead Sorting (Magnetic-Assisted Cell Sorting (MACS)) Methods MACS and FACS selections were performed similarly to as described in Ackerman et al., *Biotechnol. Prog.*, 25(3): 774 (2009). Streptavidin magnetic beads (e.g., M-280 streptavidin beads from ThermoFisher) were labeled with biotinylated antigen and incubated with yeast (typically 5-10× library diversity). Unbound yeast were removed, the beads were washed, and bound yeast were grown in selective media and induced for subsequent rounds of selection.

Fluorescence-Activated Cell Sorting (FACS) Methods

Yeast were labeled with anti-c-Myc antibody to monitor expression and biotinylated antigen (concentration varied depending on the sorting round). In some experiments, the antigen was pre-mixed with streptavidin-Alexa Fluor® 647 in order to enhance the avidity of the interaction. In other experiments, the biotinylated antigen was detected after binding and washing with streptavidin-Alexa Fluor® 647. Singlet yeast with binding were sorted using a FACS Aria III cell sorter. The sorted yeast were grown in selective media then induced for subsequent selection rounds.

After an enriched yeast population was achieved, yeast were plated on SD-CAA agar plates and single colonies were grown and induced for expression, then labeled as described above to determine their propensity to bind to the target. Positive single clones were subsequently sequenced for binding antigen, after which some clones were expressed either as a soluble Fc fragment or as fused to Fab fragments.

General Methods for Screening

Screening by ELISA

Clones were selected from panning outputs and grown in individual wells of 96-well deep-well plates. The clones were either induced for periplasmic expression using auto-induction media (obtained from EMD Millipore) or infected with helper phage for phage-display of the individual Fc variants on phage. ELISA plates were coated with antigen, typically at 0.5 mg/mL overnight, then blocked with 1% BSA before addition of phage or periplasmic extracts. After a 1-hour incubation and washing off unbound protein, HRP-conjugated secondary antibody was added (i.e., anti-Fc or anti-M13 for soluble Fc or phage-displayed Fc, respectively) and incubated for 30 minutes. The plates were washed again, and then developed with TMB reagent and quenched with 2N sulfuric acid. Absorbance at 450 nm was quantified using a plate reader (BioTek®) and binding curves were plotted using Prism software where applicable. In some assays, soluble transferrin or other competitor was added during the binding step, typically at significant molar excess.

Screening by Flow Cytometry

Fc variant polypeptides (expressed either on phage, in periplasmic extracts, or solubly as fusions to Fab fragments) were added to cells in 96-well V-bottom plates (about 100,000 cells per well in PBS+1% BSA (PBSA)), and incubated at 4° C. for 1 hour. The plates were subsequently spun and the media was removed, and then the cells were washed once with PBSA. The cells were resuspended in PBSA containing secondary antibody (typically goat anti-human-IgG-Alexa Fluor® 647 (obtained from Thermo Fisher)). After 30 minutes, the plates were spun and the media was removed, the cells were washed 1-2 times with PBSA, and then the plates were read on a flow cytometer (i.e., a FACSCanto™ II flow cytometer). Median fluorescence values were calculated for each condition using FlowJo software and binding curves were plotted with Prism software.

Example 12. Selection of TfR-Binding Polypeptide Affinity

This example describes the relationship between the affinity of a TfR-binding polypeptide for a transferrin receptor (TfR) and the resulting brain exposure to a therapeutic agent that is linked to the TfR Methods Generation of TfR$^{ms/hu}$ KI Methods for generating knock-in/knock-out mice have been published in the literature and are well known to those with skill in the art. In summary, TfR$^{ms/hu}$ KI mice were generated using CRISPR/Cas9 technology to express human Tfrc apical domain within the murine Tfrc gene; the resulting chimeric TfR was expressed in vivo under the control of the endogenous promoter. As described in International Patent Publication No. WO 2018/152285, which is incorporated by reference in its entirety herein, C57B16 mice were used to generate a knock-in of the human apical TfR mouse line via pronuclear microinjection into single cell embryos, followed by embryo transfer to pseudo pregnant females. Specifically, Cas9, single guide RNAs and a donor DNA were introduced into the embryos. The donor DNA comprised a human apical domain coding sequence that had been codon optimized for expression in mouse. The apical domain coding sequence was flanked with a left and a right homology arm. The donor sequence was designed such that the apical domain was inserted after the fourth mouse exon, and was immediately flanked at the 3' end by the ninth mouse exon. A founder male from the progeny of the female that received the embryos was bred to wild-type females to generate F1 heterozygous mice. Homozygous mice were subsequently generated from breeding of F1 generation heterozygous mice.

Mouse PK/PD

For PK/PD evaluation, TfR$^{ms/hu}$ KI mice were systemically dosed one time via tail vein injection at 50 mg/kg. Prior to perfusion, blood was collected in EDTA plasma tubes via cardiac puncture and spun at 14,000 rpm for 5 minutes. Plasma was then isolated for subsequent PK/PD analysis. Brains were extracted after perfusion and hemi-brains were isolated for homogenization in 10× by tissue weight of 1% NP-40 in PBS (for PK) or 5 M GuHCl (for PD).

Engineered TfR-binding polypeptide concentrations in mouse plasma and brain lysates were quantified using a generic human IgG assay (MSD human IgG kit # K150JLD) following the manufacturer's instructions. Briefly, pre-coated plates were blocked for 30 minutes with MSD Blocker A. Plasma samples were diluted 1:10,000 using a Hamilton Nimbus liquid handler and added in duplicate to the blocked plates. Brain samples were homogenized in 1% NP-40 lysis buffer and lysates diluted 1:10 for PK analysis. Dosing solutions were also analyzed on the same plate to confirm the correct dosage. The standard curve, 0.78-200 ng/mL IgG, was fit using a four-parameter logistic regression.

Example 13. Binding Characterization of CH3C Variants Using Biacore™

The affinity of clone variants for recombinant TfR apical domain was determined by surface plasmon resonance using a Biacore™ T200 instrument. Biacore™ Series S CM5 sensor chips were immobilized with anti-human Fab (human Fab capture kit from GE Healthcare). 5 µg/mL of polypeptide-Fab fusion was captured for 1 minute on each flow cell and serial 3-fold dilutions of human or cyno apical domain were injected at a flow rate of 30 µL/min at room temperature. Each sample was analyzed with a 45-second association and a 3-minute dissociation. After each injection, the chip was regenerated using 10 mM glycine-HCl (pH 2.1). Binding response was corrected by subtracting the RU from a flow cell capturing an irrelevant IgG at similar density. Steady-state affinities were obtained by fitting the response at equilibrium against the concentration using Biacore™ T200 Evaluation Software v3.1.

To determine the affinity of clone variants for recombinant TfR ectodomain (ECD), Biacore™ Series S CM5 sensor chips were immobilized with streptavidin. Biotinylated human or cyno TfR ECD was captured for 1 minute on each flow cell and serial 3-fold dilutions of clone variants were injected at a flow rate of 30 µL/min at room temperature. Each sample was analyzed with a 45-second association and a 3-minute dissociation. The binding response was corrected by subtracting the RU from a flow cell without TfR ECD at a similar density. Steady-state affinities were obtained by fitting the response at equilibrium against the concentration using Biacore™ T200 Evaluation Software v3.1.

The binding affinities are summarized in Table 6. Affinities were obtained by steady-state fitting.

TABLE 6

Binding affinities for exemplary CH3C variants.

| Clone | Human TfR (µM) | Cyno TfR (µM) | Human apical TfR (µM) | Cyno apical TfR (µM) |
| --- | --- | --- | --- | --- |
| CH3C.35.19.mono | 0.4 | 5.9 | 0.37 | 5.6 |
| CH3C.35.20.mono | 0.25 | 6.7 | 0.17 | 8 |
| CH3C.35.21.mono | 0.1 | 2.1 | 0.12 | 2.2 |
| CH3C.35.24.mono | 0.29 | 3.3 | 0.23 | 3 |
| CH3C.35.21.11.mono | 0.24 | 4 | 0.13 | 2.2 |
| CH3C.35.21.16.mono | 0.18 | 1.8 | 0.12 | 1.9 |
| CH3C.35.21.17.mono | 0.3 | 2.9 | 0.13 | 2.6 |
| CH3C.35.mono | 0.61 | >10 | 0.61 | >10 |
| CH3C.35.N153.mono | 0.42 | >10 | 0.95 | >10 |
| CH3C.35.bi | 0.22 | >2 | not tested | not tested |
| CH3C.35.N153.bi | 0.37 | 3.3 | not tested | not tested |
| CH3C.3.2-19.bi | 5.2 | 5.6 | not tested | not tested |
| CH3C.35.19.bi | 0.074 | 1.5 | not tested | not tested |
| CH3C.35.20.bi | 0.054 | 1.7 | not tested | not tested |
| CH3C.35.21.bi | 0.049 | 0.7 | not tested | not tested |
| CH3C.35.24.bi | 0.061 | 0.65 | not tested | not tested |

Example 14. Brain and Plasma PKPD of Polypeptide-Fab Fusions in TfR$^{ms/hu}$ Mice: CH3C.35.21, CH3C.35.20, CH3C.35, CH3C.35.23, CH3C.35.23.3

Figure 21A:
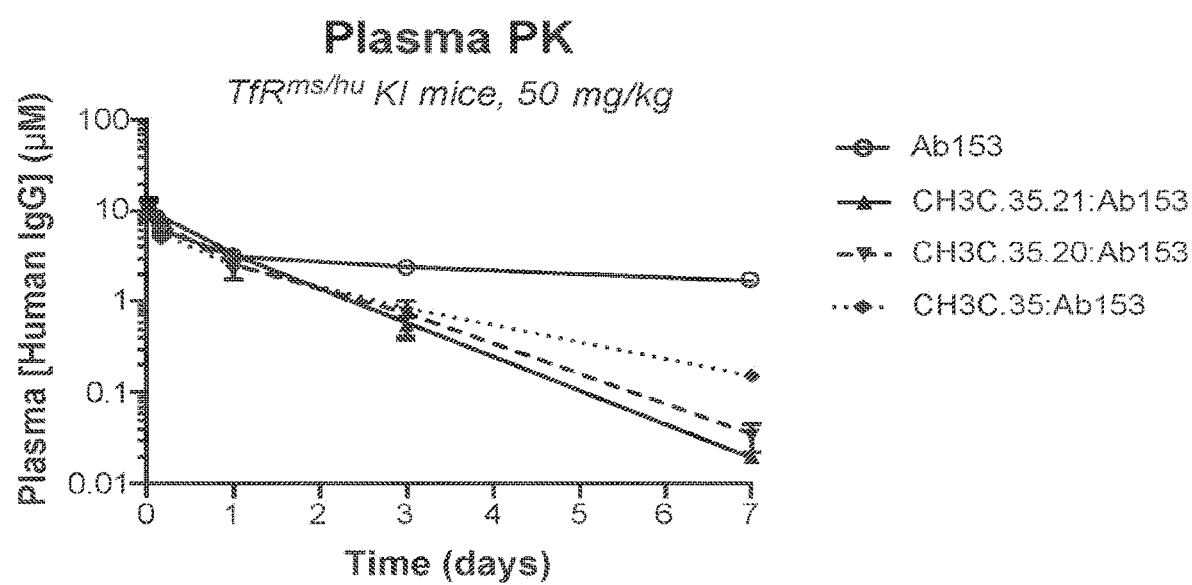
FIGS. 21A and 21B depict huIgG1 concentrations in plasma (FIG. 21A) and brain lysates (FIG. 21B) of TfR$^{ms/hu}$ knock-in (KI) mice after a single 50 mg/kg systemic injection of anti-BACE1_Ab153, CH3C35.21:Ab153, CH3C35.20:Ab153, or CH3C35:Ab153 polypeptide fusion (mean±SEM, n=5 per group).
Figure 21B:
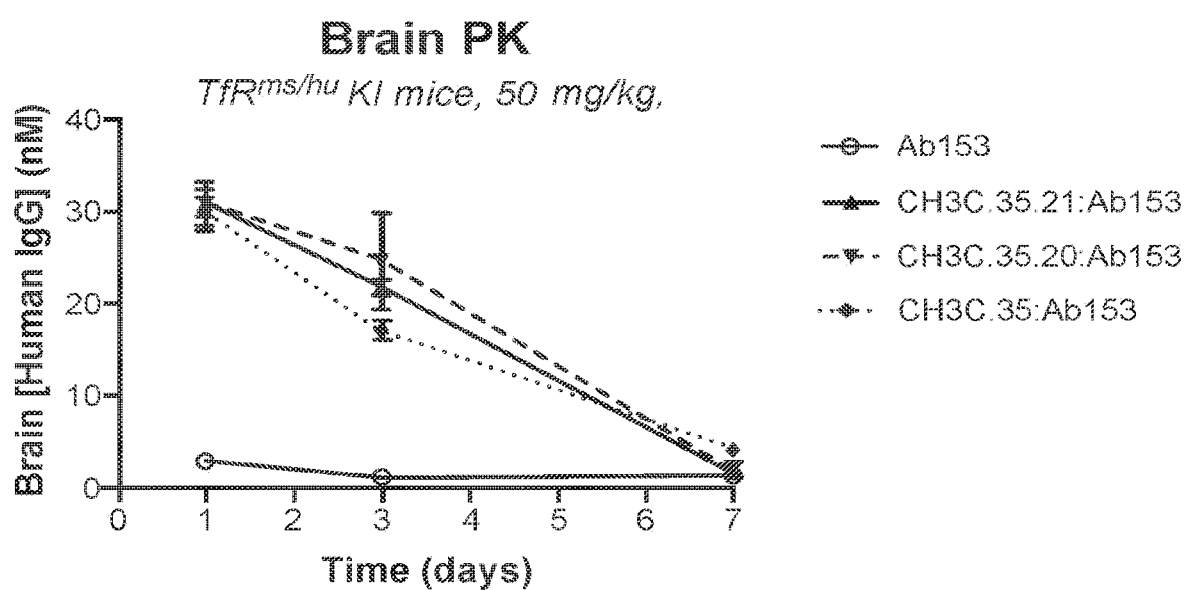
Figure 21C:
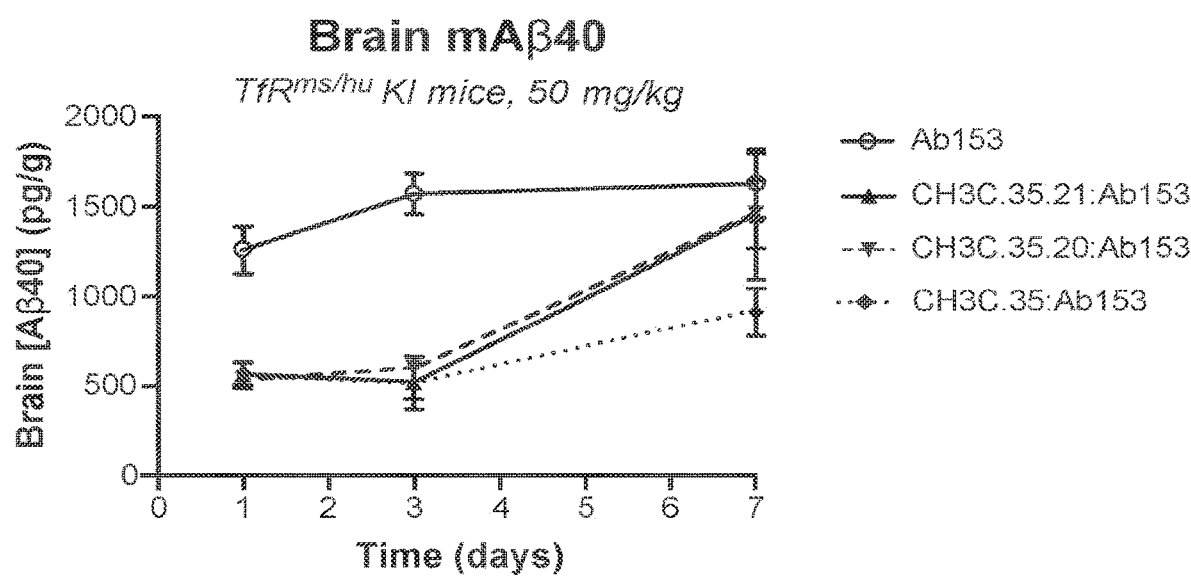
FIG. 21C depicts endogenous mouse Aβ concentration in brain lysate of TfR$^{ms/hu}$ KI mice after a single 50 mg/kg systemic injection of anti-BACE1 Ab153, CH3C35.21:Ab153, CH3C35.20:Ab153, or CH3C35:Ab153 polypeptide fusion (mean±SEM, n=5 per group).
Figure 21D:
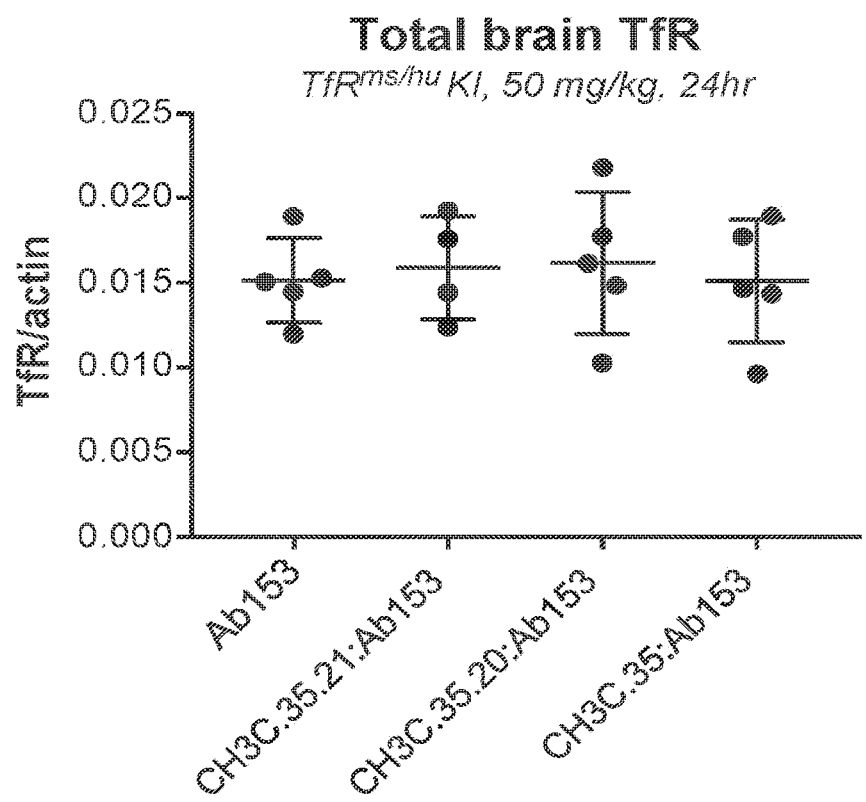
FIG. 21D depicts Western blot quantification of brain TfR protein normalized to actin in brain lysate of TfR$^{ms/hu}$ KI mice after a single 50 mg/kg systemic injection of anti- BACE1_Ab153, CH3C35.21:Ab153, CH3C35.20:Ab153, or CH3C35:Ab153 polypeptide fusion (mean±SEM, n=5 per group).

To evaluate the impact of TfR binding affinity for PK and brain uptake, anti-BACE1 Ab153 and TfR-binding polypeptide fusions (CH3C.35.21:Ab153, CH3C.35.20:Ab153, CH3C.35:Ab153 fusions) were generated that differed in their binding affinity to apical human TfR as measured by Biacore™. The binding affinities of CH3C.35.21:Ab153, CH3C.35.20:Ab153, CH3C.35:Ab153 fusions to human TfR are 100 nM, 170 nM and 620 nM, respectively. TfR$^{ms/hu}$ knock-in mice were systemically administered either Ab153 or the polypeptide-Fab fusions at 50 mg/kg, and plasma PK and brain PKPD was evaluated at 1, 3, and 7 days post-dose. Brain and plasma PKPD analysis was conducted as described above. Due to expression of TfR on peripheral tissues, CH3C.35.21:Ab153, CH3C.35.20:Ab153, and CH3C.35:Ab153 fusions exhibited faster clearance in plasma as compared to Ab153 alone, consistent with target-mediated clearance and indicative of in vivo TfR binding (FIG. 21A). Impressively, brain concentrations of CH3C.35.21:Ab153, CH3C.35.20:Ab153, and CH3C.35:Ab153 fusions were significantly increased compared to Ab153, achieving a maximum brain concentration of more than 30 nM at 1 day post-dose, compared to only about 3 nM for Ab153 at this same time point (FIG. 21B). The increase in brain exposure of CH3C.35.21:Ab153, CH3C.35.20: Ab153, and CH3C.35:Ab153 fusions resulted in about 55-60% lower endogenous mouse Aβ levels in brains of mice compared to Aβ levels in mice dosed with Ab153 (FIG. 21C). The lower brain Aβ levels were sustained while concentrations of CH3C.35.21:Ab153, CH3C.35.20:Ab153, and CH3C.35:Ab153 fusions remained elevated in brain, and returned to levels similar to Ab153 treated mice at when exposure was reduced by day 7. The reduction in brain exposure over time correlated with a reduction in peripheral exposure of CH3C.35.21:Ab153, CH3C.35.20:Ab153, and CH3C.35:Ab153 fusions, providing a clear PK/PD relationship in vivo (compare FIGS. 21A and 21C). Additionally, total brain TfR levels were comparable for Ab153-treated and polypeptide-Fab fusion-treated mice after this single high dose, indicating no significant impact of increased brain exposure of the polypeptide-Fab fusions to TfR expression in brain (FIG. 21D).

The amino acid substitutions for each clone described in the Tables (e.g., Table 5) dictate the amino acid substitutions at the register positions of that clone over the amino acids found in the sequence set forth in the Sequence Listing, in case of discrepancy.

It is understood that the examples and embodiments described herein are for illustrative purposes only and that various modifications or changes in light thereof will be suggested to persons skilled in the art and are to be included within the spirit and purview of this application and scope of the appended claims. The sequences of the sequence accession numbers cited herein are hereby incorporated by reference.

TABLE 4

CH3 Domain Modifications.

| Clone name | Group | 384 | 385 | 386 | 387 | 388 | 389 | 390 | 391 | ... | 413 | 414 | 415 | 416 | 417 | 418 | 419 | 420 | 421 |
|---|---|---|---|---|---|---|---|---|---|---|---|---|---|---|---|---|---|---|---|
| Wild-type | n/a | N | G | Q | P | E | N | N | Y | ... | D | K | S | R | W | Q | Q | G | N |
| 1 |  | L | G | L | V | W | V | G | Y | ... | A | K | S | T | W | Q | Q | G | W |
| 2 |  | Y | G | T | V | W | S | H | Y | ... | S | K | S | E | W | Q | Q | G | Y |
| 3 |  | Y | G | T | E | W | S | Q | Y | ... | E | K | S | D | W | Q | Q | G | H |
| 4 |  | V | G | T | P | W | A | L | Y | ... | L | K | S | E | W | Q | Q | G | W |
| 17 | 2 | Y | G | T | V | W | S | K | Y | ... | S | K | S | E | W | Q | Q | G | F |
| 18 | 1 | L | G | H | V | W | A | V | Y | ... | P | K | S | T | W | Q | Q | G | W |
| 21 | 1 | L | G | L | V | W | V | G | Y | ... | P | K | S | T | W | Q | Q | G | W |
| 25 | 1 | M | G | H | V | W | V | G | Y | ... | D | K | S | T | W | Q | Q | G | W |
| 34 | 1 | L | G | L | V | W | V | F | S | ... | P | K | S | T | W | Q | Q | G | W |
| 35 | 2 | Y | G | T | E | W | S | S | Y | ... | T | K | S | E | W | Q | Q | G | F |
| 44 | 2 | Y | G | T | E | W | S | N | Y | ... | S | K | S | E | W | Q | Q | G | F |
| 51 | 1/2 | L | G | H | V | W | V | G | Y | ... | S | K | S | E | W | Q | Q | G | W |
| 3.1-3 | 1 | L | G | H | V | W | V | A | T | ... | P | K | S | T | W | Q | Q | G | W |
| 3.1-9 | 1 | L | G | P | V | W | V | H | T | ... | P | K | S | T | W | Q | Q | G | W |
| 3.2-5 | 1 | L | G | H | V | W | V | D | Q | ... | P | K | S | T | W | Q | Q | G | W |
| 3.2-19 | 1 | L | G | H | V | W | V | N | Q | ... | P | K | S | T | W | Q | Q | G | W |
| 3.2-1 | 1 | L | G | H | V | W | V | N | F | ... | P | K | S | T | W | Q | Q | G | W |

TABLE 5

Additional CH3 Domain Modifications.

| Clone name | 378 | 379 | 380 | 381 | 382 | 383 | 384 | 385 | 386 | 387 | 388 | 389 | 390 | 391 |
|---|---|---|---|---|---|---|---|---|---|---|---|---|---|---|
| Wild-type | A | V | E | W | E | S | N | G | Q | P | E | N | N | Y |
| 35.20.1 | . | . | . | . | . | . | F | . | T | E | W | S | S | . |
| 35.20.2 | . | . | . | . | . | . | Y | . | T | E | W | A | S | . |
| 35.20.3 | . | . | . | . | . | . | Y | . | T | E | W | V | S | . |
| 35.20.4 | . | . | . | . | . | . | Y | . | T | E | W | S | S | . |
| 35.20.5 | . | . | . | . | . | . | F | . | T | E | W | A | S | . |
| 35.20.6 | . | . | . | . | . | . | F | . | T | E | W | V | S | . |
| 35.21.a.1 | . | . | W | . | . | . | F | . | T | E | W | S | S | . |
| 35.21.a.2 | . | . | W | . | . | . | Y | . | T | E | W | A | S | . |
| 35.21.a.3 | . | . | W | . | . | . | Y | . | T | E | W | V | S | . |
| 35.21.a.4 | . | . | W | . | . | . | Y | . | T | E | W | S | S | . |
| 35.21.a.5 | . | . | W | . | . | . | F | . | T | E | W | A | S | . |
| 35.21.a.6 | . | . | W | . | . | . | F | . | T | E | W | V | S | . |
| 35.23.1 | . | . | . | . | . | . | F | . | T | E | W | S | . | . |
| 35.23.2 | . | . | . | . | . | . | Y | . | T | E | W | A | . | . |
| 35.23.3 | . | . | . | . | . | . | Y | . | T | E | W | V | . | . |
| 35.23.4 | . | . | . | . | . | . | Y | . | T | E | W | S | . | . |
| 35.23.5 | . | . | . | . | . | . | F | . | T | E | W | A | . | . |
| 35.23.6 | . | . | . | . | . | . | F | . | T | E | W | V | . | . |
| 35.24.1 | . | . | W | . | . | . | F | . | T | E | W | S | . | . |
| 35.24.2 | . | . | W | . | . | . | Y | . | T | E | W | A | . | . |
| 35.24.3 | . | . | W | . | . | . | Y | . | T | E | W | V | . | . |
| 35.24.4 | . | . | W | . | . | . | Y | . | T | E | W | S | . | . |
| 35.24.5 | . | . | W | . | . | . | F | . | T | E | W | A | . | . |
| 35.24.6 | . | . | W | . | . | . | F | . | T | E | W | V | . | . |
| 35.21.17.1 | . | . | L | . | . | . | F | . | T | E | W | S | S | . |
| 35.21.17.2 | . | . | L | . | . | . | Y | . | T | E | W | A | S | . |
| 35.21.17.3 | . | . | L | . | . | . | Y | . | T | E | W | V | S | . |

TABLE 5-continued

Additional CH3 Domain Modifications.

| Clone | | | | | | | | | | | | | | |
|---|---|---|---|---|---|---|---|---|---|---|---|---|---|---|
| 35.21.17.4 | . | . | L | . | . | . | Y | . | T | E | W | S | S | . |
| 35.21.17.5 | . | . | L | . | . | . | F | . | T | E | W | A | S | . |
| 35.21.17.6 | . | . | L | . | . | . | F | . | T | E | W | V | S | . |
| 35.20 | . | . | . | . | . | . | Y | . | T | E | W | S | S | . |
| 35.21 | . | . | W | . | . | . | Y | . | T | E | W | S | S | . |
| 35.22 | . | . | W | . | . | . | Y | . | T | E | W | S | . | . |
| 35.23 | . | . | . | . | . | . | Y | . | T | E | W | S | . | . |
| 35.24 | . | . | W | . | . | . | Y | . | T | E | W | S | . | . |
| 35.21.17 | . | . | L | . | . | . | Y | . | T | E | W | S | S | . |
| 35.N390 | . | . | . | . | . | . | Y | . | T | E | W | S | . | . |

| Clone name | 392 | 411 | 412 | 413 | 414 | 415 | 416 | 417 | 418 | 419 | 420 | 421 | 422 | 423 |
|---|---|---|---|---|---|---|---|---|---|---|---|---|---|---|
| Wild-type | K | T | V | D | K | S | R | W | Q | Q | G | N | V | F |
| 35.20.1 | . | . | . | T | . | E | E | . | . | . | . | F | . | . |
| 35.20.2 | . | . | . | T | . | E | E | . | . | . | . | F | . | . |
| 35.20.3 | . | . | . | T | . | E | E | . | . | . | . | F | . | . |
| 35.20.4 | . | . | . | S | . | E | E | . | . | . | . | F | . | . |
| 35.20.5 | . | . | . | T | . | E | E | . | . | . | . | F | . | . |
| 35.20.6 | . | . | . | T | . | E | E | . | . | . | . | F | . | . |
| 35.21.a.1 | . | . | . | T | . | E | E | . | . | . | . | F | . | . |
| 35.21.a.2 | . | . | . | T | . | E | E | . | . | . | . | F | . | . |
| 35.21.a.3 | . | . | . | T | . | E | E | . | . | . | . | F | . | . |
| 35.21.a.4 | . | . | . | S | . | E | E | . | . | . | . | F | . | . |
| 35.21.a.5 | . | . | . | T | . | E | E | . | . | . | . | F | . | . |
| 35.21.a.6 | . | . | . | T | . | E | E | . | . | . | . | F | . | . |
| 35.23.1 | . | . | . | T | . | E | E | . | . | . | . | F | . | . |
| 35.23.2 | . | . | . | T | . | E | E | . | . | . | . | F | . | . |
| 35.23.3 | . | . | . | T | . | E | E | . | . | . | . | F | . | . |
| 35.23.4 | . | . | . | S | . | E | E | . | . | . | . | F | . | . |
| 35.23.5 | . | . | . | T | . | E | E | . | . | . | . | F | . | . |
| 35.23.6 | . | . | . | T | . | E | E | . | . | . | . | F | . | . |
| 35.24.1 | . | . | . | T | . | E | E | . | . | . | . | F | . | . |
| 35.24.2 | . | . | . | T | . | E | E | . | . | . | . | F | . | . |
| 35.24.3 | . | . | . | T | . | E | E | . | . | . | . | F | . | . |
| 35.24.4 | . | . | . | S | . | E | E | . | . | . | . | F | . | . |
| 35.24.5 | . | . | . | T | . | E | E | . | . | . | . | F | . | . |
| 35.24.6 | . | . | . | T | . | E | E | . | . | . | . | F | . | . |
| 35.21.17.1 | . | . | . | T | . | E | E | . | . | . | . | F | . | . |
| 35.21.17.2 | . | . | . | T | . | E | E | . | . | . | . | F | . | . |
| 35.21.17.3 | . | . | . | T | . | E | E | . | . | . | . | F | . | . |
| 35.21.17.4 | . | . | . | S | . | E | E | . | . | . | . | F | . | . |
| 35.21.17.5 | . | . | . | T | . | E | E | . | . | . | . | F | . | . |
| 35.21.17.6 | . | . | . | T | . | E | E | . | . | . | . | F | . | . |
| 35.20 | . | . | . | T | . | E | E | . | . | . | . | F | . | . |
| 35.21 | . | . | . | T | . | E | E | . | . | . | . | F | . | . |
| 35.22 | . | . | . | T | . | . | E | . | . | . | . | F | . | . |
| 35.23 | . | . | . | T | . | E | E | . | . | . | . | F | . | . |
| 35.24 | . | . | . | T | . | E | E | . | . | . | . | F | . | . |
| 35.21.17 | . | . | . | T | . | E | E | . | . | . | . | F | . | . |
| 35.N390 | . | . | . | T | . | . | E | . | . | . | . | F | . | . |

INFORMAL SEQUENCE LISTING

| SEQ ID NO: | Sequence | Description |
|---|---|---|
| 1 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Wild-type human Fc sequence positions 231-447 EU index numbering |
| 2 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAK | CH2 domain sequence positions 231-340 EU index numbering |
| 3 | GQPREPQVYTLPPSRDELTKNQVSLTCLVKGFYPSDIAVEWESNGQ PENNYKTTPPVLDSDGSFFLYSKLTVDKSRWQQGNVFSCSVMHEA LHNHYTQKSLSLSPGK | CH3 domain sequence Positions 341-447 EU index numbering |
| 4 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT | Clone CH3C.1 |

INFORMAL SEQUENCE LISTING

| SEQ ID NO: | Sequence | Description |
|---|---|---|
| | CLVKGFYPSDIAVEWESLGLVWVGYKTTPPVLDSDGSFFLYSKLTV<br>AKSTWQQGWVFSCSVMHEALHNHYTQKSLSLSPGK | |
| 5 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTVWSHYKTTPPVLDSDGSFFLYSKLTV<br>SKSEWQQGYVFSCSVMHEALHNHYTQKSLSLSPGK | Clone CH3C.2 |
| 6 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWSQYKTTPPVLDSDGSFFLYSKLTV<br>EKSDWQQGHVFSCSVMHEALHNHYTQKSLSLSPGK | Clone CH3C.3 |
| 7 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESVGTPWALYKTTPPVLDSDGSFFLYSKLTV<br>LKSEWQQGWVFSCSVMHEALHNHYTQKSLSLSPGK | Clone CH3C.4 |
| 8 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTVWSKYKTTPPVLDSDGSFFLYSKLTV<br>SKSEWQQGVFSCSVMHEALHNHYTQKSLSLSPGK | Clone CH3C.17 |
| 9 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESLGHVWAVYKTTPPVLDSDGSFFLYSKLTV<br>PKSTWQQGWVFSCSVMHEALHNHYTQKSLSLSPGK | Clone CH3C.18 |
| 10 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESLGLVWVGYKTTPPVLDSDGSFFLYSKLTV<br>PKSTWQQGWVFSCSVMHEALHNHYTQKSLSLSPGK | Clone CH3C.21 |
| 11 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESMGHVWVGYKTTPPVLDSDGSFFLYSKLT<br>VDKSTWQQGWVFSCSVMHEALHNHYTQKSLSLSPGK | Clone CH3C.25 |
| 12 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESLGLVWVFSKTTPPVLDSDGSFFLYSKLTVP<br>KSTWQQGWVFSCSVMHEALHNHYTQKSLSLSPGK | Clone CH3C.34 |
| 13 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWSSYKTTPPVLDSDGSFFLYSKLTV<br>TKSEWQQGFVFSCSVMHEALHNHYTQKSLSLSPGK | Clone CH3C.35 |
| 14 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWSNYKTTPPVLDSDGSFFLYSKLTV<br>SKSEWQQGFVFSCSVMHEALHNHYTQKSLSLSPGK | Clone CH3C.44 |
| 15 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESLGHVWVGYKTTPPVLDSDGSFFLYSKLTV<br>SKSEWQQGWVFSCSVMHEALHNHYTQKSLSLSPGK | Clone CH3C.51 |
| 16 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESLGHVWVATKTTPPVLDSDGSFFLYSKLTV<br>PKSTWQQGWVFSCSVMHEALHNHYTQKSLSLSPGK | Clone CH3C.3.1-3 |

| SEQ ID NO: | Sequence | Description |
|---|---|---|
| 17 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESLGPVWVHTKTTPPVLDSDGSFFLYSKLTV PKSTWQQGWVFSCSVMHEALHNHYTQKSLSLSPGK | Clone CH3C.3.1-9 |
| 18 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESLGHVWVDQKTTPPVLDSDGSFFLYSKLTV PKSTWQQGWVFSCSVMHEALHNHYTQKSLSLSPGK | Clone CH3C.3.2-5 |
| 19 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESLGHVWVNQKTTPPVLDSDGSFFLYSKLTV PKSTWQQGWVFSCSVMHEALHNHYTQKSLSLSPGK | Clone CH3C.3.2-19 |
| 20 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESLGHVWVNFKTTPPVLDSDGSFFLYSKLTV PKSTWQQGWVFSCSVMHEALHNHYTQKSLSLSPGK | Clone CH3C.3.2-1 |
| 21 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESLGHVWAVYKTTPPVLDSDGSFFLYSKLT VPKSTWQQGWVFSCSVMHEALHNHYTQKSLSLSPGK | Clone CH3C.18 variant |
| 22 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESLGHVWAVYKTTPPVLDSDGSFFLYSKLTV PKSTWQQGWVFSCSVMHEALHNHYTQKSLSLSPGK | Clone CH3C.18 variant |
| 23 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVYWESLGHVWAVYKTTPPVLDSDGSFFLYSKLTV PKSTWQQGWVFSCSVMHEALHNHYTQKSLSLSPGK | Clone CH3C.18 variant |
| 24 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESLGHVWAVYQTTPPVLDSDGSFFLYSKLTV PKSTWQQGWVFSCSVMHEALHNHYTQKSLSLSPGK | Clone CH3C.18 variant |
| 25 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESLGHVWAVYFTTPPVLDSDGSFFLYSKLTV PKSTWQQGWVFSCSVMHEALHNHYTQKSLSLSPGK | Clone CH3C.18 variant |
| 26 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESLGHVWAVYHTTPPVLDSDGSFFLYSKLTV PKSTWQQGWVFSCSVMHEALHNHYTQKSLSLSPGK | Clone CH3C.18 variant |
| 27 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESLGHVWAVYKTTPPVLDSDGSFFLYSKLT VPKSTWQQGWVFSCSVMHEALHNHYTQKSLSLSPGK | Clone CH3C.35.13 |
| 28 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESLGHVWAVYQTTPPVLDSDGSFFLYSKLTV PKSTWQQGWVFSCSVMHEALHNHYTQKSLSLSPGK | Clone CH3C.35.14 |

| SEQ ID NO: | Sequence | Description |
|---|---|---|
| 29 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESLGHVWAVYQTTPPVLDSDGSFFLYSKLT VPKSTWQQGWVFSCSVMHEALHNHYTQKSLSLSPGK | Clone CH3C.35.15 |
| 30 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESLGHVWVNQKTTPPVLDSDGSFFLYSKLT VPKSTWQQGWVFSCSVMHEALHNHYTQKSLSLSPGK | Clone CH3C.35.16 |
| 31 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESLGHVWVNQQTTPPVLDSDGSFFLYSKLTV PKSTWQQGWVFSCSVMHEALHNHYTQKSLSLSPGK | Clone CH3C.35.17 |
| 32 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESLGHVWVNQTTPPVLDSDGSFFLYSKLT VPKSTWQQGWVFSCSVMHEALHNHYTQKSLSLSPGK | Clone CH3C.35.18 |
| 33 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESYGTEWSSYKTTPPVLDSDGSFFLYSKLTV TKSEWQQGFVFSCSVMHEALHNHYTQKSLSLSPGK | Clone CH3C.35.19 |
| 34 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESYGTEWSSYKTTPPVLDSDGSFFLYSKLTV TKEEWQQGFVFSCSVMHEALHNHYTQKSLSLSPGK | Clone CH3C.35.20 |
| 35 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESYGTEWSSYKTTPPVLDSDGSFFLYSKLTV TKEEWQQGFVFSCSVMHEALHNHYTQKSLSLSPGK | Clone CH3C.35.21 |
| 36 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESYGTEWSNYKTTPPVLDSDGSFFLYSKLTV TKSEWQQGFVFSCSVMHEALHNHYTQKSLSLSPGK | Clone CH3C.35.22 |
| 37 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESYGTEWSNYKTTPPVLDSDGSFFLYSKLTV TKEEWQQGFVFSCSVMHEALHNHYTQKSLSLSPGK | Clone CH3C.35.23 |
| 38 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESYGTEWSNYKTTPPVLDSDGSFFLYSKLTV TKEEWQQGFVFSCSVMHEALHNHYTQKSLSLSPGK | Clone CH3C.35.24 |
| 39 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESYGTEWSNYKTTPPVLDSDGSFFLYSKLTV TKSEWQQGFVFSCSVMHEALHNHYTQKSLSLSPGK | Clone CH3C.35.N163 |
| 40 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESYGTEWSSYQTTPPVLDSDGSFFLYSKLTV TKSEWQQGFVFSCSVMHEALHNHYTQKSLSLSPGK | Clone CH3C.35.K165Q |

| SEQ ID NO: | Sequence | Description |
|---|---|---|
| 41 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESYGTEWSNYQTTPPVLDSDGSFFLYSKLTV TKSEWQQGFVFSCSVMHEALHNHYTQKSLSLSPGK | Clone CH3C.35.N163. K165Q |
| 42 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYKTTPPVLDSDGSFFLYSKLTV TKSEWQQGFVFSCSVMHEALHNHYTQKSLSLSPGK | Clone CH3C.35.21.1 |
| 43 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT KSEWQQGFVFSCSVMHEALHNHYTQKSLSLSPGK | Clone CH3C.35.21.2 |
| 44 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT REEWQQGFVFSCSVMHEALHNHYTQKSLSLSPGK | Clone CH3C.35.21.3 |
| 45 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT GEEWQQGFVFSCSVMHEALHNHYTQKSLSLSPGK | Clone CH3C.35.21.4 |
| 46 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT REEWQQGFVFSCWVMHEALHNHYTQKSLSLSPGK | Clone CH3C.35.21.5 |
| 47 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT KEEWQQGFVFSCWVMHEALHNHYTQKSLSLSPGK | Clone CH3C.35.21.6 |
| 48 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT REEWQQGFVFTCWVMHEALHNHYTQKSLSLSPGK | Clone CH3C.35.21.7 |
| 49 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT REEWQQGFVFTCGVMHEALHNHYTQKSLSLSPGK | Clone CH3C.35.21.8 |
| 50 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT REEWQQGFVFECWVMHEALHNHYTQKSLSLSPGK | Clone CH3C.35.21.9 |
| 51 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT REEWQQGFVFKCWVMHEALHNHYTQKSLSLSPGK | Clone CH3C.35.21.10 |
| 52 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYRTTPPVLDSDGSFFLYSKLTVT PEEWQQGFVFKCWVMHEALHNHYTQKSLSLSPGK | Clone CH3C.35.21.11 |

| INFORMAL SEQUENCE LISTING | | |
|---|---|---|
| SEQ ID NO: | Sequence | Description |
| 53 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESYGTEWSSYRTTPPVLDSDGSFFLYSKLTV<br>TREEWQQGFVFSCSVMHEALHNHYTQKSLSLSPGK | Clone CH3C.35.21.12 |
| 54 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESYGTEWSSYRTTPPVLDSDGSFFLYSKLTV<br>TGEEWQQGFVFSCSVMHEALHNHYTQKSLSLSPGK | Clone CH3C.35.21.13 |
| 55 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESYGTEWSSYRTTPPVLDSDGSFFLYSKLTV<br>TREEWQQGFVFTCWVMHEALHNHYTQKSLSLSPGK | Clone CH3C.35.21.14 |
| 56 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESYGTEWSSYRTTPPVLDSDGSFFLYSKLTV<br>TGEEWQQGFVFTCWVMHEALHNHYTQKSLSLSPGK | Clone CH3C.35.21.15 |
| 57 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESYGTEWSSYRTTPPVLDSDGSFFLYSKLTV<br>TREEWQQGFVFTCGVMHEALHNHYTQKSLSLSPGK | Clone CH3C.35.21.16 |
| 58 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVLWESYGTEWSSYKTTPPVLDSDGSFFLYSKLTV<br>TKEEWQQGFVFSCSVMHEALHNHYTQKSLSLSPGK | Clone CH3C.35.21.17 |
| 59 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVLWESYGTEWSSYRTTPPVLDSDGSFFLYSKLTVT<br>KEEWQQGFVFSCSVMHEALHNHYTQKSLSLSPGK | Clone CH3C.35.21.18 |
| 60 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESFGTEWSSYKTTPPVLDSDGSFFLYSKLTVT<br>KEEWQQGFVFSCSVMHEALHNHYTQKSLSLSPGK | Clone CH3C.35.20.1 |
| 61 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWASYKTTPPVLDSDGSFFLYSKLTV<br>TKEEWQQGFVFSCSVMHEALHNHYTQKSLSLSPGK | Clone CH3C.35.20.2 |
| 62 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWVSYKTTPPVLDSDGSFFLYSKLTV<br>TKEEWQQGFVFSCSVMHEALHNHYTQKSLSLSPGK | Clone CH3C.35.20.3 |
| 63 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWSSYKTTPPVLDSDGSFFLYSKLTVS<br>KEEWQQGFVFSCSVMHEALHNHYTQKSLSLSPGK | Clone CH3C.35.20.4 |
| 64 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESFGTEWASYKTTPPVLDSDGSFFLYSKLTV<br>TKEEWQQGFVFSCSVMHEALHNHYTQKSLSLSPGK | Clone CH3C.35.20.5 |

| SEQ ID NO: | Sequence | Description |
|---|---|---|
| 65 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESFGTEWVSYKTTPPVLDSDGSFFLYSKLTV<br>TKEEWQQGFVFSCSVMHEALHNHYTQKSLSLSPGK | Clone CH3C.35.20.6 |
| 66 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESFGTEWSSYKTTPPVLDSDGSFFLYSKLTV<br>TKEEWQQGFVFSCSVMHEALHNHYTQKSLSLSPGK | Clone CH3C.35.21.a.1 |
| 67 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESYGTEWASYKTTPPVLDSDGSFFLYSKLTV<br>TKEEWQQGFVFSCSVMHEALHNHYTQKSLSLSPGK | Clone CH3C.35.21.a.2 |
| 68 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESYGTEWVSYKTTPPVLDSDGSFFLYSKLTV<br>TKEEWQQGFVFSCSVMHEALHNHYTQKSLSLSPGK | Clone CH3C.35.21.a.3 |
| 69 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESYGTEWSSYKTTPPVLDSDGSFFLYSKLTV<br>SKEEWQQGFVFSCSVMHEALHNHYTQKSLSLSPGK | Clone CH3C.35.21.a.4 |
| 70 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESYGTEWASYKTTPPVLDSDGSFFLYSKLTV<br>TKEEWQQGFVFSCSVMHEALHNHYTQKSLSLSPGK | Clone CH3C.35.21.a.5 |
| 71 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVWWESFGTEWVSYKTTPPVLDSDGSFFLYSKLTV<br>TKEEWQQGFVFSCSVMHEALHNHYTQKSLSLSPGK | Clone CH3C.35.21.a.6 |
| 72 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESFGTEWSNYKTTPPVLDSDGSFFLYSKLTV<br>TKEEWQQGFVFSCSVMHEALHNHYTQKSLSLSPGK | Clone CH3C.35.23.1 |
| 73 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWANYKTTPPVLDSDGSFFLYSKLTV<br>TKEEWQQGFVFSCSVMHEALHNHYTQKSLSLSPGK | Clone CH3C.35.23.2 |
| 74 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWVNYKTTPPVLDSDGSFFLYSKLTV<br>TKEEWQQGFVFSCSVMHEALHNHYTQKSLSLSPGK | Clone CH3C.35.23.3 |
| 75 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWSNYKTTPPVLDSDGSFFLYSKLTV<br>SKEEWQQGFVFSCSVMHEALHNHYTQKSLSLSPGK | Clone CH3C.35.23.4 |
| 76 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESFGTEWANYKTTPPVLDSDGSFFLYSKLTV<br>TKEEWQQGFVFSCSVMHEALHNHYTQKSLSLSPGK | Clone CH3C.35.23.5 |

-continued

INFORMAL SEQUENCE LISTING

| SEQ ID NO: | Sequence | Description |
|---|---|---|
| 77 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVEWESFGTEWNYKTTPPVLDSDGSFFLYSKLTV TKEEWQQGFVFSCSVMHEALHNHYTQKSLSLSPGK | Clone CH3C.35.23.6 |
| 78 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESFGTEWSNYKTTPPVLDSDGSFFLYSKLTV TKEEWQQGFVFSCSVMHEALHNHYTQKSLSLSPGK | Clone CH3C.35.24.1 |
| 79 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESYGTEWANYKTTPPVLDSDGSFFLYSKLT VTKEEWQQGFVFSCSVMHEALHNHYTQKSLSLSPGK | Clone CH3C.35.24.2 |
| 80 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESYGTEWVNYKTTPPVLDSDGSFFLYSKLT VTKEEWQQGFVFSCSVMHEALHNHYTQKSLSLSPGK | Clone CH3C.35.24.3 |
| 81 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESYGTEWSNYKTTPPVLDSDGSFFLYSKLTV SKEEWQQGFVFSCSVMHEALHNHYTQKSLSLSPGK | Clone CH3C.35.24.4 |
| 82 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESFGTEWANYKTTPPVLDSDGSFFLYSKLTV TKEEWQQGFVFSCSVMHEALHNHYTQKSLSLSPGK | Clone CH3C.35.24.5 |
| 83 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVWWESFGTEWVNYKTTPPVLDSDGSFFLYSKLTV TKEEWQQGFVFSCSVMHEALHNHYTQKSLSLSPGK | Clone CH3C.35.24.6 |
| 84 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESFGIEWSSYKTTPPVLDSDGSFFLYSKLTVT KEEWQQGFVFSCSVMHEALHNHYTQKSLSLSPGK | Clone CH3C.35.21.17.1 |
| 85 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWASYKTTPPVLDSDGSFFLYSKLTV TKEEWQQGFVFSCSVMHEALHNHYTQKSLSLSPGK | Clone CH3C.35.21.17.2 |
| 86 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWVSYKTTPPVLDSDGSFFLYSKLTV TKEEWQQGFVFSCSVMHEALHNHYTQKSLSLSPGK | Clone CH3C.35.21.17.3 |
| 87 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESYGTEWSSYKTTPPVLDSDGSFFLYSKLTVS KEEWQQGFVFSCSVMHEALHNHYTQKSLSLSPGK | Clone CH3C.35.21.17.4 |
| 88 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLT CLVKGFYPSDIAVLWESFGTEWASYKTTPPVLDSDGSFFLYSKLTV TKEEWQQGFVFSCSVMHEALHNHYTQKSLSLSPGK | Clone CH3C.35.21.17.5 |

| SEQ ID NO: | Sequence | Description |
|---|---|---|
| 89 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVLWESFGTEWSYKTTPPVLDSDGSFFLYSKLTV<br>TKEEWQQGFVFSCSVMHEALHNHYTQKSLSLSPGK | Clone CH3C.35.21.17.6 |
| 90 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLT<br>CLVKGFYPSDIAVEWESYGTEWSNYKTTPPVLDSDGSFFLYSKLTV<br>TKSEWQQGFVFSCSVMHEALHNHYTQKSLSLSPGK | Clone CH3C.35.N390 |
| 91 | MPPPRTGRGLLWLGLVLSSVCVALGSETQANSTTDALNVLLIIVDD<br>LRPSLGCYGDKLVRSPNIDQLASHSLLFQNAFAQQAVCAPSRVSFLT<br>GRRPDTTRLYDFNSYWRVHAGNFSTIPQYFKENGYVTMSVGKVFH<br>PGISSNHTDDSPYSWSFPPYHPSSEKYENTKTCRGPDGELHANLLCP<br>VDVLDVPEGTLPDKQSTEQAIQLLEKMKTSASPFFLAVGYHKPHIPF<br>RYPKEFQKLYPLENITLAPDPEVPDGLPPVAYNPWMDIRQREDVQA<br>LNISVPYGPIPVDFQRKIRQSYFASVSYLDTQVGRLLSALDDLQLAN<br>STIIAFTSDHGWALGEHGEWAKYSNFDVATHVPLIFYVPGRTASLPE<br>AGEKLFPYLDPFDSASQLMEPGRQSMDLVELVSLFPTLAGLAGLQV<br>PPRCPVPSFHVELCREGKNLLKHFRFRDLEEDPYLPGNPRELIAYSQ<br>YPRPSDIPQWNSDKPSLKDIKIMGYSIRTIDYRYTVWVGFNPDEFLA<br>NFSDIHAGELYFVDSDPLQDHNMYNDSQGGDLFQLLMP | Full-length human iduronate sulfatase (IDS) polypeptide sequence |
| 92 | TDALNVLLIIVDDLRPSLGCYGDKLVRSPNIDQLASHSLLFQNAFAQ<br>QAVCAPSRVSFLTGRRPDTTRLYDFNSYWRVHAGNFSTIPQYFKEN<br>GYVTMSVGKVFHPGISSNHTDDSPYSWSFPPYHPSSEKYENTKTCR<br>GPDGELHANLLCPVDVLDVPEGTLPDKQSTEQAIQLLEKMKTSASP<br>FFLAVGYHKPHIPFRYPKEFQKLYPLENITLAPDPEVPDGLPPVAYN<br>PWMDIRQREDVQALNISVPYGPIPVDFQRKIRQSYFASVSYLDTQV<br>GRLLSALDDLQLANSTIIAFTSDHGWALGEHGEWAKYSNFDVATH<br>VPLIFYVPGRTASLPEAGEKLFPYLDPFDSASQLMEPGRQSMDLVEL<br>VSLFPTLAGLAGLQVPPRCPVPSFHVELCREGKNLLKHFRFRDLEED<br>PYLPGNPRELIAYSQYPRPSDIPQWNSDKPSLKDIKIMGYSIRTIDYR<br>YTVWVGFNPDEFLANFSDIHAGELYFVDSDPLQDHNMYNDSQGGD<br>LFQLLMP | Mature human iduronate sulfatase (IDS) polypeptide sequence |
| 93 | MEFSSPSREECPKPLSRVSIMAGSLTGLLLLQAVSWASGARPCIPKSF<br>GYSSVVCVCNATYCDSFDPPTFPALGTFSRYESTRSGRRMELSMGPI<br>QANHTGTGLLLTLQPEQKFQKVKGFGGAMTDAAALNILALSPPAQ<br>NLLLKSYFSEEGIGYNIIRVPMASCDFSIRTYTYADTPDDFQLHNFSL<br>PEEDTKLKIPLIHRALQLAQRPVSLLASPWTSPTWLKTNGAVNGKG<br>SLKGQPGDIYHQTWARYFVKFLDAYAEHKLQFWAVTAENEPSAGL<br>LSGYPFQCLGFTPEHQRDFIARDLGPTLANSTHHNVRLLMLDDQRL<br>LLPHWAKVVLTDPEAAKYVHGIAVHWYLDFLAPAKATLGETHRLF<br>PNTMLFASEACVGSKFWEQSVRLGSWDRGMQYSHSIITNLLYHVV<br>GWTDWNLALNPEGGPNWVRNFVDSPIIVDITKDTFYKQPMFYHLG<br>HFSKFIPEGSQRVGLVASQKNDLDAVALMHPDGSAVVVLNRSSK<br>DVPLTIKDPAVGFLETISPGYSIHTYLWRRQ | Full-length human β-glucocerbosidase polypeptide sequence |
| 94 | ARPCIPKSFGYSSVVCVCNATYCDSFDPPTFPALGTFSRYESTRSGR<br>RMELSMGPIQANHTGTGLLLTLQPEQKFQKVKGFGGAMTDAAALN<br>ILALSPPAQNLLLKSYFSEEGIGYNIIRVPMASCDFSIRTYTYADTPD<br>DFQLHNFSLPEEDTKLKIPLIHRALQLAQRPVSLLASPWTSPTWLKT<br>NGAVNGKGSLKGQPGDIYHQTWARYFVKFLDAYAEHKLQFWAVT<br>AENEPSAGLLSGYPFQCLGFTPEHQRDFIARDLGPTLANSTHHNVRL<br>LMLDDQRLLLPHWAKVVLTDPEAAKYVHGIAVHWYLDFLAPAKA<br>TLGETHRLFPNTMLFASEACVGSKFWEQSVRLGSWDRGMQYSHSII<br>TNLLYHVVGWTDWNLALNPEGGPNWVRNFVDSPIIVDITKDTFYK<br>QPMFYHLGHFSKFIPEGSQRVGLVASQKNDLDAVALMHPDGSAVV<br>VVLNRSSKDVPLTIKDPAVGFLETISPGYSIHTYLWRRQ | Mature human β-glucocerbosidase polypeptide sequence |
| 95 | EPKSCDKTHTCPPCP | Human IgG1 hinge amino acid sequence |
| 96 | MMDQARSAFSNLFGGEPLSYTRFSLARQVDGDNSHVEMKLAVDEE<br>ENADNNTKANVTKPKRCSGSICYGTIAVIVFFLIGFMIGYLGYCKGV<br>EPKTECERLAGTESPVREEPGEDFPAARRLYWDDLKRKLSEKLDST<br>DFTGTIKLLNENSYVPREAGSQKDENLALYVENQFREFKLSKVWRD<br>QHFVKIQVKDSAQNSVIIVDKNGRLVYLVENPGGYVAYSKAATVT<br>GKLVHANFGTKKDFEDLYTPVNGSIVIVRAGKITFAEKVANAESLN<br>AIGVLIYMDQTKFPIVNAELSFFGHAHLGTGDPYTPGFPSFNHTQFP<br>PSRSSGLPNIPVQTISRAAAEKLFGNMEGDCPSDWKTDSTCRMVTS | Human transferrin receptor protein 1 (TFR1) |

-continued

INFORMAL SEQUENCE LISTING

| SEQ ID NO: | Sequence | Description |
|---|---|---|
| | ESKNVKLTVSNVLKEIKILNIFGVIKGFVEPDHYVVVGAQRDAWGP GAAKSGVGTALLLKLAQMFSDMVLKDGFQPSRSIIFASWSAGDFGS VGATEWLEGYLSSLHLKAFTYINLDKAVLGTSNFKVSASPLLYTLIE KTMQNVKHPVTGQFLYQDSNWASKVEKLTLDNAAFPPLAYSGIPA VSFCFCEDTDYPYLGTTMDTYKELIERIPELNKVARAAAEVAGQFVI KLTHDVELNLDYERYNSQLLSFVRDLNQYRADIKEMGLSLQWLYS ARGDFFRATSRLTTDFGNAEKTDRFVMKKLNDRVMRVEYHFLSPY VSPKESPFRHVFWGSGSHTLPALLENLKLRKQNNGAFNETLFRNQL ALATWTIQGAANALSGDVWDIDNEF | |
| 97 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVWWESYGTEWSSYKTTPPVLDSDGSFFLYSKLT VTKEEWQQGFVFSCSVMHEALHNHYTQKSLSLSPGK | Clone CH3C.35.21 with knob mutation |
| 98 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVWWESYGTEWSSYKTTPPVLDSDGSFFLYSKLT VTKEEWQQGFVFSCSVMHEALHNHYTQKSLSLSPGK | Clone CH3C.35.21 with knob and LALA mutations |
| 99 | APELLGGPSVFLFPPKPKDTLYITREPEVTCVVVDVSHEDPEVKFNW YVDGVEVHNAKTKPREEQYNSTYRVVSVLTVLHQDWLNGKEYKC KVSNKALPAPIEKTISKAKGQPREPQVYTLPPSRDELTKNQVSLWCL VKGFYPSDIAVWWESYGTEWSSYKTTPPVLDSDGSFFLYSKLTVTK EEWQQGFVFSCSVMHEALHNHYTQKSLSLSPGK | Clone CH3C.35.21 with knob and YTE mutations |
| 100 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVWWESYGTEWSSYKTTPPVLDSDGSFFLYSKLT VTKEEWQQGFVFSCSVMHEALHNHYTQKSLSLSPGK | Clone CH3C.35.21 with knob, LALA, and YTE mutations |
| 101 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESNGQPENNYKTTPPVLDSDGSFFLVSKLTV DKSRWQQGNVFSCSVMHEALHNHYTQKSLSLSPGK | Fc sequence with hole mutations |
| 102 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESNGQPENNYKTTPPVLDSDGSFFLVSKLTV DKSRWQQGNVFSCSVMHEALHNHYTQKSLSLSPGK | Fc sequence with hole and LALA mutations |
| 103 | APELLGGPSVFLFPPKPKDTLYITREPEVTCVVVDVSHEDPEVKFNW YVDGVEVHNAKTKPREEQYNSTYRVVSVLTVLHQDWLNGKEYKC KVSNKALPAPIEKTISKAKGQPREPQVYTLPPSRDELTKNQVSLSCA VKGFYPSDIAVEWESNGQPENNYKTTPPVLDSDGSFFLVSKLTVDK SRWQQGNVFSCSVMHEALHNHYTQKSLSLSPGK | Fc sequence with hole and YTE mutations |
| 104 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESNGQPENNYKTTPPVLDSDGSFFLVSKLTV DKSRWQQGNVFSCSVMHEALHNHYTQKSLSLSPGK | Fc sequence with hole, LALA, and YTE mutations |
| 105 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVWWESYGTEWSSYKTTPPVLDSDGSFFLVSKLTV TKEEWQQGFVFSCSVMHEALHNHYTQKSLSLSPGK | Clone CH3C.35.21 with hole mutations |
| 106 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVWWESYGTEWSSYKTTPPVLDSDGSFFLVSKLTV TKEEWQQGFVFSCSVMHEALHNHYTQKSLSLSPGK | Clone CH3C.35.21 with hole and LALA mutations |
| 107 | APELLGGPSVFLFPPKPKDTLYITREPEVTCVVVDVSHEDPEVKFNW YVDGVEVHNAKTKPREEQYNSTYRVVSVLTVLHQDWLNGKEYKC KVSNKALPAPIEKTISKAKGQPREPQVYTLPPSRDELTKNQVSLSCA | Clone CH3C.35.21 with hole and YTE mutations |

| SEQ ID NO: | Sequence | Description |
|---|---|---|
| | VKGFYPSDIAVWWESYGTEWSSYKTTPPVLDSDGSFFLVSKLTVTK<br>EEWQQGFVFSCSVMHEALHNHYTQKSLSLSPGK | |
| 108 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVWWESYGTEWSSYKTTPPVLDSDGSFFLVSKLTV<br>TKEEWQQGFVFSCSVMHEALHNHYTQKSLSLSPGK | Clone CH3C.35.21 with hole, LALA, and YTE mutations |
| 109 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVEWESNGQPENNYKTTPPVLDSDGSFFLYSKLT<br>VDKSRWQQGNVFSCSVMHEALHNHYTQKSLSLSPGK | Fc sequence with knob mutation |
| 110 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVEWESNGQPENNYKTTPPVLDSDGSFFLYSKLT<br>VDKSRWQQGNVFSCSVMHEALHNHYTQKSLSLSPGK | Fc sequence with knob and LALA mutations |
| 111 | APELLGGPSVFLFPPKPKDTLYITREPEVTCVVVDVSHEDPEVKFNW<br>YVDGVEVHNAKTKPREEQYNSTYRVVSVLTVLHQDWLNGKEYKC<br>KVSNKALPAPIEKTISKAKGQPREPQVYTLPPSRDELTKNQVSLWCL<br>VKGFYPSDIAVEWESNGQPENNYKTTPPVLDSDGSFFLYSKLTVDK<br>SRWQQGNVFSCSVMHEALHNHYTQKSLSLSPGK | Fc sequence with knob and YTE mutations |
| 112 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVEWESNGQPENNYKTTPPVLDSDGSFFLYSKLT<br>VDKSRWQQGNVFSCSVMHEALHNHYTQKSLSLSPGK | Fc sequence with knob, LALA, and YTE mutations |
| 113 | DKTHTCPPCP | Portion of human IgG1 hinge sequence |
| 114 | SETQANSTTD ALNVLLIIVD DLRPSLGCYG DKLVRSPNID<br>QLASHSLLFQ NAFAQQAVCA PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDPEV PDGLPPVAYN<br>PWMDIRQRED VQALNISVPY GPIPVDFQRK IRQSYFASVS<br>YLDTQVGRLL SALDDLQLAN STIIAFTSDH GWALGEHGEW<br>AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTVWVGF<br>NPDEFLANFS DIHAGELYFV DSDPLQDHNM YNDSQGGDLF<br>QLLMP | IDS sequence (cysteine modified to formylglycine double underlined) |
| 115 | <u>SETQANSTTD ALNVLLIIVD DLRPSLGCYG DKLVRSPNID</u><br><u>QLASHSLLFQ NAFAQQAV<u>C</u>A PSRVSFLTGR RPDTTRLYDF</u><br><u>NSYWRVHAGN FSTIPQYFKE NGYVTMSVGK VFHPGISSNH</u><br><u>TDDSPYSWSF PPYHPSSEKY ENTKTCRGPD GELHANLLCP</u><br><u>VDVLDVPEGT LPDKQSTEQA IQLLEKMKTS ASPFFLAVGY</u><br><u>HKPHIPFRYP KEFQKLYPLE NITLAPDPEV PDGLPPVAYN</u><br><u>PWMDIRQRED VQALNISVPY GPIPVDFQRK IRQSYFASVS</u><br><u>YLDTQVGRLL SALDDLQLAN STIIAFTSDH GWALGEHGEW</u><br><u>AKYSNFDVAT HVPLIFYVPG RTASLPEAGE KLFPYLDPFD</u><br><u>SASQLMEPGR QSMDLVELVS LFPTLAGLAG LQVPPRCPVP</u><br><u>SFHVELCREG KNLLKHFRFR DLEEDPYLPG NPRELIAYSQ</u><br><u>YPRPSDIPQW NSDKPSLKDI KIMGYSIRTI DYRYTVWVGF</u><br><u>NPDEFLANFS DIHAGELYFV DSDPLQDHNM YNDSQGGDLF</u><br><u>QLLMP</u>GGGS DKTHTCPPCP APEAAGGPSV FLFPPKPKDT<br>LMISRTPEVT CVVVDVSHED PEVKFNWYVD GVEVHNAKTK<br>PREEQYNSTY RVVSVLTVLH QDWLNGKEYK CKVSNKALPA<br>PIEKTISKAK GQPREPQVYT LPPSRDELTK NQVSLSCAVK<br>GFYPSDIAVE WESNGQPENN YKTTPPVLDS DGSFFLVSKL<br>TVDKSRWQQG NVFSCSVMHE ALHNHYTQKS LSLSPGK | IDS-Fc fusion polypeptide with IDS sequence underlined (cysteine modified to formylglycine double underlined) and hole and LALA mutations |
| 116 | DKTHTCPPCP APEAAGGPSV FLFPPKPKDT LMISRTPEVT<br>CVVVDVSHED PEVKFNWYVD GVEVHNAKTK PREEQYNSTY<br>RVVSVLTVLH QDWLNGKEYK CKVSNKALPA PIEKTISKAK | Clone CH3C.35.21 with knob and LALA mutations and portion of |

| SEQ ID NO: | Sequence | Description |
|---|---|---|
|  | GQPREPQVYT LPPSRDELTK NQVSLWCLVK GFYPSDIAVW<br>WESYGTEWSS YKTTPPVLDS DGSFFLYSKL TVTKEEWQQG<br>FVFSCSVMHE ALHNYTQKS LSLSPGK | human IgG1 hinge sequence |
| 117 | SETQANSTTD ALNVLLIIVD DLRPSLGCYG DKLVRSPNID<br>QLASHSLLFQ NAFAQQAVCA PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDPEV PDGLPPVAYN<br>PWMDIRQRED VQALNISVPY GPIPVDFQRK IRQSYFASVS<br>YLDTQVGRLL SALDDDQLAN STIIAFTSDH GWALGEHGEW<br>AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTWVGF<br>NPDEFLANFS DIHAGELYFV DSDPLQDHNM YNDSQGGDLF<br>QLLMPGGGGS DKTHTCPPCP APELLGGPSV FLFPPKPKDT<br>LMISRTPEVT CVVVDVSHED PEVKFNWYVD GVEVHNAKTK<br>PREEQYNSTY RVVSVLTVLH QDWLNGKEYK CKVSNKALPA<br>PIEKTISKAK GQPREPQVYT LPPSRDELTK NQVSLSCAVK<br>GFYPSDIAVE WESNGQPENN YKTTPPVLDS DGSFFLVSKL<br>TVDKSRWQQG NVFSCSVMHE ALHNYTQKS LSLSPGK | IDS-Fc fusion polypeptide with IDS sequence underlined (cysteine modified to formylglycine double underlined) and hole mutations |
| 118 | SETQANSTTD ALNVLLIIVD DLRPSLGCYG DKLVRSPNID<br>QLASHSLLFQ NAFAQQAVCA PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDPEV PDGLPPVAYN<br>PWMDIRQRED VQALNISVPY GPIPVDFQRK IRQSYFASVS<br>YLDTQVGRLL SALDDDQLAN STIIAFTSDH GWALGEHGEW<br>AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTWVGF<br>NPDEFLANFS DIHAGELYFV DSDPLQDHNM YNDSQGGDLF<br>QLLMPGGGGS DKTHTCPPCP APELLGGPSV FLFPPKPKDT<br>LMISRTPEVT CVVVDVSHED PEVKFNWYVD GVEVHNAKTK<br>PREEQYNSTY RVVSVLTVLH QDWLNGKEYK CKVSNKALPA<br>PIEKTISKAK GQPREPQVYT LPPSRDELTK NQVSLWCLVK<br>GFYPSDIAVE WESNGQPENN YKTTPPVLDS DGSFFLYSKL<br>TVDKSRWQQG NVFSCSVMHE ALHNYTQKS LSLSPGK | IDS-Fc fusion polypeptide with IDS sequence underlined (cysteine modified to formylglycine double underlined) and knob mutation |
| 119 | MSCPVPACCALLLVLGLCRARPRNALLLLADDGGFESGAYNNSAIA<br>TPHLDALARRSLLFRNAFTSVSSCSPSRASLLTGLPQHQNGMYGLH<br>QDVHHFNSFDKVRSLPLLLSQAGVRTGIIGKKHVGPETVYPFDFAY<br>TEENGSVLQVGRNITRIKLLVRKFLQTQDDRPFFLYVAFHDPHRCG<br>HSQPQYGTFCEKFGNGESGMGRIPDWTPQAYDPLDVLVPYFVPNTP<br>AARADLAAQYTTVGRMDQGVGLVLQELRDAGVLNDTLVIFTSDN<br>GIPFPSGRTNLYWPGTAEPLLVSSPEHPKRWGQVSEAYVSLLDLTPT<br>ILDWFSIPYPSYAIFGSKTIHLTGRSLLPALEAEPLWATVFGSQSHHE<br>VTMSYPMRSVQHRHFRLVHNLNFKMPFPIDQDFYVSPTFQDLLNRT<br>TAGQPTGWYKDLRHYYYRARWELYDRSRDPHETQNLATDPRFAQ<br>LLEMLRDQLAKWQWETHDPWVCAPDGVLEEKLSPQCQPLHNEL | Full-length human sulfoglucosamine sulfohydrolase polypeptide sequence |
| 120 | RPRNALLLLADDGGFESGAYNNSAIATPHLDALARRSLLFRNAFTS<br>VSSCSPSRASLLTGLPQHQNGMYGLHQDVHHFNSFDKVRSLPLLLS<br>QAGVRTGIIGKKHVGPETVYPFDFAYTEENGSVLQVGRNITRIKLLV<br>RKFLQTQDDRPFFLYVAFHDPHRCGHSQPQYGTFCEKFGNGESGM<br>GRIPDWTPQAYDPLDVLVPYFVPNTPAARADLAAQYTTVGRMDQG<br>VGLVLQELRDAGVLNDTLVIFTSDNGIPFPSGRTNLYWPGTAEPLLV<br>SSPEHPKRWGQVSEAYVSLLDLTPTILDWFSIPYPSYAIFGSKTIHLT<br>GRSLLPALEAEPLWATVFGSQSHHEVTMSYPMRSVQHRHFRLVHN<br>LNFKMPFPIDQDFYVSPTFQDLLNRTTAGQPTGWYKDLRHYYYRA<br>RWELYDRSRDPHETQNLATDPRFAQLLEMLRDQLAKWQWETHDP<br>WVCAPDGVLEEKLSPQCQPLHNEL | Mature human sulfoglucosamine sulfohydrolase polypeptide sequence |
| 121 | MPRYGASLRQSCPRSGREQGQDTAGAPGLLWMGLVLALALALA<br>LALSDSRVLWAPAEAHPLSPQGHPARLHRIVPRLRDVFGWGNLTCP<br>ICKGLFTAINLGLKKEPNVARVGSVAIKLCNLLKIAPPAVCQSIVHLF<br>EDDMVEVWRRSVLSPSEACGLLLGSTCGHWDIFSSWNISLPTVKP<br>PPKPPSPPAPGAPVSRILFLTDLHWDHDYLEGTDPDCADPLCCRRGS<br>GLPPASRPGAGYWGEYSKCDLPLRTLESLLSGLGPAGPFDMVYWT | Full-length human acid sphingomyelinase polypeptide sequence |

-continued

INFORMAL SEQUENCE LISTING

| SEQ ID NO: | Sequence | Description |
|---|---|---|
|  | GDIPAHDVWHQTRQDQLRALTTVTALVRKFLGPVPVYPAVGNHES<br>TPVNSFPPPFIEGNHSSRWLYEAMAKAWEPWLPAEALRTLRIGGFY<br>ALSPYPGLRLISLNMNFCSRENFWLLINSTDPAGQLQWLVGELQAA<br>EDRGDKVHIIGHIPPGHCLKSWSWNYYRIVARYENTLAAQFFGHTH<br>VDEFEVFYDEETLSRPLAVAFLAPSATTYIGLNPGYRVYQIDGNYSG<br>SSHVVLDHETYILNLTQANIPGAIPHWQLLYRARETYGLPNTLPTA<br>WHNLVYRMRGDMQLFQTFWFLYHKGHPPSEPCGTPCRLATLCAQ<br>LSARADSPALCRHLMPDGSLPEAQSLWPRPLFC |  |
| 122 | LSDSRVLWAPAEAHPLSPQGHPARLHRIVPRLRDVFGWGNLTCPIC<br>KGLFTAINLGLKKEPNVARVGSVAIKLCNLLKIAPPAVCQSIVHLFE<br>DDMVEVWRRSVLSPSEACGLLLGSTCGHWDIFSSWNISLPTVPKPP<br>PKPPSPPAPGAPVSRILFLTDLHWDHDYLEGTDPDCADPLCCRRGSG<br>LPPASRPGAGYWGEYSKCDLPLRTLESLLSGLGPAGPFDMVYWTG<br>DIPAHDVWHQTRQDQLRALTTVTALVRKFLGPVPVYPAVGNHEST<br>PVNSFPPPFIEGNHSSRWLYEAMAKAWEPWLPAEALRTLRIGGFYA<br>LSPYPGLRLISLNMNFCSRENFWLLINSTDPAGQLQWLVGELQAAE<br>DRGDKVHIIGHIPPGHCLKSWSWNYYRIVARYENTLAAQFFGHTHV<br>DEFEVFYDEETLSRPLAVAFLAPSATTYIGLNPGYRVYQIDGNYSGS<br>SHVVLDHETYILNLTQANIPGAIPHWQLLYRARETYGLPNTLPTAW<br>HNLVYRMRGDMQLFQTFWFLYHKGHPPSEPCGTPCRLATLCAQLS<br>ARADSPALCRHLMPDGSLPEAQSLWPRPLFC | Mature human acid sphingomyelinase polypeptide sequence |
| 123 | LSDSRVLWAPAEAHPLSPQGHPARLHRIVPRLRDVFGWGNLTCPIC<br>KGLFTAINLGLKKEPNVARVGSVAIKLCNLLKIAPPAVCQSIVHLFE<br>DDMVEVWRRSVLSPSEACGLLLGSTCGHWDIFSSWNISLPTVPKPP<br>PKPPSPPAPGAPVSRILFLTDLHWDHDYLEGTDPDCADPLCCRRGSG<br>LPPASRPGAGYWGEYSKCDLPLRTLESLLSGLGPAGPFDMVYWTG<br>DIPAHDVWHQTRQDQLRALTTVTALVRKFLGPVPVYPAVGNHEST<br>PVNSFPPPFIEGNHSSRWLYEAMAKAWEPWLPAEALRTLRIGGFYA<br>LSPYPGLRLISLNMNFCSRENFWLLINSTDPAGQLQWLVGELQAAE<br>DRGDKVHIIGHIPPGHCLKSWSWNYYRIVARYENTLAAQFFGHTHV<br>DEFEVFYDEETLSRPLAVAFLAPSATTYIGLNPGYRVYQIDGNYSGS<br>SHVVLDHETYILNLTQANIPGAIPHWQLLYRARETYGLPNTLPTAW<br>HNLVYRMRGDMQLFQTFWFLYHKGHPPSEPCGTPCRLATLCAQLS<br>ARADSPALCRHLMPDGSLPEAQ | Truncated human acid sphingomyelinase polypeptide sequence |
| 124 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPRFDYVTTLPPSRDELTKNQVSLT<br>CLVKGFYPSDIAVEWESNGQPENNYKTTPPVLDSDGSFFLYSKLTV<br>DKSRWQQGNVFSCSVMHEALHNHYGFHDLSLSPGK | Clone CH3B.1 |
| 125 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPRFDMVTTLPPSRDELTKNQVSLT<br>CLVKGFYPSDIAVEWESNGQPENNYKTTPPVLDSDGSFFLYSKLTV<br>DKSRWQQGNVFSCSVMHEALHNHYGFHDLSLSPGK | Clone CH3B.2 |
| 126 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPRFEYVTTLPPSRDELTKNQVSLT<br>CLVKGFYPSDIAVEWESNGQPENNYKTTPPVLDSDGSFFLYSKLTV<br>DKSRWQQGNVFSCSVMHEALHNHYGFHDLSLSPGK | Clone CH3B.3 |
| 127 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPRFEMVTTLPPSRDELTKNQVSLT<br>CLVKGFYPSDIAVEWESNGQPENNYKTTPPVLDSDGSFFLYSKLTV<br>DKSRWQQGNVFSCSVMHEALHNHYGFHDLSLSPGK | Clone CH3B.4 |
| 128 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPRFELVTTLPPSRDELTKNQVSLT<br>CLVKGFYPSDIAVEWESNGQPENNYKTTPPVLDSDGSFFLYSKLTV<br>DKSRWQQGNVFSCSVMHEALHNHYGFHDLSLSPGK | Clone CH3B.5 |
| 129 | APELLGGPSVFLFPPKPKDTLMISRTPEVTCVVVDVSHEDPEVEFIW<br>YVDGVDVRYEWQLPREEQYNSTYRVVSVLTVLHQDWLNGKEYKC<br>KVSNKALPAPIEKTISKAKGQPREPQVYTLPPSRDELTKNQVSLTCL<br>VKGFYPSDIAVEWESNGQPENNYKTTPPVLDSDGSFFLYSKLTVDK<br>SRWQQGNVFSCSVMHEALHNHYTQKSLSLSPGK | Clone CH2A2.1 |

| SEQ ID NO: | Sequence | Description |
|---|---|---|
| 130 | APELLGGPSVFLFPPKPKDTLMISRTPEVTCVVVDVSHEDPEVGFV WYVDGVPVSWEWYWPREEQYNSTYRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2A2.2 |
| 131 | APELLGGPSVFLFPPKPKDTLMISRTPEVTCVVVDVSHEDPEVQFD WYVDGVMVRREWHRPREEQYNSTYRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2A2.3 |
| 132 | APELLGGPSVFLFPPKPKDTLMISRTPEVTCVVVDVSHEDPEVSFEW YVDGVPVRWEWQWPREEQYNSTYRVVSVLTVLHQDWLNGKEYK CKVSNKALPAPIEKTISKAKGQPREPQVYTLPPSRDELTKNQVSLTC LVKGFYPSDIAVEWESNGQPENNYKTTPPVLDSDGSFFLYSKLTVD KSRWQQGNVFSCSVMHEALHNHYTQKSLSLSPGK | Clone CH2A2.4 |
| 133 | APELLGGPSVFLFPPKPKDTLMISRTPEVTCVVVDVSHEDPEVAFTW YVDGVPVRWEWQNPREEQYNSTYRVVSVLTVLHQDWLNGKEYK CKVSNKALPAPIEKTISKAKGQPREPQVYTLPPSRDELTKNQVSLTC LVKGFYPSDIAVEWESNGQPENNYKTTPPVLDSDGSFFLYSKLTVD KSRWQQGNVFSCSVMHEALHNHYTQKSLSLSPGK | Clone CH2A2.5 |
| 134 | APELLGGPSVFLFPPKPKDTLMISRTPEVTCVVVDPQTPPWEVKFN WYVDGVEVHNAKTKPREEEYYTYYRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2C.1 |
| 135 | APELLGGPSVFLFPPKPKDTLMISRTPEVTCVVVDPPSPPWEVKFNW YVDGVEVHNAKTKPREEEYYSNYRVVSVLTVLHQDWLNGKEYKC KVSNKALPAPIEKTISKAKGQPREPQVYTLPPSRDELTKNQVSLTCL VKGFYPSDIAVEWESNGQPENNYKTTPPVLDSDGSFFLYSKLTVDK SRWQQGNVFSCSVMHEALHNHYTQKSLSLSPGK | Clone CH2C.2 |
| 136 | APELLGGPSVFLFPPKPKDTLMISRTPEVTCVVVDPQTPPWEVKFN WYVDGVEVHNAKTKPREEEYYSNYRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2C.3 |
| 137 | APELLGGPSVFLFPPKPKDTLMISRTPEVTCVVVDFRGPPWEVKFN WYVDGVEVHNAKTKPREEEYYHDYRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2C.4 |
| 138 | APELLGGPSVFLFPPKPKDTLMISRTPEVTCVVVDPQTVPWEVKFN WYVDGVEVHNAKTKPREEEYYSNYRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2C.5 |
| 139 | APELLGGPSVFLFPPKPKDTLMISRTPEVTCVVVDVSVPPRMVKFN WYVDGVEVHNAKTKSLTSQHNSTVRVVSVLTVLHQDWLNGKEYK CKVSNKALPAPIEKTISKAKGQPREPQVYTLPPSRDELTKNQVSLTC LVKGFYPSDIAVEWESNGQPENNYKTTPPVLDSDGSFFLYSKLTVD KSRWQQGNVFSCSVMHEALHNHYTQKSLSLSPGK | Clone CH2D.1 |
| 140 | APELLGGPSVFLFPPKPKDTLMISRTPEVTCVVVDVSVPPWMVKFN WYVDGVEVHNAKTKSLTSQHNSTVRVVSVLTVLHQDWLNGKEYK CKVSNKALPAPIEKTISKAKGQPREPQVYTLPPSRDELTKNQVSLTC LVKGFYPSDIAVEWESNGQPENNYKTTPPVLDSDGSFFLYSKLTVD KSRWQQGNVFSCSVMHEALHNHYTQKSLSLSPGK | Clone CH2D.2 |
| 141 | APELLGGPSVFLFPPKPKDTLMISRTPEVTCVVVDVSDMWEYVKFN WYVDGVEVHNAKTKPWVKQLNSTWRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2D.3 |

| SEQ ID NO: | Sequence | Description |
|---|---|---|
| 142 | APELLGGPSVFLFPPKPKDTLMISRTPEVTCVVVDVSDDWTWVKFN WYVDGVEVHNAKTKPWIAQPNSTWRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2D.4 |
| 143 | APELLGGPSVFLFPPKPKDTLMISRTPEVTCVVVDVSDDWEWVKFN WYVDGVEVHNAKTKPWKLQLNSTWRVVSVLTVLHQDWLNGKEY KCKVSNKALPAPIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2D.5 |
| 144 | APELLGGPSVFLFPPKPKDTLMISRTPEVTCVVVDVSHEDPWVWFY WYVDGVEVHNAKTKPREEQYNSTYRVVSVLTVLHQDWLNGKEY KCSVVNIALWWSIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2E3.1 |
| 145 | APELLGGPSVFLFPPKPKDTLMISRTPEVTCVVVDVSHEDPVVGFR WYVDGVEVHNAKTKPREEQYNSTYRVVSVLTVLHQDWLNGKEY KCRVSNSALTWKIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2E3.2 |
| 146 | APELLGGPSVFLFPPKPKDTLMISRTPEVTCVVVDVSHEDPVVGFR WYVDGVEVHNAKTKPREEQYNSTYRVVSVLTVLHQDWLNGKEY KCRVSNSALSWRIEKTISKAKGQPREPQVYTLPPSRDELTKNQVSLT CLVKGFYPSDIAVEWESNGQPENNYKTTPPVLDSDGSFFLYSKLTV DKSRWQQGNVFSCSVMHEALHNHYTQKSLSLSPGK | Clone CH2E3.3 |
| 147 | APELLGGPSVFLFPPKPKDTLMISRTPEVTCVVVDVSHEDPIVGFRW YVDGVEVHNAKTKPREEQYNSTYRVVSVLTVLHQDWLNGKEYKC RVSNSALRWRIEKTISKAKGQPREPQVYTLPPSRDELTKNQVSLTCL VKGFYPSDIAVEWESNGQPENNYKTTPPVLDSDGSFFLYSKLTVDK SRWQQGNVFSCSVMHEALHNHYTQKSLSLSPGK | Clone CH2E3.4 |
| 148 | APELLGGPSVFLFPPKPKDTLMISRTPEVTCVVVDVSHEDPAVGFE WYVDGVEVHNAKTKPREEQYNSTYRVVSVLTVLHQDWLNGKEY KCQVFNWALDWVIEKTISKAKGQPREPQVYTLPPSRDELTKNQVSL TCLVKGFYPSDIAVEWESNGQPENNYKTTPPVLDSDGSFFLYSKLT VDKSRWQQGNVFSCSVMHEALHNHYTQKSLSLSPGK | Clone CH2E3.5 |
| 149 | <u>RPRNALLLLA DDGGFESGAY NNSAIATPHL DALARRSLLF RNAFTSVSSC SPSRASLLTG LPQHQNGMYG LHQDVHHFNS FDKVRSLPLL LSQAGVRTGI IGKKHVGPET VYPFDFAYTE ENGSVLQVGR NITRIKLLVR KFLQTQDDRP FFLYVAFHDP HRCGHSQPQY GTFCEKFGNG ESGMGRIPDW TPQAYDPLDV LVPYFVPNTP AARADLAAQY TTVGRMDQGV GLVLQELRDA GVLNDTLVIF TSDNGIPFPS GRTNLYWPGT AEPLLVSSPE HPKRWGQVSE AYVSLLDLTP TILDWFSIPY PSYAIFGSKT IHLTGRSLLP ALEAEPLWAT VFGSQSHHEV TMSYPMRSVQ HRHFRLVHNL NFKMPFPIDQ DFYVSPTFQD LLNRTTAGQP TGWYKDLRHY YYRARWELYD RSRDPHETQN LATDPRFAQL LEMLRDQLAK WQWETHDPWV CAPDGVLEEK LSPQCQPLHN ELGGGGSDKT HTCPPCPAPE</u> AAGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLSCAVKGFY PSDIAVEWES NGQPENNYKT TPPVLDSDGS FFLVSKLTVD KSRWQQGNVF SCSVMHEALH NHYTQKSLSL SPGK | SGSH-Fc fusion polypeptide with mature human SGSH sequence (underlined) fused to the N-terminus of an Fc sequence with hole and LALA mutations |
| 150 | APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLSCAVK GFYPSDIAVE WESNGQPENN YKTTPPVLDS DGSFFLVSKL TVDKSRWQQG NVFSCSVMHE ALHNHYTQKS LSLSPGKGGG GS<u>RPRNALLL LADDGGFESG AYNNSAIATP HLDALARRSL LFRNAFTSVS SCSPSRASLL TGLPQHQNGM YGLHQDVHHF NSFDKVRSLP LLLSQAGVRT GIIGKKHVGP ETVYPFDFAY TEENGSVLQV GRNITRIKLL VRKFLQTQDD RPFFLYVAFH DPHRCGHSQP QYGTFCEKFG NGESGMGRIP DWTPQAYDPL DVLVPYFVPN TPAARADLAA QYTTVGRMDQ GVGLVLQELR DAGVLNDTLV IFTSDNGIPF PSGRTNLYWP GTAEPLLVSS PEHPKRWGQV SEAYVSLLDL</u> | SGSH-Fc fusion polypeptide with mature human SGSH sequence (underlined) fused to the C-terminus of an Fc sequence with hole and LALA mutations |

| SEQ ID NO: | Sequence | Description |
|---|---|---|
|  | TPTILDWFSI PYPSYAIFGS KTIHLTGRSL LPALEAEPLW<br>ATVFGSQSHH EVTMSYPMRS VQHRHFRLVH NLNFKMPFPI<br>DQDFYVSPTF QDLLNRTTAG QPTGWYKDLR HYYYRARWEL<br>YDRSRDPHET QNLATDPRFA QLLEMLRDQL AKWQWETHDP<br>WVCAPDGVLE EKLSPQCQPL HNEL |  |
| 151 | APEAAGGPSV FLFPPKPKDT LMISRTPEVT CVVVDVSHED<br>PEVKFNWYVD GVEVHNAKTK PREEQYNSTY RVVSVLTVLH<br>QDWLNGKEYK CKVSNKALPA PIEKTISKAK GQPREPQVYT<br>LPPSRDELTK NQVSLWCLVK GFYPSDIAVL WESYGTEWSS<br>YKTTPPVLDS DGSFFLYSKL TVTKEEWQQG FVFSCSVMHE<br>ALHNHYTQKS LSLSPGK | Clone CH3C.35.21.17 with knob and LALA mutations |
| 152 | RPRNALLLLA DDGGFESGAY NNSAIATPHL DALARRSLLF<br>RNAFTSVSSC SPSRASLLTG LPQHQNGMYG LHQDVHHFNS<br>FDKVRSLPLL LSQAGVRTGI IGKKHVGPET VYPFDFAYTE<br>ENGSVLQVGR NITRIKLLVR KFLQTQDDRP FFLYVAFHDP<br>HRCGHSQPQY GTFCEKFGNG ESGMGRIPDW TPQAYDPLDV<br>LVPYFVPNTP AARADLAAQY TTVGRMDQGV GLVLQELRDA<br>GVLNDTLVIF TSDNGIPFPS GRTNLYWPGT AEPLLVSSPE<br>HPKRWGQVSE AYVSLLDLTP TILDWFSIPY PSYAIFGSKT<br>IHLTGRSLLP ALEAEPLWAT VFGSQSHHEV TMSYPMRSVQ<br>HRHFRLVHNL NFKMPFPIDQ DFYVSPTFQD LLNRTTAGQP<br>TGWYKDLRHY YYRARWELYD RSRDPHETQN LATDPRFAQL<br>LEMLRDQLAK WQWETHDPWV CAPDGVLEEK LSPQCQPLHN<br>ELGGGGSDKT HTCPPCPAPE AAGGPSVFLF PPKPKDTLMI<br>SRTPEVTCVV VDVSHEDPEV KFNWYVDGVE VHNAKTKPRE<br>EQYNSTYRVV SVLTVLHQDW LNGKEYKCKV SNKALPAPIE<br>KTISKAKGQP REPQVYTLPP SRDELTKNQV SLWCLVKGFY<br>PSDIAVEWES NGQPENNYKT TPPVLDSDGS FFLYSKLTVD<br>KSRWQQGNVF SCSVMHEALH NHYTQKSLSL SPGK | SGSH-Fc fusion polypeptide with mature human SGSH sequence (underlined) fused to the N-terminus of an Fc sequence with knob and LALA mutations |
| 153 | APEAAGGPSV FLFPPKPKDT LMISRTPEVT CVVVDVSHED<br>PEVKFNWYVD GVEVHNAKTK PREEQYNSTY RVVSVLTVLH<br>QDWLNGKEYK CKVSNKALPA PIEKTISKAK GQPREPQVYT<br>LPPSRDELTK NQVSLWCLVK GFYPSDIAVE WESNGQPENN<br>YKTTPPVLDS DGSFFLYSKL TVDKSRWQQG NVFSCSVMHE<br>ALHNHYTQKS LSLSPGKGGG GSRPRNALLL LADDGGFESG<br>AYNNSAIATP HLDALARRSL LFRNAFTSVS SCSPSRASLL<br>TGLPQHQNGM YGLHQDVHHF NSFDKVRSLP LLLSQAGVRT<br>GIIGKKHVGP ETVYPFDFAY TEENGSVLQV GRNITRIKLL<br>VRKFLQTQDD RPFFLYVAFH DPHRCGHSQP QYGTFCEKFG<br>NGESGMGRIP DWTPQAYDPL DVLVPYFVPN TPAARADLAA<br>QYTTVGRMDQ GVGLVLQELR DAGVLNDTLV IFTSDNGIPF<br>PSGRTNLYWP GTAEPLLVSS PEHPKRWGQV SEAYVSLLDL<br>TPTILDWFSI PYPSYAIFGS KTIHLTGRSL LPALEAEPLW<br>ATVFGSQSHH EVTMSYPMRS VQHRHFRLVH NLNFKMPFPI<br>DQDFYVSPTF QDLLNRTTAG QPTGWYKDLR HYYYRARWEL<br>YDRSRDPHET QNLATDPRFA QLLEMLRDQL AKWQWETHDP<br>WVCAPDGVLE EKLSPQCQPL HNEL | SGSH-Fc fusion polypeptide with mature human SGSH sequence (underlined) fused to the C-terminus of an Fc sequence with knob and LALA mutations |
| 154 | RPRNALLLLA DDGGFESGAY NNSAIATPHL DALARRSLLF<br>RNAFTSVSSC SPSRASLLTG LPQHQNGMYG LHQDVHHFNS<br>FDKVRSLPLL LSQAGVRTGI IGKKHVGPET VYPFDFAYTE<br>ENGSVLQVGR NITRIKLLVR KFLQTQDDRP FFLYVAFHDP<br>HRCGHSQPQY GTFCEKFGNG ESGMGRIPDW TPQAYDPLDV<br>LVPYFVPNTP AARADLAAQY TTVGRMDQGV GLVLQELRDA<br>GVLNDTLVIF TSDNGIPFPS GRTNLYWPGT AEPLLVSSPE<br>HPKRWGQVSE AYVSLLDLTP TILDWFSIPY PSYAIFGSKT<br>IHLTGRSLLP ALEAEPLWAT VFGSQSHHEV TMSYPMRSVQ<br>HRHFRLVHNL NFKMPFPIDQ DFYVSPTFQD LLNRTTAGQP<br>TGWYKDLRHY YYRARWELYD RSRDPHETQN LATDPRFAQL<br>LEMLRDQLAK WQWETHDPWV CAPDGVLEEK LSPQCQPLHN<br>ELGGGGSDKT HTCPPCPAPE AAGGPSVFLF PPKPKDTLMI<br>SRTPEVTCVV VDVSHEDPEV KFNWYVDGVE VHNAKTKPRE<br>EQYNSTYRVV SVLTVLHQDW LNGKEYKCKV SNKALPAPIE<br>KTISKAKGQP REPQVYTLPP SRDELTKNQV SLWCLVKGFY<br>PSDIAVLWES YGTEWSSYKT TPPVLDSDGS FFLYSKLTVT<br>KEEWQQGFVF SCSVMHEALH NHYTQKSLSL SPGK | SGSH-Fc fusion polypeptide with mature human SGSH sequence (underlined) fused to the N-terminus of clone CH3C.35.21.17 with knob and LALA mutations |
| 155 | APEAAGGPSV FLFPPKPKDT LMISRTPEVT CVVVDVSHED<br>PEVKFNWYVD GVEVHNAKTK PREEQYNSTY RVVSVLTVLH<br>QDWLNGKEYK CKVSNKALPA PIEKTISKAK GQPREPQVYT<br>LPPSRDELTK NQVSLWCLVK GFYPSDIAVL WESYGTEWSS | SGSH-Fc fusion polypeptide with mature human SGSH sequence (underlined) fused to the |

INFORMAL SEQUENCE LISTING

| SEQ ID NO: | Sequence | Description |
|---|---|---|
|  | YKTTPPVLDS DGSFFLYSKL TVTKEEWQQG FVFSCSVMHE ALHNHYTQKS LSLSPGKGGG GSRPRNALLL LADDGGFESG AYNNSAIATP HLDALARRSL LFRNAFTSVS SCSPSRASLL TGLPQHQNGM YGLHQDVHHF NSFDKVRSLP LLLSQAGVRT GIIGKKHVGP ETVYPFDFAY TEENGSVLQV GRNITRIKLL VRKFLQTQDD RPFFLYVAPH DPHRCGHSQP QYGTFCEKFG NGESGMGRIP DWTPQAYDPL DVLVPYFVPN TPAARADLAA QYTTVGRMDQ GVGLVLQELR DAGVLNDTLV IFTSDNGIPF PSGRTNLYWP GTAEPLLVSS PEHPKRWGQV SEAYVSLLDL TPTILDWFSI PYPSYAIFGS KTIHLTGRSL LPALEAEPLW ATVFGSQSHH EVTMSYPMRS VQHRHFRLVH NLNFKMPFPI DQDFYVSPTF QDLLNRTTAG QPTGWYKDLR HYYYRARWEL YDRSRDPHET QNLATDPRFA QLLEMLRDQL AKWQWETHDP WVCAPDGVLE EKLSPQCQPL HNEL | C-terminus of clone CH3C.35.21.17 with knob and LALA mutations |
| 156 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVEWESFGTEWSSYKTTPPVLDSDGSFFLYSKLT VTKEEWQQGFVFSCSVMHEALHNHYTQKSLSLSPGK | Clone CH3C.35.20.1 with knob mutation |
| 157 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVEWESFGTEWSSYKTTPPVLDSDGSFFLYSKLT VTKEEWQQGFVFSCSVMHEALHNHYTQKSLSLSPGK | Clone CH3C.35.20.1 with knob and LALA mutations |
| 158 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSL WCLVKGFYPSDIAVEWESFGTEWSSYKTTPPVLDSDGSFFLYSKLT VTKEEWQQGFVFSCSVMHEALHNHYTQKSLSLSPGK | Clone CH3C.35.20.1 with knob and LALAPG mutations |
| 159 | APELLGGPSVFLFPPKPKDTLYITREPEVTCVVVDVSHEDPEVKFNW YVDGVEVHNAKTKPREEQYNSTYRVVSVLTVLHQDWLNGKEYKC KVSNKALPAPIEKTISKAKGQPREPQVYTLPPSRDELTKNQVSLWCL VKGFYPSDIAVEWESFGTEWSSYKTTPPVLDSDGSFFLYSKLTVTKE EWQQGFVFSCSVMHEALHNHYTQKSLSLSPGK | Clone CH3C.35.20.1 with knob and YTE mutations |
| 160 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVEWESFGTEWSSYKTTPPVLDSDGSFFLYSKLT VTKEEWQQGFVFSCSVMHEALHNHYTQKSLSLSPGK | Clone CH3C.35.20.1 with knob, LALA, and YTE mutations |
| 161 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSL WCLVKGFYPSDIAVEWESFGTEWSSYKTTPPVLDSDGSFFLYSKLT VTKEEWQQGFVFSCSVMHEALHNHYTQKSLSLSPGK | Clone CH3C.35.20.1 with knob, LALAPG, and YTE mutations |
| 162 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESFGTEWSSYKTTPPVLDSDGSFFLVSKLTVT KEEWQQGFVFSCSVMHEALHNHYTQKSLSLSPGK | Clone CH3C.35.20.1 with hole mutations |
| 163 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESFGTEWSSYKTTPPVLDSDGSFFLVSKLTVT KEEWQQGFVFSCSVMHEALHNHYTQKSLSLSPGK | Clone CH3C.35.20.1 with hole and LALA mutations |
| 164 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSLS CAVKGFYPSDIAVEWESFGTEWSSYKTTPPVLDSDGSFFLVSKLTVT KEEWQQGFVFSCSVMHEALHNHYTQKSLSLSPGK | Clone CH3C.35.20.1 with hole and LALAPG mutations |
| 165 | APELLGGPSVFLFPPKPKDTLYITREPEVTCVVVDVSHEDPEVKFNW YVDGVEVHNAKTKPREEQYNSTYRVVSVLTVLHQDWLNGKEYKC KVSNKALPAPIEKTISKAKGQPREPQVYTLPPSRDELTKNQVSLSCA VKGFYPSDIAVEWESFGTEWSSYKTTPPVLDSDGSFFLVSKLTVTKE EWQQGFVFSCSVMHEALHNHYTQKSLSLSPGK | Clone CH3C.35.20.1 with hole and YTE mutations |

| SEQ ID NO: | Sequence | Description |
|---|---|---|
| 166 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESFGTEWSSYKTTPPVLDSDGSFFLVSKLTVT KEEWQQGFVFSCSVMHEALHNHYTQKSLSLSPGK | Clone CH3C.35.20.1 with hole, LALA, and YTE mutations |
| 167 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSLS CAVKGFYPSDIAVEWESFGTEWSSYKTTPPVLDSDGSFFLVSKLTVT KEEWQQGFVFSCSVMHEALHNHYTQKSLSLSPGK | Clone CH3C.35.20.1 with hole, LALAPG, and YTE mutations |
| 168 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVEWESYGTEWANYKTTPPVLDSDGSFFLYSKLT VTKEEWQQGFVFSCSVMHEALHNHYTQKSLSLSPGK | Clone CH3C.35.23.2 with knob mutation |
| 169 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVEWESYGTEWANYKTTPPVLDSDGSFFLYSKLT VTKEEWQQGFVFSCSVMHEALHNHYTQKSLSLSPGK | Clone CH3C.35.23.2 with knob and LALA mutations |
| 170 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSL WCLVKGFYPSDIAVEWESYGTEWANYKTTPPVLDSDGSFFLYSKLT VTKEEWQQGFVFSCSVMHEALHNHYTQKSLSLSPGK | Clone CH3C.35.23.2 with knob and LALAPG mutations |
| 171 | APELLGGPSVFLFPPKPKDTLYITREPEVTCVVVDVSHEDPEVKFNW YVDGVEVHNAKTKPREEQYNSTYRVVSVLTVLHQDWLNGKEYC KVSNKALPAPIEKTISKAKGQPREPQVYTLPPSRDELTKNQVSLWCL VKGFYPSDIAVEWESYGTEWANYKTTPPVLDSDGSFFLYSKLTVTK EEWQQGFVFSCSVMHEALHNHYTQKSLSLSPGK | Clone CH3C.35.23.2 with knob and YTE mutations |
| 172 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVEWESYGTEWANYKTTPPVLDSDGSFFLYSKLT VTKEEWQQGFVFSCSVMHEALHNHYTQKSLSLSPGK | Clone CH3C.35.23.2 with knob, LALA, and YTE mutations |
| 173 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSL WCLVKGFYPSDIAVEWESYGTEWANYKTTPPVLDSDGSFFLYSKLT VTKEEWQQGFVFSCSVMHEALHNHYTQKSLSLSPGK | Clone CH3C.35.23.2 with knob, LALAPG, and YTE mutations |
| 174 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESYGTEWANYKTTPPVLDSDGSFFLVSKLTV TKEEWQQGFVFSCSVMHEALHNHYTQKSLSLSPGK | Clone CH3C.35.23.2 with hole mutations |
| 175 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESYGTEWANYKTTPPVLDSDGSFFLVSKLTV TKEEWQQGFVFSCSVMHEALHNHYTQKSLSLSPGK | Clone CH3C.35.23.2 with hole and LALA mutations |
| 176 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSLS CAVKGFYPSDIAVEWESYGTEWANYKTTPPVLDSDGSFFLVSKLTV TKEEWQQGFVFSCSVMHEALHNHYTQKSLSLSPGK | Clone CH3C.35.23.2 with hole and LALAPG mutations |
| 177 | APELLGGPSVFLFPPKPKDTLYITREPEVTCVVVDVSHEDPEVKFNW YVDGVEVHNAKTKPREEQYNSTYRVVSVLTVLHQDWLNGKEYC KVSNKALPAPIEKTISKAKGQPREPQVYTLPPSRDELTKNQVSLSCA VKGFYPSDIAVEWESYGTEWANYKTTPPVLDSDGSFFLVSKLTVTK EEWQQGFVFSCSVMHEALHNHYTQKSLSLSPGK | Clone CH3C.35.23.2 with hole and YTE mutations |

| SEQ ID NO: | Sequence | Description |
|---|---|---|
| 178 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESYGTEWANYKTTPPVLDSDGSFFLVSKLTV TKEEWQQGFVFSCSVMHEALHNHYTQKSLSLSPGK | Clone CH3C.35.23.2 with hole, LALA, and YTE mutations |
| 179 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSLS CAVKGFYPSDIAVEWESYGTEWANYKTTPPVLDSDGSFFLVSKLTV TKEEWQQGFVFSCSVMHEALHNHYTQKSLSLSPGK | Clone CH3C.35.23.2 with hole, LALAPG, and YTE mutations |
| 180 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVEWESYGTEWVNYKTTPPVLDSDGSFFLYSKLT VTKEEWQQGFVFSCSVMHEALHNHYTQKSLSLSPGK | Clone CH3C.35.23.3 with knob mutation |
| 181 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVEWESYGTEWVNYKTTPPVLDSDGSFFLYSKLT VTKEEWQQGFVFSCSVMHEALHNHYTQKSLSLSPGK | Clone CH3C.35.23.3 with knob and LALA mutations |
| 182 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSL WCLVKGFYPSDIAVEWESYGTEWVNYKTTPPVLDSDGSFFLYSKLT VTKEEWQQGFVFSCSVMHEALHNHYTQKSLSLSPGK | Clone CH3C.35.23.3 with knob and LALAPG mutations |
| 183 | APELLGGPSVFLFPPKPKDTLYITREPEVTCVVVDVSHEDPEVKFNW YVDGVEVHNAKTKPREEQYNSTYRVVSVLTVLHQDWLNGKEYKC KVSNKALPAPIEKTISKAKGQPREPQVYTLPPSRDELTKNQVSLWCL VKGFYPSDIAVEWESYGTEWVNYKTTPPVLDSDGSFFLYSKLTVTK EEWQQGFVFSCSVMHEALHNHYTQKSLSLSPGK | Clone CH3C.35.23.3 with knob and YTE mutations |
| 184 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSL WCLVKGFYPSDIAVEWESYGTEWVNYKTTPPVLDSDGSFFLYSKLT VTKEEWQQGFVFSCSVMHEALHNHYTQKSLSLSPGK | Clone CH3C.35.23.3 with knob, LALA, and YTE mutations |
| 185 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSL WCLVKGFYPSDIAVEWESYGTEWVNYKTTPPVLDSDGSFFLYSKLT VTKEEWQQGFVFSCSVMHEALHNHYTQKSLSLSPGK | Clone CH3C.35.23.3 with knob, LALAPG, and YTE mutations |
| 186 | APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESYGTEWVNYKTTPPVLDSDGSFFLVSKLTV TKEEWQQGFVFSCSVMHEALHNHYTQKSLSLSPGK | Clone CH3C.35.23.3 with hole mutations |
| 187 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESYGTEWVNYKTTPPVLDSDGSFFLVSKLTV TKEEWQQGFVFSCSVMHEALHNHYTQKSLSLSPGK | Clone CH3C.35.23.3 with hole and LALA mutations |
| 188 | APEAAGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSLS CAVKGFYPSDIAVEWESYGTEWVNYKTTPPVLDSDGSFFLVSKLTV TKEEWQQGFVFSCSVMHEALHNHYTQKSLSLSPGK | Clone CH3C.35.23.3 with hole and LALAPG mutations |
| 189 | APELLGGPSVFLFPPKPKDTLYITREPEVTCVVVDVSHEDPEVKFNW YVDGVEVHNAKTKPREEQYNSTYRVVSVLTVLHQDWLNGKEYKC KVSNKALPAPIEKTISKAKGQPREPQVYTLPPSRDELTKNQVSLSCA VKGFYPSDIAVEWESYGTEWVNYKTTPPVLDSDGSFFLVSKLTVTK EEWQQGFVFSCSVMHEALHNHYTQKSLSLSPGK | Clone CH3C.35.23.3 with hole and YTE mutations |

INFORMAL SEQUENCE LISTING

| SEQ ID NO: | Sequence | Description |
|---|---|---|
| 190 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVEWESYGTEWVNYKTTPPVLDSDGSFFLVSKLTV<br>TKEEWQQGFVFSCSVMHEALHNHYTQKSLSLSPGK | Clone CH3C.35.23.3 with hole, LALA, and YTE mutations |
| 191 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSLS<br>CAVKGFYPSDIAVEWESYGTEWVNYKTTPPVLDSDGSFFLVSKLTV<br>TKEEWQQGFVFSCSVMHEALHNHYTQKSLSLSPGK | Clone CH3C.35.23.3 with hole, LALAPG, and YTE mutations |
| 192 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVEWESYGTEWSNYKTTPPVLDSDGSFFLYSKLT<br>VSKEEWQQGFVFSCSVMHEALHNHYTQKSLSLSPGK | Clone CH3C.35.23.4 with knob mutation |
| 193 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVEWESYGTEWSNYKTTPPVLDSDGSFFLYSKLT<br>VSKEEWQQGFVFSCSVMHEALHNHYTQKSLSLSPGK | Clone CH3C.35.23.4 with knob and LALA mutations |
| 194 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSL<br>WCLVKGFYPSDIAVEWESYGTEWSNYKTTPPVLDSDGSFFLYSKLT<br>VSKEEWQQGFVFSCSVMHEALHNHYTQKSLSLSPGK | Clone CH3C.35.23.4 with knob and LALAPG mutations |
| 195 | APELLGGPSVFLFPPKPKDTLYITREPEVTCVVVDVSHEDPEVKFNW<br>YVDGVEVHNAKTKPREEQYNSTYRVVSVLTVLHQDWLNGKEYKC<br>KVSNKALPAPIEKTISKAKGQPREPQVYTLPPSRDELTKNQVSLWCL<br>VKGFYPSDIAVEWESYGTEWSNYKTTPPVLDSDGSFFLYSKLTVSK<br>EEWQQGFVFSCSVMHEALHNHYTQKSLSLSPGK | Clone CH3C.35.23.4 with knob and YTE mutations |
| 196 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVEWESYGTEWSNYKTTPPVLDSDGSFFLYSKLT<br>VSKEEWQQGFVFSCSVMHEALHNHYTQKSLSLSPGK | Clone CH3C.35.23.4 with knob, LALA, and YTE mutations |
| 197 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSL<br>WCLVKGFYPSDIAVEWESYGTEWSNYKTTPPVLDSDGSFFLYSKLT<br>VSKEEWQQGFVFSCSVMHEALHNHYTQKSLSLSPGK | Clone CH3C.35.23.4 with knob, LALAPG, and YTE mutations |
| 198 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVEWESYGTEWSNYKTTPPVLDSDGSFFLVSKLTV<br>SKEEWQQGFVFSCSVMHEALHNHYTQKSLSLSPGK | Clone CH3C.35.23.4 with hole mutations |
| 199 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVEWESYGTEWSNYKTTPPVLDSDGSFFLVSKLTV<br>SKEEWQQGFVFSCSVMHEALHNHYTQKSLSLSPGK | Clone CH3C.35.23.4 with hole and LALA mutations |
| 200 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSLS<br>CAVKGFYPSDIAVEWESYGTEWSNYKTTPPVLDSDGSFFLVSKLTV<br>SKEEWQQGFVFSCSVMHEALHNHYTQKSLSLSPGK | Clone CH3C.35.23.4 with hole and LALAPG mutations |
| 201 | APELLGGPSVFLFPPKPKDTLYITREPEVTCVVVDVSHEDPEVKFNW<br>YVDGVEVHNAKTKPREEQYNSTYRVVSVLTVLHQDWLNGKEYKC<br>KVSNKALPAPIEKTISKAKGQPREPQVYTLPPSRDELTKNQVSLSCA<br>VKGFYPSDIAVEWESYGTEWSNYKTTPPVLDSDGSFFLVSKLTVSK<br>EEWQQGFVFSCSVMHEALHNHYTQKSLSLSPGK | Clone CH3C.35.23.4 with hole and YTE mutations |

| SEQ ID NO: | Sequence | Description |
|---|---|---|
| 202 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVEWESYGTEWSNYKTTPPVLDSDGSFFLVSKLTV<br>SKEEWQQGFVFSCSVMHEALHNHYTQKSLSLSPGK | Clone CH3C.35.23.4 with hole, LALA, and YTE mutations |
| 203 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSLS<br>CAVKGFYPSDIAVEWESYGTEWSNYKTTPPVLDSDGSFFLVSKLTV<br>SKEEWQQGFVFSCSVMHEALHNHYTQKSLSLSPGK | Clone CH3C.35.23.4 with hole, LALAPG, and YTE mutations |
| 204 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVLWESYGTEWASYKTTPPVLDSDGSFFLYSKLT<br>VTKEEWQQGFVFSCSVMHEALHNHYTQKSLSLSPGK | Clone CH3C.35.21.17.2 with knob mutation |
| 205 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVLWESYGTEWASYKTTPPVLDSDGSFFLYSKLT<br>VTKEEWQQGFVFSCSVMHEALHNHYTQKSLSLSPGK | Clone CH3C.35.21.17.2 with knob and LALA mutations |
| 206 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSL<br>WCLVKGFYPSDIAVLWESYGTEWASYKTTPPVLDSDGSFFLYSKLT<br>VTKEEWQQGFVFSCSVMHEALHNHYTQKSLSLSPGK | Clone CH3C.35.21.17.2 with knob and LALAPG mutations |
| 207 | APELLGGPSVFLFPPKPKDTLYITREPEVTCVVVDVSHEDPEVKFNW<br>YVDGVEVHNAKTKPREEQYNSTYRVVSVLTVLHQDWLNGKEYKC<br>KVSNKALPAPIEKTISKAKGQPREPQVYTLPPSRDELTKNQVSLWCL<br>VKGFYPSDIAVLWESYGTEWASYKTTPPVLDSDGSFFLYSKLTVTK<br>EEWQQGFVFSCSVMHEALHNHYTQKSLSLSPGK | Clone CH3C.35.21.17.2 with knob and YTE mutations |
| 208 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVLWESYGTEWASYKTTPPVLDSDGSFFLYSKLT<br>VTKEEWQQGFVFSCSVMHEALHNHYTQKSLSLSPGK | Clone CH3C.35.21.17.2 with knob, LALA, and YTE mutations |
| 209 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSL<br>WCLVKGFYPSDIAVLWESYGTEWASYKTTPPVLDSDGSFFLYSKLT<br>VTKEEWQQGFVFSCSVMHEALHNHYTQKSLSLSPGK | Clone CH3C.35.21.17.2 with knob, LALAPG, and YTE mutations |
| 210 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVLWESYGTEWASYKTTPPVLDSDGSFFLVSKLTV<br>TKEEWQQGFVFSCSVMHEALHNHYTQKSLSLSPGK | Clone CH3C.35.21.17.2 with hole mutations |
| 211 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVLWESYGTEWASYKTTPPVLDSDGSFFLVSKLTV<br>TKEEWQQGFVFSCSVMHEALHNHYTQKSLSLSPGK | Clone CH3C.35.21.17.2 with hole and LALA mutations |
| 212 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSLS<br>CAVKGFYPSDIAVLWESYGTEWASYKTTPPVLDSDGSFFLVSKLTV<br>TKEEWQQGFVFSCSVMHEALHNHYTQKSLSLSPGK | Clone CH3C.35.21.17.2 with hole and LALAPG mutations |
| 213 | APELLGGPSVFLFPPKPKDTLYITREPEVTCVVVDVSHEDPEVKFNW<br>YVDGVEVHNAKTKPREEQYNSTYRVVSVLTVLHQDWLNGKEYKC<br>KVSNKALPAPIEKTISKAKGQPREPQVYTLPPSRDELTKNQVSLSCA<br>VKGFYPSDIAVLWESYGTEWASYKTTPPVLDSDGSFFLVSKLTVTK<br>EEWQQGFVFSCSVMHEALHNHYTQKSLSLSPGK | Clone CH3C.35.21.17.2 with hole and YTE mutations |

-continued

INFORMAL SEQUENCE LISTING

| SEQ ID NO: | Sequence | Description |
|---|---|---|
| 214 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVLWESYGTEWASYKTTPPVLDSDGSFFLVSKLTV<br>TKEEWQQGFVFSCSVMHEALHNHYTQKSLSLSPGK | Clone CH3C.35.21.17.2 with hole, LALA, and YTE mutations |
| 215 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSLS<br>CAVKGFYPSDIAVLWESYGTEWASYKTTPPVLDSDGSFFLVSKLTV<br>TKEEWQQGFVFSCSVMHEALHNHYTQKSLSLSPGK | Clone CH3C.35.21.17.2 with hole, LALAPG, and YTE mutations |
| 216 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVEWESYGTEWSNYKTTPPVLDSDGSFFLYSKLT<br>VTKEEWQQGFVFSCSVMHEALHNHYTQKSLSLSPGK | Clone CH3C.35.23 with knob mutation |
| 217 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVEWESYGTEWSNYKTTPPVLDSDGSFFLYSKLT<br>VTKEEWQQGFVFSCSVMHEALHNHYTQKSLSLSPGK | Clone CH3C.35.23 with knob and LALA mutations |
| 218 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSL<br>WCLVKGFYPSDIAVEWESYGTEWSNYKTTPPVLDSDGSFFLYSKLT<br>VTKEEWQQGFVFSCSVMHEALHNHYTQKSLSLSPGK | Clone CH3C.35.23 with knob and LALAPG mutations |
| 219 | APELLGGPSVFLFPPKPKDTLYITREPEVTCVVVDVSHEDPEVKFNW<br>YVDGVEVHNAKTKPREEQYNSTYRVVSVLTVLHQDWLNGKEYKC<br>KVSNKALPAPIEKTISKAKGQPREPQVYTLPPSRDELTKNQVSLWCL<br>VKGFYPSDIAVEWESYGTEWSNYKTTPPVLDSDGSFFLYSKLTVTK<br>EEWQQGFVFSCSVMHEALHNHYTQKSLSLSPGK | Clone CH3C.35.23 with knob and YTE mutations |
| 220 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSL<br>WCLVKGFYPSDIAVEWESYGTEWSNYKTTPPVLDSDGSFFLYSKLT<br>VTKEEWQQGFVFSCSVMHEALHNHYTQKSLSLSPGK | Clone CH3C.35.23 with knob, LALA, and YTE mutations |
| 221 | APEAAGGPSVFLFPPKPKDTLYITREPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSL<br>WCLVKGFYPSDIAVEWESYGTEWSNYKTTPPVLDSDGSFFLYSKLT<br>VTKEEWQQGFVFSCSVMHEALHNHYTQKSLSLSPGK | Clone CH3C.35.23 with knob, LALAPG, and YTE mutations |
| 222 | APELLGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVEWESYGTEWSNYKTTPPVLDSDGSFFLVSKLTV<br>TKEEWQQGFVFSCSVMHEALHNHYTQKSLSLSPGK | Clone CH3C.35.23 with hole mutations |
| 223 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALPAPIEKTISKAKGQPREPQVYTLPPSRDELTKNQVSLS<br>CAVKGFYPSDIAVEWESYGTEWSNYKTTPPVLDSDGSFFLVSKLTV<br>TKEEWQQGFVFSCSVMHEALHNHYTQKSLSLSPGK | Clone CH3C.35.23 with hole and LALA mutations |
| 224 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEY<br>KCKVSNKALGAPIEKTISKAKGQPREPQVYTLPPSRDELTKNQVSLS<br>CAVKGFYPSDIAVEWESYGTEWSNYKTTPPVLDSDGSFFLVSKLTV<br>TKEEWQQGFVFSCSVMHEALHNHYTQKSLSLSPGK | Clone CH3C.35.23 with hole and LALAPG mutations |
| 225 | APELLGGPSVFLFPPKPKDTLYITREPEVTCVVVDVSHEDPEVKFNW<br>YVDGVEVHNAKTKPREEQYNSTYRVVSVLTVLHQDWLNGKEYKC<br>KVSNKALPAPIEKTISKAKGQPREPQVYTLPPSRDELTKNQVSLSCA<br>VKGFYPSDIAVEWESYGTEWSNYKTTPPVLDSDGSFFLVSKLTVTK<br>EEWQQGFVFSCSVMHEALHNHYTQKSLSLSPGK | Clone CH3C.35.23 with hole and YTE mutations |

| SEQ ID NO: | Sequence | Description |
| --- | --- | --- |
| 226 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSRDELTKNQVSLS CAVKGFYPSDIAVEWESYGTEWSNYKTTPPVLDSDGSFFLVSKLTV TKEEWQQGFVFSCSVMHEALHNHYTQKSLSLSPGK | Clone CH3C.35.23 with hole, LALA, and YTE mutations |
| 227 | APEAAGGPSVFLFPPKPKDTLYITREPEVTCVVVDVSHEDPEVKFN WYVDGVEVHNAKTKPREEQYNSTYRVVSVLTVLHQDWLNGKEY KCKVSNKALGAPIEKTISKAKGQPREPQVYTLPPSRDELTKNQVSLS CAVKGFYPSDIAVEWESYGTEWSNYKTTPPVLDSDGSFFLVSKLTV TKEEWQQGFVFSCSVMHEALHNHYTQKSLSLSPGK | Clone CH3C.35.23 with hole, LALAPG, and YTE mutations |
| 228 | DKTHTCPPCPAPEAAGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLWCLVKGFYPSDIAVLWESYGTEWASYKTTPPVLDSDG SFFLYSKLTVTKEEWQQGFVFSCSVMHEALHNHYTQKSLSLSPGK | Clone CH3C.35.21.17.2 with knob and LALA mutations and portion of human IgG1 hinge sequence |
| 229 | DKTHTCPPCPAPEAAGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLWCLVKGFYPSDIAVEWESYGTEWANYKTTPPVLDSDG SFFLYSKLTVTKEEWQQGFVFSCSVMHEALHNHYTQKSLSLSPGK | Clone CH3C.35.23.2 with knob and LALA mutations and portion of human IgG1 hinge sequence |
| 230 | SETQANSTTD ALNVLLIIVD DLRPSLGCYG DKLVRSPNID QLASHSLLFQ NAFAQQAVCA PSRVSFLTGR RPDTTRLYDF NSYWRVHAGN FSTIPQYFKE NGYVTMSVGK VFHPGISSNH TDDSPYSWSF PPYHPSSEKY ENTKTCRGPD GELHANLLCP VDVLDVPEGT LPDKQSTEQA IQLLEKMKTS ASPFFLAVGY HKPHIPFRYP KEFQKLYPLE NITLAPDPEV PDGLPPVAYN PWMDIRQRED VQALNISVPY GPIPVDFQRK IRQSYFASVS YLDTQVGRLL SALDDLQLAN STIIAFTSDH GWALGEHGEW AKYSNFDVAT HVPLIFYVPG RTASLPEAGE KLFPYLDPFD SASQLMEPGR QSMDLVELVS LFPTLAGLAG LQVPPRCPVP SFHVELCREG KNLLKHFRFR DLEEDPYLPG NPRELIAYSQ YPRPSDIPQW NSDKPSLKDI KIMGYSIRTI DYRYTVWVGF NPDEFLANFS DIHAGELYFV DSDPLQDHNM YNDSQGGDLF QLLMP | IDS sequence |
| 231 | <u>SETQANSTTD ALNVLLIIVD DLRPSLGCYG DKLVRSPNID QLASHSLLFQ NAFAQQAVCA PSRVSFLTGR RPDTTRLYDF NSYWRVHAGN FSTIPQYFKE NGYVTMSVGK VFHPGISSNH TDDSPYSWSF PPYHPSSEKY ENTKTCRGPD GELHANLLCP VDVLDVPEGT LPDKQSTEQA IQLLEKMKTS ASPFFLAVGY HKPHIPFRYP KEFQKLYPLE NITLAPDPEV PDGLPPVAYN PWMDIRQRED VQALNISVPY GPIPVDFQRK IRQSYFASVS YLDTQVGRLL SALDDLQLAN STIIAFTSDH GWALGEHGEW AKYSNFDVAT HVPLIFYVPG RTASLPEAGE KLFPYLDPFD SASQLMEPGR QSMDLVELVS LFPTLAGLAG LQVPPRCPVP SFHVELCREG KNLLKHFRFR DLEEDPYLPG NPRELIAYSQ YPRPSDIPQW NSDKPSLKDI KIMGYSIRTI DYRYTVWVGF NPDEFLANFS DIHAGELYFV DSDPLQDHNM YNDSQGGDLF QLLMP</u>GGGGS DKTHTCPPCP APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLSCAVK GFYPSDIAVE WESNGQPENN YKTTPPVLDS DGSFFLVSKL TVDKSRWQQG NVFSCSVMHE ALHNHYTQKS LSLSPGK | IDS-Fc fusion polypeptide with IDS sequence underlined and hole and LALA mutations |
| 232 | <u>SETQANSTTD ALNVLLIIVD DLRPSLGCYG DKLVRSPNID QLASHSLLFQ NAFAQQAVCA PSRVSFLTGR RPDTTRLYDF NSYWRVHAGN FSTIPQYFKE NGYVTMSVGK VFHPGISSNH TDDSPYSWSF PPYHPSSEKY ENTKTCRGPD GELHANLLCP VDVLDVPEGT LPDKQSTEQA IQLLEKMKTS ASPFFLAVGY HKPHIPFRYP KEFQKLYPLE NITLAPDPEV PDGLPPVAYN PWMDIRQRED VQALNISVPY GPIPVDFQRK IRQSYFASVS YLDTQVGRLL SALDDLQLAN STIIAFTSDH GWALGEHGEW AKYSNFDVAT HVPLIFYVPG RTASLPEAGE KLFPYLDPFD SASQLMEPGR QSMDLVELVS LFPTLAGLAG LQVPPRCPVP SFHVELCREG KNLLKHFRFR DLEEDPYLPG NPRELIAYSQ YPRPSDIPQW NSDKPSLKDI KIMGYSIRTI DYRYTVWVGF NPDEFLANFS DIHAGELYFV DSDPLQDHNM YNDSQGGDLF QLLMP</u>GGGGS DKTHTCPPCP APELLGGPSV FLFPPKPKDT LMISRTPEVT CVVVDVSHED PEVKFNWYVD GVEVHNAKTK | IDS-Fc fusion polypeptide with IDS sequence underlined and hole mutations |

| SEQ ID NO: | Sequence | Description |
|---|---|---|
| | PREEQYNSTY RVVSVLTVLH QDWLNGKEYK CKVSNKALPA<br>PIEKTISKAK GQPREPQVYT LPPSRDELTK NQVSLSCAVK<br>GFYPSDIAVE WESNGQPENN YKTTPPVLDS DGSFFLVSKL<br>TVDKSRWQQG NVFSCSVMHE ALHNHYTQKS LSLSPGK | |
| 233 | <u>SETQANSTTD ALNVLLIIVD DLRPSLGCYG DKLVRSPNID<br>QLASHSLLFQ NAFAQQAVCA PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDDEV PDGLPPVAYN<br>PWMDIRQRED VQALNISVPY GPIPVDFQRK IRQSYFASVS<br>YLDTQVGRLL SALDDLQLAN STIIAFTSDH GWALGEHGEW<br>AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTVWVGF<br>NPDEFLANFS DIHAGELYFV DSDPLQDHNM YNDSQGGDLF<br>QLLMPGGGGS</u> DKTHTCPPCP APELLGGPSV FLFPPKPKDT<br>LMISRTPEVT CVVVDVSHED PEVKFNWYVD GVEVHNAKTK<br>PREEQYNSTY RVVSVLTVLH QDWLNGKEYK CKVSNKALPA<br>PIEKTISKAK GQPREPQVYT LPPSRDELTK NQVSLWCLVK<br>GFYPSDIAVE WESNGQPENN YKTTPPVLDS DGSFFLYSKL<br>TVDKSRWQQG NVFSCSVMHE ALHNHYTQKS LSLSPGK | IDS-Fc fusion polypeptide with IDS sequence underlined and knob mutation |
| 234 | SETQANSTTD ALNVLLIIVD DLRPSLGCYG DKLVRSPNID<br>QLASHSLLFQ NAFAQQAV<u>fG</u>A PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDDEV PDGLPPVAYN<br>PWMDIRQRED VQALNISVPY GPIPVDFQRK IRQSYFASVS<br>YLDTQVGRLL SALDDLQLAN STIIAFTSDH GWALGEHGEW<br>AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTVWVGF<br>NPDEFLANFS DIHAGELYFV DSDPLQDHNM YNDSQGGDLF<br>QLLMP | IDS sequence (formylglycine residue "fG" double underlined) |
| 235 | <u>SETQANSTTD ALNVLLIIVD DLRPSLGCYG DKLVRSPNID<br>QLASHSLLFQ NAFAQQAV<u>fG</u>A PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDDEV PDGLPPVAYN<br>PWMDIRQRED VQALNISVPY GPIPVDFQRK IRQSYFASVS<br>YLDTQVGRLL SALDDLQLAN STIIAFTSDH GWALGEHGEW<br>AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTVWVGF<br>NPDEFLANFS DIHAGELYFV DSDPLQDHNM YNDSQGGDLF<br>QLLMPGGGGS</u> DKTHTCPPCP APEAAGGPSV FLFPPKPKDT<br>LMISRTPEVT CVVVDVSHED PEVKFNWYVD GVEVHNAKTK<br>PREEQYNSTY RVVSVLTVLH QDWLNGKEYK CKVSNKALPA<br>PIEKTISKAK GQPREPQVYT LPPSRDELTK NQVSLSCAVK<br>GFYPSDIAVE WESNGQPENN YKTTPPVLDS DGSFFLVSKL<br>TVDKSRWQQG NVFSCSVMHE ALHNHYTQKS LSLSPGK | IDS-Fc fusion polypeptide with IDS sequence underlined (formylglycine residue "fG" double underlined) and hole and LALA mutations |
| 236 | <u>SETQANSTTD ALNVLLIIVD DLRPSLGCYG DKLVRSPNID<br>QLASHSLLFQ NAFAQQAV<u>fG</u>A PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDDEV PDGLPPVAYN<br>PWMDIRQRED VQALNISVPY GPIPVDFQRK IRQSYFASVS<br>YLDTQVGRLL SALDDLQLAN STIIAFTSDH GWALGEHGEW<br>AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTVWVGF<br>NPDEFLANFS DIHAGELYFV DSDPLQDHNM YNDSQGGDLF<br>QLLMPGGGGS</u> DKTHTCPPCP APELLGGPSV FLFPPKPKDT | IDS-Fc fusion polypeptide with IDS sequence underlined (formylglycine residue "fG" double underlined) and hole mutations |

INFORMAL SEQUENCE LISTING

| SEQ ID NO: | Sequence | Description |
|---|---|---|
| | LMISRTPEVT CVVVDVSHED PEVKFNWYVD GVEVHNAKTK<br>PREEQYNSTY RVVSVLTVLH QDWLNGKEYK CKVSNKALPA<br>PIEKTISKAK GQPREPQVYT LPPSRDELTK NQVSLSCAVK<br>GFYPSDIAVE WESNGQPENN YKTTPPVLDS DGSFFLVSKL<br>TVDKSRWQQG NVFSCSVMHE ALHNHYTQKS LSLSPGK | |
| 237 | <u>SETQANSTTD ALNVLLIIVD DLRPSLGCYG DKLVRSPNID<br>QLASHSLLFQ NAFAQQAV<u>fG</u>A PSRVSFLTGR RPDTTRLYDF<br>NSYWRVHAGN FSTIPQYFKE NGYVTMSVGK VFHPGISSNH<br>TDDSPYSWSF PPYHPSSEKY ENTKTCRGPD GELHANLLCP<br>VDVLDVPEGT LPDKQSTEQA IQLLEKMKTS ASPFFLAVGY<br>HKPHIPFRYP KEFQKLYPLE NITLAPDPEV PDGLPPVAYN<br>PWMDIRQRED VQALNISVPY GPIPVDFQRK IRQSYFASVS<br>YLDTQVGRLL SALDDLQLAN STIIAFTSDH GWALGEHGEW<br>AKYSNFDVAT HVPLIFYVPG RTASLPEAGE KLFPYLDPFD<br>SASQLMEPGR QSMDLVELVS LFPTLAGLAG LQVPPRCPVP<br>SFHVELCREG KNLLKHFRFR DLEEDPYLPG NPRELIAYSQ<br>YPRPSDIPQW NSDKPSLKDI KIMGYSIRTI DYRYTVWVGF<br>NPDEFLANFS DIHAGELYFV DSDPLQDHNM YNDSQGGDLF<br>QLLMPGGGGS</u> DKTHTCPPCP APELLGGPSV FLFPPKPKDT<br>LMISRTPEVT CVVVDVSHED PEVKFNWYVD GVEVHNAKTK<br>PREEQYNSTY RVVSVLTVLH QDWLNGKEYK CKVSNKALPA<br>PIEKTISKAK GQPREPQVYT LPPSRDELTK NQVSLWCLVK<br>GFYPSDIAVE WESNGQPENN YKTTPPVLDS DGSFFLYSKL<br>TVDKSRWQQG NVFSCSVMHE ALHNHYTQKS LSLSPGK | IDS-Fc fusion polypeptide with IDS sequence underlined (formylglycine residue "fG" double underlined) and knob mutation |
| 238 | NSVIIVDKNGRLVYLVENPGGYVAYSKAATVTGKLVHANFGTKKD<br>FEDLYTPVNGSIVIVRAGKITFAEKVANAESLNAIGVLIYMDQTKFPI<br>VNAELSFFGHAHLGTGDPYTPGFPSFNHTQFPPSRSSGLPNIPVQTIS<br>RAAAEKLFGNMEGDCPSDWKTDSTCRMVTSESKNVKLTVS | Human TfR apical domain |
| 239 | GGGGS | Glycine-rich linker |
| 240 | GGGGSGGGGS | Glycine-rich linker |
| 241 | HHHHHH | Hexahistidine tag |
| 242 | YxTEWSS | Library motif |

What is claimed is:

1. A protein comprising:
   a. a fusion polypeptide comprising a first Fc polypeptide linked to an iduronate 2-sulfatase (IDS) amino acid sequence, wherein the IDS amino acid sequence comprises a sequence having at least 90% identity to SEQ ID NO: 92, and wherein the IDS amino acid sequence is linked to the N-terminus of the first Fc polypeptide; and
   b. a second Fc polypeptide comprising a sequence having at least 90% identity to SEQ ID NO: 151 that is capable of specifically binding to a transferrin receptor.

2. The protein of claim 1, wherein the protein is capable of being transported across the blood-brain barrier of a primate.

3. The protein of claim 1, wherein the sequence having at least 90% identity to SEQ ID NO: 92 is selected from the group consisting of SEQ ID NOs: 92, 230, and 234.

4. The protein of claim 1, wherein the fusion polypeptide comprises the amino acid sequence of SEQ ID NO: 115 or 235.

5. The protein of claim 1, wherein the sequence having at least 90% identity to SEQ ID NO: 151 has at the following positions with reference to SEQ ID NO: 151:
   a. Trp, Leu, or Glu at position 150;
   b. Tyr at position 154;
   c. Thr at position 156;
   d. Glu at position 157;
   e. Trp at position 158;
   f. Ser or Ala at position 159;
   g. Ser or Asn at position 160;
   h. Thr at position 183;
   i. Glu at position 185;
   j. Glu at position 186; and
   k. Phe at position 191.

6. The protein of claim 5, wherein the sequence having at least 90% identity to SEQ ID NO: 151 has at the following positions with reference to SEQ ID NO: 151:
   a. Leu at position 150;
   b. Ala at position 159; and
   c. Ser at position 160.

7. The protein of claim 5, wherein the sequence having at least 90% identity to SEQ ID NO: 151 has at the following positions with reference to SEQ ID NO: 151:
   a. Glu at position 150;
   b. Ala at position 159; and
   c. Asn at position 160.

8. The protein of claim 5, wherein the sequence having at least 90% identity to SEQ ID NO: 151 has at the following positions with reference to SEQ ID NO: 151:
   a. Trp at position 150;
   b. Ser at position 159; and
   c. Ser at position 160.

9. The protein of claim 5, wherein the sequence having at least 90% identity to SEQ ID NO: 151 has at the following positions with reference to SEQ ID NO: 151:
   a. Leu at position 150;
   b. Ser at position 159; and
   c. Ser at position 160.

10. The protein of claim 1, wherein the fusion polypeptide comprises the sequence of SEQ ID NO: 115 or 235, and the sequence having at least 90% identity to SEQ ID NO: 151 is SEQ ID NO: 98.

11. The protein of claim 1, wherein the fusion polypeptide comprises the sequence of SEQ ID NO: 115 or 235, and the sequence having at least 90% identity to SEQ ID NO: 151 is SEQ ID NO: 116.

12. The protein of claim 1, wherein the fusion polypeptide comprises the sequence of SEQ ID NO: 115 or 235, and the sequence having at least 90% identity to SEQ ID NO: 151 is SEQ ID NO: 151.

13. The protein of claim 12, wherein the second Fc polypeptide further comprises, at the N-terminus of SEQ ID NO: 151, the amino acid sequence of SEQ ID NO: 113.

14. The protein of claim 1, wherein the fusion polypeptide comprises the sequence of SEQ ID NO: 115 or 235, and the sequence having at least 90% identity to SEQ ID NO: 151 is SEQ ID NO: 205.

15. The protein of claim 1, wherein the fusion polypeptide comprises the sequence of SEQ ID NO: 115 or 235, and the sequence having at least 90% identity to SEQ ID NO: 151 is SEQ ID NO: 228.

16. The protein of claim 1, wherein the fusion polypeptide comprises the sequence of SEQ ID NO: 115 or 235, and the sequence having at least 90% identity to SEQ ID NO: 151 is SEQ ID NO: 169.

17. The protein of claim 1, wherein the fusion polypeptide comprises the sequence of SEQ ID NO: 115 or 235, and the sequence having at least 90% identity to SEQ ID NO: 151 is SEQ ID NO: 229.

18. A pharmaceutical composition comprising the protein of claim 1 and a pharmaceutically acceptable excipient.

19. A protein comprising:
   a. a fusion polypeptide comprising a first Fc polypeptide linked to an iduronate 2-sulfatase (IDS) amino acid sequence, wherein the fusion polypeptide comprises SEQ ID NO: 235; and
   b. a second Fc polypeptide comprising a sequence having at least 90% identity to SEQ ID NO: 151 and having at the following positions with reference to SEQ ID NO: 151:
      i. Trp, Leu, or Glu at position 150;
      ii. Tyr at position 154;
      iii. Thr at position 156;
      iv. Glu at position 157;
      v. Trp at position 158;
      vi. Ser or Ala at position 159;
      vii. Ser or Asn at position 160;
      viii. Thr at position 183;
      ix. Glu at position 185;
      x. Glu at position 186; and
      xi. Phe at position 191.

20. The protein of claim 19, wherein the second Fc polypeptide is SEQ ID NO: 116.

21. The protein of claim 19, wherein the second Fc polypeptide is the combination of SEQ ID NO: 151 and SEQ ID NO: 113, wherein SEQ ID NO: 113 is at the N-terminus of SEQ ID NO: 151.

22. The protein of claim 19, wherein the second Fc polypeptide is SEQ ID NO: 228.

23. The protein of claim 19, wherein the second Fc polypeptide is SEQ ID NO: 229.

24. A pharmaceutical composition comprising the protein of claim 19 and a pharmaceutically acceptable excipient.

25. A protein comprising:
   a. a fusion polypeptide comprising a first Fc polypeptide linked to an iduronate 2-sulfatase (IDS) amino acid sequence, wherein the IDS amino acid sequence comprises a sequence having at least 90% identity to SEQ ID NO: 92, and wherein the IDS amino acid sequence is linked to the N-terminus of the first Fc polypeptide; and
   b. a second Fc polypeptide comprising a sequence having at least 90% identity to SEQ ID NO: 151 and having the following eight residues at respective positions with reference to SEQ ID NO: 151:
      i. Tyr at position 154;
      ii. Thr at position 156;
      iii. Glu at position 157;
      iv. Trp at position 158;
      v. Thr at position 183;
      vi. Glu at position 185;
      vii. Glu at position 186; and
      viii. Phe at position 191.

26. The protein of claim 25, wherein the sequence having at least 90% identity to SEQ ID NO: 151 has at the following positions with reference to SEQ ID NO: 151:
   ix. Trp, Leu, or Glu at position 150;
   x. Ser or Ala at position 159; and
   xi. Ser or Asn at position 160.

27. A pharmaceutical composition comprising the protein of claim 25 and a pharmaceutically acceptable excipient.

28. The protein of claim 25, wherein the fusion polypeptide is at least 95% identical to SEQ ID NO: 235, and the second Fc polypeptide is at least 95% identical to SEQ ID NO: 98.

29. The protein of claim 25, wherein the fusion polypeptide is at least 95% identical to SEQ ID NO: 235, and the second Fc polypeptide is at least 95% identical to SEQ ID NO: 151.

30. The protein of claim 25, wherein the fusion polypeptide is at least 95% identical to SEQ ID NO: 235, and the second Fc polypeptide is at least 95% identical to SEQ ID NO: 205.

31. The protein of claim 25, wherein the fusion polypeptide is at least 95% identical to SEQ ID NO: 235, and the second Fc polypeptide is at least 95% identical to SEQ ID NO: 169.

32. A protein comprising:
   a. a fusion polypeptide comprising a first Fc polypeptide linked to an iduronate 2-sulfatase (IDS) amino acid sequence, wherein the fusion polypeptide is at least 95% identical to SEQ ID NO: 235; and
   b. a second Fc polypeptide that is at least 95% identical to SEQ ID NO: 116.

33. A pharmaceutical composition comprising the protein of claim 32 and a pharmaceutically acceptable excipient.

34. A protein comprising:
   a. a fusion polypeptide comprising a first Fc polypeptide linked to an iduronate 2-sulfatase (IDS) amino acid sequence, wherein the fusion polypeptide is at least 95% identical to SEQ ID NO: 235; and
   b. a second Fc polypeptide that is at least 95% identical to the combination of SEQ ID NO: 151 and SEQ ID NO: 113, wherein SEQ ID NO: 113 is at the N-terminus SEQ ID NO: 151.

35. A pharmaceutical composition comprising the protein of claim 34 and a pharmaceutically acceptable excipient.

36. A protein comprising:
   a. a fusion polypeptide comprising a first Fc polypeptide linked to an iduronate 2-sulfatase (IDS) amino acid sequence, wherein the fusion polypeptide is at least 95% identical to SEQ ID NO: 235; and
   b. a second Fc polypeptide that is at least 95% identical to SEQ ID NO: 228.

37. A pharmaceutical composition comprising the protein of claim 36 and a pharmaceutically acceptable excipient.

38. A protein comprising:
   a. a fusion polypeptide comprising a first Fc polypeptide linked to an iduronate 2-sulfatase (IDS) amino acid sequence, wherein the fusion polypeptide is at least 95% identical to SEQ ID NO: 235; and
   b. a second Fc polypeptide that is at least 95% identical to SEQ ID NO: 229.

39. A pharmaceutical composition comprising the protein of claim 38 and a pharmaceutically acceptable excipient.

40. A protein comprising:
   a. a fusion polypeptide comprising a first Fc polypeptide linked to an iduronate 2-sulfatase (IDS) amino acid sequence, wherein the fusion polypeptide is SEQ ID NO: 235; and
   b. a second Fc polypeptide that is SEQ ID NO: 116.

41. A protein comprising:
a. a fusion polypeptide comprising a first Fc polypeptide linked to an iduronate 2-sulfatase (IDS) amino acid sequence, wherein the fusion polypeptide is SEQ ID NO: 235; and
b. a second Fc polypeptide that is the combination of SEQ ID NO: 113 and SEQ ID NO: 151, wherein SEQ ID NO: 113 is at the N-terminus of SEQ ID NO: 151.

42. A protein comprising:
a. a fusion polypeptide comprising a first Fc polypeptide linked to an iduronate 2-sulfatase (IDS) amino acid sequence, wherein the fusion polypeptide is SEQ ID NO: 235; and
b. a second Fc polypeptide that is SEQ ID NO: 228.

43. A protein comprising:
a. a fusion polypeptide comprising a first Fc polypeptide linked to an iduronate 2-sulfatase (IDS) amino acid sequence, wherein the fusion polypeptide is SEQ ID NO: 235; and
b. a second Fc polypeptide that is SEQ ID NO: 229.

44. The protein of claim 1, wherein the IDS amino acid sequence is linked to the first Fc polypeptide by a linker.

45. The protein of claim 1, wherein the IDS amino acid sequence is directly joined to the first Fc polypeptide.

46. The protein of claim 25, wherein the IDS amino acid sequence is linked to the first Fc polypeptide by a linker.

47. The protein of claim 25, wherein the IDS amino acid sequence is directly joined to the first Fc polypeptide.

* * * * *